(12) United States Patent
Molteni et al.

(10) Patent No.: US 8,569,345 B2
(45) Date of Patent: Oct. 29, 2013

(54) COMPOUNDS AND COMPOSITIONS AS LXR MODULATORS

(76) Inventors: Valentina Molteni, San Diego, CA (US); Xiaolin Li, San Diego, CA (US); Juliet Nabakka, San Diego, CA (US); David Archer Ellis, Fort Worth, TX (US); Beth Anaclerio, San Diego, CA (US); Enrique Saez, San Diego, CA (US); John Wityak, Carlsbad, CA (US)

( * ) Notice: Subject to any disclaimer, the term of this patent is extended or adjusted under 35 U.S.C. 154(b) by 0 days.

(21) Appl. No.: 13/414,385

(22) Filed: Mar. 7, 2012

(65) Prior Publication Data
US 2012/0214812 A1    Aug. 23, 2012

Related U.S. Application Data

(62) Division of application No. 10/589,087, filed as application No. PCT/US2005/004655 on Feb. 11, 2005, now Pat. No. 8,158,662.

(60) Provisional application No. 60/543,848, filed on Feb. 11, 2004, provisional application No. 60/623,021, filed on Oct. 27, 2004.

(51) Int. Cl.
*A61K 31/4439* (2006.01)
*A61K 31/433* (2006.01)
*C07D 417/04* (2006.01)
*C07D 417/14* (2006.01)

(52) U.S. Cl.
USPC ........... 514/335; 514/332; 514/342; 514/363; 546/261; 546/267; 546/268.7; 548/136

(58) Field of Classification Search
USPC ............... 546/268.7, 261, 267; 514/342, 332, 514/335, 363; 548/136
See application file for complete search history.

(56) References Cited

U.S. PATENT DOCUMENTS

| 5,106,859 A | 4/1992 | Hasegawa et al. |
| 6,555,563 B1 | 4/2003 | Le et al. |

FOREIGN PATENT DOCUMENTS

| JP | 1160976 | 6/1989 |
| JP | 1233282 | 9/1989 |
| WO | WO0132173 | 5/2001 |

*Primary Examiner* — Patricia L Morris
(74) *Attorney, Agent, or Firm* — Daniel E. Raymond; Genomiccs Institute of the Novartis Research Foundation

(57) ABSTRACT

The invention provides compounds, pharmaceutical compositions comprising such compounds and methods of using such compounds to treat or prevent diseases or disorders associated with the activity of liver X receptors (LXRs).

6 Claims, No Drawings

SEQUENCE LISTING

```
<160> NUMBER OF SEQ ID NOS: 13

<210> SEQ ID NO 1
<211> LENGTH: 24
<212> TYPE: DNA
<213> ORGANISM: Artificial Sequence
<220> FEATURE:
<223> OTHER INFORMATION: Chemically synthesized

<400> SEQUENCE: 1
tgtccagtcc agtaatggtt ctgt                                          24

<210> SEQ ID NO 2
<211> LENGTH: 21
<212> TYPE: DNA
<213> ORGANISM: Artificial Sequence
<220> FEATURE:
<223> OTHER INFORMATION: Chemically synthesized

<400> SEQUENCE: 2
aagcgagata tggtccggat t                                             21
```

<210> SEQ ID NO 3
<211> LENGTH: 33
<212> TYPE: DNA
<213> ORGANISM: Artificial Sequence
<220> FEATURE:
<223> OTHER INFORMATION: Chemically synthesized

<400> SEQUENCE: 3
acacctggag agaagctttc aacgagacta acc                                    33

<210> SEQ ID NO 4
<211> LENGTH: 18
<212> TYPE: DNA
<213> ORGANISM: Artificial Sequence
<220> FEATURE:
<223> OTHER INFORMATION: Chemically synthesized

<400> SEQUENCE: 4
ccacgctgct gaacatgc                                                     18

<210> SEQ ID NO 5
<211> LENGTH: 20
<212> TYPE: DNA
<213> ORGANISM: Artificial Sequence
<220> FEATURE:
<223> OTHER INFORMATION: Chemically synthesized

<400> SEQUENCE: 5
tcgaacacct gctggatgac                                                   20

<210> SEQ ID NO 6
<211> LENGTH: 26
<212> TYPE: DNA
<213> ORGANISM: Artificial Sequence
<220> FEATURE:
<223> OTHER INFORMATION: Chemically synthesized

<400> SEQUENCE: 6
aacatctccc ccttctcctt tgggct                                            26

<210> SEQ ID NO 7
<211> LENGTH: 23
<212> TYPE: DNA
<213> ORGANISM: Artificial Sequence
<220> FEATURE:
<223> OTHER INFORMATION: Chemically synthesized

<400> SEQUENCE: 7
gcaaattcga cctttctcag aac                                               23

<210> SEQ ID NO 8
<211> LENGTH: 18
<212> TYPE: DNA
<213> ORGANISM: Artificial Sequence
<220> FEATURE:
<223> OTHER INFORMATION: Chemically synthesized

<400> SEQUENCE: 8
ggaccccgtg gaatgtca                                                     18

<210> SEQ ID NO 9
<211> LENGTH: 23
<212> TYPE: DNA
<213> ORGANISM: Artificial Sequence
<220> FEATURE:
<223> OTHER INFORMATION: Chemically synthesized

<400> SEQUENCE: 9

```
accogetegg catggctatc ttc                                          23

<210> SEQ ID NO 10
<211> LENGTH: 18
<212> TYPE: DNA
<213> ORGANISM: Artificial Sequence
<220> FEATURE:
<223> OTHER INFORMATION: Chemically synthesized

<400> SEQUENCE: 10
ccacgctgct gaacatgc                                                18

<210> SEQ ID NO 11
<211> LENGTH: 20
<212> TYPE: DNA
<213> ORGANISM: Artificial Sequence
<220> FEATURE:
<223> OTHER INFORMATION: Chemically synthesized

<400> SEQUENCE: 11
tcgaacacct gctggatgac                                              20

<210> SEQ ID NO 12
<211> LENGTH: 26
<212> TYPE: DNA
<213> ORGANISM: Artificial Sequence
<220> FEATURE:
<223> OTHER INFORMATION: Chemically synthesized

<400> SEQUENCE: 12
aacatctccc ccttctcctt tgggct                                       26

<210> SEQ ID NO 13
<211> LENGTH: 26
<212> TYPE: PRT
<213> ORGANISM: Artificial Sequence
<220> FEATURE:
<223> OTHER INFORMATION: Chemically synthesized

<400> SEQUENCE: 13

Cys Pro Ser Ser His Ser Ser Leu Thr Glu Arg His Lys Ile Leu His
1               5                   10                  15

Arg Leu Leu Gln Glu Gly Ser Pro Ser Cys
            20                  25
```

COMPOUNDS AND COMPOSITIONS AS LXR MODULATORS

CROSS-REFERENCE TO RELATED APPLICATIONS

This application is a divisional application of U.S. Pat. No. 8,158,662, filed 8 Oct. 2008, which is a 371 U.S. national phase application of international application number PCT/US2005/004655 filed 11 Feb. 2005, which claims the benefit of U.S. Provisional Application No. 60/543,848, filed 11 Feb. 2004 and U.S. Provisional Application No. 60/623,021, filed 27 Oct. 2004. The full disclosures of these applications are incorporated herein by reference in their entirety for all purposes.

BACKGROUND OF THE INVENTION

1. Field of the Invention

The invention provides compounds, pharmaceutical compositions comprising such compounds and methods of using such compounds to treat or prevent diseases or disorders associated with the activity of liver X receptors (LXRs).

2. Background

Liver X receptors (LXRs), LXRα and LXRβ, are nuclear receptors that regulate the metabolism of several important lipids, including cholesterol and bile acids. While LXRβ is expressed ubiquitously in the body, LXRα is expressed in the liver and to a smaller degree in the kidneys, small intestine, adipose tissue, spleen and adrenal glands.

LXRs bind to the ATP binding cassette transporter-1 (ABCA1) promoter and increase expression of the gene to produce ABCA1 protein. ABCA1 is a membrane bound transport protein that is involved in the regulation of cholesterol efflux from extra-hepatic cells onto nascent high-density lipoprotein (HDL) particles. Mutations in the ABCA1 gene result in low levels of HDL and an accompanying increased risk of cardiovascular diseases such as atherosclerosis, myocardial infarction and ischemic stroke. LXRα and β agonists have been shown to increase ABCA1 gene expression thereby increasing HDL cholesterol and, as a consequence, decreasing both the net absorption of cholesterol and the risk of cardiovascular disease. LXR agonists also upregulate macrophage expression of apolipoprotein E (apoE) and ABCG1, both of which contribute to the efflux of cellular cholesterol. By stimulating macrophage cholesterol efflux through upregulation of ABCA1, ABCG1 and/or apoE expression, as well as increasing the expression of other target genes including cholesterol ester transfer protein and lipoprotein lipase, LXR agonists influence plasma lipoproteins.

The novel compounds of this invention modulate the activity of LXRs and are, therefore, expected to be useful in the treatment of LXR-associated diseases such as cardiovascular diseases, inflammation and disorders of glucose metabolism such as insulin resistance and obesity.

SUMMARY OF THE INVENTION

In one aspect, the present invention provides compounds of Formula I:

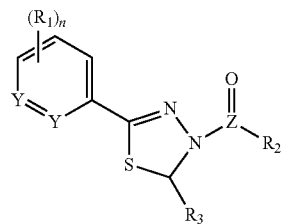

in which:

n is selected from 0, 1, 2 and 3;

Z is selected from C and S(O); each

Y is independently selected from —$CR_4$═ and —N═; wherein $R_4$ is selected from hydrogen, cyano, hydroxyl, $C_{1-6}$alkyl, $C_{1-6}$alkoxy, halo-substituted-$C_{1-6}$alkyl and halo-substituted-$C_{1-6}$alkoxy;

$R_1$ is selected from halo, cyano, hydroxyl, $C_{1-6}$alkyl, $C_{1-6}$alkoxy, halo-substituted-$C_{1-6}$alkyl, halo-substituted-$C_{1-6}$alkoxy and —C(O)$OR_4$; wherein $R_4$ is as described above;

$R_2$ is selected from $C_{6-10}$aryl, $C_{5-10}$heteroaryl, $C_{3-12}$cycloalkyl and $C_{3-8}$heterocycloalkyl; wherein any aryl, heteroaryl, cycloalkyl or heterocycloalkyl of $R_2$ is optionally substituted with 1 to 5 radicals independently selected from halo, hydroxy, cyano, nitro, $C_{1-6}$alkyl, $C_{1-6}$alkoxy, halo-substituted-$C_{1-6}$alkyl, halo-substituted-$C_{1-6}$alkoxy, —C(O)$NR_5R_5$, —$OR_5$, —OC(O)$R_5$, —$NR_5R_6$, —C(O)$R_5$ and —$NR_5$C(O)$R_5$; wherein $R_5$ and $R_6$ are independently selected from hydrogen, $C_{1-6}$alkyl, $C_{1-6}$alkoxy, halo-substituted-$C_{1-6}$alkyl, halo-substituted-$C_{1-6}$alkoxy, $C_{6-10}$aryl-$C_{0-4}$alkyl, $C_{3-8}$heteroaryl-$C_{0-4}$alkyl, $C_{3-12}$cycloalkyl-$C_{0-4}$alkyl and $C_{3-8}$heterocycloalkyl-$C_{0-4}$alkyl; or $R_5$ and $R_6$ together with the nitrogen atom to which $R_5$ and $R_6$ are attached form $C_{5-10}$heteroaryl or $C_{3-8}$heterocycloalkyl; wherein any aryl, heteroaryl, cycloalkyl or heterocycloalkyl of $R_5$ or the combination of $R_5$ and $R_6$ is optionally substituted with 1 to 4 radicals independently selected from halo, hydroxy, cyano, nitro, $C_{1-6}$alkyl, $C_{1-6}$alkoxy, halo-substituted-$C_{1-6}$alkyl and halo-substituted-$C_{1-6}$alkoxy;

$R_3$ is selected from $C_{6-10}$aryl, $C_{5-10}$heteroaryl, $C_{3-12}$cycloalkyl and $C_{3-8}$heterocycloalkyl; wherein any aryl, heteroaryl, cycloalkyl or heterocycloalkyl of $R_3$ is substituted with 1 to 5 radicals independently selected from halo, $C_{1-6}$alkoxy, halo-substituted-$C_{1-6}$alkyl, halo-substituted-$C_{1-6}$alkoxy, —$OXR_7$, —OXC(O)$NR_7R_8$, —OXC(O)$NR_7$XC(O)$OR_8$, —OXC(O)$NR_7$X$OR_8$, —OXC(O)$NR_7$X$NR_7R_8$, —OXC(O)$NR_7$XS(O)$_{0-2}R_8$, —OXC(O)$NR_7$X$NR_7$C(O)$R_8$, —OXC(O)$NR_7$XC(O)XC(O)$OR_8$, —OXC(O)$NR_7R_9$, —OXC(O)$OR_7$, —$OXOR_7$, —$OXR_9$, —$XR_9$, —OXC(O)$R_9$, —OXS(O)$_{0-2}R_9$ and —OXC(O)$NR_7CR_7$[C(O)$R_8$]$_2$;

wherein

X is a selected from a bond and $C_{1-6}$alkylene wherein any methylene of X can optionally be replaced with a divalent radical selected from C(O), $NR_7$, S(O)$_2$ and O;

$R_7$ and $R_8$ are independently selected from hydrogen, cyano, $C_{1-6}$alkyl, halo-substituted-$C_{1-6}$alkyl, $C_{2-6}$alkenyl and $C_{3-12}$cycloalkyl-$C_{0-4}$alkyl; $R_9$ is selected from $C_{6-10}$aryl-$C_{0-4}$alkyl, $C_{5-10}$heteroaryl-$C_{0-4}$alkyl, $C_{3-12}$cycloalkyl-$C_{0-4}$alkyl and $C_{3-8}$heterocycloalkyl-$C_{0-4}$alkyl; wherein any alkyl of $R_9$ can have a hydrogen replaced with —C(O)$OR_{10}$; and any aryl, heteroaryl, cycloalkyl or heterocycloalkyl of $R_9$ is optionally substituted with 1 to 4 radicals independently selected from halo, $C_{1-6}$alkyl, $C_{3-12}$cycloalkyl, halo-substituted-$C_{1-6}$alkyl, $C_{1-6}$alkoxy, halo-substituted-$C_{1-6}$alkoxy, —XC(O)OR$_{10}$, —XC(O)R$_{10}$, —XC(O)NR$_{10}$R$_{10}$, —XS(O)$_{0-2}$NR$_{10}$R$_{10}$ and —XS(O)$_{0-2}$R$_{10}$; wherein R$_{10}$ is independently selected from hydrogen and $C_{1-6}$alkyl;

and the N-oxide derivatives, prodrug derivatives, protected derivatives, individual isomers and mixture of isomers thereof; and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which modulation of LXR activity can prevent, inhibit or ameliorate the pathology and/or symptomatology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which LXR activity contributes to the pathology and/or symptomatology of the disease.

In a fifth aspect, the present invention provides a process for preparing compounds of Formula I and the N-oxide derivatives, prodrug derivatives, conjugates, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-6}$alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl can be phenyl or naphthyl, preferably phenyl. "Arylene" means a divalent radical derived from an aryl group. "Heteroaryl" is as defined for aryl where one or more of the ring members are a heteroatom. For example heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc. "$C_{6-10}$aryl$C_{0-4}$alkyl" means an aryl as described above connected via a alkylene grouping. For example, $C_{6-10}$aryl$C_{0-4}$ alkyl includes phenethyl, benzyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc. "Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, piperazinyl, piperidinyl, piperidinylone, 1,4-dioxa-8-aza-spiro[4.5]dec-8-yl, etc.

"Halogen" (or halo) preferably represents chloro or fluoro, but can also be bromo or iodo.

The term "modulate" with respect to an LXR receptor refers to regulation of the LXR receptor and its biological activities associated with the LXR pathway (e.g., transcription regulation of a target gene). Modulation of LXR receptor can be up-regulation (i.e., agonizing, activation or stimulation) or down-regulation (i.e. antagonizing, inhibition or suppression). The mode of action of an LXR modulator can be direct, e.g., through binding to the LXR receptor as a ligand. The modulation can also be indirect, e.g., through binding to and/or modifying another molecule which otherwise binds to and activates the LXR receptor, or by stimulating the generation of an endogenous LXR ligand. Thus, modulation of LXR includes a change in the bioactivities of an LXR agonist ligand (i.e., its activity in binding to and/or activating an LXR receptor) or a change in the cellular level of the ligand.

"Treat", "treating" and "treatment" refer to a method of alleviating or abating a disease and/or its attendant symptoms.

DESCRIPTION OF THE PREFERRED EMBODIMENTS

The present invention provides compounds, compositions and methods for the treatment of diseases in which modulation of LXR activity can prevent, inhibit or ameliorate the pathology and/or symptomatology of the diseases, which method comprises administering to the animal a therapeutically effective amount of a compound of Formula I.

In one embodiment, compounds of the invention are of Formula Ia:

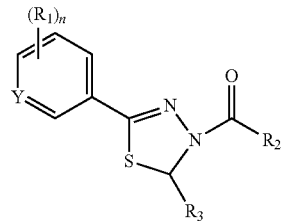

in which:
n is selected from 1, 2 and 3;
Y is selected from —CH= and —N=;
R$_1$ is selected from halo, $C_{1-6}$alkyl, and —C(O)OR$_4$; wherein R$_4$ is selected from hydrogen and $C_{1-6}$alkyl;
R$_2$ is selected from $C_{6-10}$aryl, $C_{5-10}$heteroaryl, $C_{3-12}$cycloalkyl and $C_{3-8}$heterocycloalkyl; wherein any aryl, heteroaryl, cycloalkyl or heterocycloalkyl of R$_2$ is optionally substituted with 1 to 4 radicals independently selected from halo, hydroxy, $C_{1-6}$alkyl, halo-substituted-$C_{1-6}$alkyl and —OC(O)R$_5$; wherein R$_5$ is selected from hydrogen and $C_{1-6}$alkyl; and
R$_3$ is selected from $C_{6-10}$aryl, $C_{5-10}$heteroaryl, $C_{3-12}$cycloalkyl and $C_{3-8}$heterocycloalkyl; wherein any aryl, heteroaryl, cycloalkyl or heterocycloalkyl of R$_3$ is substituted with 1 to 5 radicals independently selected from halo, hydroxyl, $C_{1-6}$alkoxy, halo-substituted-$C_{1-6}$alkyl, halo-substituted-$C_{1-6}$alkoxy, —OXR$_7$, —OXC(O)NR$_7$R$_8$, —OXC(O)NR$_7$XC(O)OR$_8$, —OXC(O)

$NR_7XOR_8$, $-OXC(O)NR_7XNR_7R_8$, $-OXC(O)NR_7XS(O)_{0-2}R_8$, $-OXC(O)NR_7XNR_7C(O)R_8$, $-OXC(O)NR_7XC(O)XC(O)OR_8$, $-OXC(O)NR_7R_9$, $-OXC(O)OR_7$, $-OXOR_7$, $-OXR_9$, $-XR_9$, $-OXC(O)R_9$ and $-OXC(O)NR_7CR_7[C(O)R_8]_2$;

wherein

X is a selected from a bond and $C_{1-6}$alkylene;

$R_7$ and $R_8$ are independently selected from hydrogen, cyano, $C_{1-6}$alkyl, halo-substituted-$C_{1-6}$alkyl, $C_{2-6}$alkenyl and $C_{3-12}$cycloalkyl-$C_{0-4}$-alkyl; $R_9$ is selected from $C_{6-10}$aryl-$C_{0-4}$alkyl, $C_{5-10}$heteroaryl-$C_{0-4}$-alkyl, $C_{3-12}$cycloalkyl-$C_{0-4}$alkyl and $C_{3-8}$heterocycloalkyl-$C_{0-4}$-alkyl; wherein any alkyl of $R_9$ can have a hydrogen replaced with $-C(O)OR_{10}$; and any aryl, heteroaryl, cycloalkyl or heterocycloalkyl of $R_9$ is optionally substituted with 1 to 4 radicals independently selected from halo, $C_{1-6}$alkyl, $C_{3-12}$cycloalkyl, halo-substituted-$C_{1-6}$alkyl, $C_{1-6}$alkoxy, halo-substituted-$C_{1-6}$alkoxy, $-XC(O)OR_{10}$, $-XC(O)R_{10}$, $-XC(O)NR_{10}R_{10}$, $-XS(O)_{0-2}NR_{10}R_{10}$ and $-XS(O)_{0-2}R_{10}$; wherein $R_{10}$ is independently selected from hydrogen and $C_{1-6}$alkyl.

In another embodiment, $R_1$ is selected from fluoro, chloro, methyl and $-C(O)OCH_3$; and $R_2$ is selected from phenyl, cyclohexyl, cyclopentyl, pyrrolyl, pyrazolyl, naphthyl, benzo[1,3]dioxolyl, thienyl, furanyl and pyridinyl; wherein any aryl, heteroaryl or cycloalkyl of $R_2$ is optionally substituted with 1 to 4 radicals independently selected from fluoro, chloro, bromo, hydroxy, methyl, ethyl, propyl, t-butyl, amino, dimethyl-amino, methoxy, trifluoromethyl, trifluoromethoxy and $-OC(O)CH_3$.

In another embodiment, $R_3$ is selected from phenyl, benzo[1,3]dioxolyl, pyridinyl, 2,2-difluoro-benzo[1,3]dioxol-5-yl and benzooxazolyl; wherein any aryl or heteroaryl of $R_3$ is substituted with 1 to 5 radicals independently selected from fluoro, chloro, bromo, methoxy, hydroxyl, difluoromethoxy, $-OCH_2C(O)NH_2$, $-OCH_2C(O)OCH_3$, $-OCH_2C(O)NHCH_3$, $-OCH_2C(O)N(CH_3)_2$, $-R_9$, $-OR_9$, $-OCH_2R_9$, $-OCH_2C(O)R_9$, $-OCH_2C(O)NHR_9$, $-OCH_2C(O)N(CH_3)R_9$, $-OCH_2C(O)NHCH_2R_9$, $-OCH_2CN$, $-OCH_2C_2H_3$, $-OCH_2C_2H_4$, $-O(CH_2)_2OH$, $-OCH_2C(O)NH(CH_2)_2C(O)OC_2H_5$, $-OCH_2C(O)NH(CH_2)_2CH_2F$, $-OCH_2C(O)NHCH_2CH_2F$, $-OCH_2C(O)NH(CH_2)_2C(O)OH$, $-OCH_2C(O)NHCH(CH_2R_9)C(O)OC_2H_5$, $-OCH_2C(O)NHC(O)(CH_2)_2C(O)OCH_3$, $-OCH_2C(O)NH(CH_2)_2NHC(O)CH_3$, $-OCH_2C(O)NHCH_2C(O)C_2H_5$, $-OCH_2C(O)NH(CH_2)_2C(O)OC_4H_9$, $-OCH_2C(O)NHCH_2C(O)OC_2H_5$, $-OCH_2C(O)NHCH[C(O)OC_2H_5]_2$, $-S(O)_2CH_3$, $-OCH_2C(O)NHCH_2CF_3$, $-OCH_2C(O)NHCH_2C(O)(CH_2)_2C(O)OCH_3$, $-OCH_2C(O)N(CH_3)CH_2C(O)OCH_3$, $-OCH_2C(O)NH(CH_2)_3OC_2H_5$, $-OCH_2C(O)NH(CH_2)_3OCH(CH_3)_2$, $-OCH_2C(O)NH(CH_2)_2SCH_3$, $-OCH_2C(O)NHCH_2CH(CH_3)_2$, $-OCH_2C(O)NHCH(CH_3)CH_2OH$, $-OCH_2C(O)NHCH_2CH(CH_3)C_2H_5$, $-OCH_2C(O)NHCH(CH_3)C(O)OC_2H_5$, $-OCH_2C(O)NHCH_2CH(CH_3)_2$ and $-OCH_2C(O)(CH_2)_3OCH(CH_3)_2$; wherein $R_9$ is phenyl, cyclopropyl-methyl, isoxazolyl, benzthiazolyl, furanyl, furanyl-methyl, tetrahydro-furanyl, pyridinyl, 4-oxo-4,5-dihydro-thiazol-2-yl, pyrazolyl, isothiazolyl, 1,3,4-thiadiazolyl, thiazolyl, phenethyl, morpholino, morpholino-propyl, isoxazolyl-methyl, pyrimidinyl, tetrahydro-pyranyl, 2-oxo-2,3-dihydro-pyrimidin-4-yl, piperazinyl, pyrrolyl, piperidinyl, pyrazinyl, imidazolyl, imidazolyl-propyl, benzo[1,3]dioxolyl, benzo[1,3]dioxolyl-propyl, 2-oxo-pyrrolidin-1-yl and 2-oxo-pyrrolidin-1-yl-propyl; wherein any alkyl of $R_9$ can have a hydrogen replaced with $-C(O)OC_2H_5$; wherein any aryl, heteroaryl or heterocycloalkyl of $R_9$ is optionally substituted with 1 to 4 radicals independently selected from methyl, ethyl, cyclopropyl, methoxy, trifluoromethyl, $-OC(O)CH_3$, $-COOH$, $-S(O)_2NH_2$, $-CH(NH_2)=NOH$, $-C(O)OC_2H_5$, $-CH_2C(O)OH$, $-CH_2C(O)OC_2H_5$, $-CH_2C(O)OCH_3$, $-C(O)OCH_3$, $-C(O)NH_2$, $-C(O)NHCH_3$ and $-C(O)CH_3$.

Preferred compounds of Formula I are detailed in the Examples and Table I, infra.

Pharmacology and Utility

Compounds of the invention modulate the activity of LXRs and, as such, are useful for treating diseases or disorders in which LXRs contribute to the pathology and/or symptomatology of the disease. This invention further provides compounds of this invention for use in the preparation of medicaments for the treatment of diseases or disorders in which LXRs contribute to the pathology and/or symptomatology of the disease. LXR mediated diseases or conditions include inflammation, cardiovascular disease including atherosclerosis, arteriosclerosis, hypercholesteremia, hyperlipidemia and disorders of glucose homeostasis, including insulin resistance, type II diabetes, and obesity.

Lipoprotein metabolism is a dynamic process comprised of the production of triglyceride and cholesterol rich particles from the liver as very low-density lipoprotein (VLDL), modification of these lipoprotein particles within the plasma (VLDL to intermediate density (IDL) to low-density lipoprotein (LDL)) and clearance of the particles from the plasma, again by the liver. This process provides the transport of triglycerides and free cholesterol to cells of the body. Reverse cholesterol transport is the proposed mechanism by which excess cholesterol is returned to the liver from extra-hepatic tissue.

The process is carried out by high-density lipoprotein (HDL) cholesterol. The combination of lipoprotein production (VLDL, HDL) from the liver, modification of particles (all) within the plasma and subsequent clearance back to the liver, accounts for the steady state cholesterol concentration in plasma. Compounds of this invention increase reverse cholesterol transport by increasing cholesterol efflux from the arteries. This invention includes the use of compounds of this invention for the preparation of a medicament for increasing reverse cholesterol transport. Additionally, this invention provides compounds for inhibiting cholesterol absorption and the use of compounds of this invention for the preparation of a medicament for inhibiting net cholesterol absorption.

The compounds of this invention can also be useful for the prevention or treatment of inflammation and neurodegenerative diseases or neurological disorders. Accordingly, this invention also provides a method for preventing or treating inflammation and a method for preventing or treating neurodegenerative diseases or neurological disorders, particularly neurodegenerative diseases or disorders characterized by neuron degeneration, neuron injury or impaired plasticity or inflammation in the CNS. Particular diseases or conditions that are characterized by neuron degeneration, inflammation, cholesterol and lipid abnormalities in the brain and thus benefiting from the growth and/or repair of neurons include stroke, Alzheimer's disease, fronto-temporal dementias (tauopathies), peripheral neuropathy, Parkinson's disease, dementia with Lewy bodies, Huntington's disease, amyotrophic lateral sclerosis and multiple sclerosis and Niemann-Pick disease. Diseases or conditions that are characterized by neuron degeneration and/or impaired plasticity include psychiatric disorders such as schizophrenia and depression. Particular diseases or conditions that are characterized by neuronal injury include those conditions associated with brain and/or spinal cord injury, including trauma. In addition, the compounds of this invention can be used to treat or prevent various diseases with an inflammatory component, such as rheumatoid arthritis, osteoarthritis, psoriasis, asthma, etc.

LXR agonists improve glucose tolerance and enhance glut4 expression (U.S. Provisional Patent Application 60/436,112, filed Dec. 23, 2002; U.S. patent application Ser. No. 10/745,334, filed Dec. 22, 2003). There is a coordinated regulation of genes involved in glucose metabolism in liver and adipose tissue. In the liver, LXR agonists inhibit expression of several genes that are important for hepatic gluconeogenesis, e.g., PGC-1α, phosphoenolpyruvate carboxykinase (PEPCK), and glucose-6-phosphatase expression. Inhibition of these gluconeogenic genes is accompanied by an induction in expression of glucokinase, which promotes hepatic glucose utilization. It was also found that glut4 mRNA levels were upregulated by LXR agonists in adipose tissue, and that glucose uptake in 3T3-L1 adipocytes was enhanced in vitro.

In accordance with these discoveries, the present invention provides methods for enhancing glut4 expression in cells in a subject by administering a compound of the invention to the subject. The present invention also provides methods for treating diabetes mellitus and related disorders, such as obesity or hyperglycemia, by administering to a subject an effective amount of a compound of the invention to ameliorate the symptoms of the disease. For example, type II diabetes is amenable to treatment with methods of the present invention. By enhancing sensitivity to insulin and glucose uptake by cells, administration with a compound of the invention can also treat other diseases characterized by insulin dysfunction (e.g., resistance, inactivity or deficiency) and/or insufficient glucose transport into cells.

Compounds of the present invention also regulate expression levels of a number of genes that play important roles in liver gluconeogenesis. Accordingly, the present invention further provides methods for reducing gluconeogenesis in a subject by modulating expression of such genes (e.g., PGC-1 and PEPCK).

In the pancreas, LXR activation stimulates insulin secretion via modulation of glucose and lipid metabolism in pancreatic β-cells, suggesting another mechanism for LXR's anti-diabetic effects. LXR modulators can thus also regulate glucose tolerance by enhancing insulin secretion from the pancreas.

In accordance with the foregoing, the present invention further provides a method for preventing or treating any of the diseases or disorders described above in a subject in need of such treatment, which method comprises administering to said subject a therapeutically effective amount (See, "Administration and Pharmaceutical Compositions", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount can vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form or in inhaled forms. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrollidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions can be sterilized and/or contain adjuvants, such as preserving, stabilizing, wetting or emulsifying agents, solution promoters, salts for regulating the osmotic pressure and/or buffers. In addition, they can also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations can also be used. Suitable formulations for topical application, e.g., to the skin and eyes, are preferably aqueous solutions, ointments, creams or gels well-known in the art. Such can contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other substances used in the treatment of cardiovascular, inflammatory and/or neurodegenerative diseases. Examples of such compounds include fibrates, TZDs, metformin, etc. Where the compounds of the invention are administered in conjunction with other therapies, dosages of the co-administered compounds will of course vary depending on the type of co-drug employed, on the specific drug employed, on the condition being treated and so forth.

The invention also provides for pharmaceutical combinations, e.g. a kit, comprising a) a first agent which is a compound of the invention as disclosed herein, in free form or in pharmaceutically acceptable salt form, and b) at least one co-agent. The kit can include instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the following Reaction Scheme I:

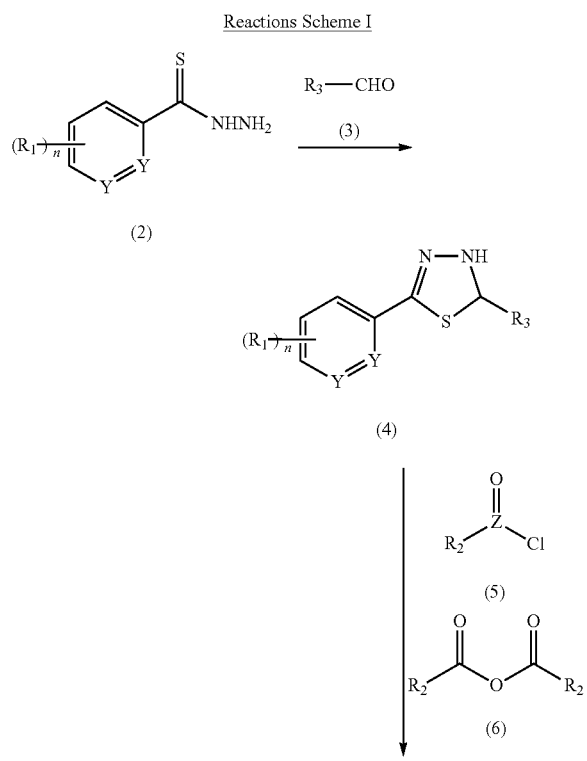

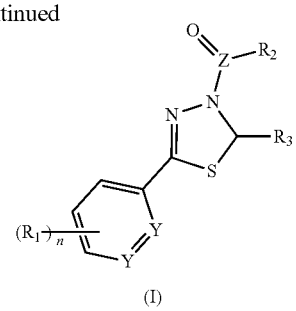

in which n, Y, Z, $R_1$, $R_2$ and $R_3$ are as defined in the Summary of the Invention. Compounds of Formula I are prepared by reacting a compound of formula 2 with a compound of formula 3 to form a compound of formula 4 which is further reacted with a compound of formula 5 or 6. The entire reaction is carried out in the presence of a suitable solvent (e.g., dichloromethane, or the like) and a suitable base (e.g., DIEA, or the like). The reaction is carried out in the temperature range of about 5 to about 30° C. and takes up to 20 hours to complete.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. Resolution of the racemic mixture may be carried out using chiral HPLC. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction scheme I; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following examples that illustrate the preparation of compounds of Formula I according to the invention.

Example 1

5-(4-Chloro-phenyl)-2-(2-difluoromethoxy-phenyl)-[1,3,4]thiadiazol-3-yl]-(2-fluoro-phenyl)-methanone

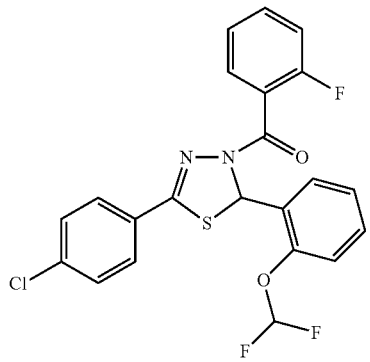 [SMILES: O=C(c1ccccc1F)N1N=C(c2ccc(Cl)cc2)SC1c1ccccc1OC(F)F]

Preparation of 4-chloro-thiobenzoic acid hydrazide

One half of volume of a solution of KOH (1.06 mol) in 400 mL of EtOH is saturated with $H_2S$. This solution is recombined with the other half of the KOH solution and the resulting solution is stirred under $N_2$ at 45-50° C. before adding 4-chlorobenzotrichloride (0.25 mol) at a rate to keep the temperature at 50-60° C. (~1.5 hours). The deep red mixture is refluxed for 30 minutes, then treated with a solution of chloroacetic acid (0.35 mol) and $NaHCO_3$ (0.35 mol) in $H_2O$ (200 mL). The reaction mixture is reheated under reflux for an additional 5 minutes. The resulting brownish-red solution is decanted from the sticky resin and acidified with concentrated HCl to pH=1. The red solution on crystallization yields (4-chloro-thiobenzoylsulfanyl)-acetic acid: $^1$H NMR (400 MHz, $CDCl_3$): δ 7.75 (d, 2H), 7.15 (d, 2H), 4.04 (s, 2H).

To a mixture of (4-chloro-thiobenzoylsulfanyl)-acetic acid (8.31 mmol) in 9 mL of NaOH (1N) is added hydrazine hydrate (36.7 mL). Glacial acetic acid (2.7 mL) is then added to the solution and the mixture is vigorously stirred. The reaction mixture is diluted with $CH_2Cl_2$ and the organic layer dried over $MgSO_4$ to yield 4-chloro-thiobenzoic acid hydrazide: LC/MS ($ES^+$) 186.9 $(M+1)^+$.

To a heterogeneous mixture of 4-chloro-thiobenzoic acid hydrazide (0.107 mmol) in $CH_2Cl_2$ (1 mL) is added 2-difluoromethoxy-benzaldehyde (0.128 mmol) and DIEA (0.128 mmol). After 10 minutes the mixture become homogenous and the reaction is complete by TLC and LCMS to give 5-(4-chloro-phenyl)-2-(2-difluoromethoxy-phenyl)-2,3-dihydro-[1,3,4]thiadiazole which is used in the next step without evaporation of the solvent.

To the solution of 5-(4-chloro-phenyl)-2-(2-difluoromethoxy-phenyl)-2,3-dihydro-[1,3,4]thiadiazole is added DIEA (0.16 mmol) and 2-fluorobenzoyl chloride (0.16 mmol) and the reaction mixture is stirred for 12 hours at room temperature. After evaporation of the solvent, the residue is purified by automated chromatography (hexane/EtOAc) to give 5-(4-chloro-phenyl)-2-(2-difluoromethoxy-phenyl)-[1,3,4]thiadiazol-3-yl]-(2-fluoro-phenyl)-methanone: $^1$H NMR (400 MHz, CDCl$_3$) δ 7.39-7.35 (m, 1H), 7.34-7.29 (m, 4H), 7.25 (dd, J$_1$=7.8 Hz, J$_2$=1.2 Hz, 1H), 7.19-7.13 (m, 3H), 7.04 (m, 1H), 6.97 (m, 2H), 6.50 (dd, J$_1$=71.6 Hz, J$_2$=71.2 Hz, 1H). LC/MS: (ES$^+$) 462.8 (M+1)$^+$.

Example 2

2-{2-[5-(4-Chloro-phenyl)-3-(2,4,6-trifluoro-benzoyl)-2,3-dihydro-[1,3,4]thiadiazol-2-yl]-phenoxy}-acetamide

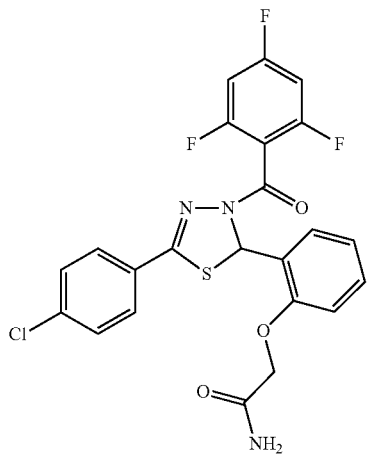 [SMILES: NC(=O)COc1ccccc1C1SC(c2ccc(Cl)cc2)=NN1C(=O)c1c(F)cc(F)cc1F]

To a heterogeneous mixture of 4-chloro-thiobenzoic acid hydrazide (1.3 mmol) in 12 mL of CH$_2$Cl$_2$ is added 2-(2-formylphenoxy)acetamide (1.53 mmol) and DIEA (1.53 mmol). After 10 minutes the mixture become homogenous and the reaction is complete by TLC and LCMS to give 2-(2-(5-(4-chlorophenyl)-2,3-dihydro-1,3,4-thiadiazol-2-yl)phenoxy)-acetamide which is used as such in the next step without evaporation of the solvent.

To the solution of 2-(2-(5-(4-chlorophenyl)-2,3-dihydro-1,3,4-thiadiazol-2-yl)phenoxy)acetamide is added DIEA (2.0 mmol) and 2,4,6-tri-fluorobenzoyl chloride (2.0 mmol) and the reaction mixture is stirred for 12 hours at room temperature. After evaporation of the solvent, the residue is purified by automated chromatography (hexane/EtOAc) to give 2-{2-[5-(4-chloro-phenyl)-3-(2,4,6-trifluoro-benzoyl)-2,3-dihydro-[1,3,4]thiadiazol-2-yl]-phenoxy}-acetamide: $^1$H NMR (400 MHz, CDCl$_3$) δ 7.43 (s, 1H), 7.27 (d, J=8.8, 2H), 7.15 (m, 2H), 7.14 (d, J=8.4 Hz, 2H) 6.99 (bs, 1H), 6.84 (t, J=6.4 Hz, 3H), 6.66 (d, J=8.4 Hz, 1H), 6.53 (t, J=8.0 Hz, 2H), 5.29 (bs, 1H), 4.47 (d, J=1.6 Hz, 2H); LC/MS: (ES$^+$) 506.2 (M+1)$^+$.

Example 3

2-{2-[5-(4-Fluoro-phenyl)-3-(2,4,6-trifluoro-benzoyl)-2,3-dihydro-[1,3,4]thiadiazol-2-yl]-6-methoxy-phenoxy}-acetamide

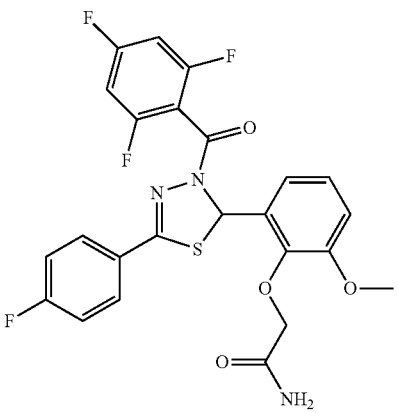 [SMILES: COc1cccc(C2SC(c3ccc(F)cc3)=NN2C(=O)c2c(F)cc(F)cc2F)c1OCC(N)=O]

Preparation of 4-fluorobenzothiohydrazide trifluoroacetic acid salt or hydrochloride salt

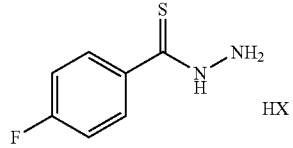

To a solution of 4-fluorobenzoic acid (35.7 mmol) in 72 mL of a mixture of DMF and THF (1:1), is added tert-butyl carbazate (37.5 mmol), EDC (39.3 mmol) and N,N-dimethylaminopyridine (0.54 mmol). After 10 minutes the mixture becomes homogeneous and stirring is continued for 3 hours until the reaction is complete by TLC and LC/MS. The reaction mixture is poured into ice. Upon addition of diethylether the organic layer is separated. The organic layer is washed with sodium bisulfite, saturated sodium bicarbonate and saturated sodium chloride solution, dried over magnesium sulfate and concentrated to yield N'-(4-fluoro-benzoyl)-hydrazinecarboxylic acid tert-butyl ester: MS: (ES$^+$) 255 (M+1)$^+$.

To a mixture of N'-(4-fluoro-benzoyl)-hydrazinecarboxylic acid tert-butyl ester (11.1 mmol) in 10 mL of dry THF is added Lawesson's reagent (11.6 mmol) and the mixture is heated in the microwave oven at 80° C. for 20 minutes The reaction mixture is concentrated and purified by automated column chromatography using hexanes/EtOAc: $^1$H NMR (400 MHz, CDCl$_3$) δ 9.8 (bs, 1H), 9.05 (bs, 1H); 8.0-7.97 (m, 2H), 7.31 (t, J=8.4 Hz, 2H), 1.73 (s, 9H). LC/MS: (ES$^+$) 271 (M+1)$^+$.

Trifluoroacetic Salt.

To a solution of N'-(4-fluoro-thiobenzoyl)-hydrazinecarboxylic acid tert-butyl ester (1.97 mmol) in CH$_2$Cl$_2$ is added trifluoroacetic acid (3 mL) and thioanisole (2.7 mmol). The mixture is stirred at room temperature for 1 hour. After evaporation of the solvent the mixture is purified by automated column chromatography (hexanes/EtOAc) to yield 4-fluoro-thiobenzoic acid hydrazide trifluoroacetic acid salt: $^1$H NMR (400 MHz, CDCl$_3$) δ 9.5 (bs, 3H), 7.8-7.76 (m, 2H), 7.05 (t, J=8.4 Hz, 2H); LC/MS: (ES$^+$) 171 (M+1)$^+$.

Hydrochloride Salt.

To N'-(4-fluoro-thiobenzoyl)-hydrazinecarboxylic acid tert-butyl ester (18.5 mmol) is added HCl (4 N) in 1,4-dioxane (185 mmol). The mixture is stirred at room temperature for 1 hour. Hexanes is added to further precipitate the product. The product is filtered off yielding 4-fluoro-thiobenzoic acid hydrazide hydrochloride salt: $^1$H NMR (400 MHz, CH$_3$OD) δ 7.8-7.75 (m, 2H), 7.09 (t, J=11.6 Hz, 2H). LC/MS: (ES$^+$) 171 (M+1)$^+$.

Preparation of
3-methoxy-2-triisopropylsilanyloxy-benzaldehyde

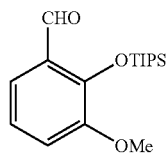

O-vanillin (26.3 mmol) is mixed with TIPSCl (39.6 mmol) and imidazole (78.7 mmol) in a microwave vessel. The mixture is heated in the microwave at 100° C. for 3 minutes. The oily mixture is diluted with EtOAc (100 mL) and washed with NaHSO$_4$ (1 M) (2×50 mL) and brine (50 mL). After drying with MgSO$_4$, the filtrate is concentrated. The resultant crude mixture is purified by silica flash chromatography (2% EtOAc/hexane) to yield 3-methoxy-2-triisopropylsilanyloxy-benzaldehyde as an oil: $^1$H NMR (400 MHz, CDCl$_3$) δ 10.6 (s, 1H), 7.38 (dd, J$_1$=1.6 Hz, J$_2$=8 Hz, 1H), 7.04 (dd, J$_1$=1.6 Hz, J$_2$=8 Hz, 1H), 6.93 (td, J$_1$=8 Hz, J$_2$=0.8 Hz, 1H), 3.82 (s, 3H), 1.34-1.25 (m, 3H), 1.1 (s, 18H); LC/MS (ES$^+$): 309 (M+1)$^+$.

To a heterogeneous mixture of 4-fluoro-thiobenzoic acid hydrazide salt (2.06 mmol) in 8 mL of CH$_2$Cl$_2$ is added 3-methoxy-2-triisopropylsilanyloxy-benzaldehyde (2.27 mmol) and DIEA (4.13 mmol). After 15 minutes the mixture becomes homogenous and the reaction is complete by TLC and LCMS to give 5-(4-fluoro-phenyl)-2-(3-methoxy-2-triisopropylsilanyloxy-phenyl)-2,3-dihydro-[1,3,4]thiadiazole which is used in the next step without evaporation of the solvent.

To the solution of 5-(4-fluoro-phenyl)-2-(3-methoxy-2-triisopropylsilanyloxy-phenyl)-2,3-dihydro-[1,3,4]thiadiazole is added DIEA (3.09 mmol) and 2,4,6-tri-fluorobenzoyl chloride (3.09 mmol) and the reaction mixture is stirred for 12 hours at room temperature. After concentration, the residue is purified by automated column chromatography (hexane/EtOAc) to yield [5-(4-fluoro-phenyl)-2-(3-methoxy-2-triisopropylsilanyloxy-phenyl)-[1,3,4]thiadiazol-3-yl]-(2,4,6-trifluoro-phenyl)-methanone.

To [5-(4-fluoro-phenyl)-2-(3-methoxy-2-triisopropylsilanyloxy-phenyl)-[1,3,4]thiadiazol-3-yl]-(2,4,6-trifluoro-phenyl)-methanone (32.3 μmol) is added tetrabutylammonium fluoride in tetrahydrofuran (1 M) (48.5 μmol). The mixture is stirred for an hour and 2-bromo-acetamide (48.5 μmol) is added. The mixture is stirred at room temperature for 12 hours. After evaporation of the solvent the residue is purified by preparative LC/MS (20-100% MeCN/H$_2$O) to give 2-{2-[5-(4-fluoro-phenyl)-3-(2,4,6-trifluoro-benzoyl)-2,3-dihydro-[1,3,4]thiadiazol-2-yl]-6-methoxy-phenoxy}-acetamide: $^1$H NMR (400 MHz, CDCl$_3$): δ 7.63-7.62 (m, 2H), 7.57 (s, 1H), 7.22-7.12 (m, 3H), 7.02 (dd, J$_1$=8.4 Hz, J$_2$=2 Hz, 2H), 6.9 (bs, 1H), 6.85 (t, J=8.4 Hz, 2H), 6.10 (s, 1H), 4.83 (d, J=15.2 Hz, 1H), 4.68 (d, J=15.2 Hz, 1H), 3.94 (s, 3H).

Example 4

3-{3-[5-(4-Fluoro-phenyl)-3-(2,4,6-trifluoro-benzoyl)-2,3-dihydro-[1,3,4]thiadiazol-2-yl]-2-methoxy-phenoxymethyl}-benzoic acid methyl ester

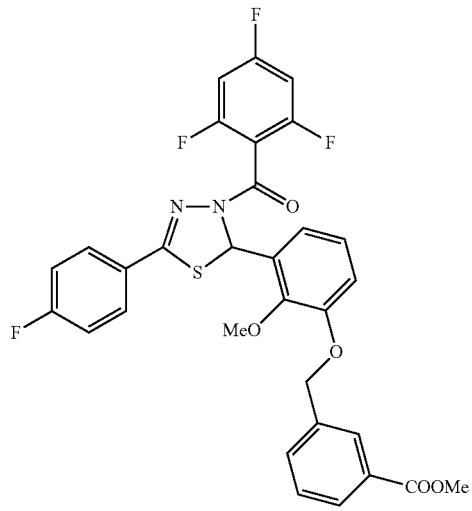 [SMILES: COC(=O)c1cccc(COc2cccc(C3SC(c4ccc(F)cc4)=NN3C(=O)c3c(F)cc(F)cc3F)c2OC)c1]

Preparation of
2-Methoxy-3-triisopropylsilanyloxy-benzaldehyde

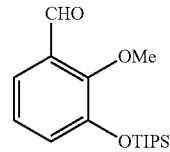

Guaiacol (2-methoxy-phenol, 34.6 mmol) is mixed with TIPSCl (51.9 mmol) and imidazole (103.8 mmol) in a tube. The mixture is heated in the microwave oven at 180° C. for 3 minutes. The oily mixture is diluted with EtOAc (100 mL) and washed with NaHSO$_4$ (1 M) (2×50 mL) and brine (50 mL). After drying over anhydrous Na$_2$SO$_4$, the filtrate is concentrated. The resultant crude mixture is purified by silica flash chromatography (2% EtOAc/hexane) to yield triisopropyl-(2-methoxy-phenoxy)-silane as a colorless oil. Yield: 69%. $^1$H NMR (400 MHz, CDCl$_3$) δ 6.8-6.89 (m, 4H), 3.8 (s, 3H), 1.22-1.28 (m, 3H), 1.1 (s, 9H), 1.08 (s, 9H). LC/MS (ES$^+$): (M+1), 281.2. R$_f$=0.8 (5% EtOAc/hexane). (Note: Alternatively, conventional heating might be adopted in which case NMP is the solvent of choice).

nBuLi (2.5 M in hexanes) (36 mmol) is mixed with TMEDA (36 mmol) at 0° C. in a dry round bottom flask for 10 minutes. A solution of triisopropyl-(2-methoxy-phenoxy)-silane (24 mmol) in 25 mL of dry THF is added to the above mixture. The mixture is warmed up to room temperature in 2 hours by removal of the ice bath. The slightly yellow solution is then transferred to another dry flask containing dry 7.5 mL of DMF at room temperature. The mixture is stirred overnight. HCl (1 M) is added to the mixture to quench the reaction. The mixture is diluted with EtOAc (100 mL), washed with HCl (1 M) (2×100 mL) and brine (50 mL) and finally dried over anhydrous Na$_2$SO$_4$. Purification is accomplished by silica flash chromatography (5% EtOAc/hexane) to yield 3-methoxy-2-triisopropylsilanyloxy-benzaldehyde as a colorless oil which needs to be stored at low temperatures: $^1$H NMR (400 MHz, CDCl$_3$) δ 10.4 (s, 1H), 7.42 (dd, J$_1$=7.7 Hz, J$_2$=1.7 Hz, 1H), 7.67 (d, J$_1$=8 Hz, J$_2$=1.7 Hz, 1H), 7.04 (t, J=8.4 Hz, 1H), 3.96 (s, 3H), 1.26-1.35 (m, 3H), 1.13 (s, 9H), 1.12 (s, 9H). LC/MS (ES$^+$): (M+1) 309.2. R$_f$=0.4 (5% EtOAc/hexane).

N'-(4-fluoro-thiobenzoyl)-hydrazinecarboxylic acid tert-butyl ester (1.23 mmol) is dissolved in 5 mL of CH$_2$Cl$_2$ at room temperature in a dry round bottom flask. Removal of the ester group is accomplished adding TFA (2 mL) to the solution at room temperature. The reaction is complete after 30 minutes as determined by LC/MS. Solvent is removed in vacuo. The resultant oil is dried on the vacuum line for 30 minutes and dissolved in 1 mL of dry CH$_2$Cl$_2$. This solution is added to a mixture of 3-methoxy-2-triisopropylsilanyloxy-benzaldehyde (1.23 mmol) and DIEA (4.9 mmol) in 1 mL of dry CH$_2$Cl$_2$. The mixture is allowed to stand at room temperature in the presence of molecular sieves for 5 minutes. 2,4,6-Trifluorobenzoyl chloride (1.6 mmol) is added and the reaction mixture is kept at room temperature for 16 hours. HCl (1 M) (10 mL) is added to the mixture to quench the reaction. The mixture is diluted with EtOAc (50 mL), washed with HCl (1 M) (2×10 mL) and brine (50 mL) and dried over anhydrous Na$_2$SO$_4$. Purification is accomplished by silica flash chromatography (5% EtOAc/hexane) to give [5-(4-fluoro-phenyl)-2-(2-methoxy-3-triisopropylsilanyloxy-phenyl)-[1,3,4]thiadiazol-3-yl]-(2,4,6-trifluoro-phenyl)-methanone as a colorless oil: $^1$H NMR (400 MHz, CDCl$_3$) δ 7.54 (dd, J$_1$=8.8 Hz, J$_2$=5.3 Hz, 2H), 7.51 (s, 1H), 7.04 (t, J=8.6 Hz, 2H), 6.95 (t, J=7.8 Hz, 1H), 6.87 (t, J=8.8 Hz, 2H), 6.77 (t, J=7.9 Hz, 2H), 4.03 (s, 3H), 1.27-1.36 (m, 3H), 1.14 (dd, J$_1$=J$_2$=6.3 Hz, 18H); LC/MS (ES$^+$): (M+1) 309.2. R$_f$=0.4 (5% EtOAc/hexanes).

[5-(4-fluoro-phenyl)-2-(2-methoxy-3-triisopropylsilanyloxy-phenyl)-[1,3,4]thiadiazol-3-yl]-(2,4,6-trifluoro-phenyl)-methanone (0.02 mmol) is treated with tetrabutylammonium fluoride (1 M in THF) (0.04 mmol) at room temperature for 30 minutes. 3-Bromomethyl-benzoic acid methyl ester (0.04 mmol) is then added. After 30 minutes, the reaction is complete as determined by LC/MS. The mixture is diluted with acetonitrile and purified by preparative LC/MS (20-100% MeCN/H$_2$O) to give 3-{3-[5-(4-fluoro-phenyl)-3-(2,4,6-trifluoro-benzoyl)-2,3-dihydro-[1,3,4]thiadiazol-2-yl]-2-methoxy-phenoxymethyl}-benzoic acid methyl ester as white solid after evaporation of solvent: $^1$H NMR (400 MHz, CDCl$_3$) δ 8.14 (s, 1H), 8.02 (d, J=7.8 Hz, 1H), 7.67 (d, J=7.7 Hz, 1H), 7.47-7.55 (m, 4H), 7.01-7.07 (m, 3H), 6.94 (t, J=8.3 Hz, 2H), 6.77 (t, J=8.5 Hz, 2H), 5.16 (s, 2H), 4.07 (s, 3H), 3.94 (s, 3H). LC/MS (ES$^+$): (M+1) 610.9.

Example 5

4-{3-[5-(4-Fluoro-phenyl)-3-(2,4,6-trifluoro-benzoyl)-2,3-dihydro-[1,3,4]thiadiazol-2-yl]-2-methoxy-phenoxymethyl}-benzoic acid

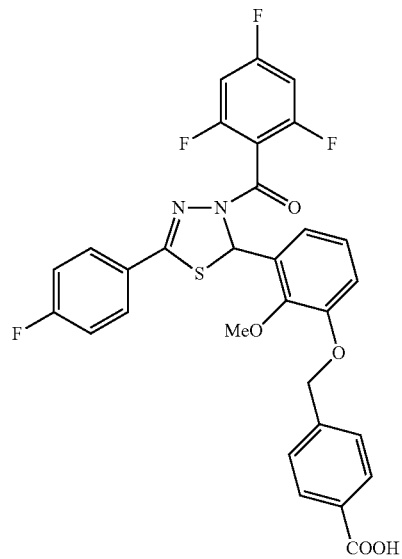 [SMILES: COc1c(OCc2ccc(C(=O)O)cc2)cccc1C1SC(c2ccc(F)cc2)=NN1C(=O)c1c(F)cc(F)cc1F]

[5-(4-fluoro-phenyl)-2-(2-methoxy-3-triisopropylsilanyloxy-phenyl)-[1,3,4]thiadiazol-3-yl]-(2,4,6-trifluoro-phenyl)-methanone (0.02 mmol) is treated with tetrabutylammonium fluoride (1.0 M in THF) (0.04 mmol) at room temperature for 30 minutes. The reaction is complete by LC/MS analysis. 4-Bromomethyl-benzoic acid methyl ester (0.04 mmol) is added. After 30 minutes, the reaction is complete as determined by LC/MS. After dilution with MeOH (0.5 mL), LiOH (1 M) (0.5 mL) is added. After stirring for 1 hour, the solvent is removed from the reaction mixture. A mixture of MeOH/DMSO is added to the residue and resultant solution is filtered. The clear solution is purified by preparative LC/MS (20-100% MeCN/H$_2$O) to give 4-{3-[5-(4-fluoro-phenyl)-3-(2,4,6-trifluoro-benzoyl)-2,3-dihydro-[1,3,4]thiadiazol-2-yl]-2-methoxy-phenoxymethyl}-benzoic acid as white solid after removal of solvent: $^1$H NMR (400 MHz, CDCl$_3$) δ 8.14 (d, J=8 Hz, 2H), 7.53-7.58 (m, 5H), 7.03-7.05 (m, 3H), 6.94-6.95 (m, 2H), 6.77 (t, J=8.2 Hz, 2H), 5.2 (s, 2H), 4.08 (s, 3H); LC/MS (ES+): (M+1) 597.3.

Example 6

2-{2-[5-(4-Chloro-phenyl)-3-(2,4,6-trifluoro-benzoyl)-2,3-dihydro-[1,3,4]thiadiazol-2-yl]-phenoxy}-N-methyl-acetamide

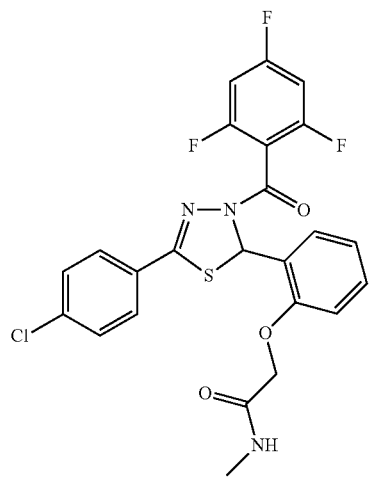 [SMILES: CNC(=O)COc1ccccc1C1SC(c2ccc(Cl)cc2)=NN1C(=O)c1c(F)cc(F)cc1F]

(2-Formyl-phenoxy)-acetic acid (0.5 mmol) is dissolved in 1 mL of $CH_2Cl_2$. Oxalyl chloride (0.066 mL) is added along with one drop of DMF. After 1 hour, the solvent is removed from the mixture. The resultant residue is dissolved in 1 mL of $CH_2Cl_2$ and added to 1 mL of $NH_2Me$ in THF (2 M) at ambient temperature. After 16 hours of stiffing, the solvent is removed and the mixture is purified by preparative TLC (10% MeOH/EtOAc) to yield the product 2-(2-formyl-phenoxy)-N-methyl-acetamide as an off white solid: LC/MS (ES+): 194.1 (M+1)+.

The 2-(2-formyl-phenoxy)-N-methyl-acetamide (0.0311 mmol) is added to 4-chloro-thiobenzoic acid hydrazide (0.0342 mmol) in 0.1 mL of $CH_2Cl_2$. After 10 minutes, DIEA (0.05 mL) and 2,4,6-trifluoro-benzoyl chloride (0.0467 mmol) are added. The mixture is kept at room temperature overnight. After removal of solvent, the residue is purified by preparative HPLC (20-100% MeCN/$H_2O$ gradient) to give the product 2-{2-[5-(4-chloro-phenyl)-3-(2,4,6-trifluoro-benzoyl)-2,3-dihydro-[1,3,4]thiadiazol-2-yl]-phenoxy}-N-methyl-acetamide as an off white solid: LC/MS (ES+): 520.1 (M+1)+.

Example 7

N-Cyclopropylmethyl-2-{3-[5-(4-fluoro-phenyl)-3-(2,4,6-trifluoro-benzoyl)-2,3-dihydro-[1,3,4]thiadiazol-2-yl]-2-methoxy-phenoxy}-acetamide

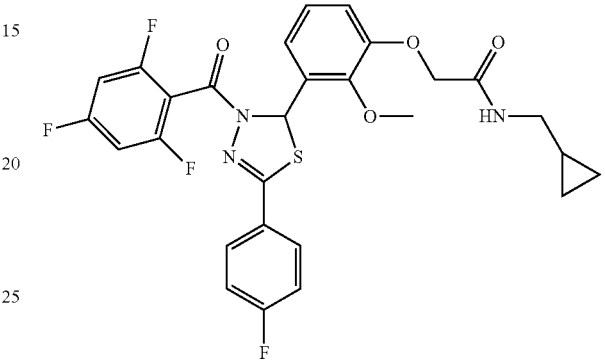

[5-(4-fluoro-phenyl)-2-(2-methoxy-3-triisopropylsilanyloxy-phenyl)-[1,3,4]thiadiazol-3-yl]-(2,4,6-trifluoro-phenyl)-methanone (3.31 mmol), prepared as described in example 4, is treated with tetrabutylammonium fluoride (1 M in THF) (4.97 mmol) at room temperature for 40 minutes. Methyl bromoacetate (4.97 mmol) is then added. After 12 hours, the reaction is complete as determined by LC/MS. Purification is accomplished by silica flash chromatography (25% EtOAc/hexane) to give {3-[5-(4-fluoro-phenyl)-3-(2,4,6-trifluoro-benzoyl)-2,3-dihydro-[1,3,4]thiadiazol-2-yl]-2-methoxy-phenoxy}-acetic acid methyl ester: $^1H$ NMR (400 MHz, $CDCl_3$) δ 7.52 (m, 3H), 7.04 (m, 3H), 6.95 (dd, $J_1$=8.4 Hz, $J_2$=1.6 Hz, 1H), 6.82 (dd, $J_1$=8 Hz, $J_2$=1.6 Hz), 6.76 (m, 2H), 4.7 (s, 2H), 4.1 (s, 3H); LC/MS (ES+): 505.1 (M+1)+.

To a solution of {3-[5-(4-fluoro-phenyl)-3-(2,4,6-trifluoro-benzoyl)-2,3-dihydro-[1,3,4]thiadiazol-2-yl]-2-methoxy-phenoxy}-acetic acid methyl ester (2.47 mmol) in 30 mL of a mixture of THF and MeOH (3:2), is added LiOH (1 M) (25 mL). After stiffing for 12 hours the reaction is complete as determined by LC/MS. The reaction is diluted with ethyl acetate and water, washed with brine and dried over $MgSO_4$ and the solvent is removed from the reaction mixture to yield {3-[5-(4-fluoro-phenyl)-3-(2,4,6-trifluoro-benzoyl)-2,3-dihydro-[1,3,4]thiadiazol-2-yl]-2-methoxy-phenoxy}-acetic acid: LC/MS (ES+): 521.1 (M+1)+.

To a solution of {3-[5-(4-fluoro-phenyl)-3-(2,4,6-trifluoro-benzoyl)-2,3-dihydro-[1,3,4]thiadiazol-2-yl]-2-methoxy-phenoxy}-acetic acid (0.029 mmol) in 1 mL of DMF is added DIEA (0.058 mmol), HATU (0.058 mmol) and cyclopropyl methylamine (0.058 mmol). The reaction mixture is stirred for 12 hours. The mixture is purified by preparative LC/MS (20-100% MeCN/$H_2O$) to give N-cyclopropylmethyl-2-{3-[5-(4-fluoro-phenyl)-3-(2,4,6-trifluoro-benzoyl)-2,3-dihydro-[1,3,4]thiadiazol-2-yl]-2-methoxy-phenoxy}-acetamide: $^1H$ NMR (400 MHz, $CDCl_3$) δ 7.55-7.51 (m, 3H), 7.12-6.99 (m, 4H), 6.9 (d, J=7.6 Hz, 2H), 6.77 (t, J=8.4 Hz, 2H), 4.56 (s, 2H), 4.08 (s, 3H), 3.26-3.2 (m, 2H), 1.02-0.99 (m, 1H), 0.57-0.52 (m, 2H), 0.25 (m, 2H); LC/MS (ES$^+$): 574.1 (M+1)$^+$.

Example 8

2-{2-[5-(4-Fluoro-phenyl)-3-(2,4,6-trifluoro-benzoyl)-2,3-dihydro-[1,3,4]thiadiazol-2-yl]-phenoxy}-N-(5-methyl-isoxazol-3-yl)-acetamide

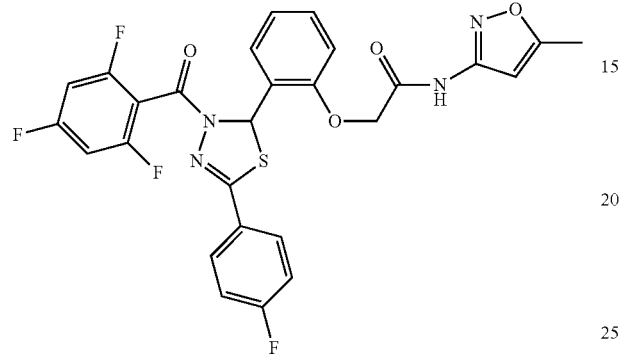

[5-(4-Fluoro-phenyl)-2-(2-triisopropylsilanyloxy-phenyl)-[1,3,4]thiadiazol-3-yl]-(2,4,6-trifluoro-phenyl)-methanone (3.4 mmol), prepared in a similar manner as described for [5-(4-fluoro-phenyl)-2-(3-methoxy-2-triisopropylsilanyloxy-phenyl)-[1,3,4]thiadiazol-3-yl]-(2,4,6-trifluoro-phenyl)-methanone in example 3, is treated with tetrabutylammonium fluoride (1.0 M in THF) (5.1 mmol) at room temperature for 40 minutes. Methyl bromoacetate (5.1 mmol) is then added. After 12 hours, the reaction is complete as determined by LC/MS. Purification is accomplished by silica flash chromatography (25% EtOAc/hexane) to give {2-[5-(4-fluoro-phenyl)-3-(2,4,6-trifluoro-benzoyl)-2,3-dihydro-[1,3,4]thiadiazol-2-yl]-phenoxy}-acetic acid methyl ester: $^1$H NMR (400 MHz, CDCl$_3$) δ 7.61 (s, 1H), 7.54 (m, 2H), 7.04 (m, 3H), 7.01 (d, J=8.4 Hz, 1H) 6.95 (bs, 2H), 4.94 (s, 2H), 4.01 (s, 3H). MS: (ES$^+$) 535.1 (M+1); LC/MS (ES$^+$): 535.1 (M+1)$^+$.

To a solution of {2-[5-(4-fluoro-phenyl)-3-(2,4,6-trifluoro-benzoyl)-2,3-dihydro-[1,3,4]thiadiazol-2-yl]-phenoxy}-acetic acid methyl ester (2.93 mmol) in 30 mL of a mixture of THF and MeOH (3:2), is added LiOH (1 M) (30 mL). After stirring for 12 hours the reaction is complete as determined by LC/MS. The reaction is diluted with ethyl acetate and water, washed with brine and dried over MgSO$_4$ and the solvent is removed from the reaction mixture to yield {2-[5-(4-Fluoro-phenyl)-3-(2,4,6-trifluoro-benzoyl)-2,3-dihydro-[1,3,4]thiadiazol-2-yl]-phenoxy}-acetic acid: $^1$H NMR (400 MHz, acetone-d$_6$) δ 7.66 (m, 3H), 7.39 (m, 1H), 7.3 (dd, J$_1$=7.6 Hz, J$_2$=1.6 Hz, 1H), 7.22 (m, 4H), 7.13 (m, 1H), 7.07 (t, J=7.6 Hz, 1H), 4.94 (s, 2H); LC/MS (ES$^+$): 491.0 (M+1)$^+$.

To a solution of {2-[5-(4-fluoro-phenyl)-3-(2,4,6-trifluoro-benzoyl)-2,3-dihydro-[1,3,4]thiadiazol-2-yl]-phenoxy}-acetic acid (0.031 mmol) in DMF (1 mL) is added DIEA (0.058 mmol), HATU (0.058 mmol) and 5-methyl-isoxazol-3-ylamine (0.058 mmol). The reaction mixture is stirred for 12 hours. The mixture is purified by preparative LC/MS (20-100% MeCN/H$_2$O) to give 2-{2-[5-(4-fluoro-phenyl)-3-(2,4,6-trifluoro-benzoyl)-2,3-dihydro-[1,3,4]thiadiazol-2-yl]-phenoxy}-N-(5-methyl-isoxazol-3-yl)-acetamide: $^1$H NMR (400 MHz, CDCl$_3$) δ 7.55-7.51 (m, 3H), 7.35-7.26 (m, 2H), 7.05-6.96 (m, 3H), 6.85 (d, J=8 Hz, 1H), 6.69 (t, J=7.6 Hz, 2H), 6.56 (s, 1H), 4.72 (s, 2H), 2.33 (s, 3H); LC/MS (ES$^+$): 571.1 (M+1)$^+$.

Example 9

3-{2-[5-(4-Fluoro-phenyl)-3-(2,4,6-trifluoro-benzoyl)-2,3-dihydro-[1,3,4]thiadiazol-2-yl]-phenoxymethyl}-benzamide

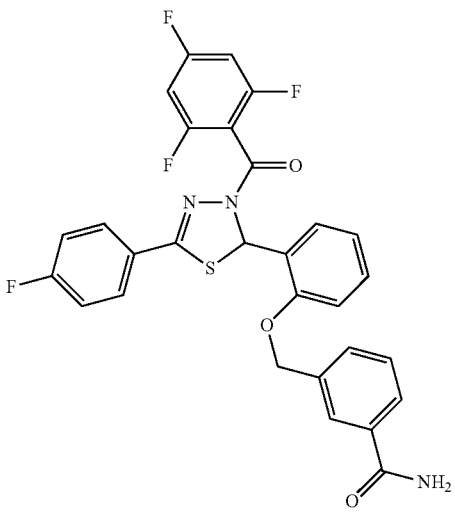 [SMILES: NC(=O)c1cccc(COc2ccccc2C2SC(c3ccc(F)cc3)=NN2C(=O)c2c(F)cc(F)cc2F)c1]

[5-(4-Fluoro-phenyl)-2-(2-triisopropylsilanyloxy-phenyl)-[1,3,4]thiadiazol-3-yl]-(2,4,6-trifluoro-phenyl)-methanone (41 μmol), prepared in a similar manner as described for [5-(4-fluoro-phenyl)-2-(3-methoxy-2-triisopropylsilanyloxy-phenyl)-[1,3,4]thiadiazol-3-yl]-(2,4,6-trifluoro-phenyl)-methanone in example 3, is treated with tetrabutylammonium fluoride (1.0 M in THF) (48 μmol) at room temperature for 40 minutes. The solvent is removed in vacuo and dried over MgSO$_4$ to yield [5-(4-fluoro-phenyl)-2-(2-hydroxy-phenyl)-[1,3,4]thiadiazol-3-yl]-(2,4,6-trifluoro-phenyl)-methanone to be used without further purification.

To [5-(4-fluoro-phenyl)-2-(2-hydroxy-phenyl)-[1,3,4]thiadiazol-3-yl]-(2,4,6-trifluoro-phenyl)-methanone (41 μmol) dissolved in acetonitrile (1 mL) is added K$_2$CO$_3$ (61.5 μmol) and 3-bromomethyl-benzamide (94.2 μmol) and the mixture is heated at 90° C. After 12 hours, the reaction is complete as determined by LC/MS. Purification is accomplished by preparative LC/MS (20-100% MeCN/H$_2$O) to give 3-{2-[5-(4-fluoro-phenyl)-3-(2,4,6-trifluoro-benzoyl)-2,3-dihydro-[1,3,4]thiadiazol-2-yl]-phenoxymethyl}-benzamide: $^1$H NMR (400 MHz, CDCl$_3$) δ 8.09 (s, 1H), 7.9 (d, J=7.6 Hz, 1H), 7.7 (s, 1H), 7.6-7.5 (m, 4H) 7.35 (d, J=7.6 Hz, 1H), 7.06 (t, J=8.4 Hz, 1H), 6.99 (t, J=7.6 Hz, 2H), 6.88 (d, J=8 Hz), 6.79 (t, J=8.4 Hz, 2H), 6.26 (bs, 1H), 5.33 (d, J=7.6 Hz); LC/MS (ES+): 566.1 (M+1)+.

Example 10

2-{2-[5(4-Fluoro-phenyl)-3-(2,4,6-trifluoro-benzoyl)-2,3-dihydro-[1,3,4]thiadiazol-2-yl]-phenoxymethyl}-furan-3-carboxylic acid

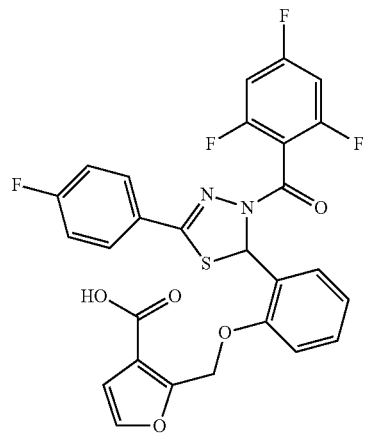 [SMILES: O=C(O)c1ccoc1COc1ccccc1C1SC(c2ccc(F)cc2)=NN1C(=O)c1c(F)cc(F)cc1F]

[5-(4-Fluoro-phenyl)-2-(2-triisopropylsilanyloxy-phenyl)-[1,3,4]thiadiazol-3-yl]-(2,4,6-trifluoro-phenyl)-methanone (0.67 mmol), prepared as described for [5-(4-fluorophenyl)-2-(3-methoxy-2-triisopropylsilanyloxy-phenyl)-[1,3,4]thiadiazol-3-yl]-(2,4,6-trifluoro-phenyl)-methanone in example 3, is treated with tetrabutylammonium fluoride (1.0 M in THF) (1.3 mmol) at room temperature. After 15 minutes, methyl 2-(bromomethyl)-3-furoate (0.74 mmol) is added and the mixture is stirred for an additional 12 hours. The solvent is removed in vacuo and the residue is purified on silica to yield 2-{2-[5(4-fluoro-phenyl)-3-(2,4,6-trifluoro-benzoyl)-2,3-dihydro-[1,3,4]thiadiazol-2-yl]-phenoxymethyl}-furan-3-carboxylic acid methyl ester as a yellow solid: LC/MS (ES+): 571.1 (M+1)+.

To a solution of 2-{2-[5-(4-fluoro-phenyl)-3-(2,4,6-trifluoro-benzoyl)-2,3-dihydro-[1,3,4]thiadiazol-2-yl]-phenoxymethyl}-furan-3-carboxylic acid methyl ester (0.49 mmol) in THF/MeOH/H$_2$O (3:2:1), is added LiOH (3 N) (4.9 mmol). After stirring for 12 hours, the reaction is acidified with HCl (1 N) and extracted with ethyl acetate. The organic layer is dried over MgSO$_4$, filtered, and concentrated. The residue is purified using preparative LC/MS to give 2-{2-[5-(4-fluoro-phenyl)-3-(2,4,6-trifluoro-benzoyl)-2,3-dihydro-[1,3,4]thiadiazol-2-yl]-phenoxymethyl}-furan-3-carboxylic acid as a white solid: $^1$H NMR (400 MHz, CDCl$_3$) δ 7.26-7.23 (m, 3H), 7.20 (d, J=1.9, 1H), 7.10-7.05 (m, 1H), 7.03-6.99 (m, 1H), 6.86 (d, J=8.1, 1H), 6.78-6.74 (m, 3H), 6.55 (d, J=1.9, 1H), 6.55-6.50 (m, 2H), 5.38-5.21 (m, 2H); LC/MS (ES+): 557.1 (M+1)+.

Example 11

[2-(2-Difluoromethoxy-phenyl)-5-(6-methyl-pyridin-3-yl)-[1,3,4]thiadiazol-3-yl]-(2,4,6-trifluoro-phenyl)-methanone

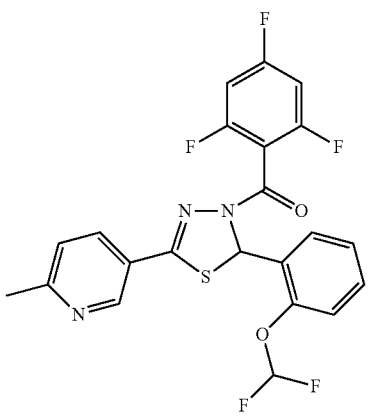 [SMILES: Cc1ccc(C2=NN(C(=O)c3c(F)cc(F)cc3F)C(c3ccccc3OC(F)F)S2)cn1]

N'-(6-Methyl-pyridine-3-carbothioyl)-hydrazinecarboxylic acid tert-butyl ester (0.1 mmol) prepared as described in example 3 for N'-(4-fluoro-benzoyl)-hydrazinecarboxylic acid tert-butyl ester, is treated with TFA (1 mmol) in dry CH$_2$Cl$_2$ (1 mL) at room temperature for 30 minutes. Solvent is removed and the residue is dissolved in dry CH$_2$Cl$_2$ (1 mL). DIEA (0.287 mmol) is added to the solution and the mixture is treated with 2-difluoromethoxy-benzaldehyde (0.12 mmol) in the presence of 4 Å molecular sieves. 2,4,6-Trifluorobenzoyl chloride (0.15 mmol) is added after 5 minutes. The mixture is kept at ambient temperature for 16 hours and purified by preparative HPLC (20-100% MeCN/H$_2$O) to yield [2-(2-difluoromethoxy-phenyl)-5-(6-methyl-pyridin-3-yl)-[1,3,4]thiadiazol-3-yl]-(2,4,6-trifluoro-phenyl)-methanone: $^1$H NMR (400 MHz, CDCl$_3$) 8.71 (d, J=2.1 Hz, 1H), 7.81 (dd, J$_1$=8.2 Hz, J$_2$=2.2 Hz, 1H), 7.53 (s, 1H), 7.36-7.4 (m, 2H), 7.26 (d, J=8.1 Hz, 2H), 7.18 (d, J=8.3 Hz, 1H), 6.78

(t, J=8.3 Hz, 2H), 6.67 (dd, $J_1$=75.0 Hz, $J_2$=71.7 Hz, 1H), 2.64 (s, 3H); LC/MS (ES+): (M+1) 480.1.

Example 12

[2-(2-Difluoromethoxy-phenyl)-5-(6-methyl-pyridin-3-yl)-[1,3,4]thiadiazol-3-yl]-(2-hydroxy-phenyl)-methanone

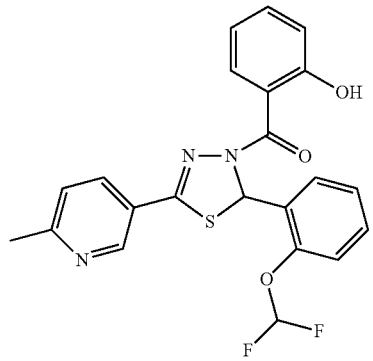 [SMILES: Cc1ccc(C2=NN(C(=O)c3ccccc3O)C(c3ccccc3OC(F)F)S2)cn1]

(2-(2-(Difluoromethoxy)phenyl)-5-(6-methylpyridin-3-yl)-1,3,4-thiadiazol-3(2H)-yl)(2-acetoxyphenyl)methanone (0.02 mmol) prepared in a similar manner as described in experiment 11 for [2-(2-difluoromethoxy-phenyl)-5-(6-methyl-pyridin-3-yl)-[1,3,4]thiadiazol-3-yl]-(2,4,6-trifluoro-phenyl)-methanone, is dissolved in THF/MeOH (1 mL/0.5 mL) and treated with aqueous LiOH (1 M) (0.5 mL) at room temperature for 30 minutes. Aqueous HCl (3 M) is added to adjust the pH to 5-6. Solvent is removed and the residue is purified by preparative HPLC (20-100% MeCN/$H_2O$) to yield [2-(2-difluoromethoxy-phenyl)-5-(6-methyl-pyridin-3-yl)-[1,3,4]thiadiazol-3-yl]-(2-hydroxy-phenyl)-methanone: $^1$H NMR (400 MHz, CDCl$_3$) 9.02 (d, J=2.0 Hz, 1H), 8.41 (d, J=8.6 Hz, 1H), 8.23 (dd, $J_1$=8.2 Hz, $J_2$=2.2 Hz, 1H), 7.77 (d, J=7.5 Hz, 1H), 7.65 (s, 1H), 7.62 (dd, $J_1$=7.8 Hz, $J_2$=1.3 Hz, 1H), 7.45-7.53 (m, 5H), 6.97-7.01 (m, 2H), 2.79 (s, 3H); LC/MS (ES+): (M+1) 442.1.

Example 13

[2-(2-Difluoromethoxy-phenyl)-5-(6-fluoro-pyridin-3-yl)-[1,3,4]thiadiazol-3-yl]-(2,4,6-trifluoro-phenyl)-methanone

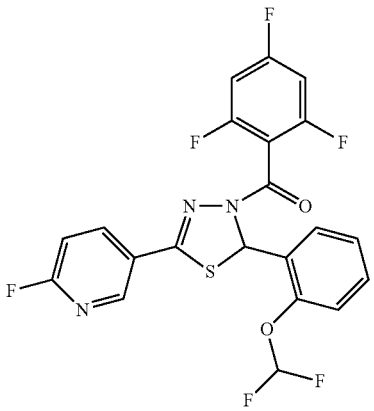 [SMILES: O=C(c1c(F)cc(F)cc1F)N1N=C(c2ccc(F)nc2)SC1c1ccccc1OC(F)F]

N'-(6-fluoro-pyridine-3-carbothioyl)-hydrazinecarboxylic acid tert-butyl ester (0.044 mmol) prepared as described in example 3 for N'-(4-fluoro-benzoyl)-hydrazinecarboxylic acid tert-butyl ester, is treated with TFA (0.44 mmol) and thioanisole (0.44 mmol) in dry $CH_2Cl_2$ (1 mL) at room temperature for 30 minutes. The solvent is removed and the residue is dissolved in dry $CH_2Cl_2$ (1 mL). DIEA (0.22 mmol) is added to the solution and the mixture is treated with 2-difluoromethoxy-benzaldehyde (0.067 mmol) in the presence of 4 Å molecular sieves. 2,4,6-Trifluorobenzoyl chloride (0.089 mmol) is added after 5 minutes. The mixture is kept at room temperature for 16 hours and purified by preparative silica gel TLC (30% EtOAc/hexane) to yield [2-(2-difluoromethoxy-phenyl)-5-(6-fluoro-pyridin-3-yl)-[1,3,4]thiadiazol-3-yl]-(2,4,6-trifluoro-phenyl)-methanone: $^1$H NMR (400 MHz, CDCl$_3$) 8.39 (s, 1H), 7.93-7.97 (m, 1H), 7.54 (s, 1H), 7.37-7.41 (m, 2H), 7.24-7.27 (m, 1H), 7.19 (d, J=8.1 Hz, 1H), 6.97 (dd, $J_1$=8.6 Hz, $J_2$=2.7 Hz, 1H), 6.78 (t, J=8.3 Hz, 2H), 6.67 (dd, $J_1$=75.0 Hz, $J_2$=71.7 Hz, 1H); LC/MS (ES$^+$): (M+1) 484.1.

Example 14

3-{4-[5-(3,4-Difluoro-phenyl)-3-(2,4,6-trifluoro-benzoyl)-2,3-dihydro-[1,3,4]thiadiazol-2-yl]-benzooxazol-2-yl}-benzoic acid

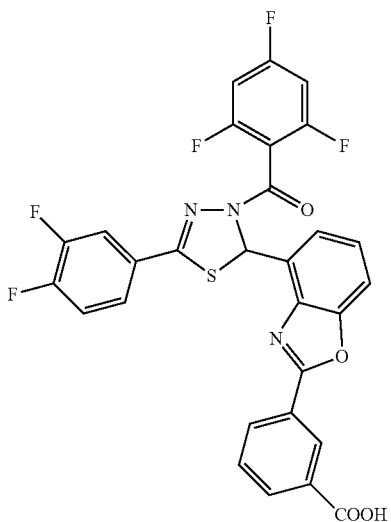 [SMILES: O=C(O)c1cccc(-c2nc3c(C4SC(c5ccc(F)c(F)c5)=NN4C(=O)c4c(F)cc(F)cc4F)cccc3o2)c1]

2-Amino-3-methyl-phenol (6.09 mmol) is heated with 3-formyl-benzoic acid methyl ester (6.09 mmol) in MeOH (6 mL) at 60° C. for 30 minutes. The solvent is removed from the mixture to obtain a dark red oil which is dissolved in dry CH$_2$Cl$_2$ (6 mL) at room temperature and treated with DDQ (6.4 mmol) for 16 hours. The mixture is diluted with EtOAc and poured onto saturated aqueous NaHCO$_3$. The aqueous phase is further extracted with EtOAc and the combined organic phases are dried over Na$_2$SO$_4$. Filtration and removal of the solvent yields a residue which is purified by silica gel chromatography (5-10% EtOAc/hexane) to yield 3-(4-methyl-benzooxazol-2-yl)-benzoic acid methyl ester as a white solid: $^1$H NMR (400 MHz, CDCl$_3$) 8.92 (d, J=1.6 Hz, 1H), 8.47 (dt, $J_1$=7.8 Hz, $J_2$=1.5 Hz, 1H), 8.2 (dt, $J_1$=7.8 Hz, $J_2$=1.4 Hz, 1H), 7.61 (t, J=7.9 Hz, 1H), 7.43 (d, J=8.1 Hz, 1H), 7.27 (t, J=7.7 Hz, 1H), 7.17 (t, J=7.5 Hz, 1H), 3.99 (s, 3H), 2.69 (s, 3H); LC/MS (ES$^+$): (M+1) 268.1.

A solution of 3-(4-methyl-benzooxazol-2-yl)-benzoic acid methyl ester (1.2 mmol), N-bromo succinimide (1.5 mmol) and AIBN (0.3 mmol) in CCl$_4$ are heated in microwave at 100° C. for 30 minutes (1 mL). The mixture is filtered and concentrated to yield the crude 3-(4-bromomethyl-benzooxazol-2-yl)-benzoic acid methyl ester. LC/MS (ES$^+$): (M$^+$) 346.1, 348.1, (M-Br) 266.1, 268.1.

The crude 3-(4-bromomethyl-benzooxazol-2-yl)-benzoic acid methyl ester is treated with HMTA (1.8 mmol) in acetic acid/H$_2$O (3 mL/1.5 mL) in a microwave oven at 130° C. for 20 minutes. The solvent is removed and the mixture is purified by silica gel chromatography (10-20% EtOAc/hexane) to yield 3-(4-formyl-benzooxazol-2-yl)-benzoic acid methyl ester as a white solid. Yield: 32%. $^1$H NMR (400 MHz, CDCl$_3$) 10.8 (s, 1H), 8.97 (s, 1H), 8.53 (d, J=7.8 Hz, 1H), 8.26 (d, J=7.8 Hz, 1H), 7.94 (dd, $J_1$=7.7 Hz, $J_2$=1 Hz, 1H), 7.86 (d, J=8.1 Hz, 1H), 7.66 (t, J=7.8 Hz, 1H), 7.51 (t, J=7.9 Hz, 1H), 4.0 (s, 3H). LC/MS (ES$^+$): (M+1) 282.1, (M+Na) 304.1.

N'-(3,4-Difluoro-thiobenzoyl)-hydrazinecarboxylic acid tert-butyl ester (0.1 mmol) prepared as described in example 3 for N'-(4-fluoro-benzoyl)-hydrazinecarboxylic acid tert-butyl ester, is treated with TFA (1 mmol) in dry CH$_2$Cl$_2$ (1 mL) at room temperature for 30 minutes. Solvent is removed and the residue is dissolved in dry CH$_2$Cl$_2$ (1 mL). DIEA (0.57 mmol) is added to the solution and the mixture is treated with 3-(4-formyl-benzooxazol-2-yl)-benzoic acid methyl ester (0.064 mmol) in the presence of 4 Å molecular sieves. 2,4,6-Trifluorobenzoyl chloride (0.15 mmol) is added after 5 minutes. The mixture is kept at room temperature for 16 hours and purified by preparative HPLC (20-100% MeCN/H$_2$O) to yield 3-{4-[5-(3,4-difluoro-phenyl)-3-(2,4,6-trifluoro-benzoyl)-2,3-dihydro-[1,3,4]thiadiazol-2-yl]-benzooxazol-2-yl}-benzoic acid methyl ester. LC/MS (ES$^+$): (M+1) 610.0, (M+Na) 632.0.

3-{4-[5-(3,4-Difluoro-phenyl)-3-(2,4,6-trifluoro-benzoyl)-2,3-dihydro-[1,3,4]thiadiazol-2-yl]-benzooxazol-2-yl}-benzoic acid methyl ester (0.02 mmol) is dissolved in THF/MeOH (1 mL/0.5 mL) and treated with aqueous LiOH (1 M) (0.5 mL) at room temperature for 30 minutes. Aqueous HCl (3 M) is added to adjust the pH to 5-6. The solvent is removed and the residue is purified by preparative HPLC (20-100% MeCN/H$_2$O) to yield 3-{4-[5-(3,4-difluoro-phenyl)-3-(2,4,6-trifluoro-benzoyl)-2,3-dihydro-[1,3,4]thiadiazol-2-yl]-benzooxazol-2-yl}-benzoic acid: $^1$H NMR (400 MHz, CDCl$_3$) 8.95 (s, 1H), 8.48 (d, J=7.9 Hz, 1H), 8.27 (d, J=7.8 Hz, 1H), 7.92 (s, 1H), 7.66 (t, J=7.8 Hz, 1H), 7.6 (dd, $J_1$=7.7 Hz, $J_2$=1.2 Hz, 1H), 7.46 (m, 1H), 7.29-7.42 (m, 3H), 7.19 (q, J=8.2 Hz, 1H), 6.76-6.81 (m, 2H); LC/MS (ES$^+$): (M+1) 596.0, (M+Na) 618.0.

Example 15

4-{3-[5-4-Fluoro-phenyl)-3-(2-hydroxy-benzoyl)-2,3-dihydro-[1,3,4]thiadiazol-2-yl]-2-methoxy-phenoxymethyl}-benzene sulfonamide

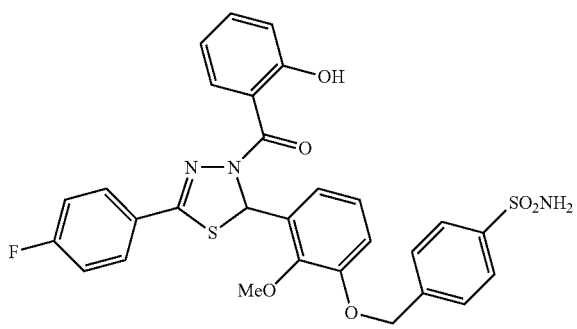 [SMILES: COc1c(OCc2ccc(S(N)(=O)=O)cc2)cccc1C1SC(c2ccc(F)cc2)=NN1C(=O)c1ccccc1O]

4-(3-Formyl-2-methoxy-phenoxymethyl)-N,N-bis-(4-methoxy-benzyl)-benzenesulfonamide

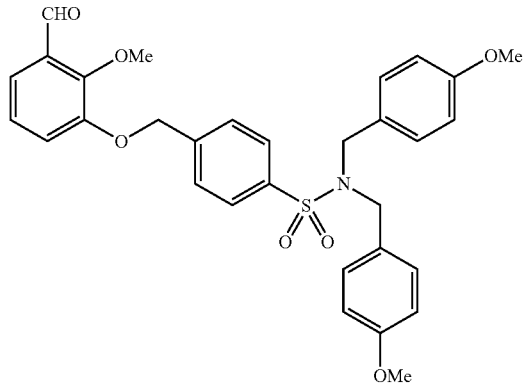 [SMILES: COc1ccc(CN(Cc2ccc(OC)cc2)S(=O)(=O)c2ccc(COc3cccc(C=O)c3OC)cc2)cc1]

A solution of 4-(bromomethyl)benzenesulfonyl chloride (5.6 mmol) in 5 mL of $CH_2Cl_2$ at 25° C. is treated with $Et_3N$ (8.4 mmol) followed by bis-(4-methoxy-benzyl)-amine (5.8 mmol). The reaction is stirred for 12 hours, diluted with $H_2O$, extracted with $CH_2Cl_2$, dried ($MgSO_4$), filtered and concentrated. The resultant crude material is purified by silica flash chromatography (20% EtOAc/hexanes) to yield 4-bromomethyl-N,N-bis-(4-methoxy-benzyl)-benzenesulfonamide: $^1$H NMR (400 MHz, $CDCl_3$): δ 7.72 (apparent t, J=8.4 Hz, 2H), 7.44 (dd, $J_1$=1.6 Hz, $J_2$=8.4 Hz, 2H), 6.91-6.86 (m, 4H), 6.69 (d, J=8.8 Hz, 4H), 4.5 (s, 2H), 4.19 (s, 4H), 3.71 (s, 3H); LC/MS: ($ES^+$) 490.1 (M+1)$^+$.

2-Methoxy-3-triisopropylsilanyloxy-benzaldehyde (2.9 mmol), prepared as described in example 4, and 4-bromomethyl-N,N-bis-(4-methoxy-benzyl)-benzenesulfonamide (3.0 mmol) in anhydrous THF (4 mL) are treated with 4.4 mL of a 1.0 M solution of TBAF in THF. The reaction is stirred for 12 hours at ambient temperature and concentrated. The resultant material was purified by silica flash chromatography (30% EtOAc/hexanes) to yield 4-(3-formyl-2-methoxy-phenoxymethyl)-N,N-bis(4-methoxy-benzyl)-benzamide: $^1$H NMR (400 MHz, $CDCl_3$): δ 10.45 (s, 1H), 7.85 (d, J=8 Hz, 2H), 7.58 (d, J=8 Hz, 2H), 7.48 (dd, $J_1$=1.2 Hz, $J_2$=7.6 Hz, 1H), 7.11-7.19 (m, 2H), 6.97 (d, J=8.8 Hz, 4H), 6.74 (d, T=8.4 Hz, 4H), 5.23 (s, 2H), 4.26 (s, 4H), 4.05 (s, 3H), 3.77 (s, 6H); LC/MS: ($ES^+$) 562.6 (M+1)$^+$.

4-Fluorobenzothiohydrazide hydrochloride salt (0.045 mmol) as prepared in example 3 is dissolved in $CH_2Cl_2$ (1 mL). DIEA (0.133 mmol) is added to the solution and the mixture is treated with 4-(3-formyl-2-methoxy-phenoxymethyl)-N,N-bis(4-methoxy-benzyl)-benzamide (0.047 mmol) in the presence of 4 Å molecular sieves. Acetic acid 2-chlorocarbonyl-phenyl ester (0.047 mmol) is added after 5 minutes. The mixture was kept at ambient temperature for 16 hours and concentrated. The resultant material is dissolved in trifluoroacetic acid. After 3 hours, the reaction mixture is concentrated. The crude material is dissolved in DMSO and purified by preparative LC/MS (20-100% MeCN/$H_2O$) to give 4-{3-[5-4-fluoro-phenyl)-3-(2-hydroxy-benzoyl)-2,3-dihydro-[1,3,4]thiadiazol-2-yl]-2-methoxy-phenoxymethyl}-benzenesulfonamide as a white solid after evaporation of solvent: $^1$H NMR (400 MHz, $CDCl_3$): δ 11.27 (s, 1H), 8.55 (dd, $J_1$=1.2 Hz, $J_2$=8 Hz, 1H), 7.96 (d, J=8 Hz, 2H), 7.71-7.77 (m, 2H), 7.59-7.64 (m, 3H), 7.42-7.47 (m, 1H), 7.12-7.8 (m, 2H), 6.95-7.03 (m, 3H), 6.86-6.92 (m, 2H), 5.2 (s, 2H), 4.77 (s, 2H), 4.07 (s, 3H); LC/MS: ($ES^+$) 594.0 (M+1)$^+$.

Example 16

3-{3-[5-(4-Fluoro-phenyl)-3-(2,4,6-trifluoro-benzoyl)-2,3-dihydro-[1,3,4]thiadiazol-2-yl]-2-methoxy-phenoxymethyl}-N-hydroxy-benzamidine

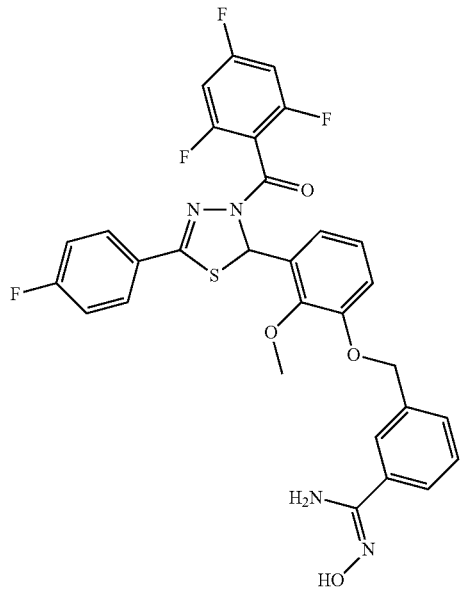 [SMILES: COc1c(OCc2cccc(/C(N)=N/O)c2)cccc1C1SC(c2ccc(F)cc2)=NN1C(=O)c1c(F)cc(F)cc1F]

To 3-{2-[5-(4-fluoro-phenyl)-3-(2,4,6-trifluoro-benzoyl)-2,3-dihydro-[1,3,4]thiadiazol-2-yl]-phenoxymethyl}-benzamide (0.1 mmol) is charged 1 mL of $SOCl_2$. The mixture is heated at 100° C. in the microwave oven for 25 minutes. Solvent is removed. The residue is dissolved in EtOH (1 mL). $NH_2OH$ (50% aqueous solution, 0.06 mL) is charged. The mixture is heated at 100° C. in microwave for 25 minutes. Purification by preparative LC/MS (20-100% MeCN/$H_2O$) to give 3-{3-[5-(4-fluoro-phenyl)-3-(2,4,6-trifluoro-benzoyl)-2,3-dihydro-[1,3,4]thiadiazol-2-yl]-2-methoxy-phenoxymethyl}-N-hydroxy-benzamidine. $^1$H NMR (400 MHz, $CDCl_3$) δ 7.7 (d, J=7 Hz, 1H), 7.64 (s, 1H), 7.52-7.61 (m, 4H), 7.5 (s, 1H), 7.03-7.08 (m, 2H), 7.0 (d, J=8.2 Hz, 1H), 6.95 (d, J=7.9 Hz, 1H), 6.9 (d, J=6.8 Hz, 1H), 6.76 (t, J=8 Hz, 2H), 6.41 (bs, 2NH), 5.21 (dd, J=14.5, 12.8 Hz, 2H), 4.04 (s, 3H); LC/MS (ES$^+$): 611.1 (M+1)$^+$.

Example 17

2-{3-[5-(4-Fluoro-phenyl)-3-(2-hydroxy-benzoyl)-2,3-dihydro-[1,3,4]thiadiazol-2-yl]-2-methoxy-phenoxy}-N-(2-hydroxy-1-methyl-ethyl)-acetamide

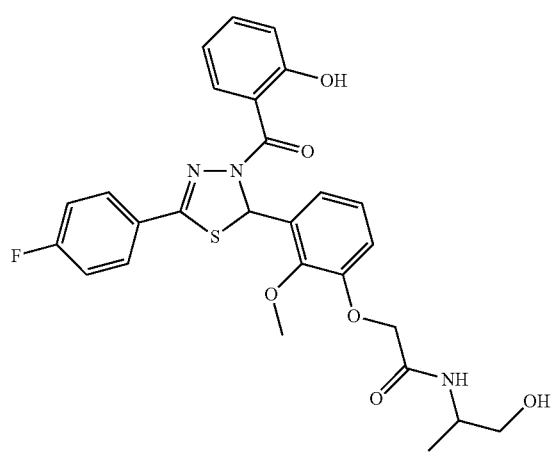 [SMILES: COc1c(OCC(=O)NC(C)CO)cccc1C1SC(c2ccc(F)cc2)=NN1C(=O)c1ccccc1O]

To {3-[5-(4-Fluoro-phenyl)-3-(2-hydroxy-benzoyl)-2,3-dihydro-[1,3,4]thiadiazol-2-yl]-2-methoxy-phenoxy}-acetic acid (0.27 mmol) in dry DMF (0.5 mL) is added HATU (1.35 mmol), DIEA (0.45 mL, 2.7 mmol) and 2-amino-propan-1-ol. The mixture is kept at ambient temperature for 16 hours. The residue is diluted with EtOH (1 mL). Purification of the mixture by preparative LC/MS (30-100% MeCN/H$_2$O) gives 2-{3-[5-(4-fluoro-phenyl)-3-(2-hydroxy-benzoyl)-2,3-dihydro-[1,3,4]thiadiazol-2-yl]-2-methoxy-phenoxy}-N-(2-hydroxy-1-methyl-ethyl)-acetamide. $^1$H NMR (400 MHz, CDCl$_3$) δ 11.2 (s, 1H), 8.53 (m, 1H), 7.73 (m, 2H), 7.6 (s, 1H), 7.44 (t, J=8.4 Hz, 1H), 7.15 (t, J=8 Hz, 2H), 6.9-7.1 (m, 5H), 4.58 (s, 2H), 4.14 (m, 1H), 4.06 (s, 3H), 3.69 (m, 1H), 3.59 (m, 1H), 2.1 (bs, 2H), 1.23 (m, 3H); LC/MS (ES$^+$): 540.1 (M+1)$^+$.

Example 18

6-{2-Cyanomethoxy-3-[5-(4-fluoro-phenyl)-3-(2,4,6-trifluoro-benzoyl)-2,3-dihydro-[1,3,4]thiadiazol-2-yl]-phenoxymethyl}-pyridine-2-carboxylic acid ethyl ester To 2,3-dihydroxybenaldehyde (1 mmol) in dry DMSO (2.5 mL) is added NaH (60% suspension in oil, 2.5 mmol). After 10 minutes, 6-bromomethyl-pyridine-2-carboxylic acid ethyl ester (1 mmol) is added. After 1 hour, bromoacetonitrile (0.07 mL, 1 mmol) is introduced at ambient temperature and mixture is stirred for 16 hours. Saturated aqueous NH$_4$Cl solution is used to quench the reaction and the mixture is extracted with EtOAc. After drying over sodium sulfate, solvent is removed. Purification of the mixture by preparative HPLC (20-70% MeCN/H$_2$O) gives 6-(2-cyanomethoxy-3-formyl-phenoxymethyl)-pyridine-2-carboxylic acid ethyl ester. $^1$H NMR (400 MHz, CDCl$_3$) δ 10.4 (s, 1H), 8.1 (d, J=7.7 Hz, 1H), 7.9 (t, J=7.9 Hz, 1H), 7.7 (d, J=8.2 Hz, 1H), 7.5 (dd, J=8.2, 2.4 Hz, 1H), 7.24 (m, 2H), 5.42 (s, 2H), 5.14 (s, 2H), 4.5 (q, J=7.2 Hz, 2H), 1.45 (t, J=7 Hz, 3H); LC/MS (ES$^+$): 341.2 (M+1)$^+$.

6-{2-Cyanomethoxy-3-[5-(4-fluoro-phenyl)-3-(2,4,6-trifluoro-benzoyl)-2,3-dihydro-[1,3,4]thiadiazol-2-yl]-phenoxymethyl}-pyridine-2-carboxylic acid ethyl ester is prepared in a similar manner as described for [5-(4-fluoro-phenyl)-2-(3-methoxy-2-triisopropylsilanyloxy-phenyl)-[1,3,4]thiadiazol-3-yl]-(2,4,6-trifluoro-phenyl)-methanone in example 3 using 6-(2-cyanomethoxy-3-formyl-phenoxymethyl)-pyridine-2-carboxylic acid ethyl ester. $^1$H NMR (400 MHz, CDCl$_3$) δ 8.1 (d, J=7.9 Hz, 1H), 7.94 (t, J=7.9 Hz, 1H), 7.76 (d, J=7.5 Hz, 1H), 7.54-7.58 (m, 3H), 7.05-7.14 (m, 3H), 7.01 (d, J=7.3 Hz, 1H), 6.96 (d, J=8.9 Hz, 1H), 6.76 (t, J=8.5 Hz, 2H), 5.4 (s, 2H), 5.12 (d, J=4.4 Hz, 2H), 4.5 (q, J=7.2 Hz, 2H), 1.45 (t, J=7.3 Hz, 3H); LC/MS (ES$^+$): 651.2 (M+1)$^+$.

Example 19

6-{3-[5-(4-Fluoro-phenyl)-3-(2,4,6-trifluoro-benzoyl)-2,3-dihydro-[1,3,4]thiadiazol-2-yl]-2-methoxy-carbonylmethoxy-phenoxymethyl}-pyridine-2-carboxylic acid

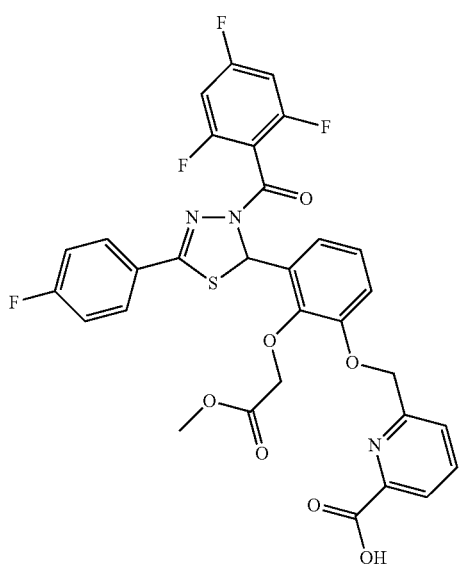 [SMILES: COC(=O)COc1c(OCc2cccc(C(=O)O)n2)cccc1C1SC(c2ccc(F)cc2)=NN1C(=O)c1c(F)cc(F)cc1F]

6-{2-Cyanomethoxy-3-[5-(4-fluoro-phenyl)-3-(2,4,6-trifluoro-benzoyl)-2,3-dihydro-[1,3,4]thiadiazol-2-yl]-phenoxymethyl}-pyridine-2-carboxylic acid ethyl ester is dissolved in THF (1.5 mL) and MeOH (1.0 mL), LiOH (1 M) (0.5 mL) is added. After stirring for 1 hour, the solvent is removed from the reaction mixture. A mixture of MeOH/DMSO is added to the residue and resultant solution is filtered. The clear solution is purified by preparative LC/MS (20-100% MeCN/H$_2$O) to give 6-{3-[5-(4-fluoro-phenyl)-3-(2,4,6-trifluoro-benzoyl)-2,3-dihydro-[1,3,4]thiadiazol-2-yl]-2-methoxycarbonylmethoxy-phenoxymethyl}-pyridine-2-carboxylic acid as white solid after removal of solvent: $^1$H NMR (400 MHz, CDCl$_3$) δ 8.21 (d, J=7.9 Hz, 1H), 8.03 (t, J=7.3 Hz, 1H), 7.81 (d, 10.1 Hz, 1H), 7.8 (s, 1H), 7.55 (dd, J=8.9, 5.3 Hz, 2H), 7.0-7.1 (m, 4H), 6.92 (d, J=8 Hz, 1H), 6.76 (t, J=7.5 Hz, 2H), 5.31 (s, 2H), 4.94 (d, J=7.8 Hz, 2H), 4.8 (bs, 1H), 3.8 (s, 3H); LC/MS (ES$^+$): (M+1) 656.3.

By repeating the procedures described in the above examples, using appropriate starting materials, the following compounds of Formula I, as identified in Table 1 and 2, are obtained.

TABLE 1

| Example | Structure | MS (m/z) (M + 1)$^+$ | NMR |
|---|---|---|---|
| 1 | 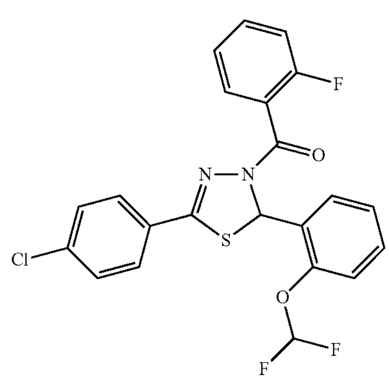 [SMILES: O=C(c1ccccc1F)N1N=C(c2ccc(Cl)cc2)SC1c1ccccc1OC(F)F] | 462.8 | $^1$H NMR (400 MHz, CDCl$_3$) δ 7.39-7.35 (m, 1H), 7.34-7.29 (m, 4H), 7.25 (dd, J$_1$ = 7.8 Hz, J$_2$ = 1.2 Hz, 1H), 7.19-7.13 (m, 3H), 7.07-7.03 (m, 1H), 6.99-6.96 (m, 2H), 6.50 (dd, J$_1$ = 71.6 Hz, J$_2$ = 71.2 Hz, 1H). |

TABLE 1-continued

| Example | Structure | MS (m/z) (M + 1)+ | NMR |
|---|---|---|---|
| 2 | 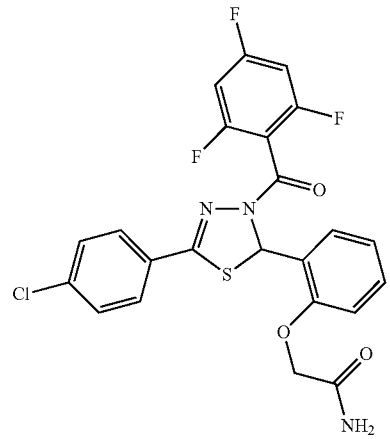 [SMILES: NC(=O)COc1ccccc1C1SC(c2ccc(Cl)cc2)=NN1C(=O)c1c(F)cc(F)cc1F] | 506.2 | ¹H NMR (400 MHz, CDCl$_3$) δ 7.43 (s, 1H), 7.27 (d, J = 8.8, 2H), 7.15 (m, 2H), 7.14 (d, J = 8.4 Hz, 2H) 6.99 (bs, 1H), 6.84 (t, J = 6.4 Hz, 3H), 6.66 (d, J = 8.4 Hz, 1H), 6.53 (t, J = 8.0 Hz, 2H), 5.29 (bs, 1H), 4.47 (d, J = 1.6 Hz, 2H). |
| 3 | 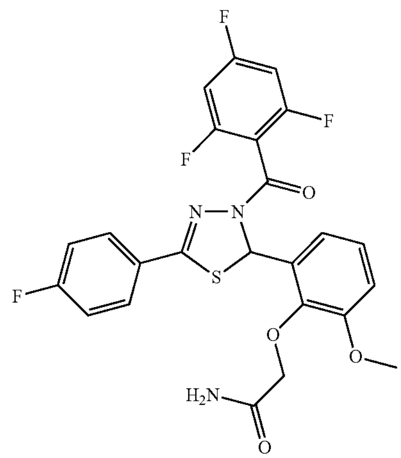 [SMILES: COc1cccc(C2SC(c3ccc(F)cc3)=NN2C(=O)c2c(F)cc(F)cc2F)c1OCC(N)=O] | 520.3 | ¹H NMR (400 MHz, CDCl$_3$) δ 7.63-7.62 (m, 2H), 7.57 (s, 1H), 7.22-7.12 (m, 3H), 7.02 (dd, 2H, J$_1$ = 8.4 Hz, J$_2$ = 2 Hz), 6.9 (bs, 1H), 6.85 (t, 2H, J = 8.4 Hz), 6.10 (s, 1H), 4.83 (d, 1H, J = 15.2 Hz), 4.68 (d, 1H, J = 15.2 Hz), 3.94 (s, 3H). |
| 4 | 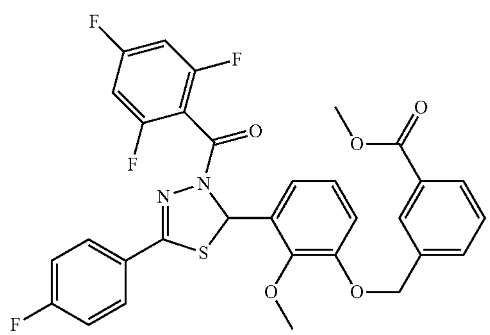 [SMILES: COC(=O)c1cccc(COc2cccc(C3SC(c4ccc(F)cc4)=NN3C(=O)c3c(F)cc(F)cc3F)c2OC)c1] | 610.9 | ¹H NMR (400 MHz, CDCl$_3$) δ 8.14 (s, 1H), 8.02 (d, J = 7.8 Hz, 1H), 7.67 (d, J = 7.7 Hz, 1H), 7.47-7.55 (m, 4H), 7.01-7.07 (m, 3H), 6.94 (t, J = 8.3 Hz, 2H), 6.77 (t, J = 8.5 Hz, 2H), 5.16 (s, 2H), 4.07 (s, 3H), 3.94 (s, 3H). |
| 5 | 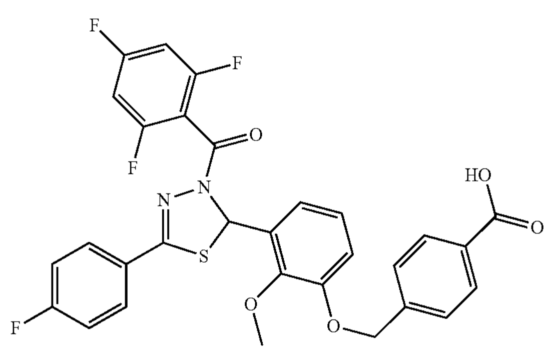 [SMILES: COc1c(OCc2ccc(C(=O)O)cc2)cccc1C1SC(c2ccc(F)cc2)=NN1C(=O)c1c(F)cc(F)cc1F] | 597.3 | ¹H NMR (400 MHz, CDCl$_3$) δ 8.14 (d, J = 8 Hz, 2H), 7.53-7.58 (m, 5H), 7.03-7.05 (m, 3H), 6.94-6.95 (m, 2H), 6.77 (t, J = 8.2 Hz, 2H), 5.2 (s, 2H), 4.08 (s, 3H). |

| Example | Structure | MS (m/z) (M + 1)+ | NMR |
|---|---|---|---|
| 6 | 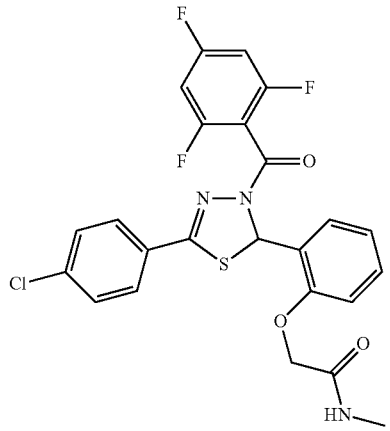 [SMILES: CNC(=O)COc1ccccc1C1SC(c2ccc(Cl)cc2)=NN1C(=O)c1c(F)cc(F)cc1F] | 520.2 | ¹H NMR (400 MHz, CDCl$_3$) δ 7.55-7.51 (m, 3H), 7.12-6.99 (m, 4H), 6.9 (d, J = 7.6 Hz, 2H), 6.77 (t, J = 8.4 Hz, 2H), 4.56 (s, 2H), 4.08 (s, 3H), 3.26-3.2 (m, 2H), 1.02-0.99 (m, 1H), 0.57-0.52 (m, 2H), 0.25 (m, 2H). |
| 7 | 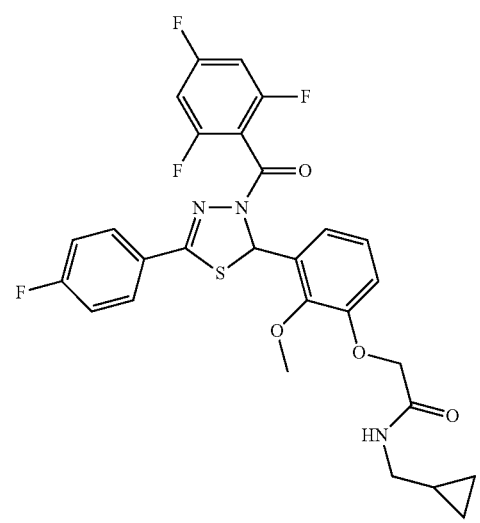 [SMILES: COc1c(OCC(=O)NCC2CC2)cccc1C1SC(c2ccc(F)cc2)=NN1C(=O)c1c(F)cc(F)cc1F] | 574.2 | ¹H NMR (400 MHz, CDCl$_3$) δ 7.55-7.51 (m, 3H), 7.35-7.26 (m, 2H), 7.05-6.96 (m, 3H), 6.85 (d, J = 8 Hz, 1H), 6.69 (t, J = 7.6 Hz, 2H), 6.56 (s, 1H), 4.72 (s, 2H), 2.33 (s, 3H). |
| 8 | 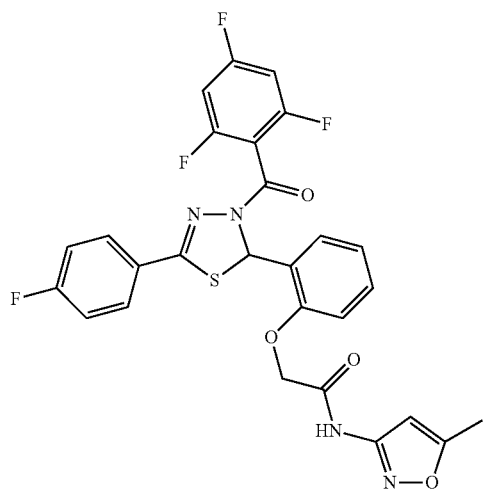 [SMILES: Cc1cc(NC(=O)COc2ccccc2C2SC(c3ccc(F)cc3)=NN2C(=O)c2c(F)cc(F)cc2F)no1] | 571.1 | ¹H NMR (400 MHz, CDCl$_3$) δ 8.09 (s, 1H), 7.9 (d, J = 7.6 Hz, 1H), 7.7 (s, 1H), 7.6-7.5 (m, 4H) 7.35 (d, J = 7.6 Hz, 1H), 7.06 (t, J = 8.4 Hz, 1H), 6.99 (t, J = 7.6 Hz, 2H), 6.88 (d, J = 8 Hz), 6.79 (t, J = 8.4 Hz, 2H), 6.26 (bs, 1H), 5.33 (d, J = 7.6 Hz). |

TABLE 1-continued

| Example | Structure | MS (m/z) (M + 1)+ | NMR |
|---------|-----------|-------------------|-----|
| 9 | 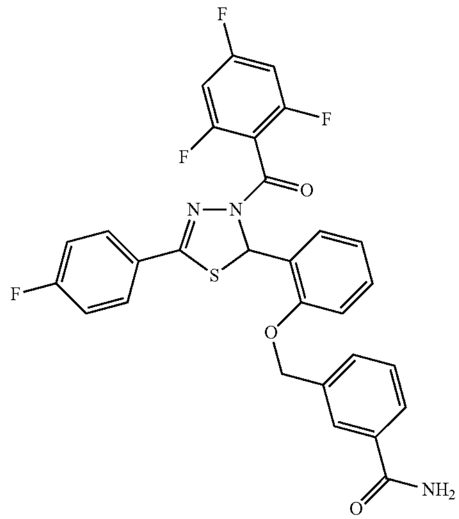 [SMILES: NC(=O)c1cccc(COc2ccccc2C2SC(c3ccc(F)cc3)=NN2C(=O)c2c(F)cc(F)cc2F)c1] | 566.1 | ¹H NMR (400 MHz, CDCl₃) δ 7.26-7.23 (m, 3H), 7.20 (d, J = 1.9 Hz, 1H), 7.10-7.05 (m, 1H), 7.03-6.99 (m, 1H), 6.86 (d, J = 8.1 Hz, 1H), 6.78-6.74 (m, 3H), 6.55 (d, J = 1.9 Hz, 1H), 6.55-6.50 (m, 2H), 5.38-5.21 (m, 2H). |
| 10 | 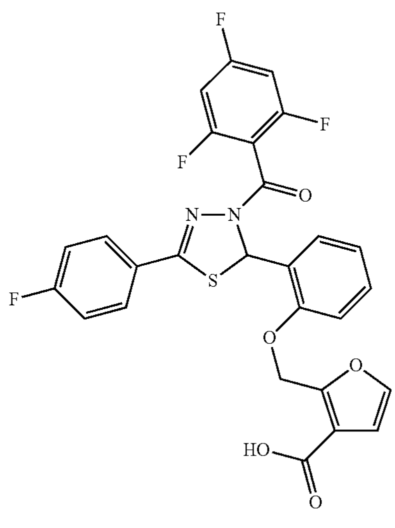 [SMILES: O=C(O)c1ccoc1COc1ccccc1C1SC(c2ccc(F)cc2)=NN1C(=O)c1c(F)cc(F)cc1F] | 556.5 | ¹H NMR (400 MHz, CDCl₃) δ 8.71 (d, J = 2.1 Hz, 1H), 7.81 (dd, J₁ = 8.2 Hz, J₂ = 2.2 Hz, 1H), 7.53 (s, 1H), 7.36-7.4 (m, 2H), 7.26 (d, J = 8.1 Hz, 2H), 7.18 (d, J = 8.3 Hz, 1H), 6.78 (t, J = 8.3 Hz, 2H), 6.67 (dd, J₁ = 75.0 Hz, J₂ = 71.7 Hz, 1H), 2.64 (s, 3H). |
| 11 | 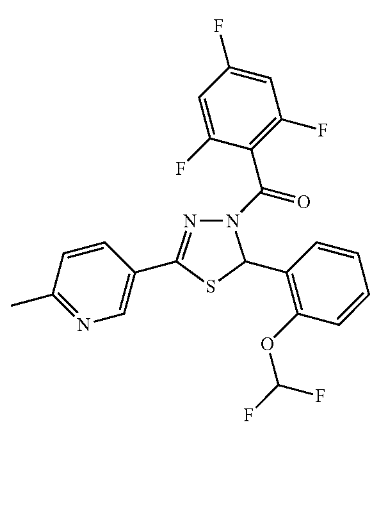 [SMILES: Cc1ccc(C2=NN(C(=O)c3c(F)cc(F)cc3F)C(c3ccccc3OC(F)F)S2)cn1] | 480.0 | ¹H NMR (400 MHz, CDCl₃) δ 9.02 (d, J = 2.0 Hz, 1H), 8.41 (d, J = 8.6 Hz, 1H), 8.23 (dd, J₁ = 8.2 Hz, J₂ = 2.2 Hz, 1H), 7.77 (d, J = 7.5 Hz, 1H), 7.65 (s, 1H), 7.62 (dd, J₁ = 7.8 Hz, J₂ = 1.3 Hz, 1H), 7.45-7.53 (m, 5H), 6.97-7.01 (m, 2H), 2.79 (s, 3H). |

TABLE 1-continued

| Example | Structure | MS (m/z) (M + 1)+ | NMR |
|---|---|---|---|
| 12 | 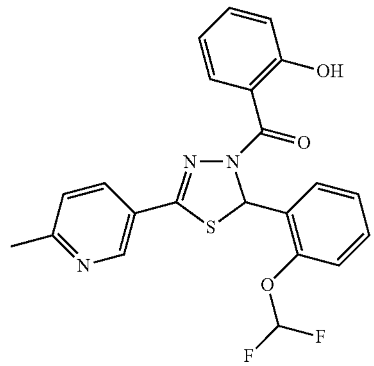 [SMILES: Cc1ccc(C2=NN(C(=O)c3ccccc3O)C(c3ccccc3OC(F)F)S2)cn1] | 442.1 | ¹H NMR (400 MHz, CDCl₃) δ 7.55-7.51 (m, 3H), 7.12-6.99 (m, 4H), 6.9 (d, J = 7.6 Hz, 2H), 6.77 (t, J = 8.4 Hz, 2H), 4.56 (s, 2H), 4.08 (s, 3H), 3.26-3.2 (m, 2H), 1.02-0.99 (m, 1H), 0.57-0.52 (m, 2H), 0.25 (m, 2H). |
| 13 | 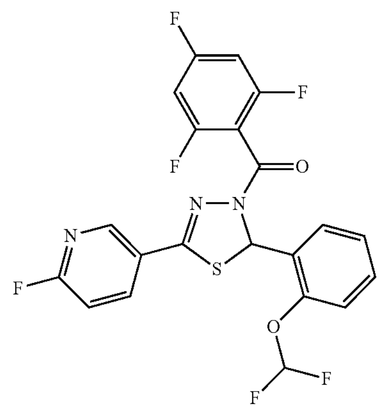 [SMILES: O=C(c1c(F)cc(F)cc1F)N1N=C(c2ccc(F)nc2)SC1c1ccccc1OC(F)F] | 484.4 | ¹H NMR (400 MHz, CDCl₃) δ 8.39 (s, 1H), 7.93-7.97 (m, 1H), 7.54 (s, 1H), 7.37-7.41 (m, 2H), 7.24-7.27 (m, 1H), 7.19 (d, J = 8.1 Hz, 1H), 6.97 (dd, J₁ = 8.6 Hz, J₂ = 2.7 Hz, 1H), 6.78 (t, J = 8.3 Hz, 2H), 6.67 (dd, J₁ = 75.0 Hz, J₂ = 71.7 Hz, 1H). |
| 14 | 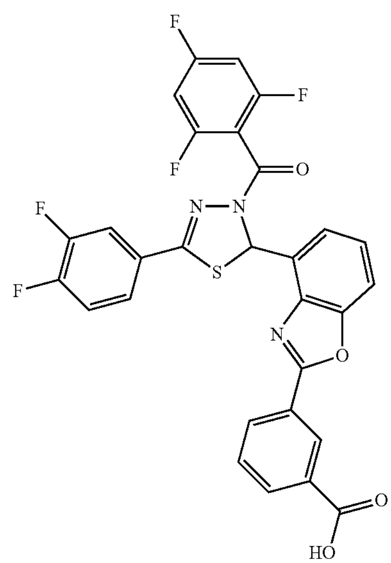 [SMILES: O=C(O)c1cccc(-c2nc3c(C4SC(c5ccc(F)c(F)c5)=NN4C(=O)c4c(F)cc(F)cc4F)cccc3o2)c1] | 596.2 | ¹H NMR (400 MHz, CDCl₃) δ 8.95 (s, 1H), 8.48 (d, J = 7.9 Hz, 1H), 8.27 (d, J = 7.8 Hz, 1H), 7.92 (s, 1H), 7.66 (t, J = 7.8 Hz, 1H), 7.6 (dd, J₁ = 7.7 Hz, J₂ = 1.2 Hz, 1H), 7.46 (m, 1H), 7.29-7.42 (m, 3H), 7.19 (q, J = 8.2 Hz, 1H), 6.76-6.81 (m, 2H). |

TABLE 1-continued

| Example | Structure | MS (m/z) (M + 1)+ | NMR |
|---|---|---|---|
| 15 | 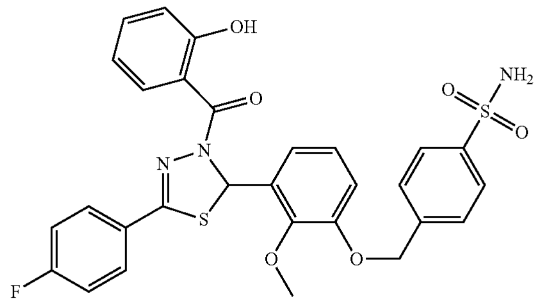 [SMILES: COc1c(OCc2ccc(S(N)(=O)=O)cc2)cccc1C1SC(c2ccc(F)cc2)=NN1C(=O)c1ccccc1O] | 594.0 | $^1$H NMR (400 MHz, CDCl$_3$) δ 11.27 (s, 1H), 8.55 (dd, J$_1$ = 1.2 Hz, J$_2$ = 8 Hz, 1H), 7.96 (d, J = 8 Hz, 2H), 7.71-7.77 (m, 2H), 7.59-7.64 (m, 3H), 7.42-7.47 (m, 1H), 7.12-7.8 (m, 2H), 6.95-7.03 (m, 3H), 6.86-6.92 (m, 2H), 5.2 (s, 2H), 4.77 (s, 2H), 4.07 (s, 3H). |
| 16 | 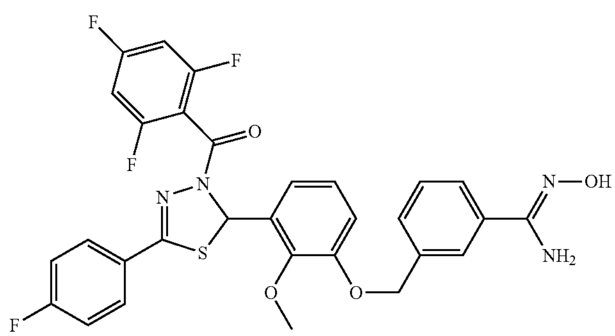 [SMILES: COc1c(OCc2cccc(/C(N)=N/O)c2)cccc1C1SC(c2ccc(F)cc2)=NN1C(=O)c1c(F)cc(F)cc1F] | 611.1 | $^1$H NMR (400 MHz, CDCl$_3$) δ 7.7 (d, J = 7 Hz, 1H), 7.64 (s, 1H), 7.52-7.61 (m, 4H), 7.5 (s, 1H), 7.03-7.08 (m, 2H), 7.0 (d, J = 8.2 Hz, 1H), 6.95 (d, J = 7.9 Hz, 1H), 6.9 (d, J = 6.8 Hz, 1H), 6.76 (t, J = 8 Hz, 2H), 6.41 (bs, 2NH), 5.21 (dd, J = 14.5, 12.8 Hz, 2H), 4.04 (s, 3H). |
| 17 | 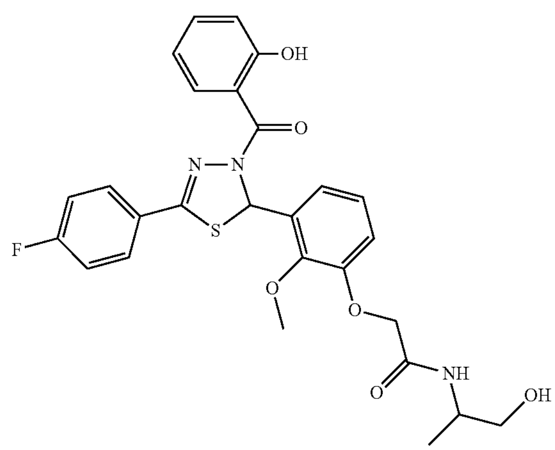 [SMILES: COc1c(OCC(=O)NC(C)CO)cccc1C1SC(c2ccc(F)cc2)=NN1C(=O)c1ccccc1O] | 540.1 | $^1$H NMR (400 MHz, CDCl$_3$) δ 11.2 (s, 1H), 8.53 (m, 1H), 7.73 (m, 2H), 7.6 (s, 1H), 7.44 (t, J = 8.4 Hz, 1H), 7.15 (t, J = 8 Hz, 2H), 6.9-7.1 (m, 5H), 4.58 (s, 2H), 4.14 (m, 1H), 4.06 (s, 3H), 3.69 (m, 1H), 3.59 (m, 1H), 2.1 (bs, 2H), 1.23 (m, 3H). |

TABLE 1-continued

| Example | Structure | MS (m/z) (M + 1)+ | NMR |
|---|---|---|---|
| 18 | 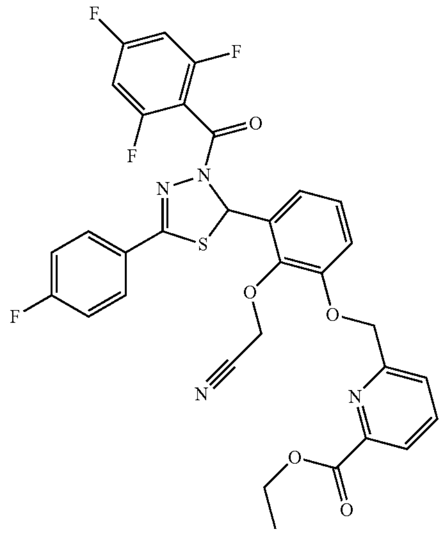 [SMILES: CCOC(=O)c1cccc(COc2cccc(C3SC(c4ccc(F)cc4)=NN3C(=O)c3c(F)cc(F)cc3F)c2OCC#N)n1] | 651.0 | ¹H NMR (400 MHz, CDCl₃) δ 8.1 (d, J = 7.9 Hz, 1H), 7.94 (t, J = 7.9 Hz, 1H), 7.76 (d, J = 7.5 Hz, 1H), 7.54-7.58 (m, 3H), 7.05-7.14 (m, 3H), 7.01 (d, J = 7.3 Hz, 1H), 6.96 (d, J = 8.9 Hz, 1H), 6.76 (t, J = 8.5 Hz, 2H), 5.4 (s, 2H), 5.12 (d, J = 4.4 Hz, 2H), 4.5 (q, J = 7.2 Hz, 2H), 1.45 (t, J = 7.3 Hz, 3H). |
| 19 | 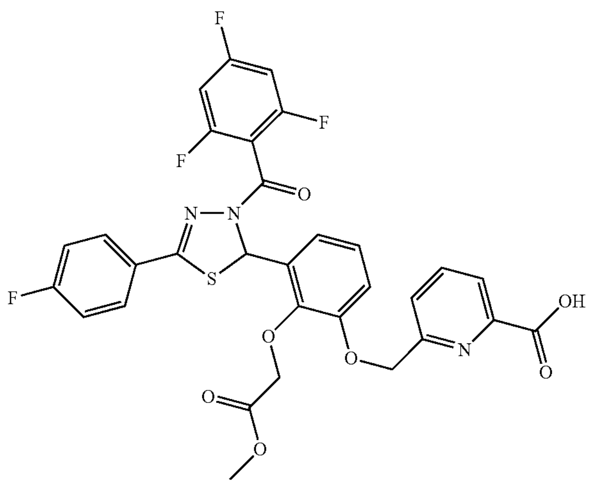 [SMILES: COC(=O)COc1c(OCc2cccc(C(=O)O)n2)cccc1C1SC(c2ccc(F)cc2)=NN1C(=O)c1c(F)cc(F)cc1F] | 656.0 | ¹H NMR (400 MHz, CDCl₃) δ 8.21 (d, J = 7.9 Hz, 1H), 8.03 (t, J = 7.3 Hz, 1H), 7.81 (d, 10.1 Hz, 1H), 7.8 (s, 1H), 7.55 (dd, J = 8.9, 5.3 Hz, 2H), 7.0-7.1 (m, 4H), 6.92 (d, J = 8 Hz, 1H), 6.76 (t, J = 7.5 Hz, 2H), 5.31 (s, 2H), 4.94 (d, J = 7.8 Hz, 2H), 4.8 (bs, 1H), 3.8 (s, 3H). |
| 20 | 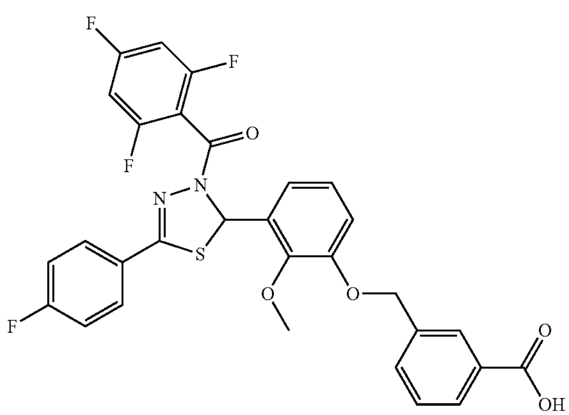 [SMILES: COc1c(OCc2cccc(C(=O)O)c2)cccc1C1SC(c2ccc(F)cc2)=NN1C(=O)c1c(F)cc(F)cc1F] | 597.3 | ¹H NMR (400 MHz, CDCl₃) δ 8.21 (s, 1H), 8.09 (d, J = 7.8 Hz, 1H), 7.73 (d, J = 7.6 Hz, 1H), 7.51-7.55 (m, 4H), 7.05 (m, 3H), 6.95 (t, J = 8.6 Hz, 2H), 6.77 (t, J = 8.3 Hz, 2H), 5.18 (s, 2H), 4.08 (s, 3H). |

TABLE 1-continued

| Example | Structure | MS (m/z) (M + 1)+ | NMR |
|---|---|---|---|
| 21 | 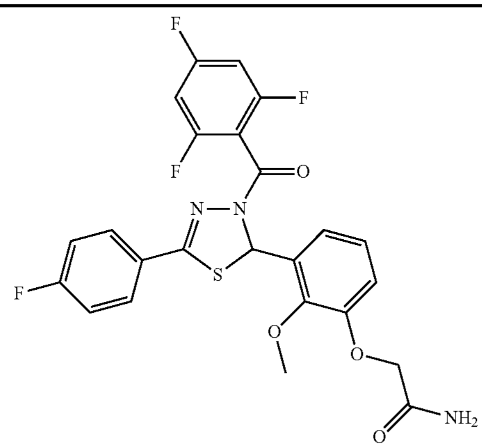 | 520.3 | ¹H NMR (400 MHz, CDCl₃) δ 7.54 (m, 2H), 7.5 (s, 1H), 7.0-7.13 (m, 4H), 6.92 (d, J = 8.2 Hz, 1H), 6.82 (s, 1H), 6.77 (t, J = 8.3 Hz, 1H), 5.78 (s, 1H), 4.58 (s, 2H), 4.06 (s, 3H). |
| 22 | 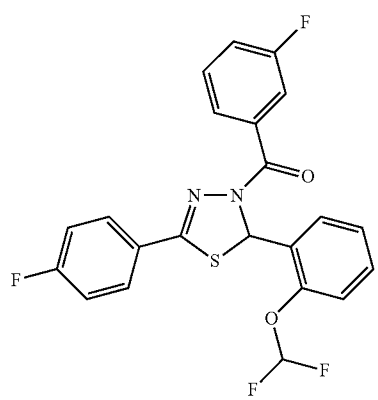 [SMILES: O=C(c1cccc(F)c1)N1N=C(c2ccc(F)cc2)SC1c1ccccc1OC(F)F] | 447.0 | ¹H NMR (400 MHz, CDCl₃) δ 7.78 (d, J = 7.7 Hz, 1H), 7.73 (d, J = 9.6 Hz, 1H), 7.66 (dd, $J_1$ = 8.7 Hz, $J_2$ = 5.3 Hz, 2H), 7.56 (s, 1H), 7.44 (q, J = 8.0 Hz, 1H), 7.33-7.37 (m, 2H), 7.17-7.26 (m, 3H), 7.12 (t, J = 8.5 Hz, 2H), 6.7 (dd, $J_1$ = 76 Hz, $J_2$ = 71 Hz, 1H). |
| 23 | 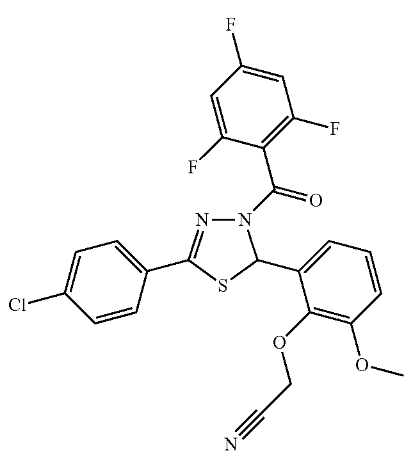 [SMILES: COc1cccc(C2SC(c3ccc(Cl)cc3)=NN2C(=O)c2c(F)cc(F)cc2F)c1OCC#N] | 518.2 | ¹H NMR (400 MHz, CDCl₃) δ 7.39 (s, 1H), 7.35 (d, J = 8.0 Hz, 2H), 7.21 (d, J = 8.0 Hz, 2H), 7.02 (t, 1H), 6.82 (t, J = 8.0 Hz, 2H), 6.62 (t, J = 8.0 Hz, 2H), 4.86 (d, J = 6.8 Hz, 2H), 3.78 (s, 3H). |

TABLE 1-continued
| Example | Structure | MS (m/z) (M + 1)+ | NMR |
|---|---|---|---|
| 24 | 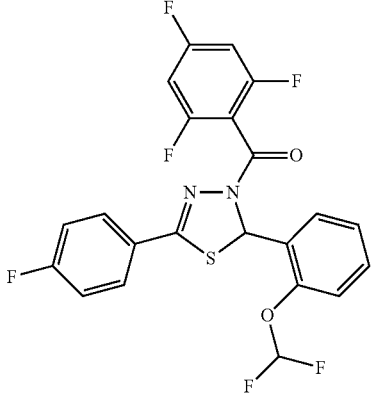 [SMILES: O=C(c1c(F)cc(F)cc1F)N1N=C(c2ccc(F)cc2)SC1c1ccccc1OC(F)F] | 483.0 | ¹H NMR (400 MHz, CDCl$_3$) 7.54 (dd, J$_1$ = 8.7 Hz, J$_2$ = 5.2 Hz, 2H), 7.5 (s, 1H), 7.4 (d, J = 8.0 Hz, 1H), 7.36 (d, J = 8.7 Hz, 1H), 7.24 (t, J = 7.6 Hz, 1H), 7.18 (d, J = 8.0 Hz, 1H), 7.06 (t, J = 8.5 Hz, 2H), 6.77 (t, J = 8.4 Hz, 2H), 6.68 (dd, J$_1$ = 75 Hz, J$_2$ = 72 Hz, 1H). |
| 25 | 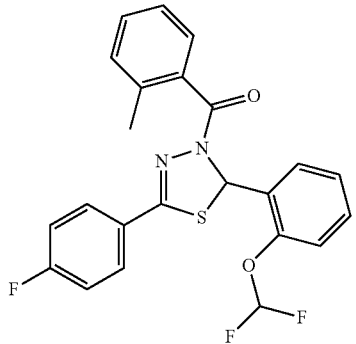 [SMILES: Cc1ccccc1C(=O)N1N=C(c2ccc(F)cc2)SC1c1ccccc1OC(F)F] | 443.0 | ¹H NMR (400 MHz, CDCl$_3$) 7.4-7.44 (m, 2H), 7.23-7.32 (m, 3H), 7.12-7.16 (m, 5H), 7.08 (t, J = 7.9 Hz, 1H), 6.93 (t, J = 8.5 Hz, 2H), 6.6 (dd, J$_1$ = 71 Hz, J$_2$ = 76 Hz, 1H), 2.24 (s, 3H). |
| 26 | 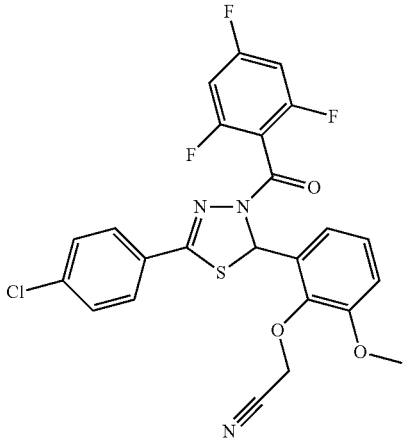 [SMILES: COc1cccc(C2SC(c3ccc(Cl)cc3)=NN2C(=O)c2c(F)cc(F)cc2F)c1OCC#N] | 518.0 | ¹H NMR (400 MHz, CDCl$_3$) δ 7.40-7.35 (m, 3H), 7.22 (d, 2H, J = 8.8 Hz), 7.05 (t, 1H, J = 8 Hz), 6.85-6.80 (m, 2H), 6.63 (m, 2H), 4.87 (d, 2H, J = 7.2 Hz), 3.79 (s, 3H). |

TABLE 1-continued
| Example | Structure | MS (m/z) (M + 1)+ | NMR |
|---|---|---|---|
| 27 | 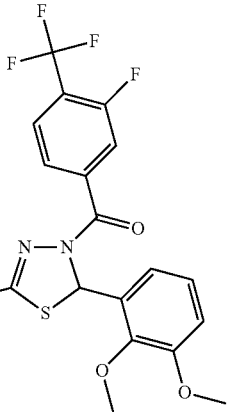 | 509.3 | ¹H NMR (400 MHz, CDCl$_3$) δ 7.88-7.85 (m, 2H), 7.71 (t, 1H, J = 7.6 Hz), 7.67-7.62 (m, 2H), 7.55 (s, 1H), 7.11 (t, 2H, J = 11.6 Hz), 7.03 (t, 1H, J = 8 Hz), 6.90 (dd, 1H, J$_1$ = 8 Hz, J$_2$ = 1.6 Hz), 6.82 (dd, 1H, J$_1$ = 7.6 Hz, J$_2$ = 1.2 Hz), 4.03 (s, 3H), 3.88 (s, 3H). |
| 28 | 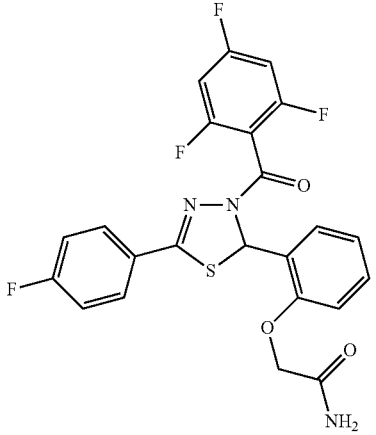 [SMILES: NC(=O)COc1ccccc1C1SC(c2ccc(F)cc2)=NN1C(=O)c1c(F)cc(F)cc1F] | 490.2 | ¹H NMR (400 MHz, CDCl$_3$) δ 7.58 (s, 1H), 7.49 (m, 2H), 7.33 (dd, J$_1$ = 7.6 Hz, J$_2$ = 1.2 Hz, 1H), 7.25 (td, J$_1$ = 8.4 Hz, J$_2$ = 1.2 Hz, 1H), 7.13 (bs, 1H), 6.99 (m, 3H), 6.81 (d, J = 8 Hz, 1H), 6.68 (t, J = 8.4 Hz, 2H), 5.76 (bs, 1H), 4.61 (d, J = 1.6 Hz, 2H). |
| 29 | 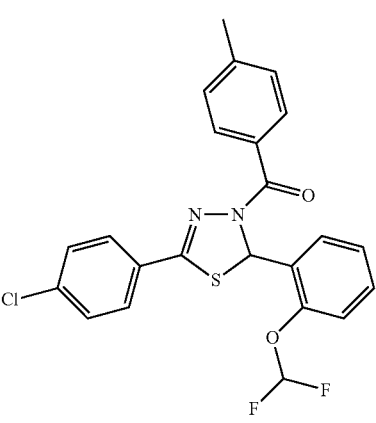 [SMILES: Cc1ccc(C(=O)N2N=C(c3ccc(Cl)cc3)SC2c2ccccc2OC(F)F)cc1] | 459.0 | ¹H NMR (400 MHz, CDCl$_3$) δ 7.91 (d, 2H, J = 8 Hz), 7.61-7.57 (m, 3H), 7.39-7.30 (m, 4H), 7.29-7.26 (m, 2H), 7.21-7.16 (m, 2H), 6.7 (dd, 1H, J$_1$ = 76 Hz, J$_2$ = 71.2 Hz). |

TABLE 1-continued
| Example | Structure | MS (m/z) (M + 1)+ | NMR |
|---|---|---|---|
| 30 | 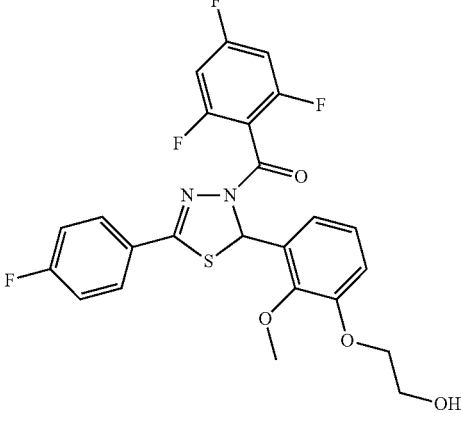 | 507.3 | ¹H NMR (400 MHz, CDCl₃) δ 7.53 (dd, $J_1$ = 8.7 Hz, $J_2$ = 5.3 Hz, 2H), 7.5 (s, 1H), 7.03-7.08 (m, 3H), 6.94 (d, J = 8.4 Hz, 2H), 6.77 (t, J = 8.5 Hz, 2H), 4.15 (t, J = 4.5 Hz, 2H), 4.05 (s, 3H), 3.98-4.02 (m, 2H). |
| 31 | 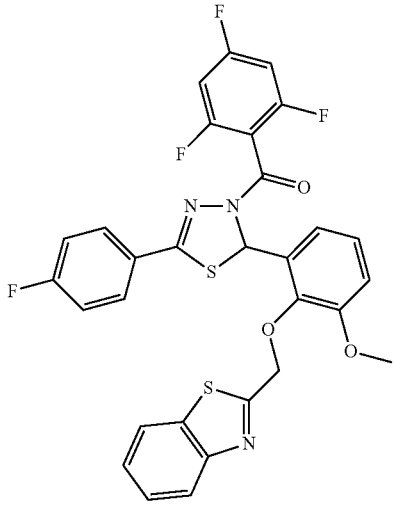 [SMILES: COc1cccc(C2SC(c3ccc(F)cc3)=NN2C(=O)c2c(F)cc(F)cc2F)c1OCc1nc2ccccc2s1] | 610.3 | ¹H NMR (400 MHz, CDCl₃) δ 8.05 (d, 1H, J = 8 Hz), 7.95 (d, 1H, J = 8 Hz), 7.65 (s, 1H), 7.53-7.42 (m, 4H), 7.13 (t, 1H, J = 8 Hz), 7.03-6.94 (m, 4H), 6.77 (bs, 2H), 5.7 (s, 2H), 3.90 (s, 3H). |
| 32 | 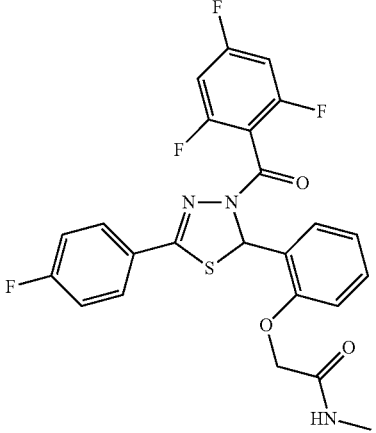 [SMILES: CNC(=O)COc1ccccc1C1SC(c2ccc(F)cc2)=NN1C(=O)c1c(F)cc(F)cc1F] | 504.1 | ¹H NMR (400 MHz, CDCl₃) δ 7.63 (s, 1H), 7.6-7.55 (m, 2H), 7.41-7.39 (m, 1H), 7.35-7.31 (m, 1H), 7.25-7.21 (bs, 1H), 7.11-7.04 (m, 3H), 6.87 (d, J = 8.4 Hz, 1H), 6.76 (t, J = 8.4 Hz, 1H), 4.69 (d, J = 7.2 Hz, 2H), 2.81 (d, J = 4.8 Hz, 3H). |

TABLE 1-continued

| Example | Structure | MS (m/z) (M + 1)+ | NMR |
|---|---|---|---|
| 33 | 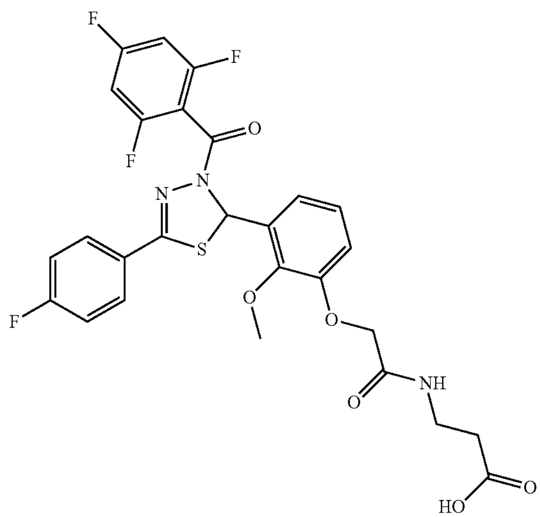 [SMILES: COc1c(OCC(=O)NCCC(=O)O)cccc1C1SC(c2ccc(F)cc2)=NN1C(=O)c1c(F)cc(F)cc1F] | 591.2 | $^1$H NMR (400 MHz, CDCl$_3$) δ 7.36 (m, 4H), 6.89-6.59 (m, 6H), 4.38 (s, 2H), 3.8 (s, 3H), 3.44 (m, 1H), 3.32 (m, 1H), 2.29 (s, 1H). |
| 34 | 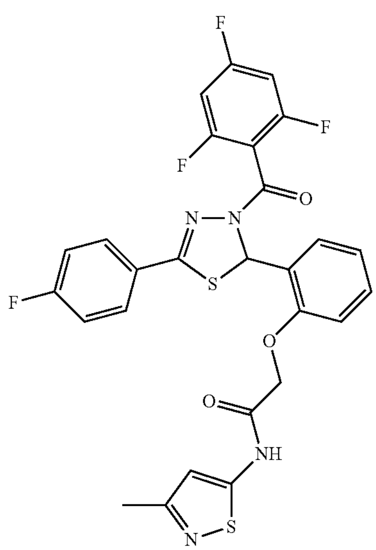 [SMILES: Cc1cc(NC(=O)COc2ccccc2C2SC(c3ccc(F)cc3)=NN2C(=O)c2c(F)cc(F)cc2F)sn1] | 587.1 | $^1$H NMR (400 MHz, CDCl$_3$) δ 7.53 (dd, J$_1$ = 8.7 Hz, J$_2$ = 5.3 Hz, 2H), 7.5 (s, 1H), 7.16 (d, J = 3.4 Hz, 1H). 7.02-7.07 (m, 3H), 6.94-6.97 (m, 2H), 6.77 (t, J = 8.4 Hz, 2H), 6.54 (d, J = 3.4 Hz, 1H), 5.12 (s, 2H), 4.04 (s, 3H), 3.9 (s, 3H). |
| 35 | 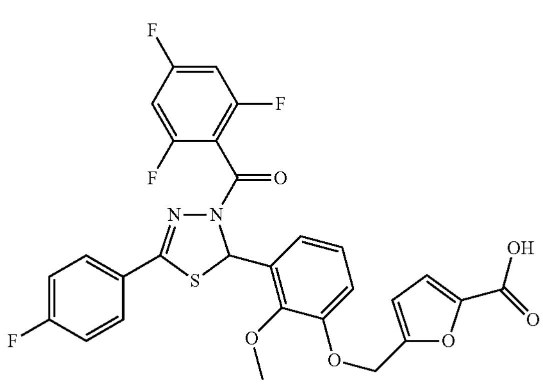 [SMILES: COc1c(OCc2ccc(C(=O)O)o2)cccc1C1SC(c2ccc(F)cc2)=NN1C(=O)c1c(F)cc(F)cc1F] | 588.1 | $^1$H NMR (400 MHz, CDCl$_3$) δ 7.53 (dd, J$_1$ = 8.9 Hz, J$_2$ = 5.2 Hz, 2H), 7.5 (s, 1H), 7.3 (d, J = 3.5 Hz, 1H). 7.03-7.07 (m, 3H), 6.96 (d, J = 8.3 Hz, 2H), 6.77 (t, J = 8.3 Hz, 2H), 6.58 (d, J = 3.5 Hz, 1H), 5.15 (s, 2H), 4.05 (s, 3H), 2.9 (bs, 1H). |

TABLE 1-continued

| Example | Structure | MS (m/z) (M + 1)+ | NMR |
|---|---|---|---|
| 36 | 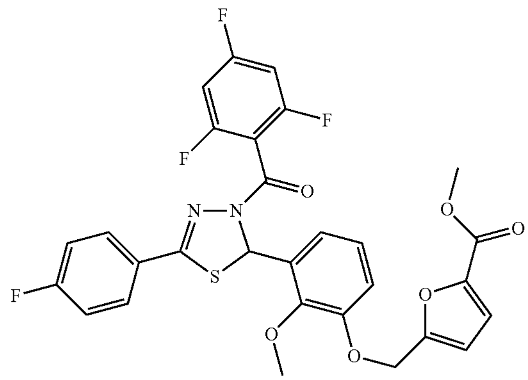 [SMILES: COC(=O)c1ccc(COc2cccc(C3SC(c4ccc(F)cc4)=NN3C(=O)c3c(F)cc(F)cc3F)c2OC)o1] | 601.0 | ¹H NMR (400 MHz, CDCl₃) δ 7.53 (dd, J₁ = 8.7 Hz, J₂ = 5.3 Hz, 2H), 7.5 (s, 1H), 7.16 (d, J = 3.4 Hz, 1H). 7.02-7.07 (m, 3H), 6.94-6.97 (m, 2H), 6.77 (t, J = 8.4 Hz, 2H), 6.54 (d, J = 3.4 Hz, 1H), 5.12 (s, 2H), 4.04 (s, 3H), 3.9 (s, 3H). |
| 37 | 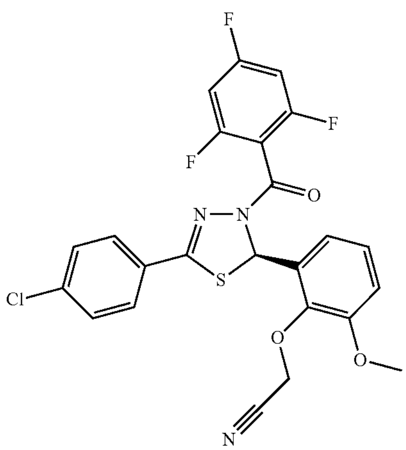 [SMILES: COc1cccc([C@H]2SC(c3ccc(Cl)cc3)=NN2C(=O)c2c(F)cc(F)cc2F)c1OCC#N] | 518.0 | ¹H NMR (400 MHz, CDCl₃) δ 7.39 (s, 1H), 7.35 (d, J = 8.0 Hz, 2H), 7.21 (d, J = 8.0 Hz, 2H), 7.02 (t, 1H), 6.82 (t, J = 8.0 Hz, 2H), 6.62 (t, J = 8.0 Hz, 2H), 4.86 (d, J = 6.8 Hz, 2H), 3.78 (s, 3H). |
| 38 | 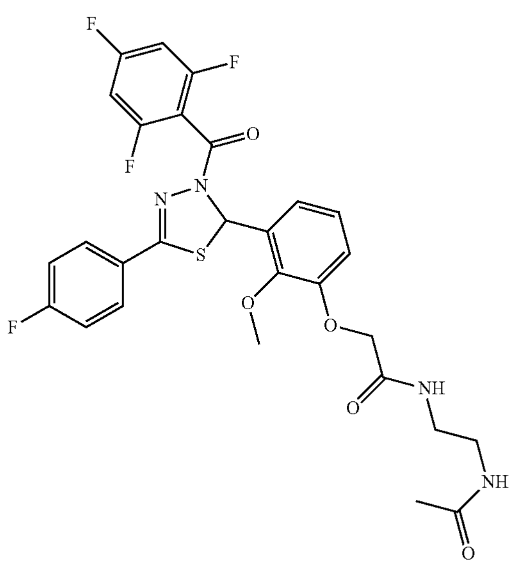 [SMILES: COc1c(OCC(=O)NCCNC(C)=O)cccc1C1SC(c2ccc(F)cc2)=NN1C(=O)c1c(F)cc(F)cc1F] | 605.2 | ¹H NMR (400 MHz, CDCl₃) δ 7.74-7.7 (m, 3H), 7.3-7.18 (m, 4H), 7.11 (d, J = 8.4 Hz, 1H), 6.97 (t, J₁ = 8.4 Hz, J₂ = 2 Hz), 6.33 (bs, 1H), 4.79 (s, 2H), 4.27 (s, 3H), 3.74-3.54 (m, 4H), 2.3 (s, 1H), 2.15 (s, 3H). |

TABLE 1-continued

| Example | Structure | MS (m/z) (M + 1)+ | NMR |
|---------|-----------|-------------------|-----|
| 39 | 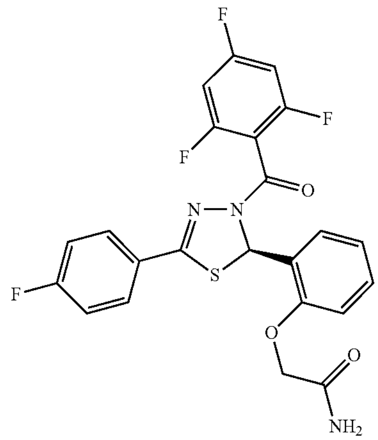 [SMILES: NC(=O)COc1ccccc1[C@H]1SC(c2ccc(F)cc2)=NN1C(=O)c1c(F)cc(F)cc1F] | 490.0 | ¹H NMR (400 MHz, CDCl$_3$) δ 7.63-7.62 (m, 2H), 7.57 (s, 1H), 7.22-7.12 (m, 3H), 7.02 (dd, 2H, J$_1$ = 8.4 Hz, J$_2$ = 2 Hz), 6.9 (bs, 1H), 6.85 (t, 2H, J = 8.4 Hz), 6.10 (s, 1H), 4.83 (d, 1H, J = 15.2 Hz), 4.68 (d, 1H, J = 15.2 Hz), 3.94 (s, 3H). |
| 40 | 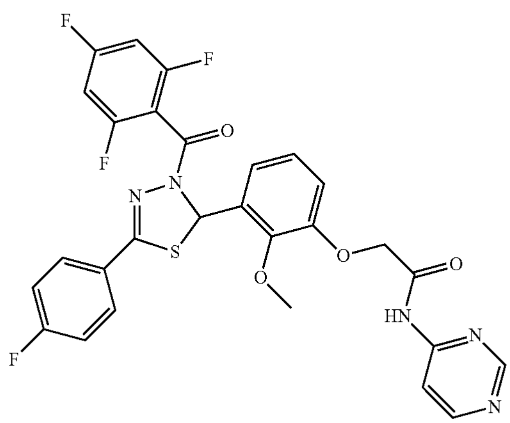 [SMILES: COc1c(OCC(=O)Nc2ccncn2)cccc1C1SC(c2ccc(F)cc2)=NN1C(=O)c1c(F)cc(F)cc1F] | 598.2 | ¹H NMR (400 MHz, CDCl$_3$) δ 9.33 (bs, 1H), 9.02 (s, 1H), 8.77 (d, J = 6 Hz, 1H), 8.31 (d, J = 6 Hz, 1H), 7.63-7.60 (m, 3H), 7.22-7.12 (m, 4H), 7.04 (d, J = 8 Hz, 1H), 6.86 (t, J = 8 Hz, 2H), 4.8 (s, 2H), 4.23 (s, 3H). |
| 41 | 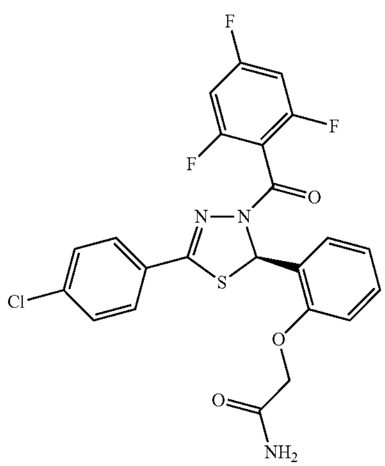 [SMILES: NC(=O)COc1ccccc1[C@H]1SC(c2ccc(Cl)cc2)=NN1C(=O)c1c(F)cc(F)cc1F] | 506.0 | ¹H NMR (400 MHz, CDCl$_3$) δ 7.43 (s, 1H), 7.27 (d, J = 8.8, 2H), 7.15 (m, 2H), 7.14 (d, J = 8.4 Hz, 2H) 6.99 (bs, 1H), 6.84 (t, J = 6.4 Hz, 3H), 6.66 (d, J = 8.4 Hz, 1H), 6.53 (t, J = 8.0 Hz, 2H), 5.29 (bs, 1H), 4.47 (d, J = 1.6 Hz, 2H). |

TABLE 1-continued

| Example | Structure | MS (m/z) (M + 1)+ | NMR |
|---|---|---|---|
| 42 | 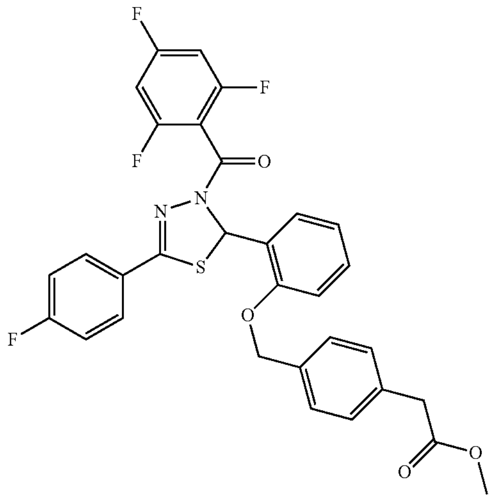 [SMILES: COC(=O)Cc1ccc(COc2ccccc2C2SC(c3ccc(F)cc3)=NN2C(=O)c2c(F)cc(F)cc2F)cc1] | 595.2 | ¹H NMR (400 MHz, CDCl₃) δ 7.41-7.36 (m, 3H), 7.32(d, J = 8 Hz, 2H), 7.2(d, J = 7.6 Hz, 2H), 7.16 (m, 1H), 6.92-6.85 (m, 4H), 6.72-6.58 (bs, 3H), 5.05 (s, 2H), 3.59 (s, 3H), 3.53 (s, 2H). |
| 43 | 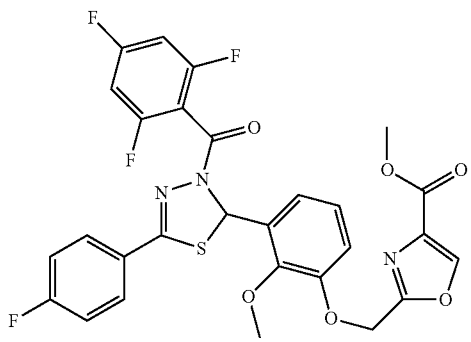 [SMILES: COC(=O)c1coc(COc2cccc(C3SC(c4ccc(F)cc4)=NN3C(=O)c3c(F)cc(F)cc3F)c2OC)n1] | 602.1 | ¹H NMR (400 MHz, CDCl₃) δ 8.28 (s, 1H), 7.53 (m, 2H), 7.49 (s, 1H), 7.02-7.07 (m, 4H), 6.97 (dd, J₁ = 6.0 Hz, J₂ = 3.2 Hz, 1H), 6.77 (t, J = 8.2 Hz, 2H), 5.25 (d, J = 1.8 Hz, 2H), 4.05 (s, 3H), 3.94 (s, 3H). |
| 44 | 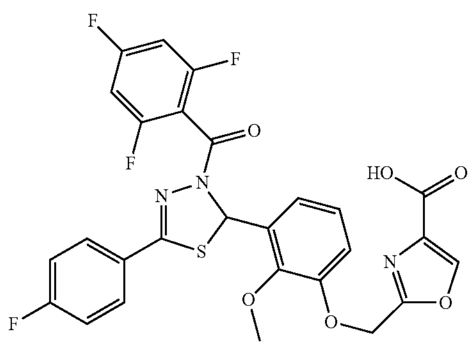 [SMILES: COc1c(OCc2nc(C(=O)O)co2)cccc1C1SC(c2ccc(F)cc2)=NN1C(=O)c1c(F)cc(F)cc1F] | 588.1 | ¹H NMR (400 MHz, CDCl₃) δ 8.35 (s, 1H), 7.53 (d, J = 8.7 Hz, 1H), 7.52 (d, J = 8.6 Hz, 1H), 7.49 (s, 1H), 7.01-7.07 (m, 4H), 6.98 (d, J = 7.2 Hz, 1H), 6.77 (t, J = 8.2 Hz, 2H), 5.26 (s, 2H), 4.05 (s, 3H). |
| 45 | 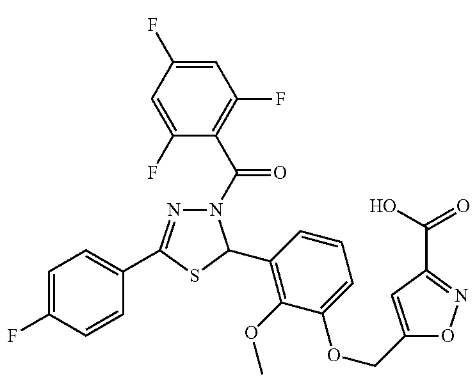 [SMILES: COc1c(OCc2cc(C(=O)O)no2)cccc1C1SC(c2ccc(F)cc2)=NN1C(=O)c1c(F)cc(F)cc1F] | 588.1 | ¹H NMR (400 MHz, CDCl₃) δ 7.54 (dd, J₁ = 8.8 Hz, J₂ = 5.2 Hz, 2H), 7.5 (s, 1H), 7.03-7.09 (m, 3H), 7.0 (dd, J₁ = 6.7 Hz, J₂ = 1.2 Hz, 1H), 6.95 (dd, J₁ = 8.0 Hz, J₂ = 1.2 Hz, 1H), 6.84 (s, 1H), 6.77 (t, J = 8.2 Hz, 2H), 5.27 (s, 2H), 4.05 (s, 3H). |

TABLE 1-continued

| Example | Structure | MS (m/z) (M + 1)+ | NMR |
|---|---|---|---|
| 46 | 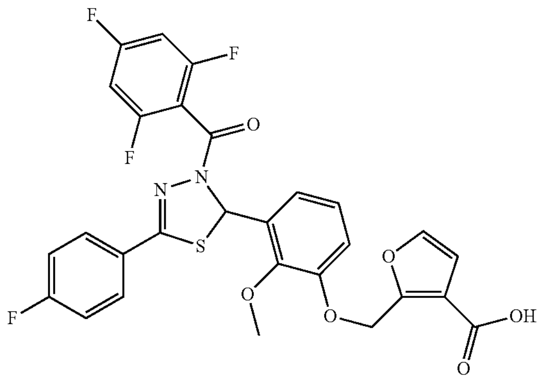 [SMILES: COc1c(OCc2occc2C(=O)O)cccc1C1SC(c2ccc(F)cc2)=NN1C(=O)c1c(F)cc(F)cc1F] | 587.1 | ¹H NMR (400 MHz, CDCl₃) 7.51-7.55 (m, 2H), 7.5 (s, 1H), 7.45 (d, J = 1.9 Hz, 1H), 6.98-7.07 (m, 5H), 6.94 (dd, $J_1$ = 7.1 Hz, $J_2$ = 2.0 Hz, 1H), 6.77 (t, J = 8 Hz, 2H), 5.46 (d, J = 12.7 Hz, 2H), 5.38 (d, J = 12.8 Hz, 1H), 4.04 (s, 3H). |
| 47 | 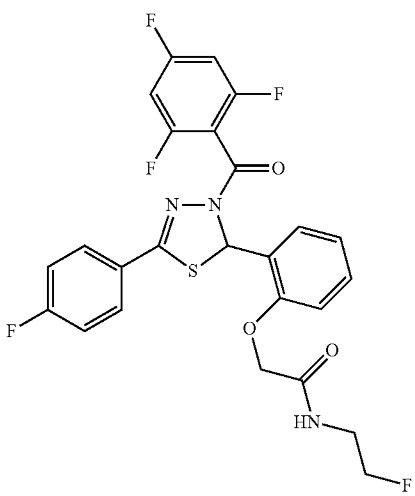 [SMILES: O=C(COc1ccccc1C1SC(c2ccc(F)cc2)=NN1C(=O)c1c(F)cc(F)cc1F)NCCF] | 536.1 | ¹H NMR (400 MHz, CDCl₃) δ 7.79-7.77 (m, 2H), 7.73-7.69 (m, 2H), 7.55 (dd, $J_1$ = 6.1 Hz, $J_2$ = 1.5 Hz, 1H), 7.50-7.45 (m, 1H), 7.24-7.18 (m, 3H), 7.02 (d, J = 8.1 Hz, 1H), 6.92-6.87 (m, 2H), 4.89 (d, J = 6.8 Hz, 2H), 4.66-4.63 (m, 1H), 4.54-4.51 (m, 1H), 3.84-3.62 (m, 2H). |
| 48 | 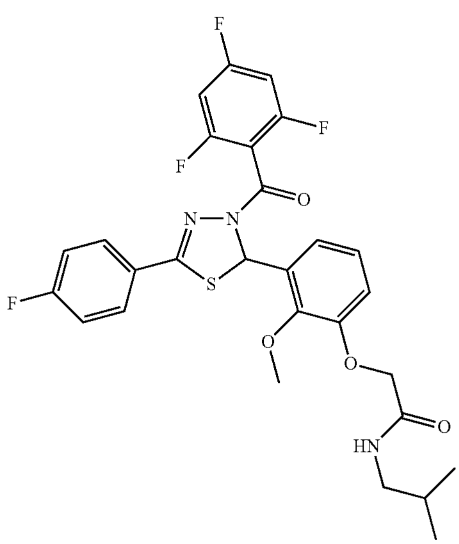 [SMILES: COc1c(OCC(=O)NCC(C)C)cccc1C1SC(c2ccc(F)cc2)=NN1C(=O)c1c(F)cc(F)cc1F] | 576.2 | ¹H NMR (400 MHz, CDCl₃) δ 7.64-7.61 (m, 2H), 7.59 (s, 1H), 7.21-7.13 (m, 3H), 7.09 (dd, $J_1$ = 6.5 Hz, $J_2$ = 1.1 Hz, 1H), 7.05 (bs, 1H), 7.01 (dd, $J_1$ = 6.7 Hz, $J_2$ = 1.3 Hz, 1H), 6.87 (m, 2H), 4.69 (s, 2H), 4.15 (s, 3H), 3.29 (t, J = 6.6 Hz, 2H), 1.98-1.88 (m, 1H), 1.03 (d, J = 6.6 Hz, 6H). |

TABLE 1-continued

| Example | Structure | MS (m/z) (M + 1)+ | NMR |
|---|---|---|---|
| 49 | 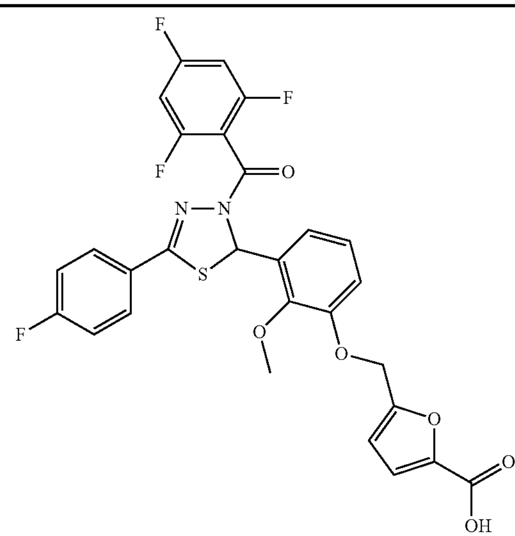 | 587.1 | ¹H NMR (400 MHz, CDCl₃) δ 7.54 (d, J = 8.8 Hz, 2H), 7.53 (t, J = 8.7 Hz, 1H), 7.5 (s, 1H), 7.31 (d, J = 3.5 Hz, 1H), 7.03-7.07 (m, 3H), 6.97 (d, J = 2.2 Hz, 1H), 6.95 (s, 1H), 6.77 (t, J = 8.3 Hz, 2H), 6.59 (d, J = 3.5 Hz, 1H), 5.15 (d, 2H), 4.05 (s, 3H). |
| 50 | 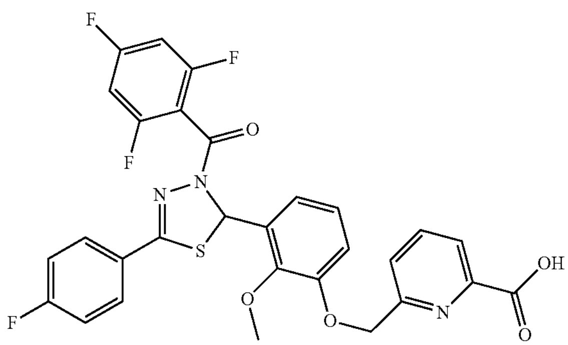 [SMILES: COc1c(OCc2cccc(C(=O)O)n2)cccc1C1SC(c2ccc(F)cc2)=NN1C(=O)c1c(F)cc(F)cc1F] | 598.2 | ¹H NMR (400 MHz, CDCl₃) δ 8.2 (d, J = 7.7 Hz, 1H), 8.03 (t, J = 7.8 Hz, 1H), 7.87 (d, J = 7.8 Hz, 1H), 7.52-7.56 (m, 3H), 7.03-7.08 (m, 3H), 6.97 (d, J = 7.9 Hz, 1H), 6.92 (d, J = 7.1 Hz, 1H), 6.77 (t, J = 8.4 Hz, 2H), 5.32 (s, 2H), 4.11 (s, 3H). |
| 51 | 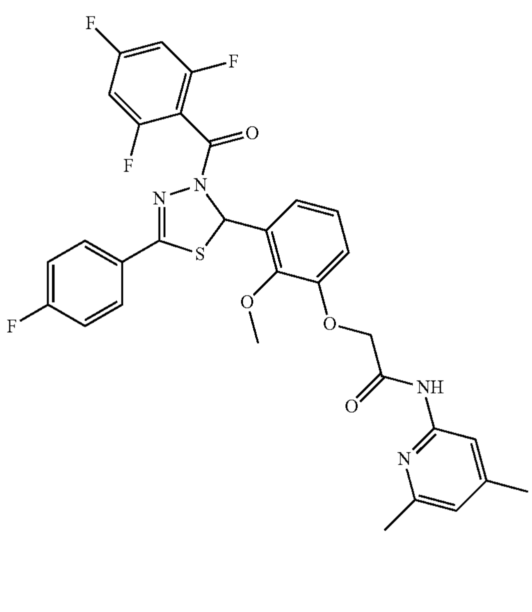 [SMILES: COc1c(OCC(=O)Nc2cc(C)cc(C)n2)cccc1C1SC(c2ccc(F)cc2)=NN1C(=O)c1c(F)cc(F)cc1F] | 625.2 | ¹H NMR (400 MHz, CDCl₃) δ 8.91 (bs, 1H), 7.82 (s, 1H), 7.46-7.42 (m, 3H), 7.00-6.85 (m, 5H), 6.69-6.65 (m, 3H), 4.58 (s, 2H), 4.05 (s, 3H), 2.34 (s, 3H), 2.25 (s, 3H). |

TABLE 1-continued

| Example | Structure | MS (m/z) (M + 1)+ | NMR |
|---|---|---|---|
| 52 | 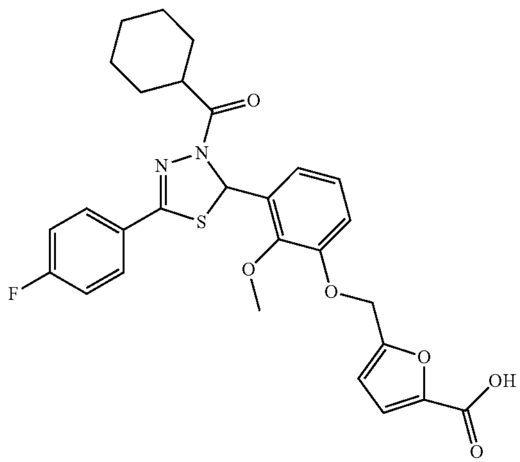 [SMILES: COc1c(OCc2ccc(C(=O)O)o2)cccc1C1SC(c2ccc(F)cc2)=NN1C(=O)C1CCCCC1] | 539.1 | ¹H NMR (400 MHz, CDCl₃) δ 7.70 (dd, $J_1$ = 5.2 Hz, $J_2$ = 8.8 Hz, 2H), 7.28 (m, 2H), 7.11 (m, 2H), 6.9 (m, 2H), 6.74 (dd, 1H), 6.56 (d, J = 3.6 Hz, 1H), 5.11 (s, 2H), 3.98 (s, 3H), 3.24 (m, 1H), 2.08 (m, 1H), 1.90-1.83 (m, 3H), 1.72 (m, 1H), 1.59-1.3 (m, 5H). |
| 53 | 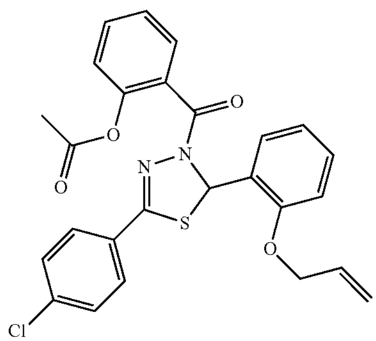 [SMILES: C=CCOc1ccccc1C1SC(c2ccc(Cl)cc2)=NN1C(=O)c1ccccc1OC(C)=O] | 493.1 | ¹H NMR (400 MHz, CDCl₃) δ 7.75 (d, J = 6.4 Hz, 1H), 7.60 (m, 4H), 7.45-7.36 (m, 6H), 7.04 (m, 2H), 6.22 (m, 1H), 5.58 (d, J = 17.2 Hz, 1H), 5.44 (d, J = 10.4 Hz, 1H), 4.77 (d, J = 4.8 Hz, 2H), 2.27 (s, 3H). |
| 54 | 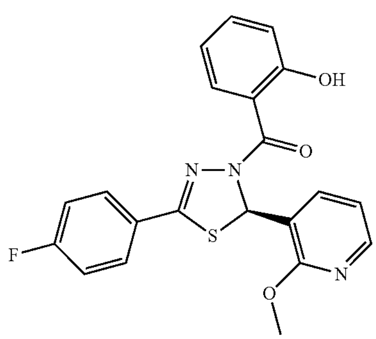 [SMILES: COc1ncccc1[C@H]1SC(c2ccc(F)cc2)=NN1C(=O)c1ccccc1O] | 410.0 | ¹H NMR (400 MHz, CDCl₃) δ 11.22 (bs, 1H), 8.56 (dd, J = 8.4 Hz, 1H), 8.14 (dd, $J_1$ = 1.6 Hz, $J_2$ = 5.2 Hz, 1H), 7.72 (m, 2H), 7.47 (m, 2H), 7.38 (dd, $J_1$ = 1.2 Hz, $J_2$ = 7.2 Hz, 1H), 7.14 (t, J = 8.4 Hz, 2H), 7.01 (m, 2H), 6.86 (dd, $J_1$ = 5.2 Hz, $J_2$ = 7.2 Hz, 1H), 4.08 (s, 3H). |
| 55 | 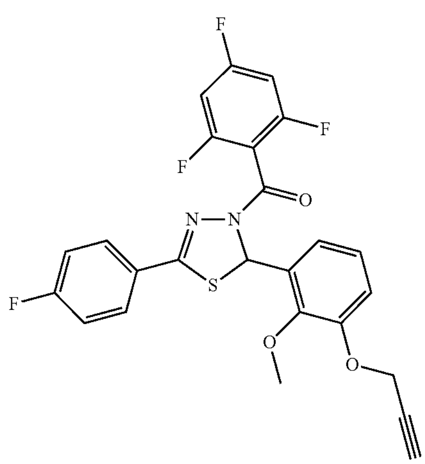 [SMILES: C#CCOc1cccc(C2SC(c3ccc(F)cc3)=NN2C(=O)c2c(F)cc(F)cc2F)c1OC] | 501.3 | ¹H NMR (400 MHz, CDCl₃) δ 7.53 (dd, $J_1$ = 8.8 Hz, $J_2$ = 5.2 Hz, 2H), 7.5 (s, 1H), 7.04-7.07 (m, 4H), 6.95 (d, J = 6.8 Hz, 2H), 6.77 (t, J = 8.2 Hz, 2H), 4.76 (d, J = 2.3 Hz, 2H), 4.05 (s, 3H), 2.53 (t, J = 2.4 Hz, 1H). |

TABLE 1-continued

| Example | Structure | MS (m/z) (M + 1)+ | NMR |
|---|---|---|---|
| 56 | 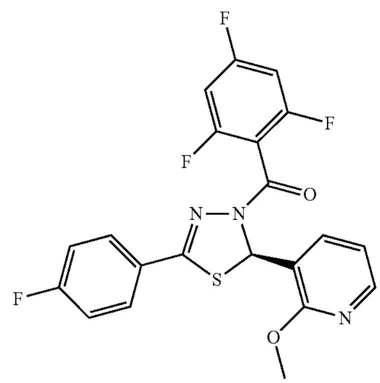 [SMILES: COc1ncccc1[C@H]1SC(c2ccc(F)cc2)=NN1C(=O)c1c(F)cc(F)cc1F] | 448.0 | ¹H NMR (400 MHz, CDCl₃) δ 8.19 (dd, J₁ = 1.6 Hz, J₂ = 4.8 Hz, 1H), 7.56 (m, 3H), 7.41 (s, 1H), 7.09 (t, J = 8.4 Hz, 2H), 6.95 (dd, J₁ = 5.2 Hz, J₂ = 7.2 Hz, 1H), 6.83 (bs, 2H), 4.11 (s, 3H). |
| 57 | 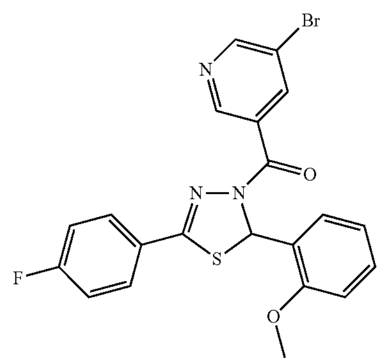 [SMILES: COc1ccccc1C1SC(c2ccc(F)cc2)=NN1C(=O)c1cncc(Br)c1] | 472.0 | ¹H NMR (400 MHz, CDCl₃) δ 9.23 (s, 1H), 8.82 (s, 1H), 8.47 (s, 1H), 7.64-7.67 (m, 2H), 7.53 (s, 1H), 7.32 (dt, J₁ = 7.3 Hz, J₂ = 1.5 Hz, 1H), 7.07-7.14 (m, 3H), 6.92-6.96 (m, 2H), 3.94 (s, 3H). |
| 58 | 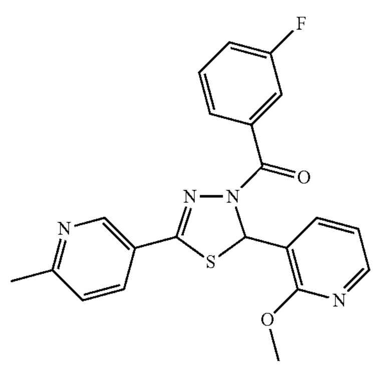 [SMILES: COc1ncccc1C1SC(c2ccc(C)nc2)=NN1C(=O)c1cccc(F)c1] | 409.1 | ¹H NMR (400 MHz, CDCl₃) δ 8.92 (d, J = 1.3 Hz, 1H), 8.27 (dd, J₁ = 8.3 Hz, J₂ = 1.7 Hz, 1H), 8.18 (dd, J₁ = 5.1 Hz, J₂ = 1.7 Hz, 1H), 7.78 (d, J = 7.8 Hz, 1H), 7.68 (d, J = 9.4 Hz, 1H), 7.57 (d, J = 8.3 Hz, 1H), 7.52 (s, 1H), 7.49 (dd, J₁ = 8.1 Hz, J₂ = 2.5 Hz, 1H), 7.39 (dd, J₁ = 7.4 Hz, J₂ = 1.5 Hz, 1H), 7.29 (dd, J₁ = 8.3 Hz, J₂ = 2.5 Hz, 1H), 6.91 (dd, J₁ = 7.4 Hz, J₂ = 5.1 Hz, 1H), 4.08 (s, 3H), 2.81 (s, 3H). |
| 59 | 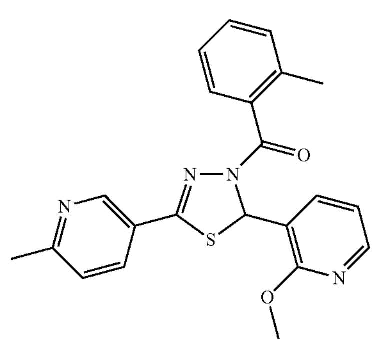 [SMILES: COc1ncccc1C1SC(c2ccc(C)nc2)=NN1C(=O)c1ccccc1C] | 405.1 | ¹H NMR (400 MHz, CDCl₃) δ 8.76 (m, 1H), 8.21 (m, 2H), 7.39-7.56 (m, 5H), 7.29 (d, J = 6.9 Hz, 1H), 6.95 (dd, J₁ = 7.3 Hz, J₂ = 5.2 Hz, 1H), 4.08 (s, 3H), 2.81 (s, 3H), 2.38 (s, 3H). |

TABLE 1-continued

| Example | Structure | MS (m/z) (M + 1)+ | NMR |
|---|---|---|---|
| 60 | 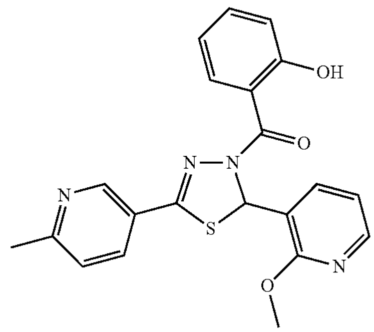 [SMILES: COc1ncccc1C1SC(c2ccc(C)nc2)=NN1C(=O)c1ccccc1O] | 407.1 | $^1$H NMR (400 MHz, CDCl$_3$) δ 9.04 (d, J = 1.0 Hz, 1H), 8.39 (d, J = 8.1 Hz, 1H), 8.35 (dd, J$_1$ = 8.3 Hz, J$_2$ = 1.6 Hz, 1H), 8.20 (dd, J$_1$ = 5.0 Hz, J$_2$ = 1.4 Hz, 1H), 7.63 (d, J = 8.3 Hz, 1H), 7.58 (s, 1H), 7.49 (t, J = 8.3 Hz, 1H), 7.42 (d, J = 7.4 Hz, 1H), 7.04 (d, J = 8.1 Hz, 1H), 7.0 (d, J = 7.4 Hz, 1H), 6.92 (dd, J$_1$ = 7.4 Hz, J$_2$ = 5.1 Hz, 1H), 4.1 (s, 3H), 2.85 (s, 3H). |
| 61 | 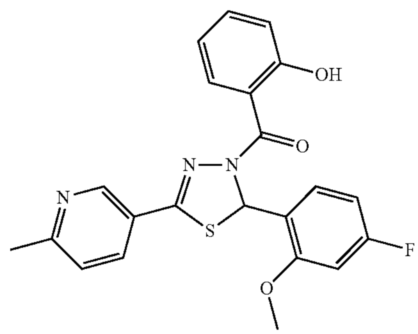 [SMILES: COc1cc(F)ccc1C1SC(c2ccc(C)nc2)=NN1C(=O)c1ccccc1O] | 424.1 | $^1$H NMR (400 MHz, CDCl$_3$) δ 8.96 (s, 1H), 8.49 (d, J = 8.2 Hz, 1H), 8.15 (dd, J$_1$ = 8.3 Hz, J$_2$ = 2.0 Hz, 1H), 7.59 (s, 1H), 7.48 (d, J = 8.5 Hz, 1H), 7.44 (d, J = 8.5 Hz, 1H), 7.07 (dd, J$_1$ = 8.5 Hz, J$_2$ = 6.3 Hz, 1H), 7.02 (d, J = 8.6 Hz, 1H), 6.98 (d, J = 7.7 Hz, 1H), 6.69 (dd, J$_1$ = 10.5 Hz, J$_2$ = 2.2 Hz, 1H), 6.62 (dd, J$_1$ = 8.3 Hz, J$_2$ = 2.3 Hz, 1H), 3.94 (s, 3H), 2.74 (s, 3H). |
| 62 | 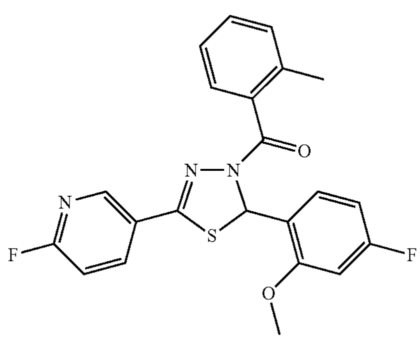 [SMILES: COc1cc(F)ccc1C1SC(c2ccc(F)nc2)=NN1C(=O)c1ccccc1C] | 425.5 | $^1$H NMR (400 MHz, CDCl$_3$) δ 8.34 (s, 1H), 7.93 (dd, J$_1$ = 8.8 Hz, J$_2$ = 2.2 Hz, 1H), 7.52 (s, 1H), 7.44 (d, J = 7.4 Hz, 1H), 7.37 (t, J = 7.5 Hz, 1H), 7.26-7.28 (m, 2H), 7.15 (dd, J$_1$ = 8.4 Hz, J$_2$ = 6.4 Hz, 1H), 6.92 (dd, J$_1$ = 8.3 Hz, J$_2$ = 1.8 Hz, 1H), 6.64-6.71 (m, 2H), 3.93 (s, 3H), 2.39 (s, 3H). |
| 63 | 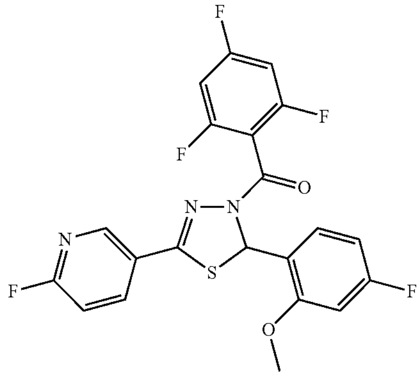 [SMILES: COc1cc(F)ccc1C1SC(c2ccc(F)nc2)=NN1C(=O)c1c(F)cc(F)cc1F] | 465.4 | $^1$H NMR (400 MHz, CDCl$_3$) δ 8.36 (d, J = 2.3 Hz, 1H), 7.94 (dt, J$_1$ = 8.5 Hz, J$_2$ = 2.5 Hz, 1H), 7.46 (s, 1H), 7.18 (dt, J$_1$ = 8.1 Hz, J$_2$ = 2.3 Hz, 1H), 6.95 (dd, J$_1$ = 8.6 Hz, J$_2$ = 2.9 Hz, 1H), 6.78 (bm, 2H), 6.65-6.7 (m, 2H), 6.76-6.82 (m, 2H), 3.93 (s, 3H). |

TABLE 1-continued

| Example | Structure | MS (m/z) (M + 1)+ | NMR |
|---------|-----------|-------------------|-----|
| 64 | 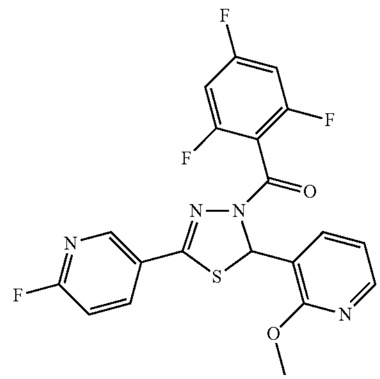 [SMILES: COc1ncccc1C1SC(c2ccc(F)nc2)=NN1C(=O)c1c(F)cc(F)cc1F] | 449 | ¹H NMR (400 MHz, CDCl₃) δ 8.36 (d, J = 2.2 Hz, 1H), 8.17 (dd, J₁ = 5.1 Hz, J₂ = 1.5 Hz, 1H), 7.93 (dd, J₁ = 8.4 Hz, J₂ = 1.8 Hz, 1H), 7.49 (dd, J₁ = 7.5 Hz, J₂ = 1.3 Hz, 1H), 7.41 (s, 1H), 6.92-6.97 (m, 2H), 6.76-6.82 (m, 2H), 4.07 (s, 3H). |
| 65 | 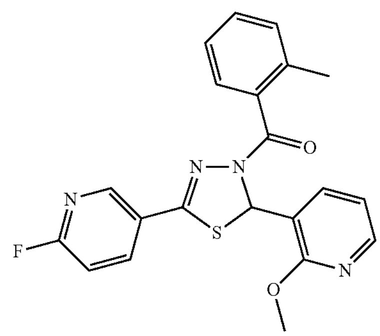 [SMILES: COc1ncccc1C1SC(c2ccc(F)nc2)=NN1C(=O)c1ccccc1C] | 409.1 | ¹H NMR (400 MHz, CDCl₃) δ 8.35 (d, J = 1.6 Hz, 1H), 8.18 (dd, J₁ = 5.0 Hz, J₂ = 1.6 Hz, 1H), 7.93 (dd, J₁ = 8.6 Hz, J₂ = 2.4 Hz, 1H), 7.47 (s, 2H), 7.45 (s, 1H), 7.38 (t, J = 7.6 Hz, 1H), 7.27-7.31 (m, 2H), 6.9-6.93 (m, 2H), 4.07 (s, 3H), 2.4 (s, 3H). |
| 66 | 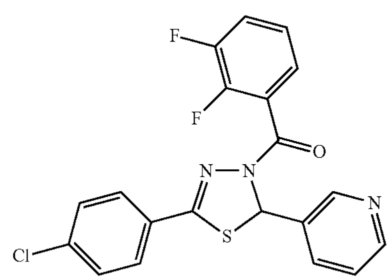 [SMILES: O=C(c1cccc(F)c1F)N1N=C(c2ccc(Cl)cc2)SC1c1cccnc1] | 416.2 | ¹H NMR (400 MHz, CDCl₃) δ 8.76 (s, 1H), 8.62 (d, J = 4.8 Hz, 1H), 7.82 (d, J = 7.8 Hz, 1H), 7.53 (d, J = 8.5 Hz, 2H), 7.26-7.39 (m, 5H), 7.17 (m, 1H). |
| 67 | 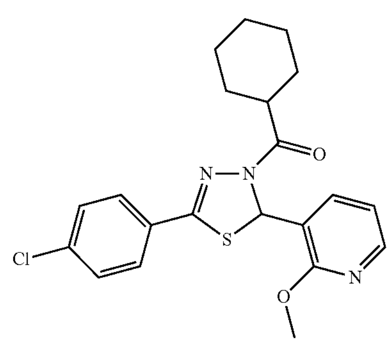 [SMILES: COc1ncccc1C1SC(c2ccc(Cl)cc2)=NN1C(=O)C1CCCCC1] | 416.3 | ¹H NMR (400 MHz, CDCl₃) δ 8.16 (d, J = 5.3 Hz, 1H), 7.68 (d, J = 8.5 Hz, 2H), 7.45 (d, J = 8.5 Hz, 2H), 7.32 (s, 1H), 7.31 (d, J = 6.7 Hz, 1H), 6.9 (dd, , J = 7.5, 5.1 Hz, 1H), 4.1 (s, 3H), 3.31 (t, J = 11.1 Hz, 1H), 2.16 (d, , J = 11.4 Hz, 1H), 1.92 (m, 3H), 1.79 (d, J = 12.3 Hz, 1H), 1.32-1.64 (m, 5H). |

TABLE 1-continued

| Example | Structure | MS (m/z) (M + 1)+ | NMR |
|---|---|---|---|
| 68 | 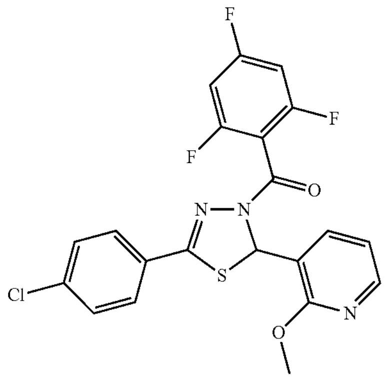 [SMILES: COc1ncccc1C1SC(c2ccc(Cl)cc2)=NN1C(=O)c1c(F)cc(F)cc1F] | 464.2 | ¹H NMR (400 MHz, CDCl₃) δ 8.16 (d, J = 6.1 Hz, 1H), 7.49 (d, J = 7.5 Hz, 2H), 7.45 (d, J = 8.5 Hz, 2H), 7.37 (s, 1H), 7.33 (d, J = 8.7 Hz, 1H), 6.92 (dd, J = 7.3, 4.8 Hz, 1H), 6.79 (m, 2H), 4.1 (s, 3H). |
| 69 | 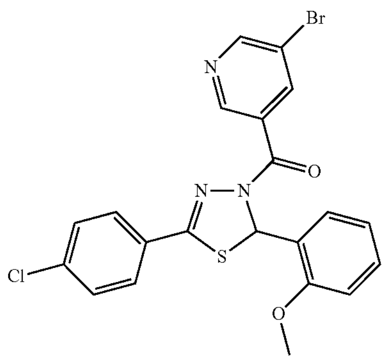 [SMILES: COc1ccccc1C1SC(c2ccc(Cl)cc2)=NN1C(=O)c1cncc(Br)c1] | 488.0 | 1H NMR (400 MHz, CDCl₃) δ 9.26 (s, 1H), 8.73 (s, 1H), 8.54 (s, 1H), 7.48 (d, J = 8.4 Hz, 2H), 7.38 (s, 1H), 7.26 (d, J = 8.4 Hz, 2H), 7.19 (t, J = 7.2 Hz, 1H), 6.98 (d, J = 7.6 Hz, 1H), 6.86 (m, 2H) 3.8 (s, 3H). |
| 70 | 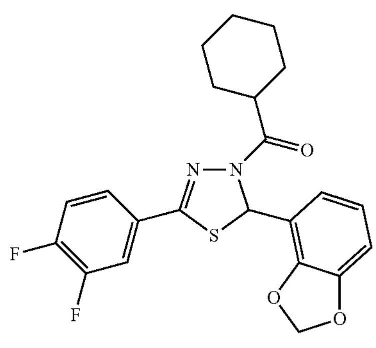 [SMILES: O=C(C1CCCCC1)N1N=C(c2ccc(F)c(F)c2)SC1c1cccc2c1OCO2] | 431.1 | 1H NMR (400 MHz, CDCl₃) δ 7.61 (t, J = 8.4 Hz, 1H), 7.4 (m, 1H), 7.23 (dd, J = 16.9, 8 Hz, 1H), 7.17 (s, 1H), 6.73-6.79 (m, 2H), 6.66 (d, J = 7.4 Hz, 1H), 5.99 (d, J = 4.6 Hz, 2H), 3.17 (d, J = 11.8 Hz, 1H), 1.99 (d, , J = 11.4 Hz, 1H), 1.84 (m, 3H), 1.72 (d, J = 12.8 Hz, 1H), 1.19-1.65 (m, 5H). |
| 71 | 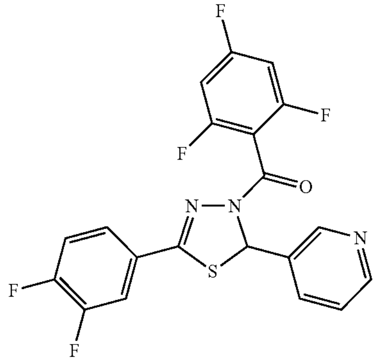 [SMILES: O=C(c1c(F)cc(F)cc1F)N1N=C(c2ccc(F)c(F)c2)SC1c1cccnc1] | 436.0 | ¹H NMR (400 MHz, CDCl₃) δ 8.77 (s, 1H), 8.64 (s, 1H), 7.87 (d, J = 7.5 Hz, 1H), 7.4-7.45 (m, 2H), 7.28-7.32 (m, 2H), 7.21 (dd, J = 17.4, 9.1 Hz, 1H), 6.77 (t, J = 8.2 Hz, 2H). |

TABLE 1-continued

| Example | Structure | MS (m/z) (M + 1)+ | NMR |
|---|---|---|---|
| 72 | 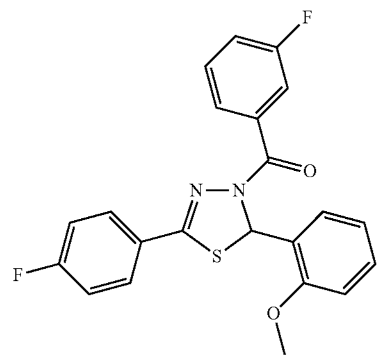 | 411.3 | ¹H NMR (400 MHz, CDCl₃) δ 7.84 (d, J = 7.6 Hz, 1H), 7.77 (m, 1H), 7.67 (m, 2H), 7.55 (s, 1H), 7.48 (m, 1H), 7.32 (m, 1H), 7.26 (m, 2H), 7.15 (d, J = 7.6 Hz, 1H), 7.09 (t, J = 8.4 Hz, 2H), 6.95 (m, 2H), 3.95 (s, 3H). |
| 73 | 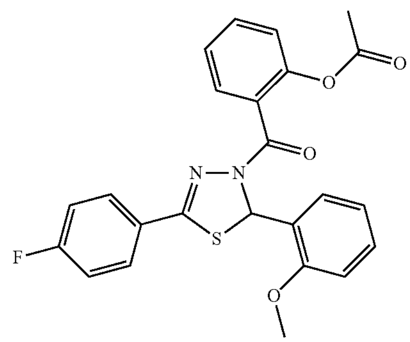 [SMILES: COc1ccccc1C1SC(c2ccc(F)cc2)=NN1C(=O)c1ccccc1OC(C)=O] | 451.1 | ¹H NMR (400 MHz, CDCl₃) δ 7.65 (dd, J₁ = 1.6 Hz, J₂ = 1.6 Hz, 1H), 7.56 (m, 4H), 7.35 (m, 4H), 7.02 (t, J = 8.4 Hz, 2H), 6.97 (m, 2H), 3.95 (s, 3H), 2.12 (s, 3H). |
| 74 | 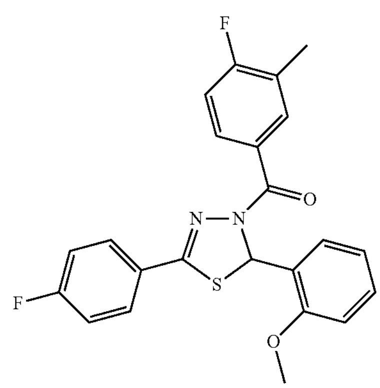 [SMILES: COc1ccccc1C1SC(c2ccc(F)cc2)=NN1C(=O)c1ccc(F)c(C)c1] | 425.3 | ¹H NMR (400 MHz, CDCl₃) δ 7.9 (m, 2H), 7.66 (m, 2H), 7.54 (s, 1H), 7.32 (m, 1H), 7.15 (m, 4H), 6.95 (m, 2H), 3.97 (s, 3H), 2.35 (s, 3H). |
| 75 | 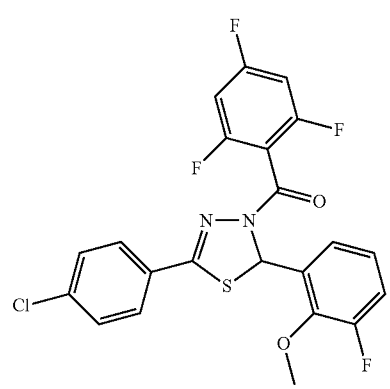 [SMILES: COc1c(F)cccc1C1SC(c2ccc(Cl)cc2)=NN1C(=O)c1c(F)cc(F)cc1F] | 481.2 | ¹H NMR (400 MHz, CDCl₃) δ 7.46-7.48 (m, 3H), 7.34 (d, J = 8.7 Hz, 1H), 7.29 (d, J = 8.4 Hz, 1H), 7.15 (d, J = 8.5 Hz, 1H), 6.98-7.11 (m, 3H), 6.78 (t, J = 8.5 Hz, 2H), 4.11 (d, J = 2.7 Hz, 3H). |

TABLE 1-continued

| Example | Structure | MS (m/z) (M + 1)+ | NMR |
|---|---|---|---|
| 76 | 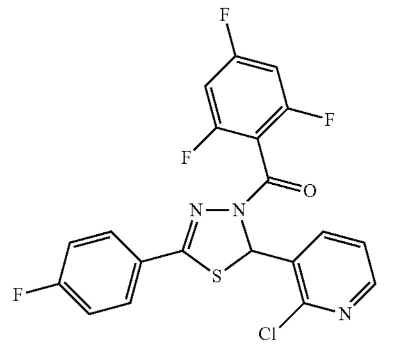 [SMILES: O=C(c1c(F)cc(F)cc1F)N1N=C(c2ccc(F)cc2)SC1c1cccnc1Cl] | 452.2 | ¹H NMR (400 MHz, CDCl₃) δ 8.4 (d, J = 3.1 Hz, 1H), 7.66 (d, J = 7.9 Hz, 1H), 7.53 (dd, J = 9.9, 5.5 Hz, 2H), 7.48 (s, 1H), 7.31 (dd, J = 8, 4.6 Hz, 1H), 7.07 (t, J = 8.6 Hz, 2H), 6.81 (t, J = 8.5 Hz, 2H). |
| 77 | 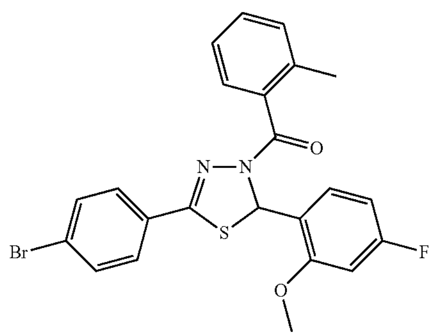 [SMILES: COc1cc(F)ccc1C1SC(c2ccc(Br)cc2)=NN1C(=O)c1ccccc1C] | 485.2 | ¹H NMR (400 MHz, CDCl₃) δ 8.1 (d, J = 7.8 Hz, 1H), 7.43-7.49 (m, 4H), 7.38 (d, J = 8.9 Hz, 2H), 7.25-7.3 (m, 2H), 7.16 (dd, J = 8.2, 6.3 Hz, 1H), 6.6-6.7 (m, 2H), 3.92 (s, 3H), 2.39 (s, 3H). |
| 78 | 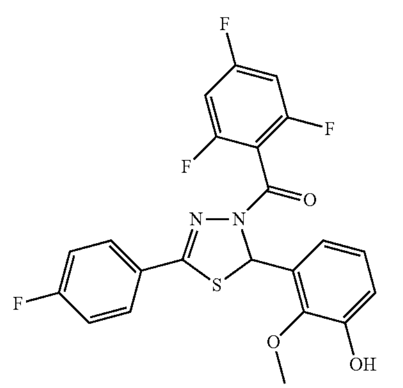 [SMILES: COc1c(O)cccc1C1SC(c2ccc(F)cc2)=NN1C(=O)c1c(F)cc(F)cc1F] | 463.2 | ¹H NMR (400 MHz, CDCl₃) δ 7.54 (dd, J = 8.9, 5.3 Hz, 2H), 7.47 (s, 1H), 7.01-7.08 (m, 3H), 6.93 (d, J = 8.1 Hz, 1H), 6.87 (d, J = 7.9 Hz, 1H), 6.77 (t, J = 8.4 Hz, 2H), 5.3 (bs, 1H), 4.03 (s, 3H). |
| 79 | 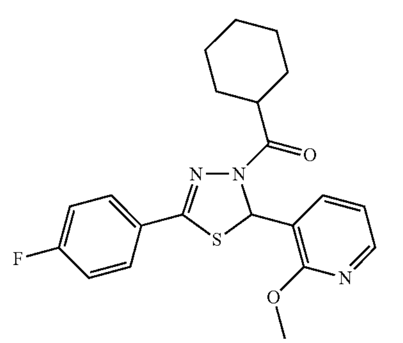 [SMILES: COc1ncccc1C1SC(c2ccc(F)cc2)=NN1C(=O)C1CCCCC1] | 400.1 | ¹H NMR (400 MHz, CDCl₃): δ 8.09 (dd, J₁ = 1.6 Hz, J₂ = 5.2 Hz, 1H), 7.69 (dd, J₁ = 5.2 Hz, J₂ = 8.8 Hz, 2H), 7.24 (dd, J₁ = 1.2 Hz, J₂ = obscureδ by CDCl₃, 1H), 7.2 (s, 1H), 7.11 (t, J = 8.8 Hz, 2H), 6.83 (dd, J₁ = 4.8 Hz, J₂ = 7.2 Hz, 1H), 4.03 (s, 3H), 3.21-3.29 (m, 1H), 2.11 (d, J = 12 Hz, 1H), 1.81-1.92 (m, 3H), 1.74 (d, J = 12 Hz, 1H), 1.21-1.67 (m, 7H). |

TABLE 1-continued

| Example | Structure | MS (m/z) (M + 1)+ | NMR |
|---|---|---|---|
| 80 | 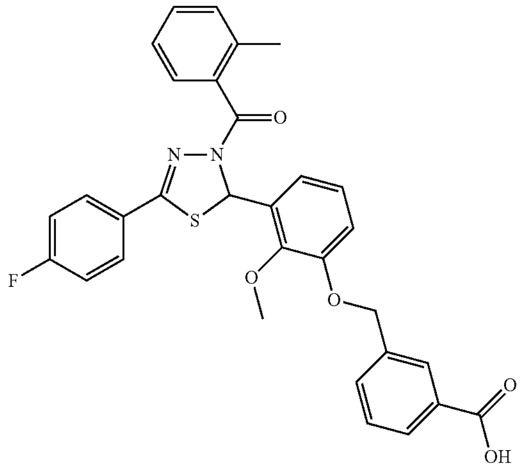 [SMILES: COc1c(OCc2cccc(C(=O)O)c2)cccc1C1SC(c2ccc(F)cc2)=NN1C(=O)c1ccccc1C] | 557.2 | ¹H NMR (400 MHz, CDCl₃) δ 8.03(s, 1H), 7.92 (d, J = 8 Hz, 1H), 7.57 (d, J = 7.6 Hz, 1H), 7.43 (s, 1H), 7.37 (t, J = 6.8 Hz, 3H), 7.28 (d, J = 7.2 Hz, 1H), 7.19 (s, 1H), 7.11 (m, 2H), 6.89 (m, 3H), 6.79 (m, 2H), 5.02 (s, 2H), 3.94 (s, 3H), 2.22 (s, 3H). |
| 81 | 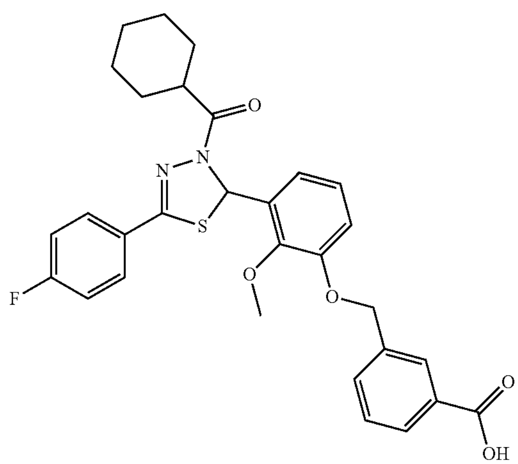 [SMILES: COc1c(OCc2cccc(C(=O)O)c2)cccc1C1SC(c2ccc(F)cc2)=NN1C(=O)C1CCCCC1] | 548.2 | ¹H NMR (400 MHz, CDCl₃) δ 7.88 (s, 1H), 7.78 (d, J = 8.0 Hz, 1H), 7.72 (m, 2H), 7.61 (d, J = 7.6 Hz, 1H), 7.47 (t, J = 7.6 Hz, 1H), 7.34 (s, 1H), 7.11 (t, J = 8.4 Hz, 2H), 6.94 (t, J = 8 Hz, 1H), 6.88 (dd, J₁ = 8.0 Hz, J₂ = 1.2 Hz, 1H), 6.72 (dd, J₁ = 8.0 Hz, J₂ = 1.2 Hz, 1H), 6.22 (s, 1H), 5.81 (bs, 2H), 5.14 (s, 2H), 4.01 (s, 3H), 3.28 (m, 1H), 2.1 (m, 1H), 1.91 (m, 3H), 1.77 (m, 1H), 1.59 (m, 4H), 1.29 (m, 1H). |
| 82 | 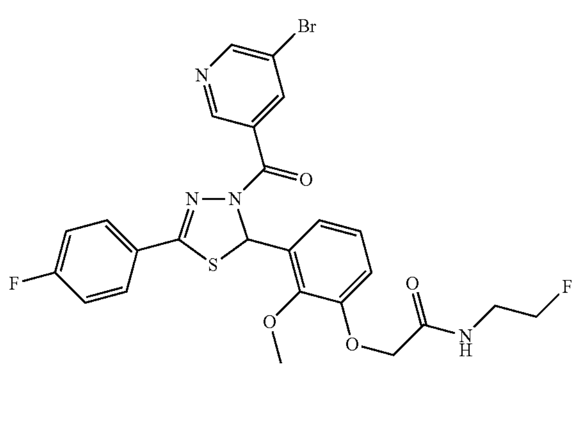 [SMILES: COc1c(OCC(=O)NCCF)cccc1C1SC(c2ccc(F)cc2)=NN1C(=O)c1cncc(Br)c1] | 591.1 | ¹H NMR (400 MHz, CDCl₃) δ 9.46 (s, 1H), 9.01 (s, 1H), 8.71 (s, 1H), 7.89 (m, 2H), 7.73 (s, 1H), 7.34 (m, 3H), 7.15 (m, 2H), 4.78 (s, 2H), 4.25 (s, 2H), 3.93 (m, 2H). |

TABLE 1-continued

| Example | Structure | MS (m/z) (M + 1)+ | NMR |
| --- | --- | --- | --- |
| 83 | 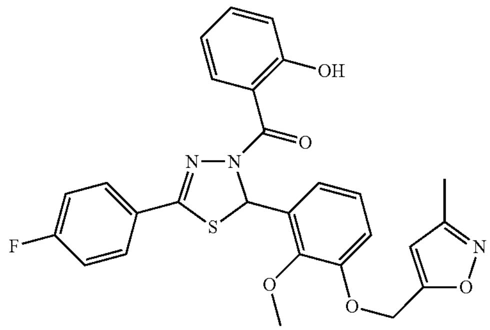 [SMILES: COc1c(OCc2cc(C)no2)cccc1C1SC(c2ccc(F)cc2)=NN1C(=O)c1ccccc1O] | 520.2 | ¹H NMR (400 MHz, CDCl$_3$) δ 8.62 (d, J = 8 Hz, 1H), 7.82 (m, 2H), 7.68 (s, 1H), 7.51 (t, J = 7.6 Hz, 1H), 7.21 (t, J = 8.4 Hz, 2H), 7.08 (m, 4H), 6.95 (m, 1H), 6.21 (s, 1H), 5.23 (s, 2H), 4.11 (s, 3H), 2.52 (s, 3H. |
| 84 | 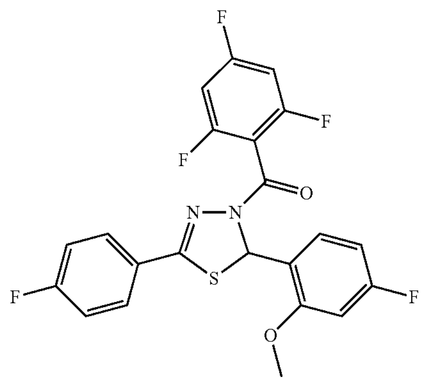 [SMILES: COc1cc(F)ccc1C1SC(c2ccc(F)cc2)=NN1C(=O)c1c(F)cc(F)cc1F] | 465.0 | ¹H NMR (400 MHz, CDCl$_3$) δ 7.54 (m, 2H), 7.42 (s, 1H), 7.21 (m, 1H), 7.06 (m, 2H), 6.83 (m, 2H), 6.69 (m, 2H), 3.92 (s, 3H). |
| 85 | 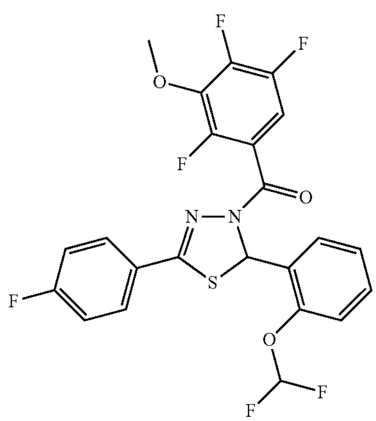 [SMILES: COc1c(F)c(F)cc(C(=O)N2N=C(c3ccc(F)cc3)SC2c2ccccc2OC(F)F)c1F] | 513.0 | ¹H NMR (400 MHz, CDCl$_3$) δ 7.59 (m, 2H), 7.48 (s, 1H), 7.41 (m, 2H), 7.26 (m, 1H), 7.18 (d, J = 8 Hz, 1H), 7.11 (m, 3H), 6.68 (dd, J1 = 75.6 Hz, J2 = 4.4 Hz, 1H), 4.09 (s, 1H). |
| 86 | 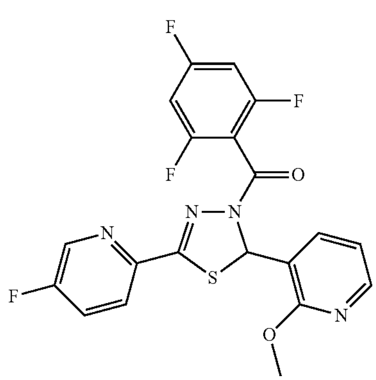 [SMILES: COc1ncccc1C1SC(c2ccc(F)cn2)=NN1C(=O)c1c(F)cc(F)cc1F] | 449.1 | ¹H NMR (400 MHz, CDCl$_3$) δ 8.41 (d, J = 2.7 Hz, 1H), 8.14 (d, J = 5.1 Hz, 1H), 7.77 (dd, J = 8.7, 4.1 Hz, 1H), 7.5 (d, J = 8.9 Hz, 1H), 7.41 (dt, J = 8.5, 2.7 Hz, 1H), 7.3 (s, 1H), 6.91 (dd, J = 7.7, 5 Hz, 1H), 6.79 (m, 2H), 4.06 (m, 3H). |

TABLE 1-continued

| Example | Structure | MS (m/z) (M + 1)+ | NMR |
|---|---|---|---|
| 87 | 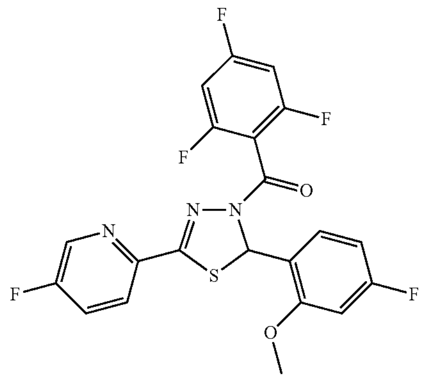 [SMILES: COc1cc(F)ccc1C1SC(c2ccc(F)cn2)=NN1C(=O)c1c(F)cc(F)cc1F] | 466.0 | ¹H NMR (400 MHz, CDCl$_3$) δ 8.31 (d, J = 4.1 Hz, 1H), 7.68 (dd, J = 8.9, 4.4 Hz, 1H), 7.31 (dt, J = 8, 2.9 Hz, 1H), 7.17 (s, 1H), 7.1 (dd, J = 9, 6.1 Hz, 1H), 6.69 (m, 2H), 6.53-6.58 (m, 2H), 3.82 (s, 3H). |
| 88 | 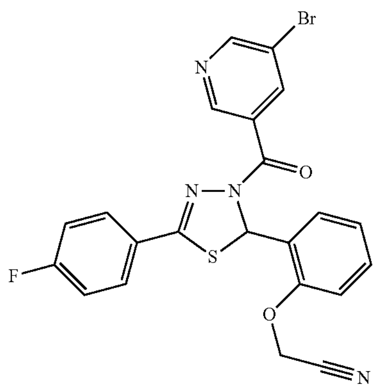 [SMILES: N#CCOc1ccccc1C1SC(c2ccc(F)cc2)=NN1C(=O)c1cncc(Br)c1] | 498.9 | ¹H NMR (400 MHz, CDCl$_3$) δ 9.23 (s, 1H), 8.82 (s, 1H), 8.48 (t, J = 2 Hz, 1H), 7.67 (dd, J$_1$ = 5.2 Hz, J$_2$ = 8.8 Hz, 2H), 7.52 (s, 1H), 7.39 (apparent t, J = 7.6 Hz, 1H), 7.06-7.16 (m, 3H), 7.05 (d, J = 8.4 Hz, 1H), 4.92 (dd, J$_1$ = 16 Hz, J$_2$ = 27 Hz, 2H). |
| 89 | 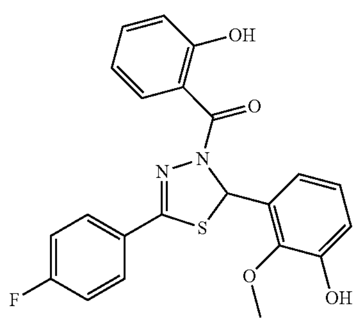 [SMILES: COc1c(O)cccc1C1SC(c2ccc(F)cc2)=NN1C(=O)c1ccccc1O] | 425.0 | ¹H NMR (400 MHz, CDCl$_3$) δ 11.23 (s, 1H), 8.54 (dd, J1 = 0.8 Hz, J2 = 8.4 Hz, 1H), 7.73 (dd, J1 = 5.2 Hz, J2 = 8.8 Hz, 2H), 7.59 (s, 1H), 7.44 (apparent t, J = 7.2 Hz, 1H), 7.15 (t, J = 7.6 Hz, 2H), 6.89-7.03-7.16 (m, 4H), 6.81 (dd, J1 = 1.6 Hz, J2 = 7.6 Hz, 1H), 5.49 (s, 1H), 4.03 (s, 3H). |
| 90 | 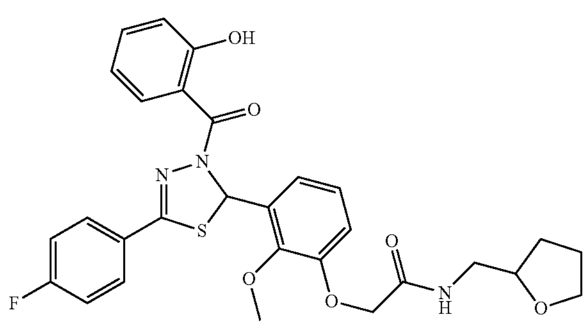 [SMILES: COc1c(OCC(=O)NCC2CCCO2)cccc1C1SC(c2ccc(F)cc2)=NN1C(=O)c1ccccc1O] | 566.1 | ¹H NMR (400 MHz, CDCl$_3$) δ 11.14 (d, J = 3.6 Hz, 1H), 8.44 (dt, J = 1.6 Hz, J$_2$ = 8.4 Hz, 1H), 7.63 (dd, J$_1$ = 5.2 Hz, J$_2$ = 8 Hz, 2H), 7.51 (d, J = 2 Hz, 1H), 7.34 (apparent t, J = 7.2 Hz, 1H), 7.04 (t, J = 8.4 Hz, 2H), 6.75-6.99 (m, 6H), 4.46 (d, J = 1.61 Hz, 2H), 3.97 (s, 3H), 3.86-3.94 (m, 1H), 3.69-3.77 (m, 1H), 3.61-3.67 (m, 1H), 3.47-3.56 (m, 1H), 3.17-3.29 (m, 1H), 1.71-1.92 (m, 3H), 1.38-1.48 (m partially obscuredδ by H2O, 1H). |

TABLE 1-continued
| Example | Structure | MS (m/z) (M + 1)+ | NMR |
|---|---|---|---|
| 91 | 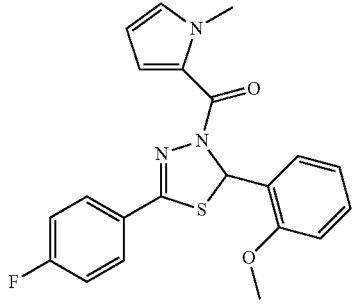 [SMILES: COc1ccccc1C1SC(c2ccc(F)cc2)=NN1C(=O)c1cccn1C] | 396.0 | $^1$H NMR (400 MHz, CDCl$_3$) δ 7.87 (m, 2H), 7.66 (s, 1H), 7.61 (m, 1H), 7.4 (m, 1H), 7.26 (m, 3H), 7.05 (m, 2H) 6.95 (m, 1H), 6.36 (m, 1H), 4.05 (s, 6H). |
| 92 | 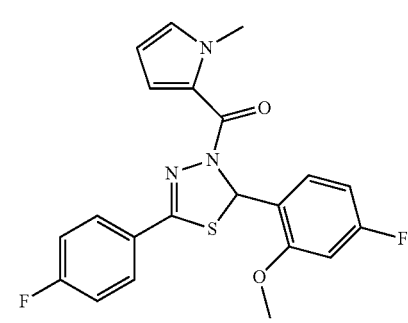 [SMILES: COc1cc(F)ccc1C1SC(c2ccc(F)cc2)=NN1C(=O)c1cccn1C] | 414.0 | $^1$H NMR (400 MHz, CDCl$_3$) δ 7.74 (m, 2H), 7.48 (m, 2H), 7.13 (m, 3H), 6.83 (s, 1H), 6.65 (dd, J$_1$ = 10.8 Hz, J$_2$ = 2.0 Hz, 1H), 6.59 (m, 1H), 3.92 (s, 6H). |
TABLE 2
| Example | Structure | MS (m/z) (M + 1)+ |
|---|---|---|
| 93 | 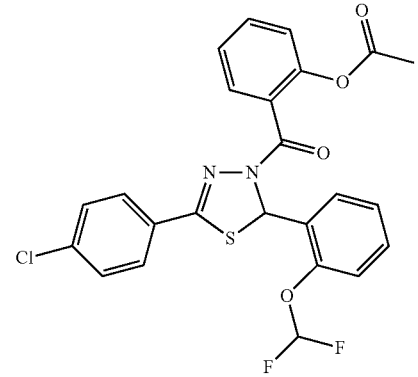 [SMILES: CC(=O)Oc1ccccc1C(=O)N1N=C(c2ccc(Cl)cc2)SC1c1ccccc1OC(F)F] | 503.0 |
| 94 | 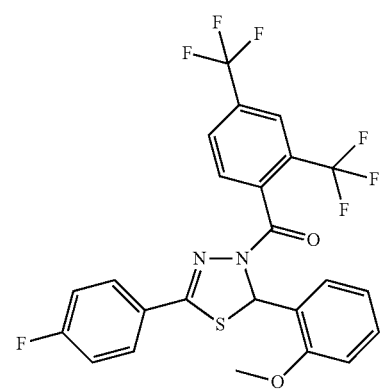 [SMILES: COc1ccccc1C1SC(c2ccc(F)cc2)=NN1C(=O)c1ccc(C(F)(F)F)cc1C(F)(F)F] | 529.1 |

TABLE 2-continued

| Example | Structure | MS (m/z) (M + 1)+ |
|---|---|---|
| 95 | 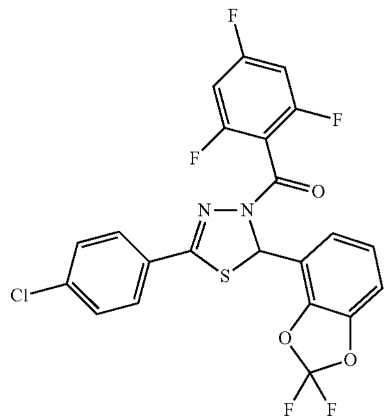 [SMILES: O=C(c1c(F)cc(F)cc1F)N1N=C(c2ccc(Cl)cc2)SC1c1cccc2c1OC(F)(F)O2] | 513.0 |
| 96 | 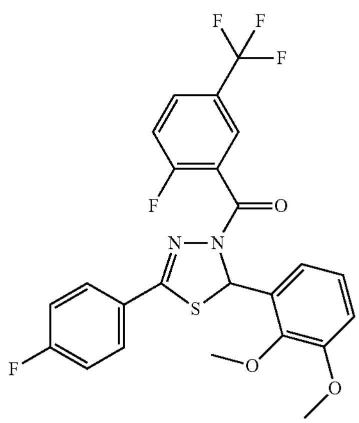 [SMILES: COc1cccc(C2SC(c3ccc(F)cc3)=NN2C(=O)c2cc(C(F)(F)F)ccc2F)c1OC] | 509.2 |
| 97 | 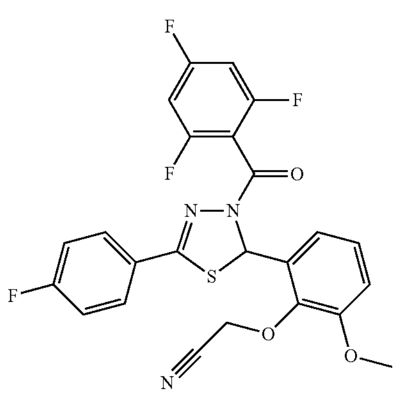 [SMILES: COc1cccc(C2SC(c3ccc(F)cc3)=NN2C(=O)c2c(F)cc(F)cc2F)c1OCC#N] | 502.2 |

TABLE 2-continued

| Example | Structure | MS (m/z) (M + 1)+ |
|---|---|---|
| 98 | 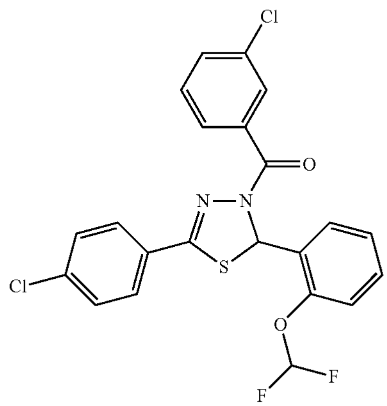 | 479.0 |
| 99 | 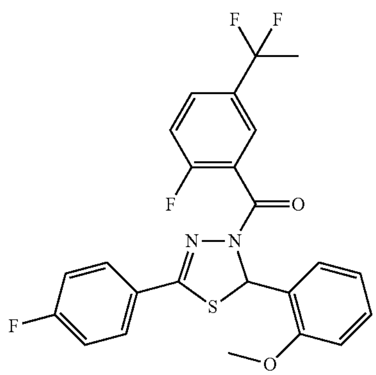 [SMILES: COc1ccccc1C1SC(c2ccc(F)cc2)=NN1C(=O)c1cc(C(C)(F)F)ccc1F] | 479.3 |
| 100 | 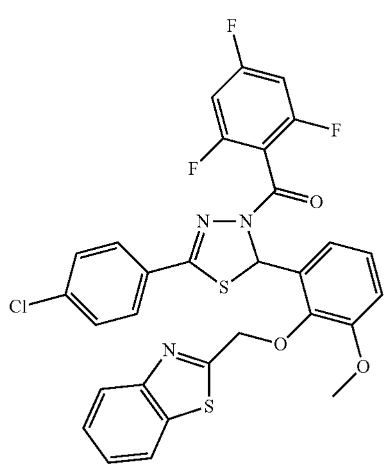 [SMILES: COc1cccc(C2SC(c3ccc(Cl)cc3)=NN2C(=O)c2c(F)cc(F)cc2F)c1OCc1nc2ccccc2s1] | 626.3 |

TABLE 2-continued

| Example | Structure | MS (m/z) (M + 1)+ |
|---|---|---|
| 101 | 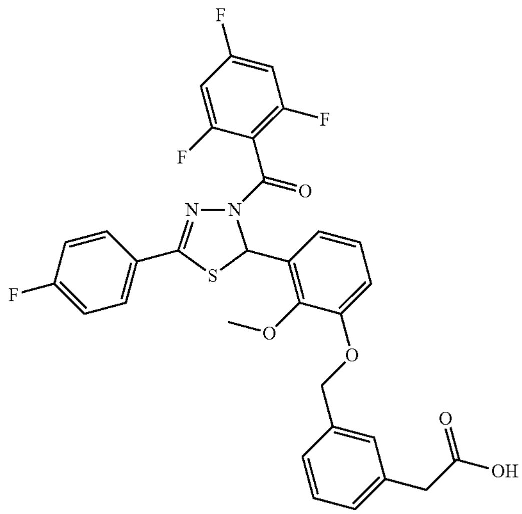 [SMILES: COc1c(OCc2cccc(CC(=O)O)c2)cccc1C1SC(c2ccc(F)cc2)=NN1C(=O)c1c(F)cc(F)cc1F] | 611.2 |
| 102 | 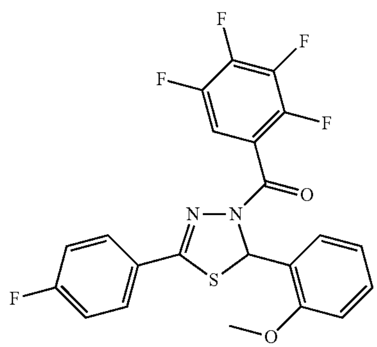 [SMILES: COc1ccccc1C1SC(c2ccc(F)cc2)=NN1C(=O)c1cc(F)c(F)c(F)c1F] | 465.2 |
| 103 | 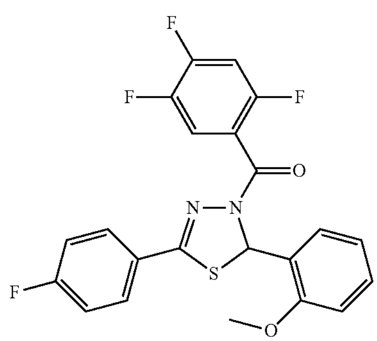 [SMILES: COc1ccccc1C1SC(c2ccc(F)cc2)=NN1C(=O)c1cc(F)c(F)cc1F] | 447.2 |
| 104 | 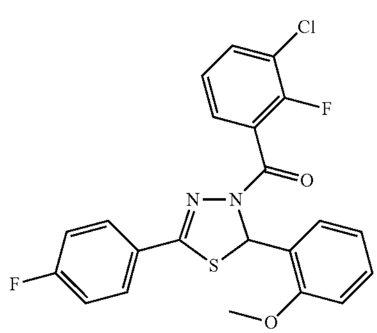 [SMILES: COc1ccccc1C1SC(c2ccc(F)cc2)=NN1C(=O)c1cccc(Cl)c1F] | 445.2 |

TABLE 2-continued
| Example | Structure | MS (m/z) (M + 1)+ |
|---|---|---|
| 105 | 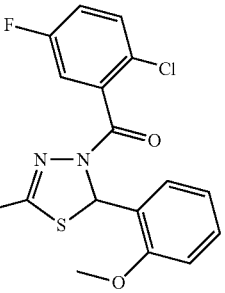 | 445.2 |
| 106 | 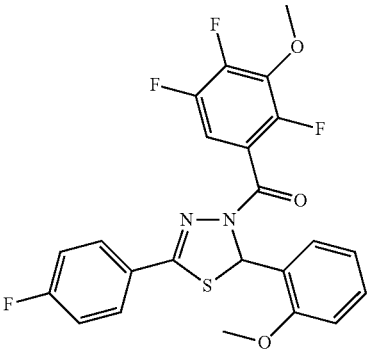 [SMILES: COc1ccccc1C1SC(c2ccc(F)cc2)=NN1C(=O)c1cc(F)c(F)c(OC)c1F] | 447.3 |
| 107 | 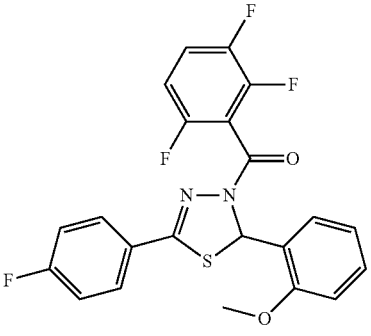 [SMILES: COc1ccccc1C1SC(c2ccc(F)cc2)=NN1C(=O)c1c(F)ccc(F)c1F] | 447.3 |
| 108 | 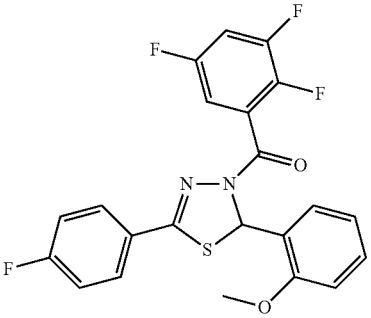 [SMILES: COc1ccccc1C1SC(c2ccc(F)cc2)=NN1C(=O)c1cc(F)cc(F)c1F] | 447.3 |

TABLE 2-continued

| Example | Structure | MS (m/z) (M + 1)+ |
|---|---|---|
| 109 | 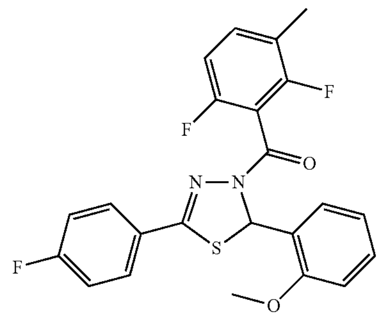 [SMILES: COc1ccccc1C1SC(c2ccc(F)cc2)=NN1C(=O)c1c(F)ccc(C)c1F] | 443.3 |
| 110 | 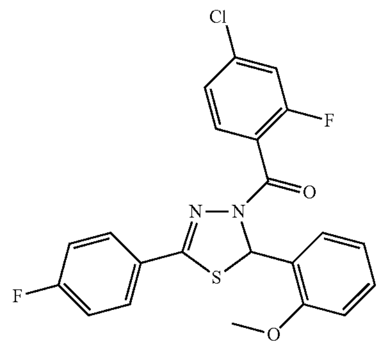 [SMILES: COc1ccccc1C1SC(c2ccc(F)cc2)=NN1C(=O)c1ccc(Cl)cc1F] | 445.2 |
| 111 | 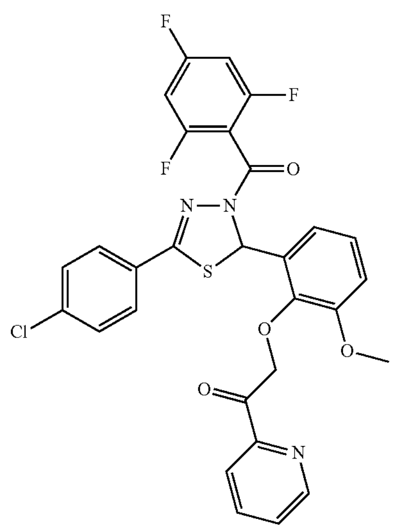 [SMILES: COc1cccc(C2SC(c3ccc(Cl)cc3)=NN2C(=O)c2c(F)cc(F)cc2F)c1OCC(=O)c1ccccn1] | 598.2 |
| 112 | 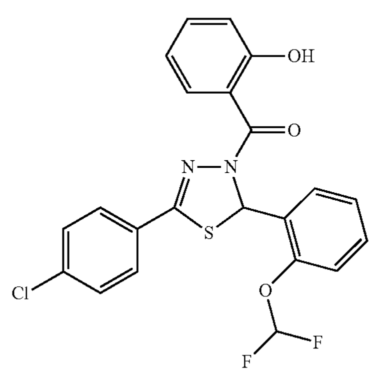 [SMILES: O=C(c1ccccc1O)N1N=C(c2ccc(Cl)cc2)SC1c1ccccc1OC(F)F] | 461.2 |

TABLE 2-continued

| Example | Structure | MS (m/z) (M + 1)+ |
|---|---|---|
| 113 | 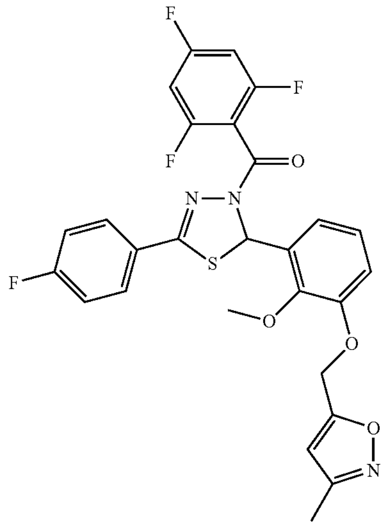 [SMILES: COc1c(OCc2cc(C)no2)cccc1C1SC(c2ccc(F)cc2)=NN1C(=O)c1c(F)cc(F)cc1F] | 558.2 |
| 114 | 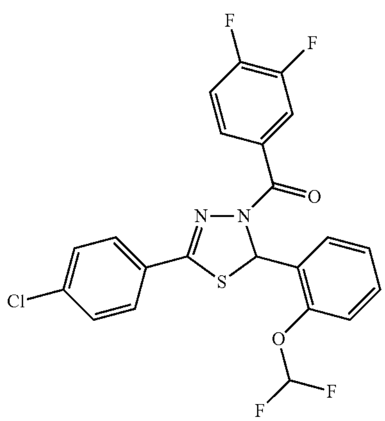 [SMILES: O=C(c1ccc(F)c(F)c1)N1N=C(c2ccc(Cl)cc2)SC1c1ccccc1OC(F)F] | 481.0 |
| 115 | 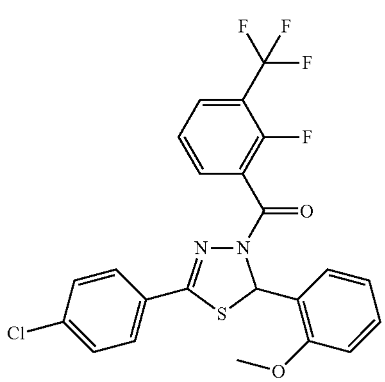 [SMILES: COc1ccccc1C1SC(c2ccc(Cl)cc2)=NN1C(=O)c1cccc(C(F)(F)F)c1F] | 495.0 |

TABLE 2-continued

| Example | Structure | MS (m/z) (M + 1)+ |
|---|---|---|
| 116 | 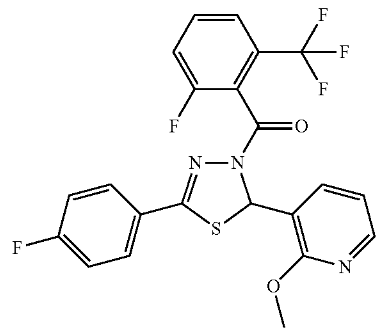 [SMILES: COc1ncccc1C1SC(c2ccc(F)cc2)=NN1C(=O)c1c(F)cccc1C(F)(F)F] | 480.0 |
| 117 | 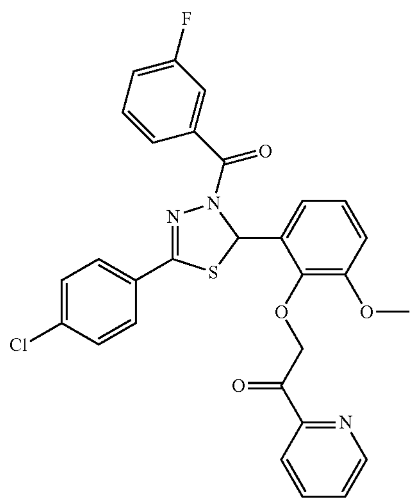 [SMILES: COc1cccc(C2SC(c3ccc(Cl)cc3)=NN2C(=O)c2cccc(F)c2)c1OCC(=O)c1ccccn1] | 562.1 |
| 118 | 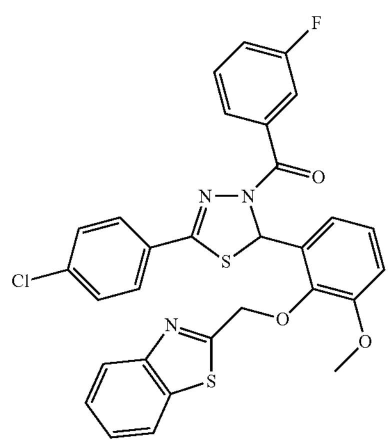 [SMILES: COc1cccc(C2SC(c3ccc(Cl)cc3)=NN2C(=O)c2cccc(F)c2)c1OCc1nc2ccccc2s1] | 589.9 |

TABLE 2-continued

| Example | Structure | MS (m/z) (M + 1)+ |
|---|---|---|
| 119 | 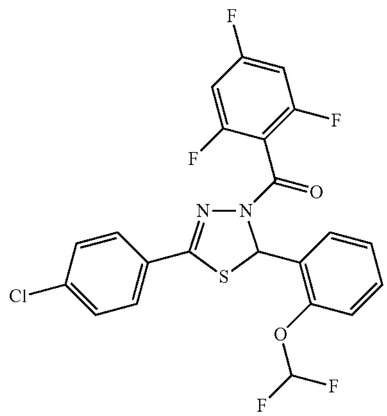 [SMILES: O=C(c1c(F)cc(F)cc1F)N1N=C(c2ccc(Cl)cc2)SC1c1ccccc1OC(F)F] | 499.2 |
| 120 | 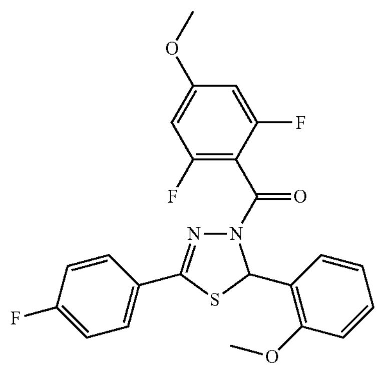 [SMILES: COc1cc(F)c(C(=O)N2N=C(c3ccc(F)cc3)SC2c2ccccc2OC)c(F)c1] | 459.3 |
| 121 | 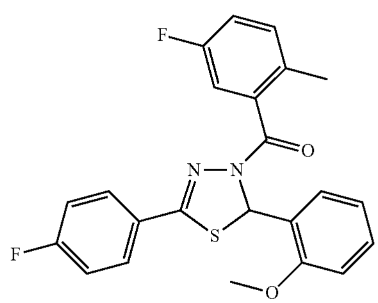 [SMILES: COc1ccccc1C1SC(c2ccc(F)cc2)=NN1C(=O)c1cc(F)ccc1C] | 425.3 |
| 122 | 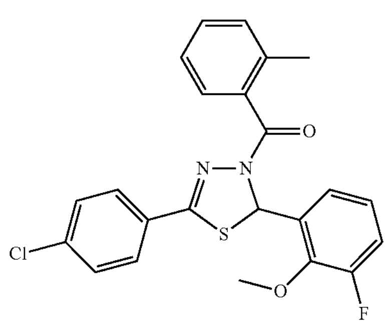 [SMILES: COc1c(F)cccc1C1SC(c2ccc(Cl)cc2)=NN1C(=O)c1ccccc1C] | 441.2 |

TABLE 2-continued

| Example | Structure | MS (m/z) (M + 1)+ |
|---------|-----------|-------------------|
| 123 | 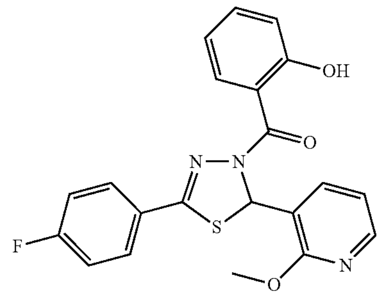 [SMILES: COc1ncccc1C1SC(c2ccc(F)cc2)=NN1C(=O)c1ccccc1O] | 410.2 |
| 124 | 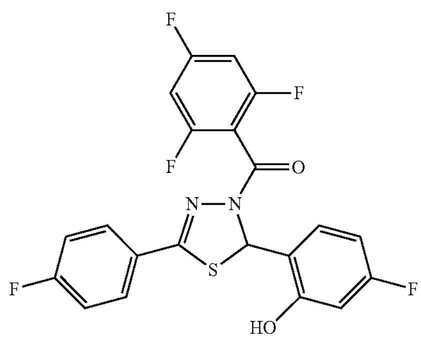 [SMILES: O=C(c1c(F)cc(F)cc1F)N1N=C(c2ccc(F)cc2)SC1c1ccc(F)cc1O] | 451.2 |
| 125 | 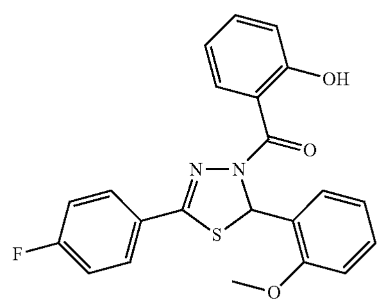 [SMILES: COc1ccccc1C1SC(c2ccc(F)cc2)=NN1C(=O)c1ccccc1O] | 409.2 |
| 126 | 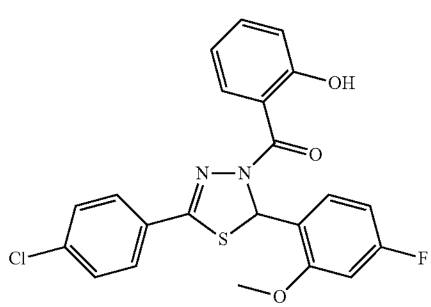 [SMILES: COc1cc(F)ccc1C1SC(c2ccc(Cl)cc2)=NN1C(=O)c1ccccc1O] | 443.2 |

TABLE 2-continued
| Example | Structure | MS (m/z) (M + 1)+ |
|---|---|---|
| 127 | 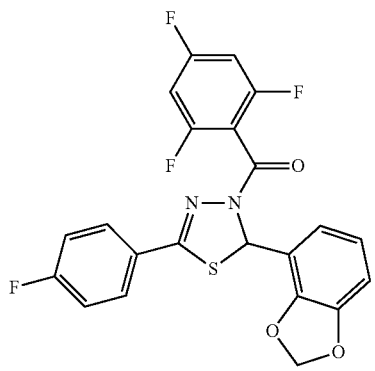 [SMILES: O=C(c1c(F)cc(F)cc1F)N1N=C(c2ccc(F)cc2)SC1c1cccc2c1OCO2] | 461.2 |
| 128 | 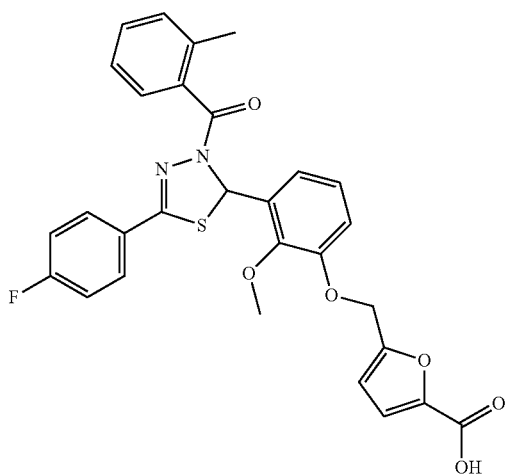 [SMILES: COc1c(OCc2ccc(C(=O)O)o2)cccc1C1SC(c2ccc(F)cc2)=NN1C(=O)c1ccccc1C] | 547.1 |
| 129 | 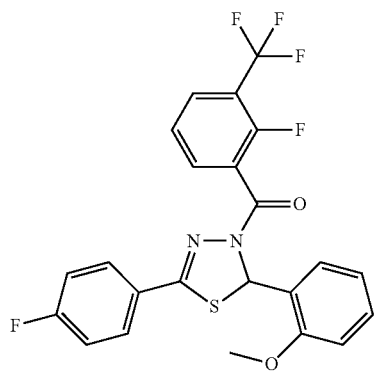 [SMILES: COc1ccccc1C1SC(c2ccc(F)cc2)=NN1C(=O)c1cccc(C(F)(F)F)c1F] | 479.2 |

TABLE 2-continued
| Example | Structure | MS (m/z) (M + 1)+ |
|---|---|---|
| 130 | 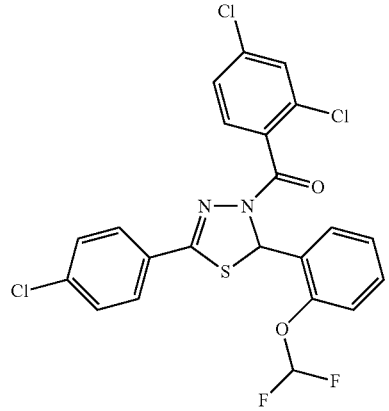 [SMILES: O=C(c1ccc(Cl)cc1Cl)N1N=C(c2ccc(Cl)cc2)SC1c1ccccc1OC(F)F] | 514.9 |
| 131 | 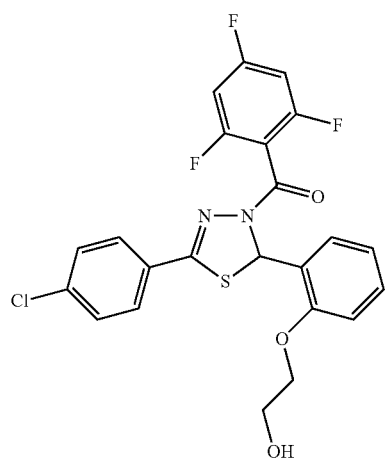 [SMILES: O=C(c1c(F)cc(F)cc1F)N1N=C(c2ccc(Cl)cc2)SC1c1ccccc1OCCO] | 493.0 |
| 132 | 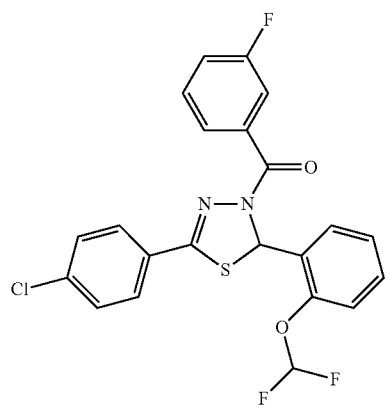 [SMILES: O=C(c1cccc(F)c1)N1N=C(c2ccc(Cl)cc2)SC1c1ccccc1OC(F)F] | 463.0 |

TABLE 2-continued

| Example | Structure | MS (m/z) (M + 1)+ |
|---|---|---|
| 133 | 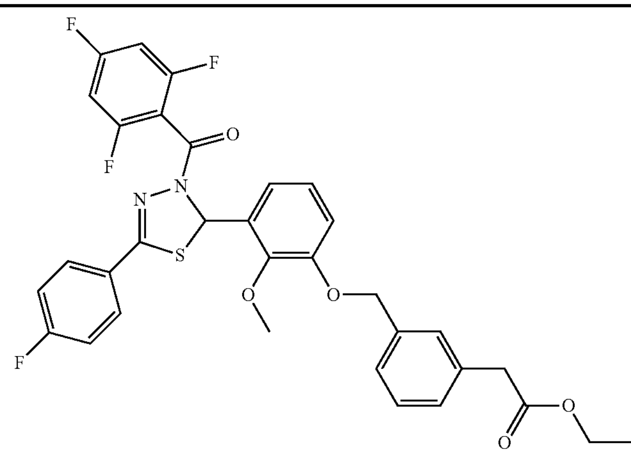 | 639.3 |
| 134 | 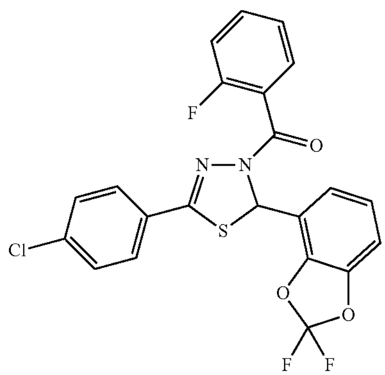 [SMILES: O=C(c1ccccc1F)N1N=C(c2ccc(Cl)cc2)SC1c1cccc2c1OC(F)(F)O2] | 476.8 |
| 135 | 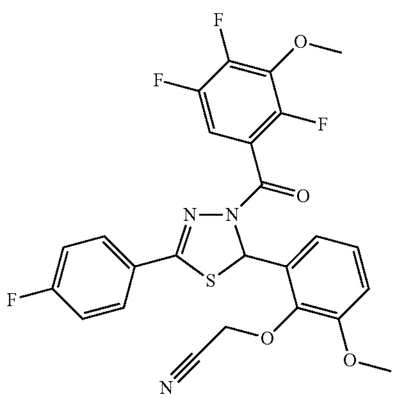 [SMILES: COc1cccc(C2SC(c3ccc(F)cc3)=NN2C(=O)c2cc(F)c(F)c(OC)c2F)c1OCC#N] | 532.3 |
| 136 | 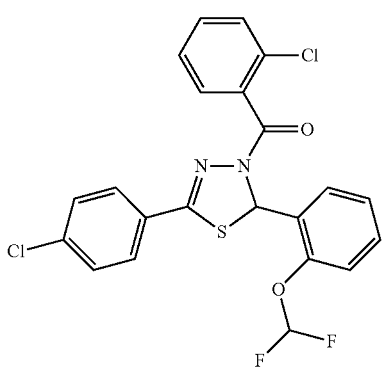 [SMILES: O=C(c1ccccc1Cl)N1N=C(c2ccc(Cl)cc2)SC1c1ccccc1OC(F)F] | 479.0 |

TABLE 2-continued

| Example | Structure | MS (m/z) (M + 1)+ |
|---|---|---|
| 137 | 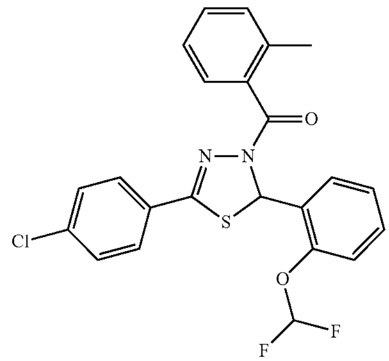 [SMILES: Cc1ccccc1C(=O)N1N=C(c2ccc(Cl)cc2)SC1c1ccccc1OC(F)F] | 459.0 |
| 138 | 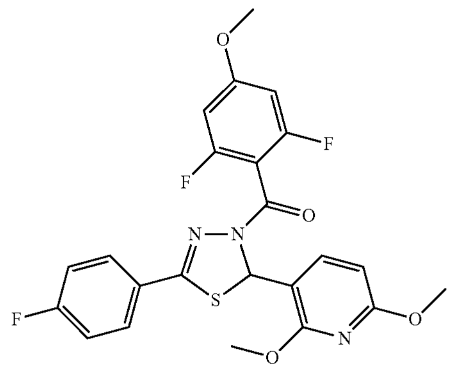 [SMILES: COc1cc(F)c(C(=O)N2N=C(c3ccc(F)cc3)SC2c2ccc(OC)nc2OC)c(F)c1] | 490.1 |
| 139 | 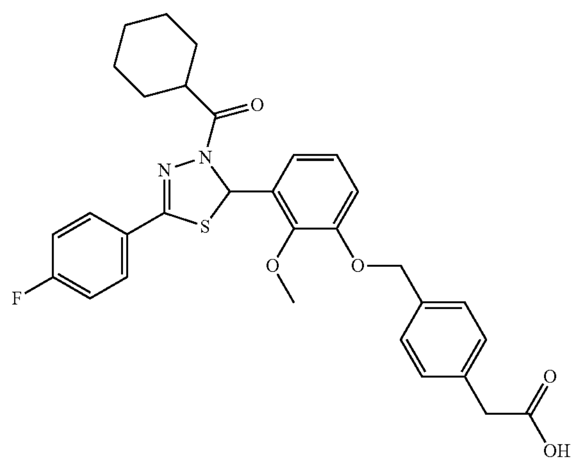 [SMILES: COc1c(OCc2ccc(CC(=O)O)cc2)cccc1C1SC(c2ccc(F)cc2)=NN1C(=O)C1CCCCC1] | 563.2 |
| 140 | 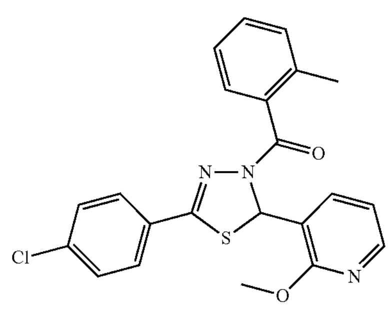 [SMILES: COc1ncccc1C1SC(c2ccc(Cl)cc2)=NN1C(=O)c1ccccc1C] | 424.0 |

TABLE 2-continued

| Example | Structure | MS (m/z) (M + 1)+ |
|---|---|---|
| 141 | 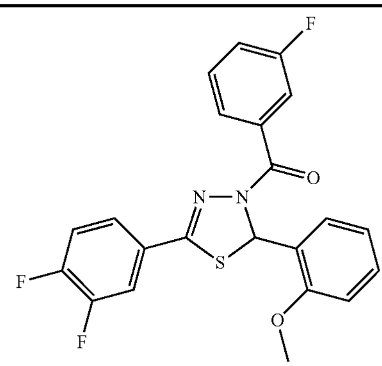 | 429.0 |
| 142 | 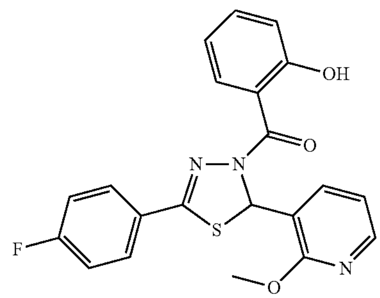 | 410.0 |
| 143 | 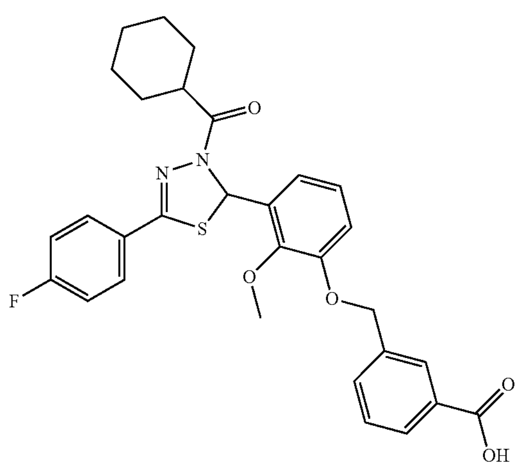 [SMILES: COc1c(OCc2cccc(C(=O)O)c2)cccc1C1SC(c2ccc(F)cc2)=NN1C(=O)C1CCCCC1] | 549.2 |
| 144 | 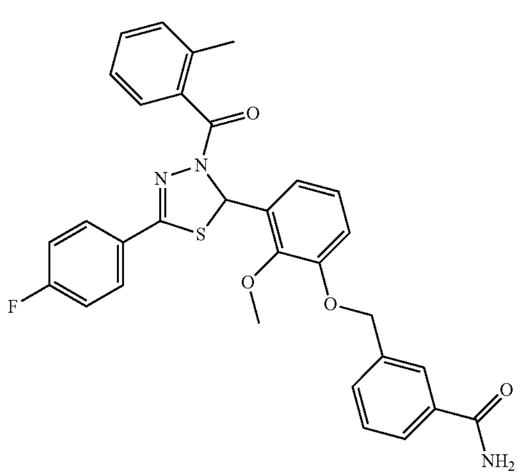 [SMILES: COc1c(OCc2cccc(C(N)=O)c2)cccc1C1SC(c2ccc(F)cc2)=NN1C(=O)c1ccccc1C] | 556.2 |

TABLE 2-continued

| Example | Structure | MS (m/z) (M + 1)+ |
|---|---|---|
| 145 | 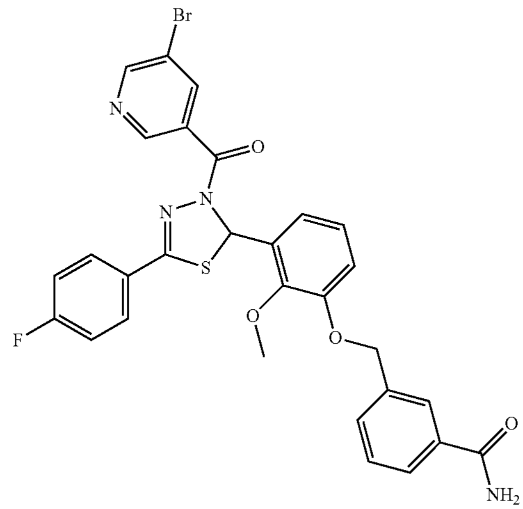 [SMILES: COc1c(OCc2cccc(C(N)=O)c2)cccc1C1SC(c2ccc(F)cc2)=NN1C(=O)c1cncc(Br)c1] | 621.1 |
| 146 | 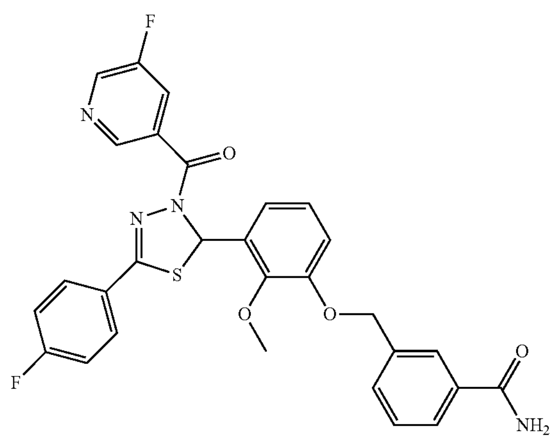 [SMILES: COc1c(OCc2cccc(C(N)=O)c2)cccc1C1SC(c2ccc(F)cc2)=NN1C(=O)c1cncc(F)c1] | 561.1 |
| 147 | 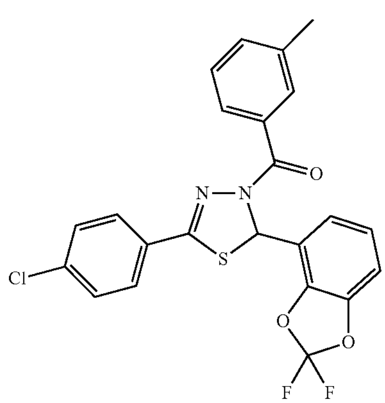 [SMILES: Cc1cccc(C(=O)N2N=C(c3ccc(Cl)cc3)SC2c2cccc3c2OC(F)(F)O3)c1] | 472.9 |

TABLE 2-continued
| Example | Structure | MS (m/z) (M + 1)+ |
|---|---|---|
| 148 | 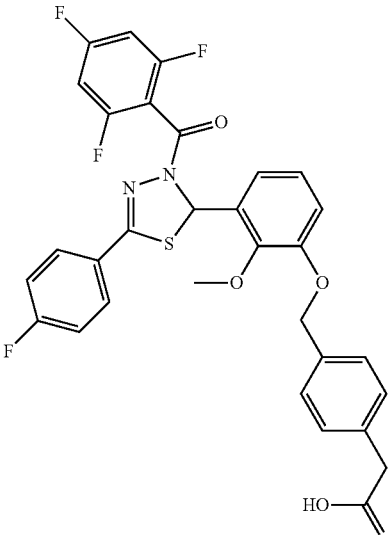 | 611.3 |
| 149 | 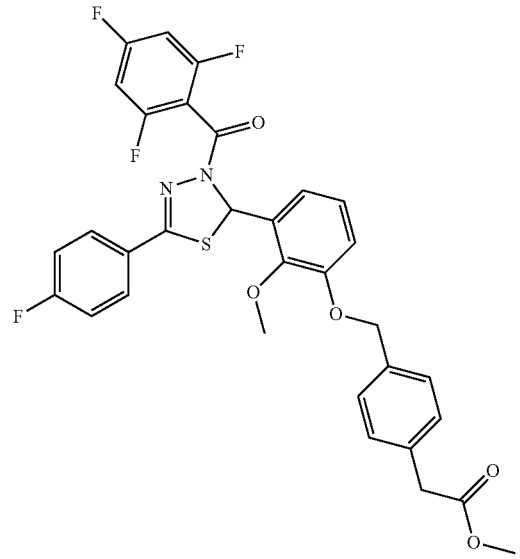 [SMILES: COC(=O)Cc1ccc(COc2cccc(C3SC(c4ccc(F)cc4)=NN3C(=O)c3c(F)cc(F)cc3F)c2OC)cc1] | 625.1 |
| 150 | 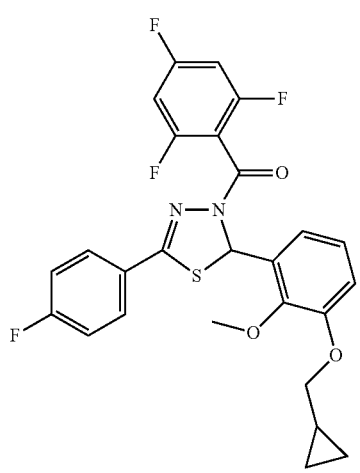 [SMILES: COc1c(OCC2CC2)cccc1C1SC(c2ccc(F)cc2)=NN1C(=O)c1c(F)cc(F)cc1F] | 517.3 |

TABLE 2-continued

| Example | Structure | MS (m/z) (M + 1)+ |
|---|---|---|
| 151 | 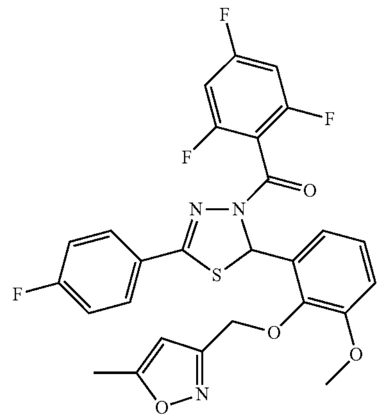 [SMILES: COc1cccc(C2SC(c3ccc(F)cc3)=NN2C(=O)c2c(F)cc(F)cc2F)c1OCc1cc(C)on1] | 558.3 |
| 152 | 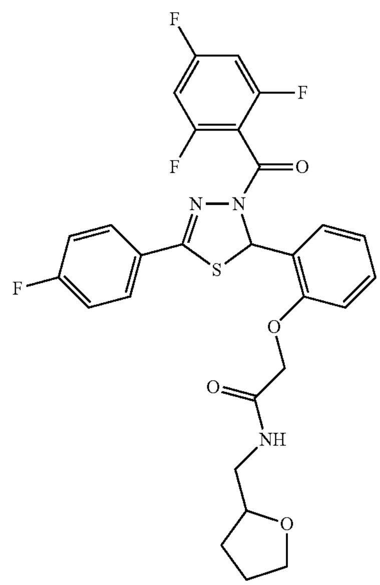 [SMILES: O=C(COc1ccccc1C1SC(c2ccc(F)cc2)=NN1C(=O)c1c(F)cc(F)cc1F)NCC1CCCO1] | 574.4 |
| 153 | 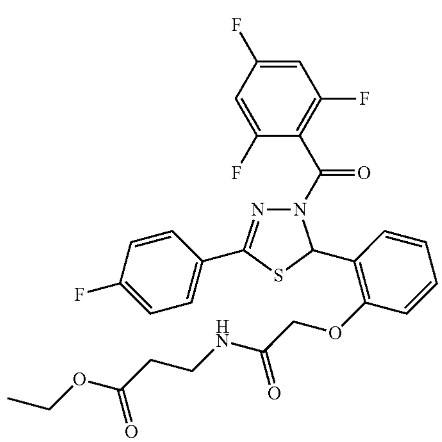 [SMILES: CCOC(=O)CCNC(=O)COc1ccccc1C1SC(c2ccc(F)cc2)=NN1C(=O)c1c(F)cc(F)cc1F] | 590.4 |

TABLE 2-continued

| Example | Structure | MS (m/z) (M + 1)+ |
|---|---|---|
| 154 | 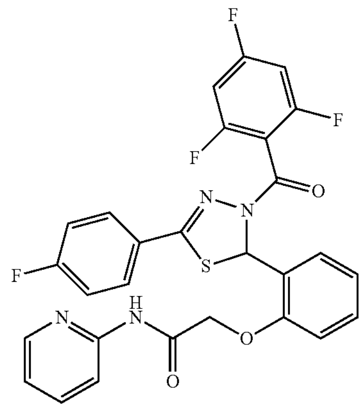 [SMILES: O=C(COc1ccccc1C1SC(c2ccc(F)cc2)=NN1C(=O)c1c(F)cc(F)cc1F)Nc1ccccn1] | 567.3 |
| 155 | 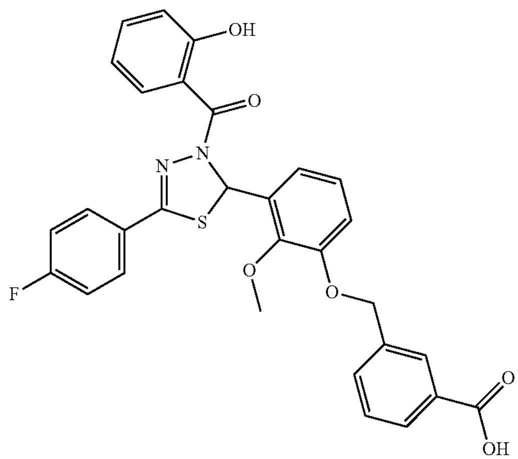 [SMILES: COc1c(OCc2cccc(C(=O)O)c2)cccc1C1SC(c2ccc(F)cc2)=NN1C(=O)c1ccccc1O] | 559.1 |
| 156 | 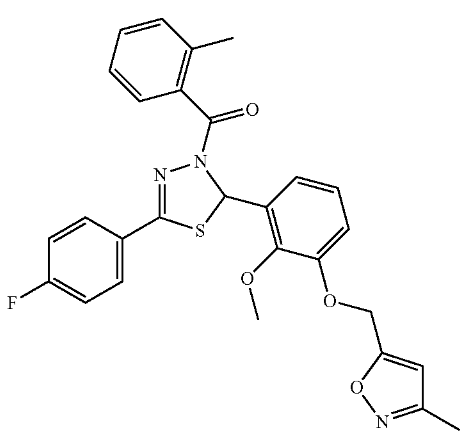 [SMILES: COc1c(OCc2cc(C)no2)cccc1C1SC(c2ccc(F)cc2)=NN1C(=O)c1ccccc1C] | 518.2 |

TABLE 2-continued

| Example | Structure | MS (m/z) (M + 1)+ |
|---|---|---|
| 157 | 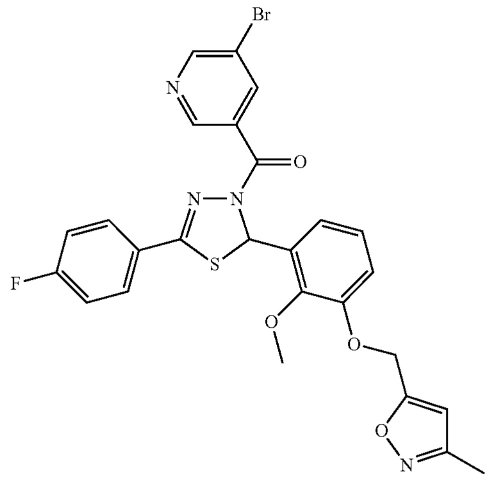 [SMILES: COc1c(OCc2cc(C)no2)cccc1C1SC(c2ccc(F)cc2)=NN1C(=O)c1cncc(Br)c1] | 583.0 |
| 158 | 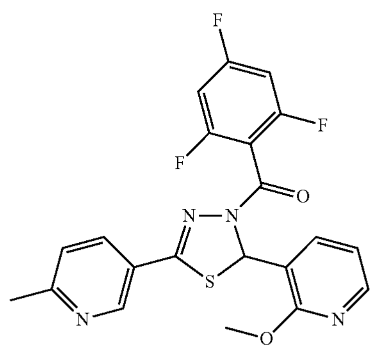 [SMILES: COc1ncccc1C1SC(c2ccc(C)nc2)=NN1C(=O)c1c(F)cc(F)cc1F] | 445.1 |
| 159 | 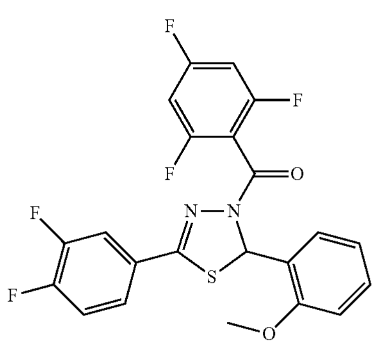 [SMILES: COc1ccccc1C1SC(c2ccc(F)c(F)c2)=NN1C(=O)c1c(F)cc(F)cc1F] | 465.1 |

TABLE 2-continued

| Example | Structure | MS (m/z) (M + 1)+ |
|---|---|---|
| 160 | 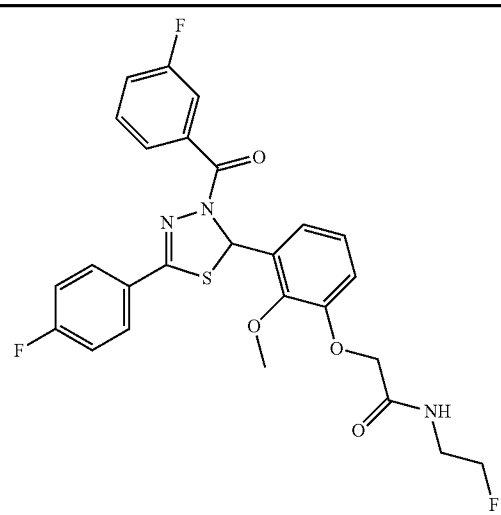 | 530.2 |
| 161 | 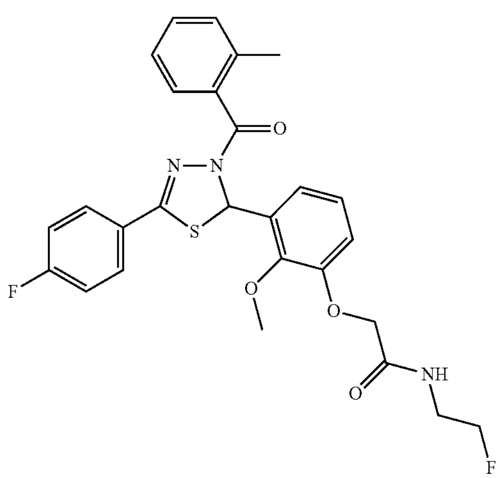 [SMILES: COc1c(OCC(=O)NCCF)cccc1C1SC(c2ccc(F)cc2)=NN1C(=O)c1ccccc1C] | 526.2 |
| 162 | 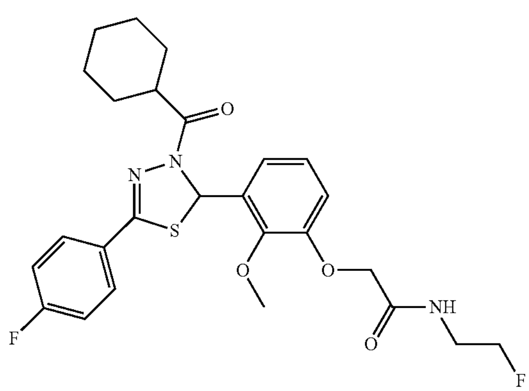 [SMILES: COc1c(OCC(=O)NCCF)cccc1C1SC(c2ccc(F)cc2)=NN1C(=O)C1CCCCC1] | 518.2 |

TABLE 2-continued
| Example | Structure | MS (m/z) (M + 1)+ |
|---|---|---|
| 163 | 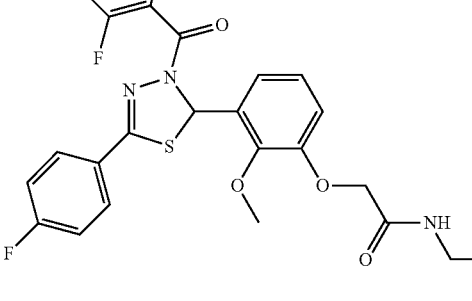 | 578.2 |
| 164 | 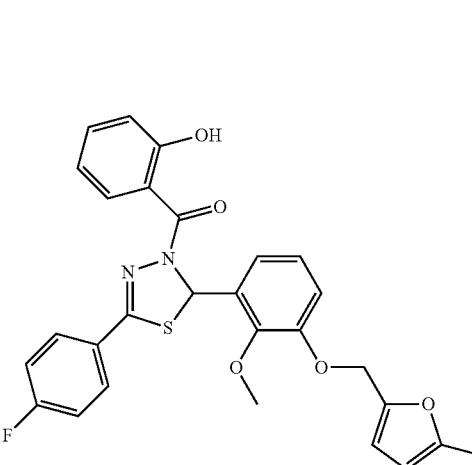 | 549.1 |
| 165 | 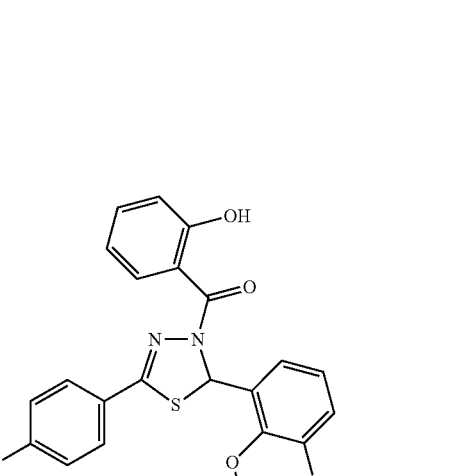 | 571.3 |

TABLE 2-continued
| Example | Structure | MS (m/z) (M + 1)+ |
|---|---|---|
| 166 | 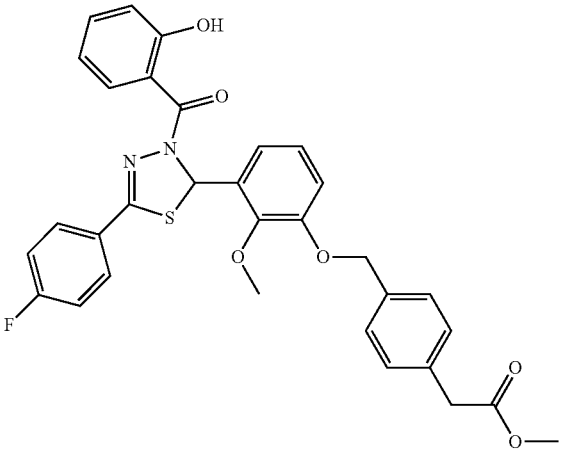 [SMILES: COC(=O)Cc1ccc(COc2cccc(C3SC(c4ccc(F)cc4)=NN3C(=O)c3ccccc3O)c2OC)cc1] | 587.2 |
| 167 | 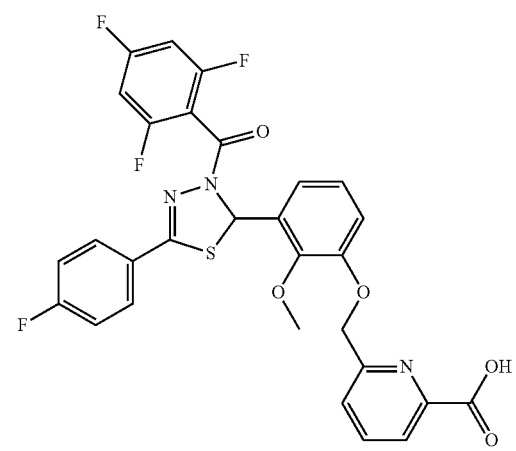 [SMILES: COc1c(OCc2cccc(C(=O)O)n2)cccc1C1SC(c2ccc(F)cc2)=NN1C(=O)c1c(F)cc(F)cc1F] | 598.1 |
| 168 | 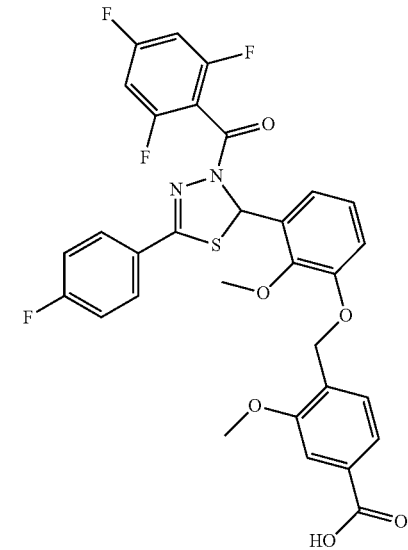 [SMILES: COc1cc(C(=O)O)ccc1COc1cccc(C2SC(c3ccc(F)cc3)=NN2C(=O)c2c(F)cc(F)cc2F)c1OC] | 627.1 |

TABLE 2-continued
| Example | Structure | MS (m/z) (M + 1)+ |
|---|---|---|
| 169 | 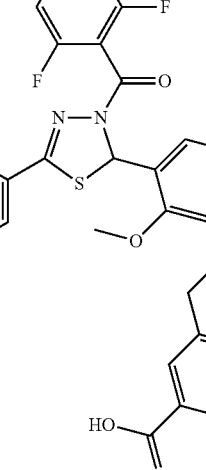 | 627.1 |
| 170 | 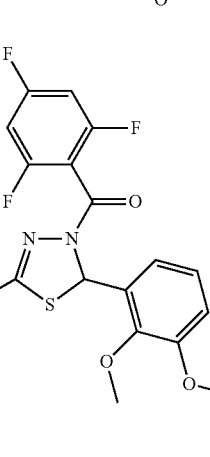 | 566.2 |
| 171 | 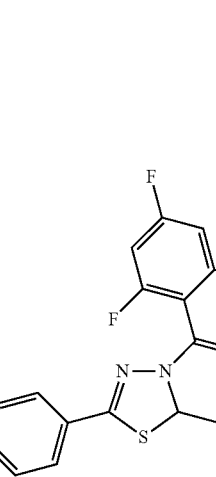 | 472.0 |

TABLE 2-continued

| Example | Structure | MS (m/z) (M + 1)+ |
|---|---|---|
| 172 | 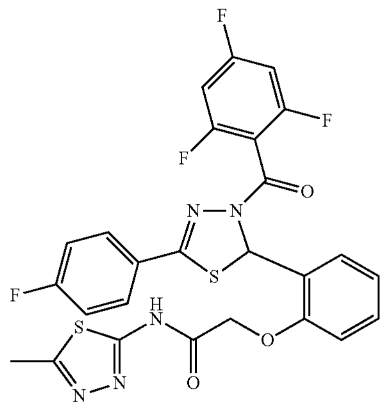 [SMILES: Cc1nnc(NC(=O)COc2ccccc2C2SC(c3ccc(F)cc3)=NN2C(=O)c2c(F)cc(F)cc2F)s1] | 588.1 |
| 173 | 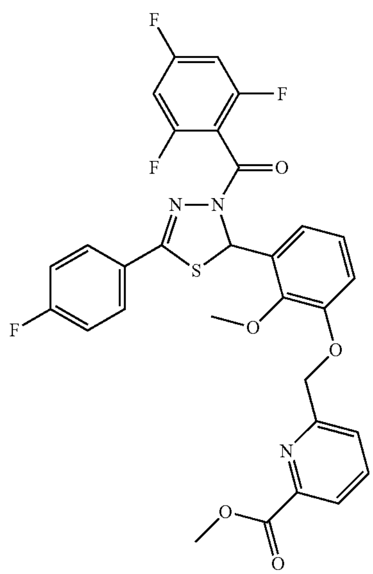 [SMILES: COC(=O)c1cccc(COc2cccc(C3SC(c4ccc(F)cc4)=NN3C(=O)c3c(F)cc(F)cc3F)c2OC)n1] | 612.2 |
| 174 | 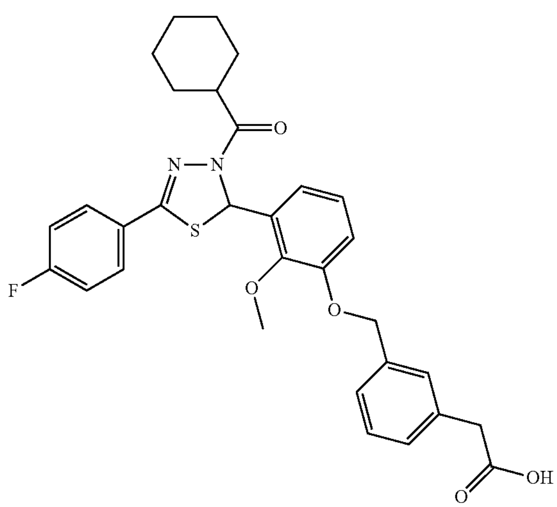 [SMILES: COc1c(OCc2cccc(CC(=O)O)c2)cccc1C1SC(c2ccc(F)cc2)=NN1C(=O)C1CCCCC1] | 563.2 |

TABLE 2-continued
| Example | Structure | MS (m/z) (M + 1)+ |
|---|---|---|
| 175 | 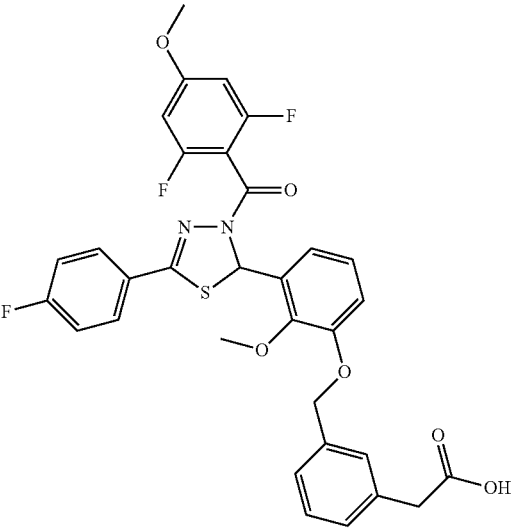 [SMILES: COc1cc(F)c(C(=O)N2N=C(c3ccc(F)cc3)SC2c2cccc(OCc3cccc(CC(=O)O)c3)c2OC)c(F)c1] | 623.2 |
| 176 | 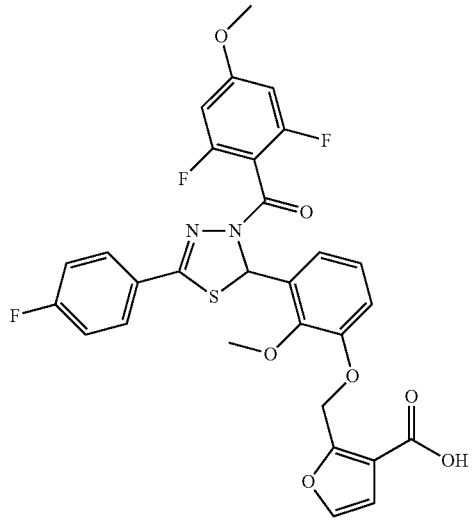 [SMILES: COc1cc(F)c(C(=O)N2N=C(c3ccc(F)cc3)SC2c2cccc(OCc3occc3C(=O)O)c2OC)c(F)c1] | 599.1 |
| 177 | 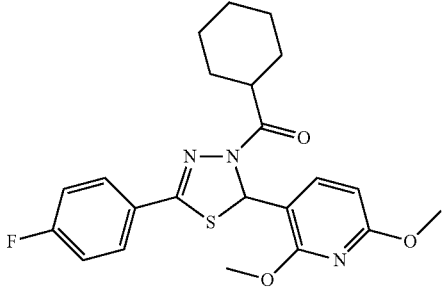 [SMILES: COc1ccc(C2SC(c3ccc(F)cc3)=NN2C(=O)C2CCCCC2)c(OC)n1] | 430.1 |

TABLE 2-continued

| Example | Structure | MS (m/z) (M + 1)+ |
|---|---|---|
| 178 | 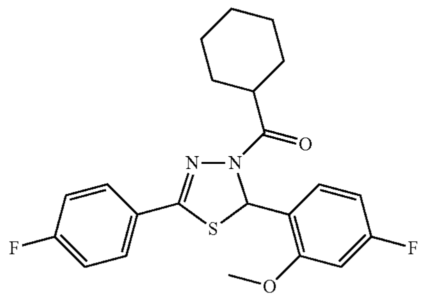 [SMILES: COc1cc(F)ccc1C1SC(c2ccc(F)cc2)=NN1C(=O)C1CCCCC1] | 417.1 |
| 179 | 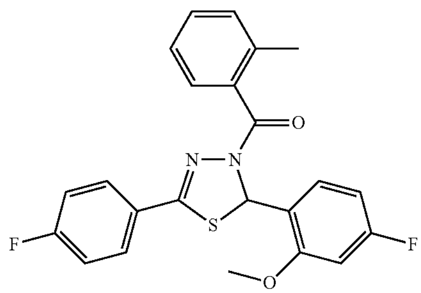 [SMILES: COc1cc(F)ccc1C1SC(c2ccc(F)cc2)=NN1C(=O)c1ccccc1C] | 425.0 |
| 180 | 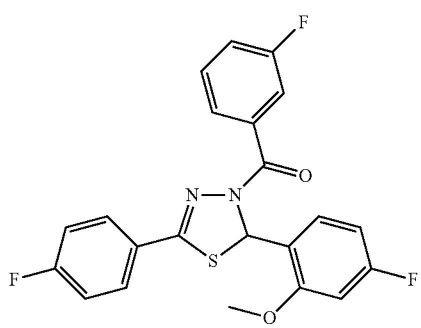 [SMILES: COc1cc(F)ccc1C1SC(c2ccc(F)cc2)=NN1C(=O)c1cccc(F)c1] | 429.1 |
| 181 | 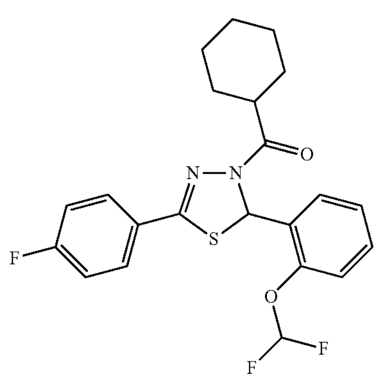 [SMILES: O=C(C1CCCCC1)N1N=C(c2ccc(F)cc2)SC1c1ccccc1OC(F)F] | 435.1 |

TABLE 2-continued
| Example | Structure | MS (m/z) (M + 1)+ |
|---------|-----------|-------------------|
| 182 | 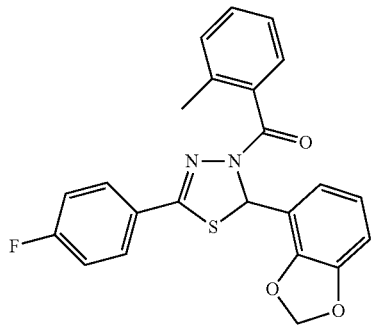 [SMILES: Cc1ccccc1C(=O)N1N=C(c2ccc(F)cc2)SC1c1cccc2c1OCO2] | 421.0 |
| 183 | 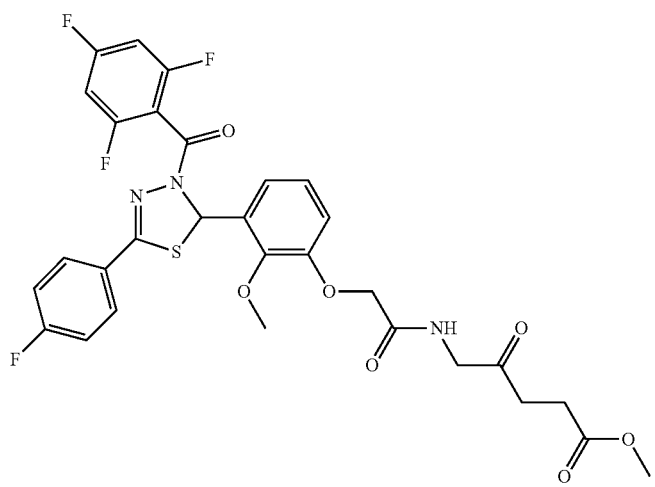 [SMILES: COC(=O)CCC(=O)CNC(=O)COc1cccc(C2SC(c3ccc(F)cc3)=NN2C(=O)c2c(F)cc(F)cc2F)c1OC] | 648.2 |
| 184 | 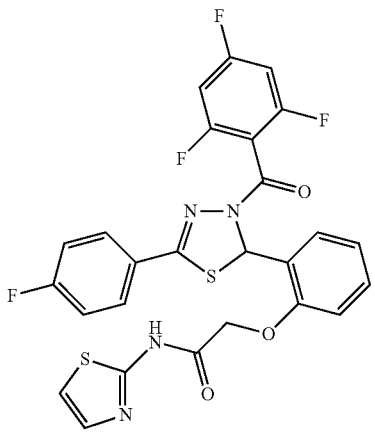 [SMILES: O=C(COc1ccccc1C1SC(c2ccc(F)cc2)=NN1C(=O)c1c(F)cc(F)cc1F)Nc1nccs1] | 573.1 |

TABLE 2-continued
| Example | Structure | MS (m/z) (M + 1)+ |
|---|---|---|
| 185 | 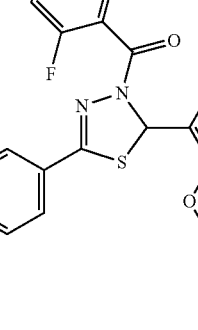 | 615.2 |
| 186 | 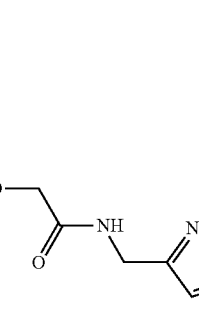 | 696.2 |
| 187 | 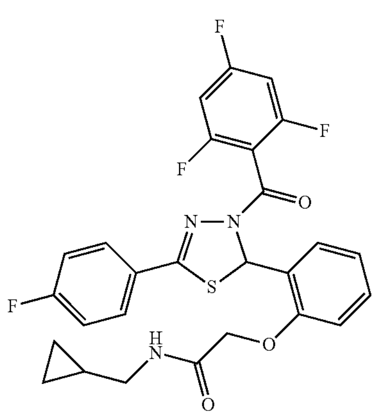 [SMILES: O=C(COc1ccccc1C1SC(c2ccc(F)cc2)=NN1C(=O)c1c(F)cc(F)cc1F)NCC1CC1] | 544.2 |

TABLE 2-continued

| Example | Structure | MS (m/z) (M + 1)+ |
|---|---|---|
| 188 | 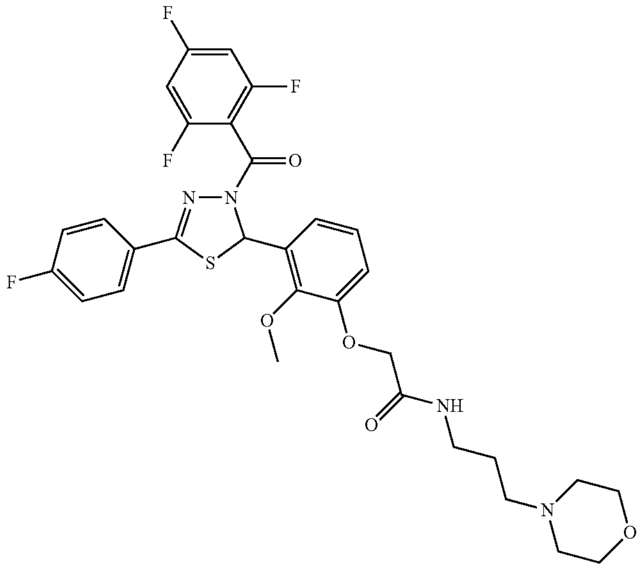 [SMILES: COc1c(OCC(=O)NCCCN2CCOCC2)cccc1C1SC(c2ccc(F)cc2)=NN1C(=O)c1c(F)cc(F)cc1F] | 647.2 |
| 189 | 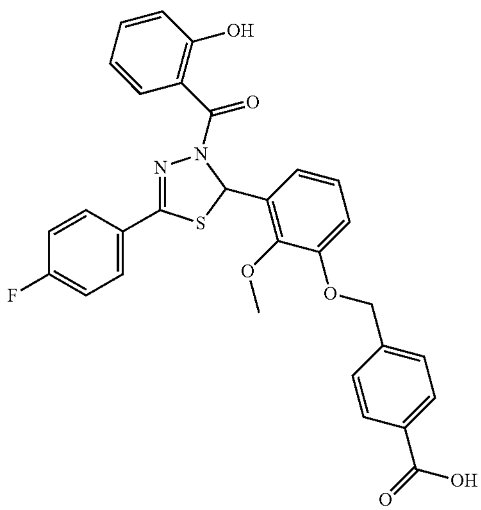 [SMILES: COc1c(OCc2ccc(C(=O)O)cc2)cccc1C1SC(c2ccc(F)cc2)=NN1C(=O)c1ccccc1O] | 559.1 |
| 190 | 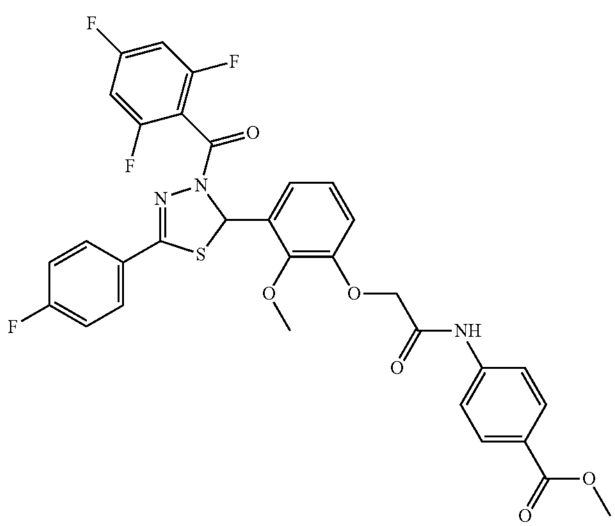 [SMILES: COC(=O)c1ccc(NC(=O)COc2cccc(C3SC(c4ccc(F)cc4)=NN3C(=O)c3c(F)cc(F)cc3F)c2OC)cc1] | 654.2 |

TABLE 2-continued
| Example | Structure | MS (m/z) (M + 1)+ |
|---|---|---|
| 191 | 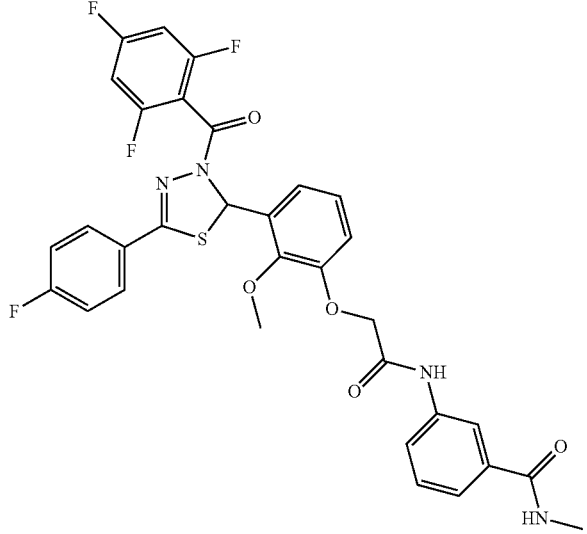 [SMILES: CNC(=O)c1cccc(NC(=O)COc2cccc(C3SC(c4ccc(F)cc4)=NN3C(=O)c3c(F)cc(F)cc3F)c2OC)c1] | 653.2 |
| 192 | 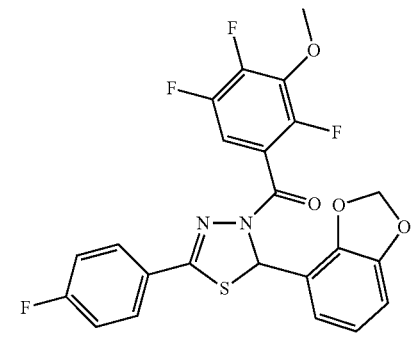 [SMILES: COc1c(F)c(F)cc(C(=O)N2N=C(c3ccc(F)cc3)SC2c2cccc3c2OCO3)c1F] | 491.0 |
| 193 | 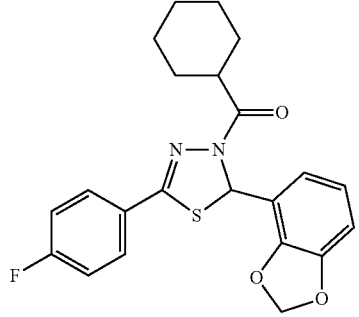 [SMILES: O=C(C1CCCCC1)N1N=C(c2ccc(F)cc2)SC1c1cccc2c1OCO2] | 413.1 |

TABLE 2-continued
| Example | Structure | MS (m/z) (M + 1)+ |
|---|---|---|
| 194 | 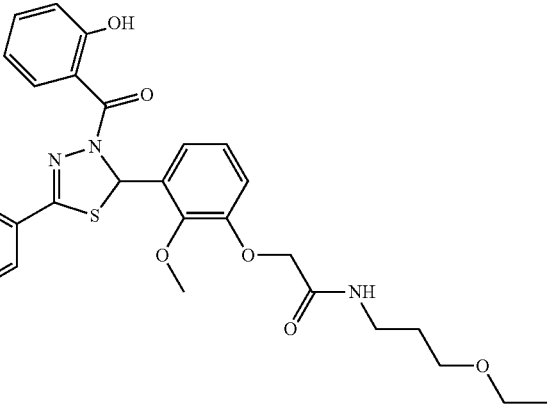 | 568.2 |
| 195 | 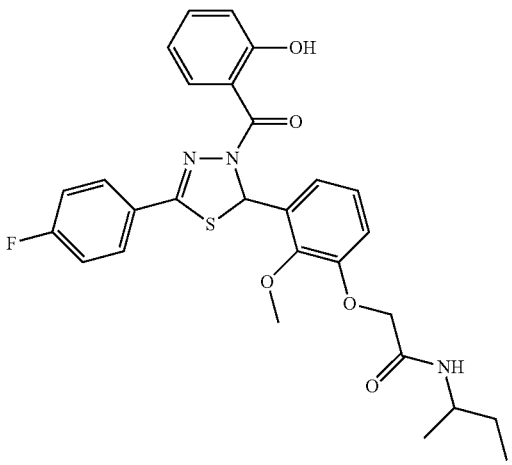 [SMILES: CCC(C)NC(=O)COc1cccc(C2SC(c3ccc(F)cc3)=NN2C(=O)c2ccccc2O)c1OC] | 538.2 |
| 196 | 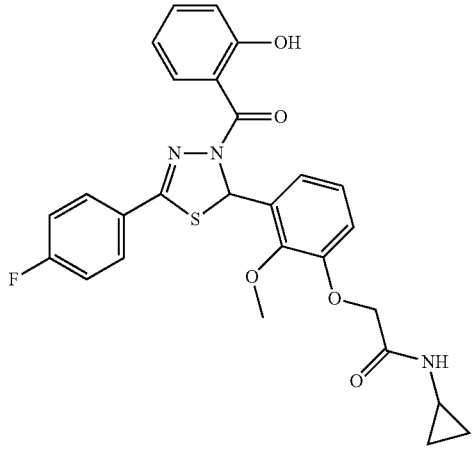 [SMILES: COc1c(OCC(=O)NC2CC2)cccc1C1SC(c2ccc(F)cc2)=NN1C(=O)c1ccccc1O] | 522.1 |

TABLE 2-continued
| Example | Structure | MS (m/z) (M + 1)+ |
|---|---|---|
| 197 | 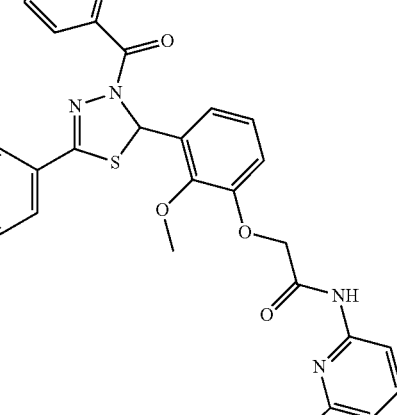 | 587.2 |
| 198 | 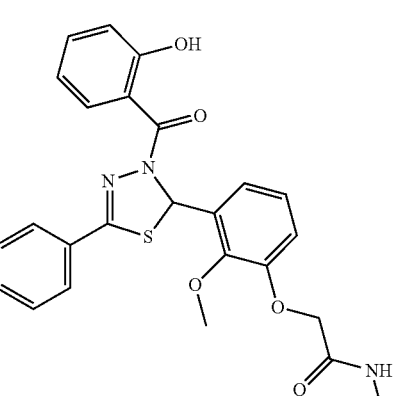 | 522.1 |
| 199 | 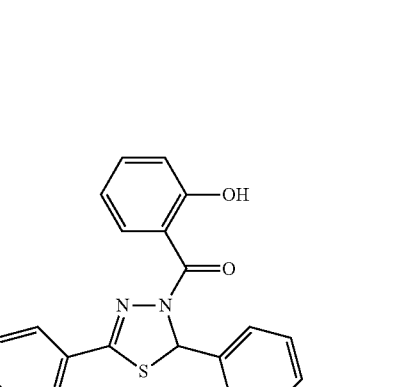 | 524.2 |

TABLE 2-continued
| Example | Structure | MS (m/z) (M + 1)+ |
|---|---|---|
| 200 | 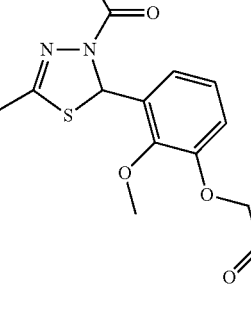 | 538.2 |
| 201 | 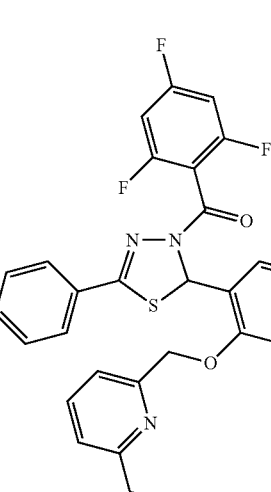 | 568.1 |
| 202 | 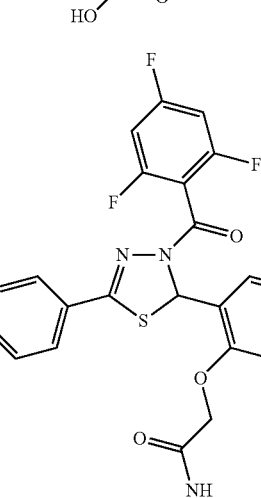 | 585.2 |

TABLE 2-continued

| Example | Structure | MS (m/z) (M + 1)+ |
|---|---|---|
| 203 | 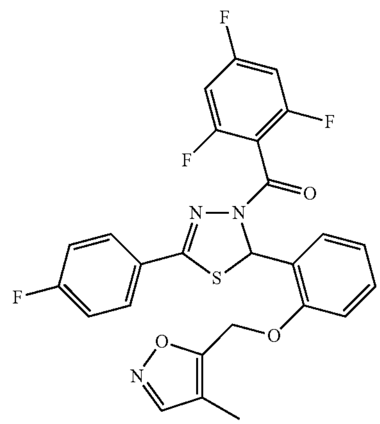 [SMILES: Cc1cnoc1COc1ccccc1C1SC(c2ccc(F)cc2)=NN1C(=O)c1c(F)cc(F)cc1F] | 528.0 |
| 204 | 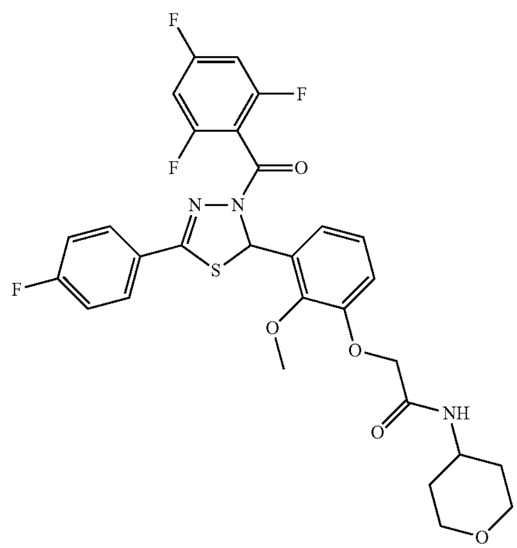 [SMILES: COc1c(OCC(=O)NC2CCOCC2)cccc1C1SC(c2ccc(F)cc2)=NN1C(=O)c1c(F)cc(F)cc1F] | 604.2 |
| 205 | 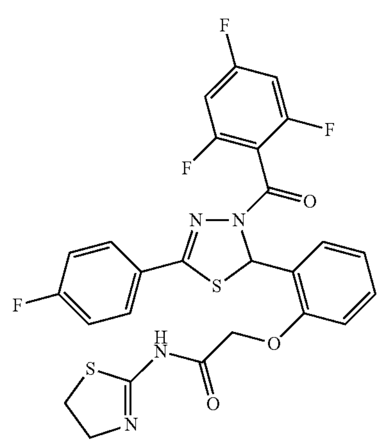 [SMILES: O=C(COc1ccccc1C1SC(c2ccc(F)cc2)=NN1C(=O)c1c(F)cc(F)cc1F)NC1=NCCS1] | 575.1 |

TABLE 2-continued
| Example | Structure | MS (m/z) (M + 1)+ |
|---|---|---|
| 206 | 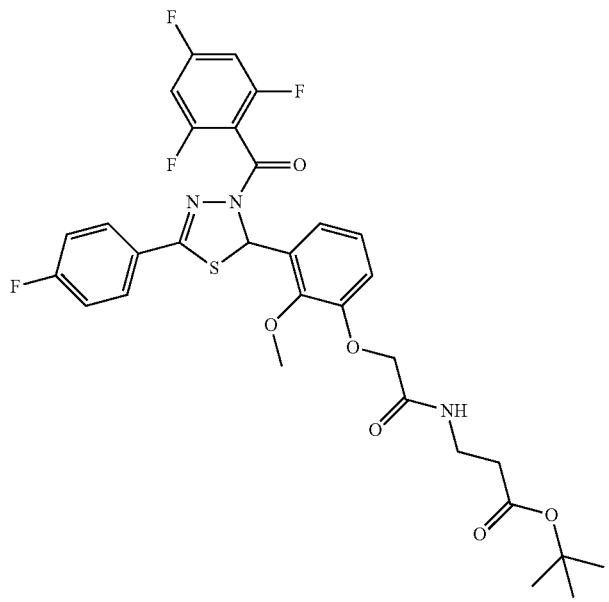 [SMILES: COc1c(OCC(=O)NCCC(=O)OC(C)(C)C)cccc1C1SC(c2ccc(F)cc2)=NN1C(=O)c1c(F)cc(F)cc1F] | 670.2 [M + 23] |
| 207 | 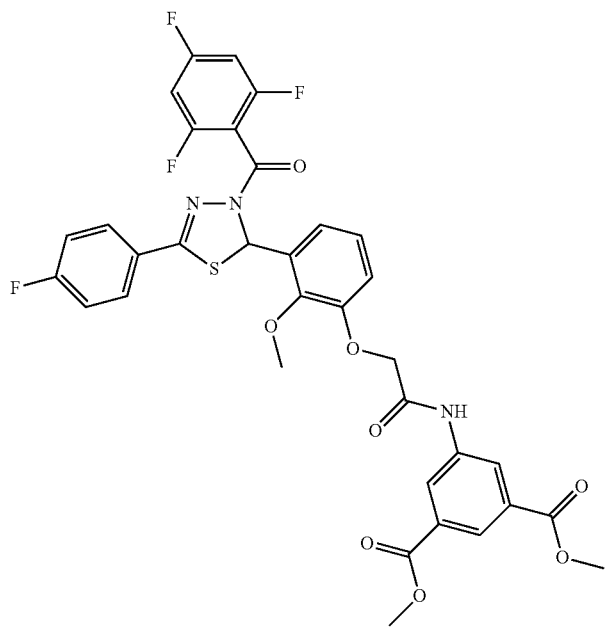 [SMILES: COC(=O)c1cc(NC(=O)COc2cccc(C3SC(c4ccc(F)cc4)=NN3C(=O)c3c(F)cc(F)cc3F)c2OC)cc(C(=O)OC)c1] | 712.2 |

TABLE 2-continued

| Example | Structure | MS (m/z) (M + 1)+ |
|---|---|---|
| 208 | 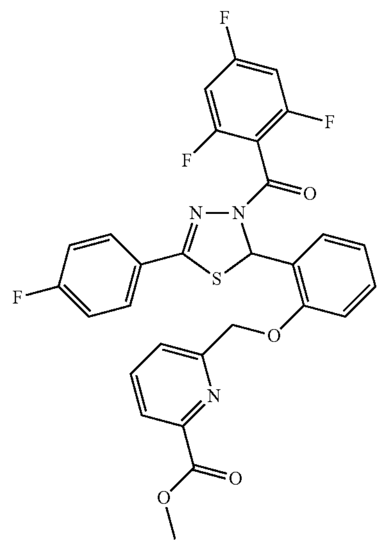 [SMILES: COC(=O)c1cccc(COc2ccccc2C2SC(c3ccc(F)cc3)=NN2C(=O)c2c(F)cc(F)cc2F)n1] | 582.0 |
| 209 | 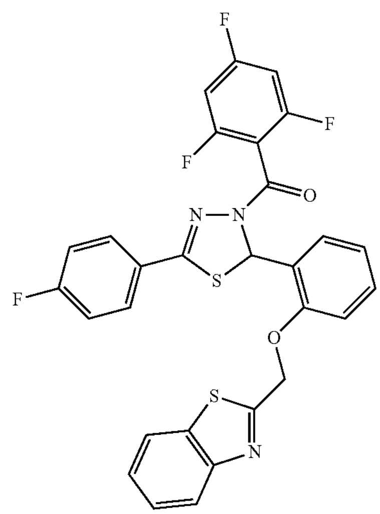 [SMILES: O=C(c1c(F)cc(F)cc1F)N1N=C(c2ccc(F)cc2)SC1c1ccccc1OCc1nc2ccccc2s1] | 580.0 |
| 210 | 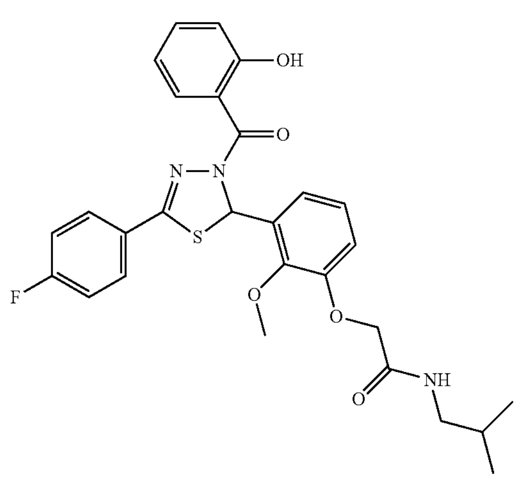 [SMILES: COc1c(OCC(=O)NCC(C)C)cccc1C1SC(c2ccc(F)cc2)=NN1C(=O)c1ccccc1O] | 538.2 |

TABLE 2-continued
| Example | Structure | MS (m/z) (M + 1)+ |
|---|---|---|
| 211 | 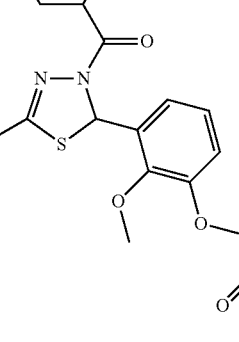 | 540.1 |
| 212 | 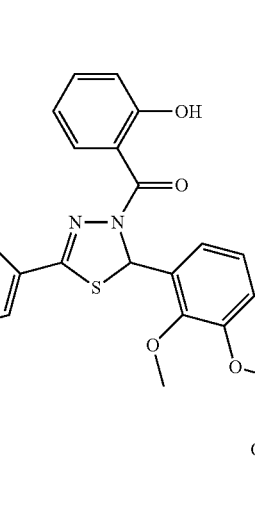 | 550.2 |
| 213 | 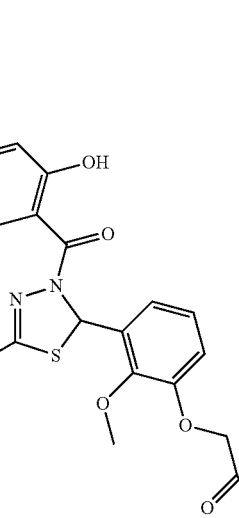 | 553.1 |

TABLE 2-continued
| Example | Structure | MS (m/z) (M + 1)+ |
|---|---|---|
| 214 | 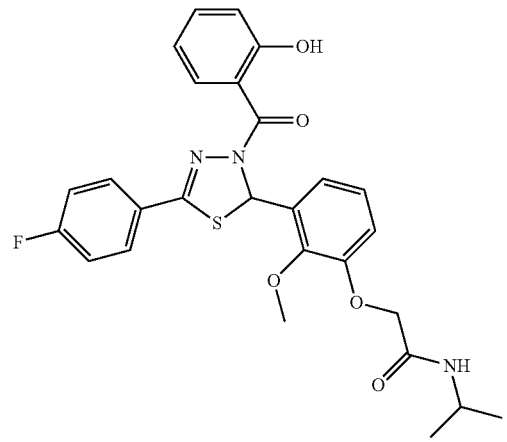 [SMILES: COc1c(OCC(=O)NC(C)C)cccc1C1SC(c2ccc(F)cc2)=NN1C(=O)c1ccccc1O] | 524.2 |
| 215 | 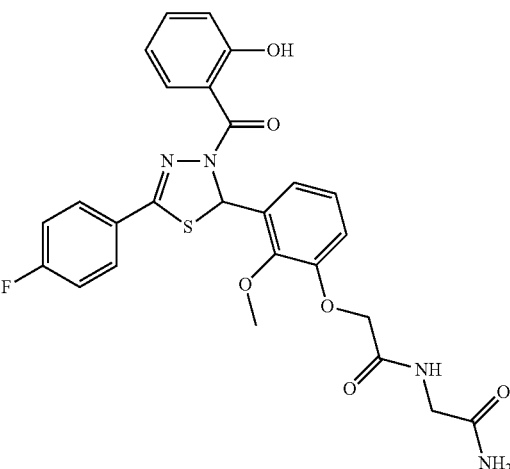 [SMILES: COc1c(OCC(=O)NCC(N)=O)cccc1C1SC(c2ccc(F)cc2)=NN1C(=O)c1ccccc1O] | 539.1 |
| 216 | 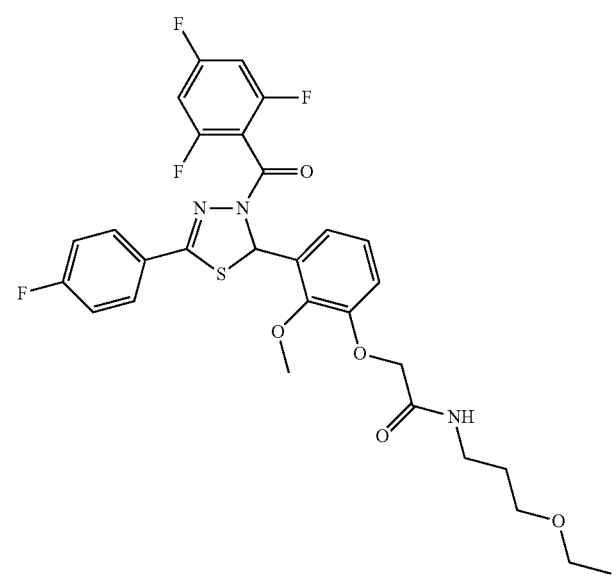 [SMILES: CCOCCCNC(=O)COc1cccc(C2SC(c3ccc(F)cc3)=NN2C(=O)c2c(F)cc(F)cc2F)c1OC] | 606.2 |

TABLE 2-continued

| Example | Structure | MS (m/z) (M + 1)+ |
|---|---|---|
| 217 | 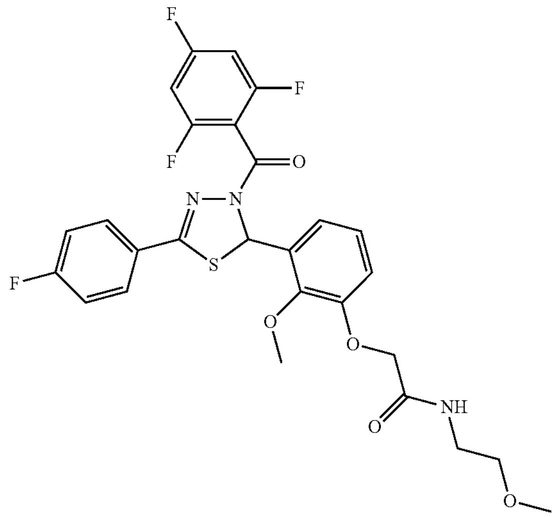 [SMILES: COCCNC(=O)COc1cccc(C2SC(c3ccc(F)cc3)=NN2C(=O)c2c(F)cc(F)cc2F)c1OC] | 578.1 |
| 218 | 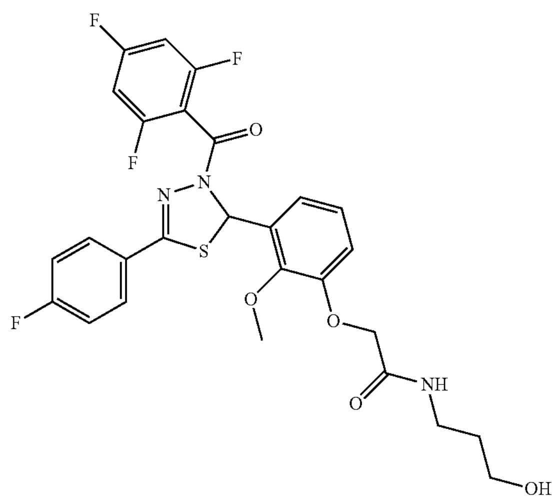 [SMILES: COc1c(OCC(=O)NCCCO)cccc1C1SC(c2ccc(F)cc2)=NN1C(=O)c1c(F)cc(F)cc1F] | 578.1 |
| 219 | 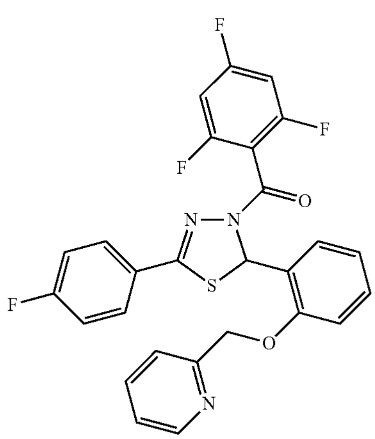 [SMILES: O=C(c1c(F)cc(F)cc1F)N1N=C(c2ccc(F)cc2)SC1c1ccccc1OCc1ccccn1] | 524.0 |

TABLE 2-continued
| Example | Structure | MS (m/z) (M + 1)+ |
|---|---|---|
| 220 | 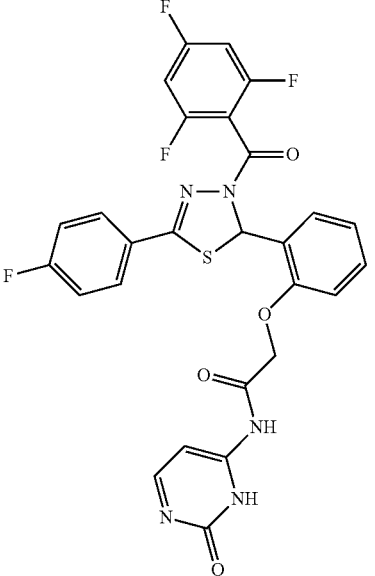 [SMILES: O=C(COc1ccccc1C1SC(c2ccc(F)cc2)=NN1C(=O)c1c(F)cc(F)cc1F)Nc1ccnc(=O)[nH]1] | 584.2 |
| 221 | 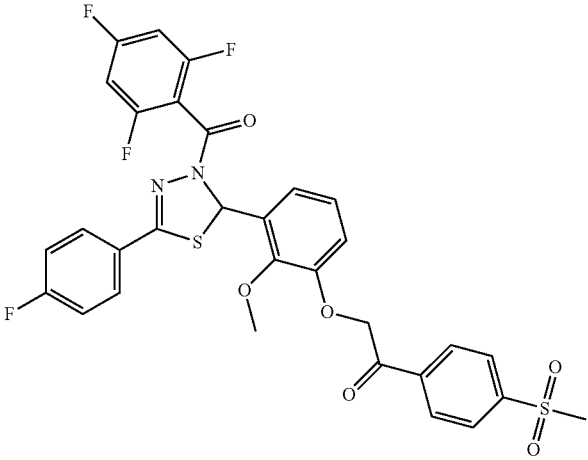 [SMILES: COc1c(OCC(=O)c2ccc(S(C)(=O)=O)cc2)cccc1C1SC(c2ccc(F)cc2)=NN1C(=O)c1c(F)cc(F)cc1F] | 659.1 |
| 222 | 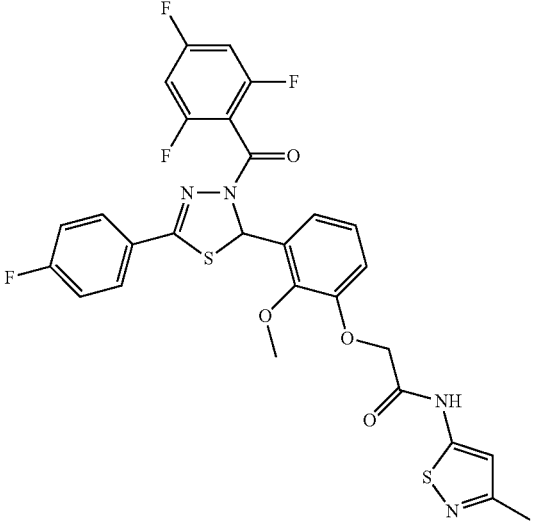 [SMILES: COc1c(OCC(=O)Nc2cc(C)ns2)cccc1C1SC(c2ccc(F)cc2)=NN1C(=O)c1c(F)cc(F)cc1F] | 617.1 |

TABLE 2-continued

| Example | Structure | MS (m/z) (M + 1)+ |
|---|---|---|
| 223 | 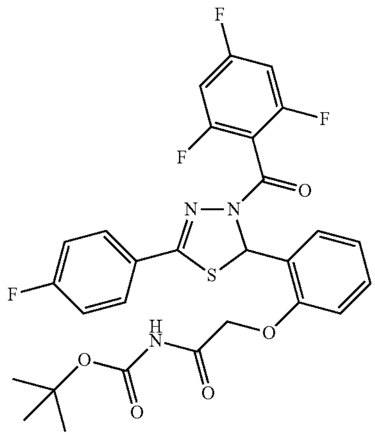 [SMILES: CC(C)(C)OC(=O)NC(=O)COc1ccccc1C1SC(c2ccc(F)cc2)=NN1C(=O)c1c(F)cc(F)cc1F] | 640.2 [M + 23] |
| 224 | 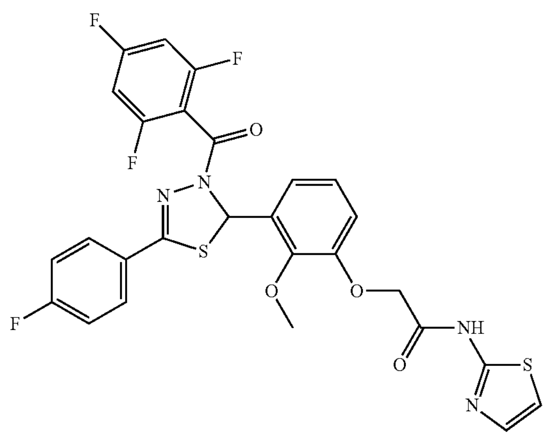 [SMILES: COc1c(OCC(=O)Nc2nccs2)cccc1C1SC(c2ccc(F)cc2)=NN1C(=O)c1c(F)cc(F)cc1F] | 603.1 |
| 225 | 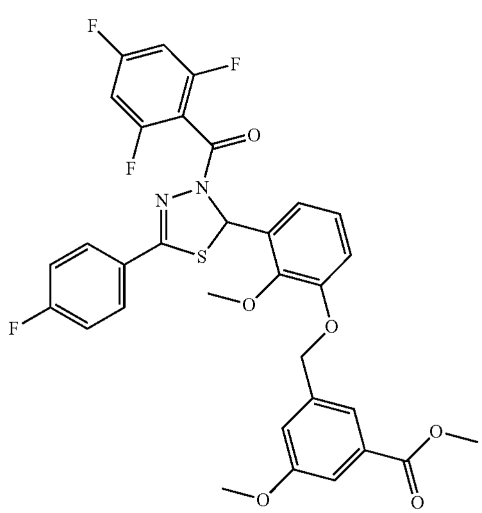 [SMILES: COC(=O)c1cc(COc2cccc(C3SC(c4ccc(F)cc4)=NN3C(=O)c3c(F)cc(F)cc3F)c2OC)cc(OC)c1] | 641.1 |

TABLE 2-continued

| Example | Structure | MS (m/z) (M + 1)+ |
|---|---|---|
| 226 | 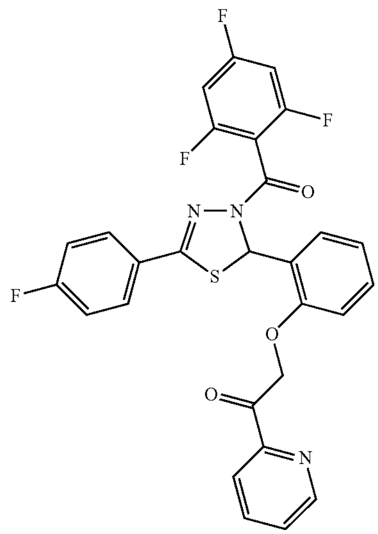 [SMILES: O=C(COc1ccccc1C1SC(c2ccc(F)cc2)=NN1C(=O)c1c(F)cc(F)cc1F)c1ccccn1] | 552.1 |
| 227 | 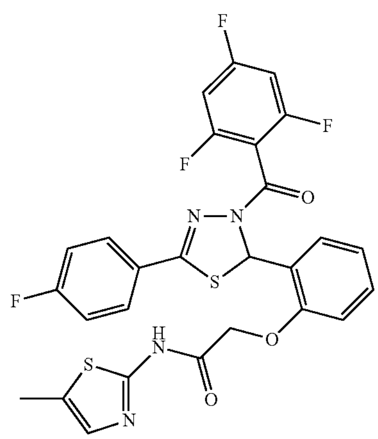 [SMILES: Cc1cnc(NC(=O)COc2ccccc2C2SC(c3ccc(F)cc3)=NN2C(=O)c2c(F)cc(F)cc2F)s1] | 587.1 |
| 228 | 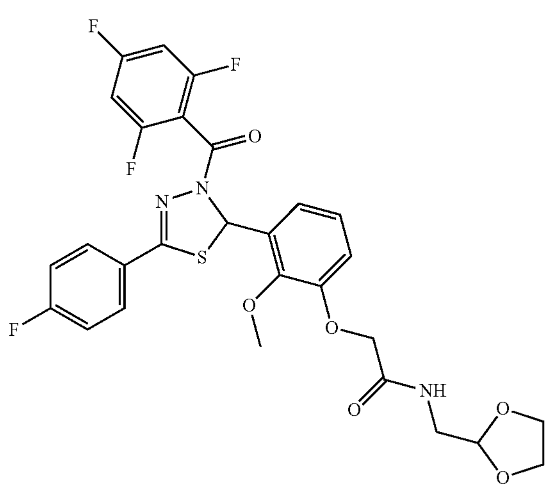 [SMILES: COc1c(OCC(=O)NCC2OCCO2)cccc1C1SC(c2ccc(F)cc2)=NN1C(=O)c1c(F)cc(F)cc1F] | 606.1 |

TABLE 2-continued

| Example | Structure | MS (m/z) (M + 1)+ |
|---------|-----------|-------------------|
| 229 | 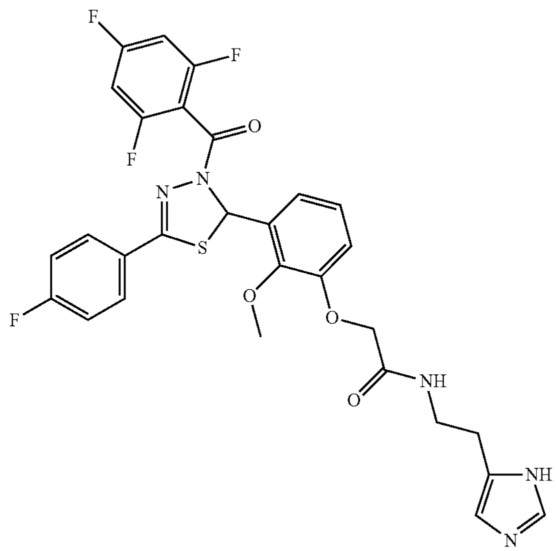 [SMILES: COc1c(OCC(=O)NCCc2cnc[nH]2)cccc1C1SC(c2ccc(F)cc2)=NN1C(=O)c1c(F)cc(F)cc1F] | 614.1 |
| 230 | 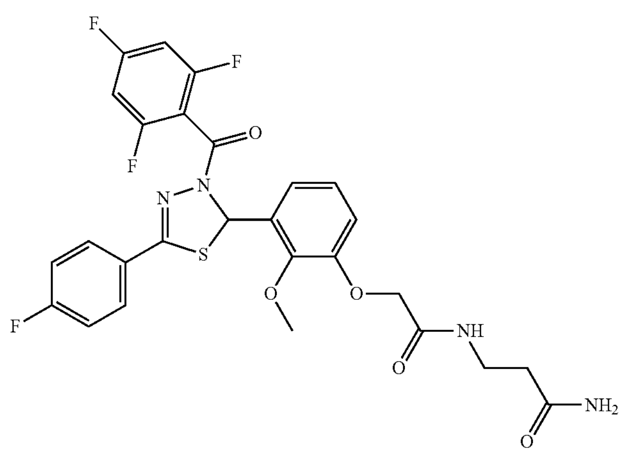 [SMILES: COc1c(OCC(=O)NCCC(N)=O)cccc1C1SC(c2ccc(F)cc2)=NN1C(=O)c1c(F)cc(F)cc1F] | 591.1 |
| 231 | 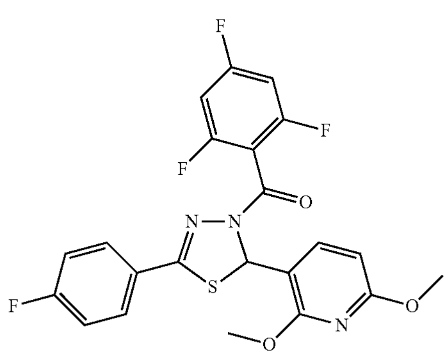 [SMILES: COc1ccc(C2SC(c3ccc(F)cc3)=NN2C(=O)c2c(F)cc(F)cc2F)c(OC)n1] | 478.0 |

TABLE 2-continued

| Example | Structure | MS (m/z) (M + 1)+ |
|---|---|---|
| 232 | 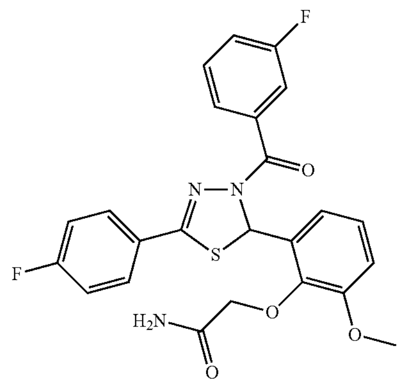 [SMILES: COc1cccc(C2SC(c3ccc(F)cc3)=NN2C(=O)c2cccc(F)c2)c1OCC(N)=O] | 484.0 |
| 233 | 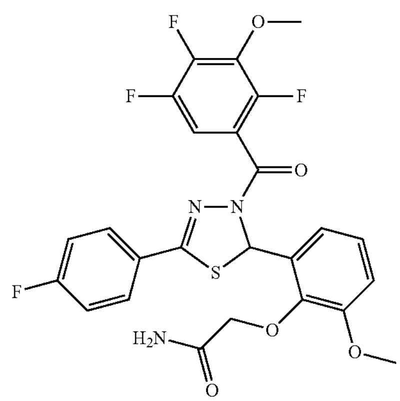 [SMILES: COc1cccc(C2SC(c3ccc(F)cc3)=NN2C(=O)c2cc(F)c(F)c(OC)c2F)c1OCC(N)=O] | 550.0 |
| 234 | 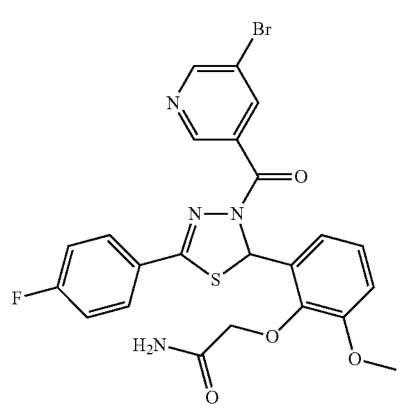 [SMILES: COc1cccc(C2SC(c3ccc(F)cc3)=NN2C(=O)c2cncc(Br)c2)c1OCC(N)=O] | 544.9 |

TABLE 2-continued

| Example | Structure | MS (m/z) (M + 1)+ |
|---|---|---|
| 235 | 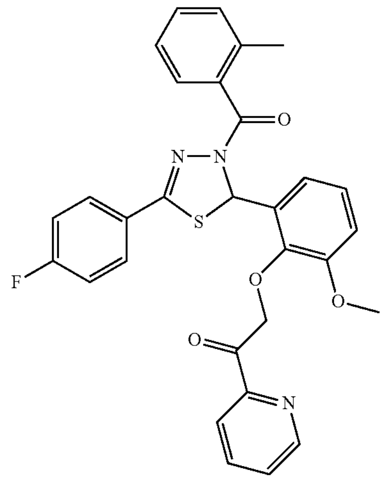 [SMILES: COc1cccc(C2SC(c3ccc(F)cc3)=NN2C(=O)c2ccccc2C)c1OCC(=O)c1ccccn1] | 542.1 |
| 236 | 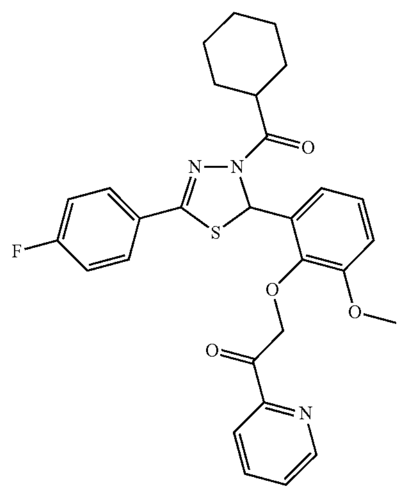 [SMILES: COc1cccc(C2SC(c3ccc(F)cc3)=NN2C(=O)C2CCCCC2)c1OCC(=O)c1ccccn1] | 534.1 |
| 237 | 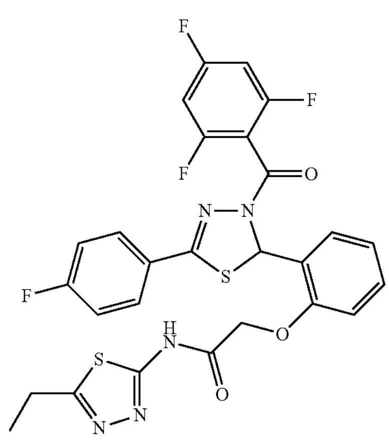 [SMILES: CCc1nnc(NC(=O)COc2ccccc2C2SC(c3ccc(F)cc3)=NN2C(=O)c2c(F)cc(F)cc2F)s1] | 602.1 |

TABLE 2-continued

| Example | Structure | MS (m/z) (M + 1)+ |
|---|---|---|
| 238 | 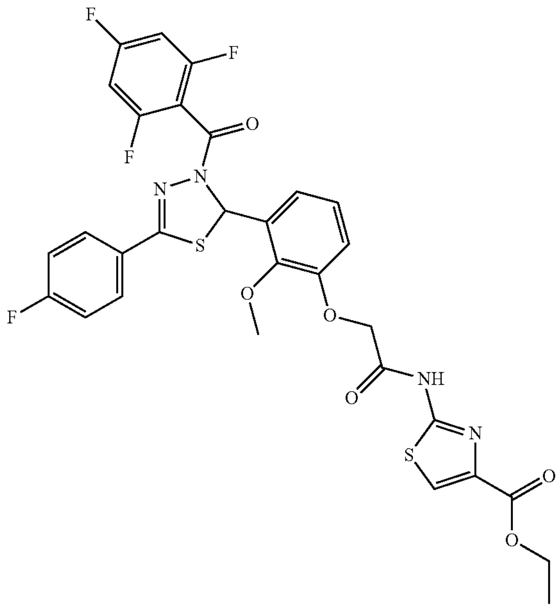 [SMILES: CCOC(=O)c1csc(NC(=O)COc2cccc(C3SC(c4ccc(F)cc4)=NN3C(=O)c3c(F)cc(F)cc3F)c2OC)n1] | 675.2 |
| 239 | 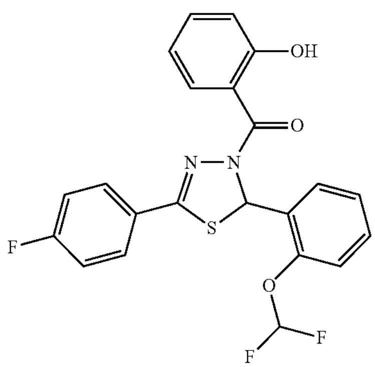 [SMILES: O=C(c1ccccc1O)N1N=C(c2ccc(F)cc2)SC1c1ccccc1OC(F)F] | 445.0 |
| 240 | 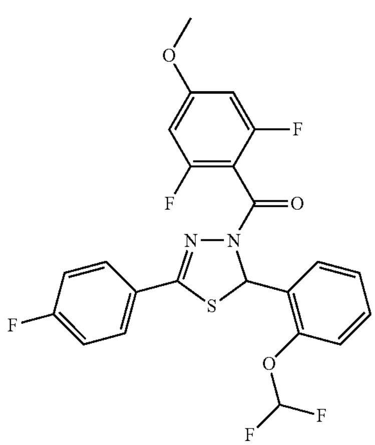 [SMILES: COc1cc(F)c(C(=O)N2N=C(c3ccc(F)cc3)SC2c2ccccc2OC(F)F)c(F)c1] | 495.1 |

TABLE 2-continued
| Example | Structure | MS (m/z) (M + 1)+ |
|---|---|---|
| 241 | 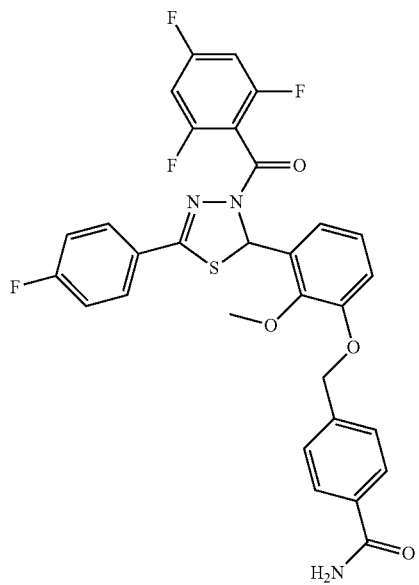 [SMILES: COc1c(OCc2ccc(C(N)=O)cc2)cccc1C1SC(c2ccc(F)cc2)=NN1C(=O)c1c(F)cc(F)cc1F] | 596.1 |
| 242 | 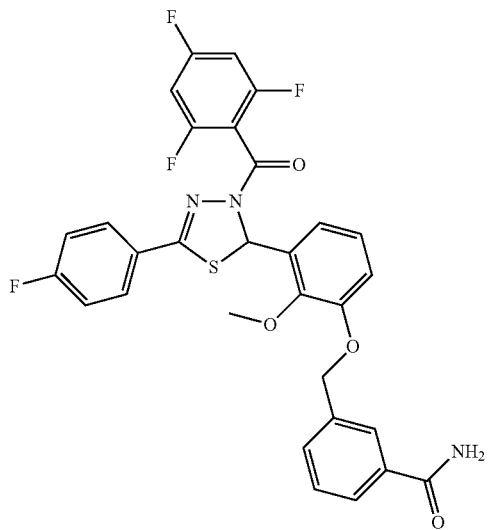 [SMILES: COc1c(OCc2cccc(C(N)=O)c2)cccc1C1SC(c2ccc(F)cc2)=NN1C(=O)c1c(F)cc(F)cc1F] | 596.2 |

TABLE 2-continued

| Example | Structure | MS (m/z) (M + 1)+ |
|---|---|---|
| 243 | 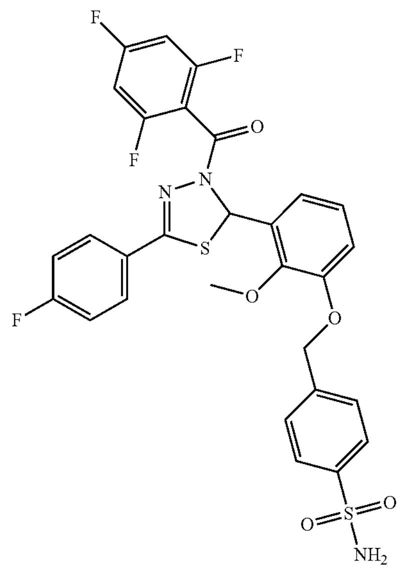 [SMILES: COc1c(OCc2ccc(S(N)(=O)=O)cc2)cccc1C1SC(c2ccc(F)cc2)=NN1C(=O)c1c(F)cc(F)cc1F] | 632.1 |
| 244 | 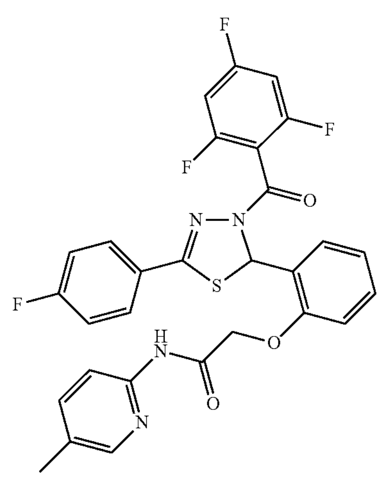 [SMILES: Cc1ccc(NC(=O)COc2ccccc2C2SC(c3ccc(F)cc3)=NN2C(=O)c2c(F)cc(F)cc2F)nc1] | 581.1 |
| 245 | 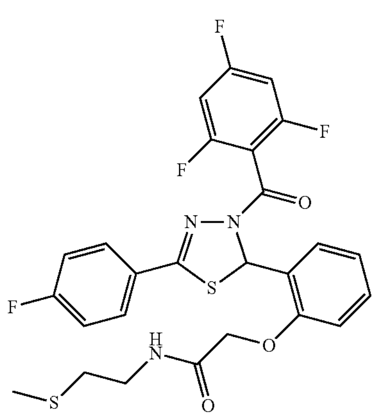 [SMILES: CSCCNC(=O)COc1ccccc1C1SC(c2ccc(F)cc2)=NN1C(=O)c1c(F)cc(F)cc1F] | 564.1 |

TABLE 2-continued

| Example | Structure | MS (m/z) (M + 1)+ |
|---|---|---|
| 246 | 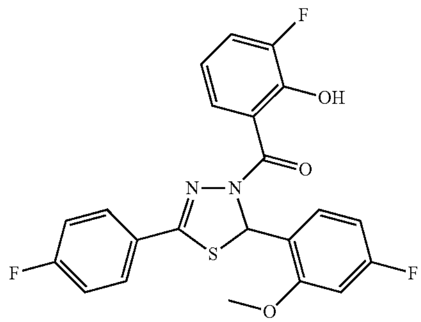 [SMILES: COc1cc(F)ccc1C1SC(c2ccc(F)cc2)=NN1C(=O)c1cccc(F)c1O] | 445.0 |
| 247 | 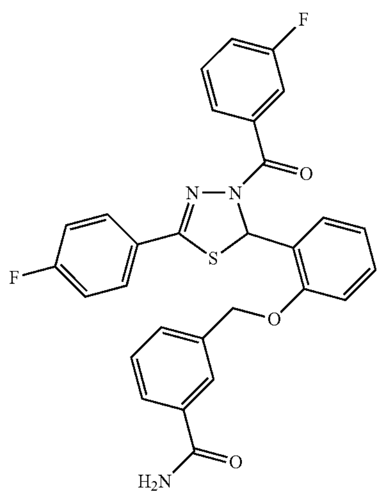 [SMILES: NC(=O)c1cccc(COc2ccccc2C2SC(c3ccc(F)cc3)=NN2C(=O)c2cccc(F)c2)c1] | 530.0 |
| 248 | 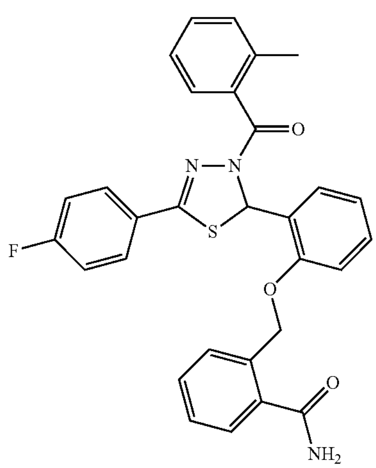 [SMILES: Cc1ccccc1C(=O)N1N=C(c2ccc(F)cc2)SC1c1ccccc1OCc1ccccc1C(N)=O] | 526.1 |

TABLE 2-continued

| Example | Structure | MS (m/z) (M + 1)+ |
|---|---|---|
| 249 | 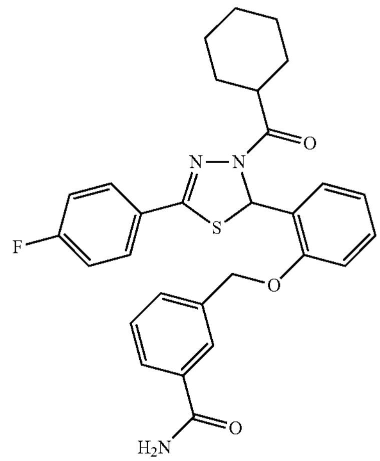 [SMILES: NC(=O)c1cccc(COc2ccccc2C2SC(c3ccc(F)cc3)=NN2C(=O)C2CCCCC2)c1] | 518.1 |
| 250 | 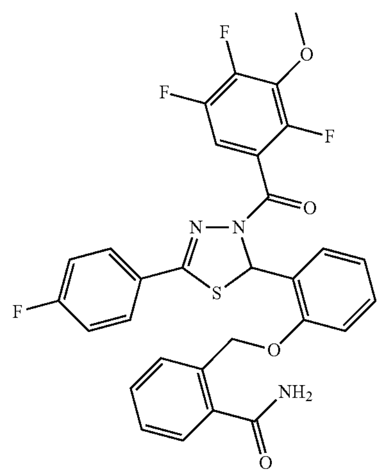 [SMILES: COc1c(F)c(F)cc(C(=O)N2N=C(c3ccc(F)cc3)SC2c2ccccc2OCc2ccccc2C(N)=O)c1F] | 596.1 |
| 251 | 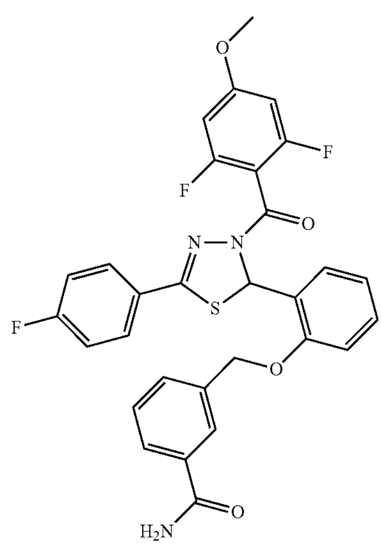 [SMILES: COc1cc(F)c(C(=O)N2N=C(c3ccc(F)cc3)SC2c2ccccc2OCc2cccc(C(N)=O)c2)c(F)c1] | 578.1 |

TABLE 2-continued

| Example | Structure | MS (m/z) (M + 1)+ |
|---|---|---|
| 252 | 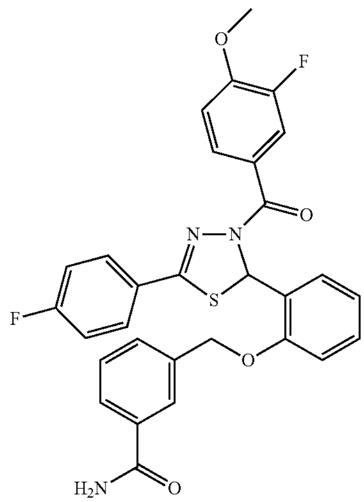 [SMILES: COc1ccc(C(=O)N2N=C(c3ccc(F)cc3)SC2c2ccccc2OCc2cccc(C(N)=O)c2)cc1F] | 560.1 |
| 253 | 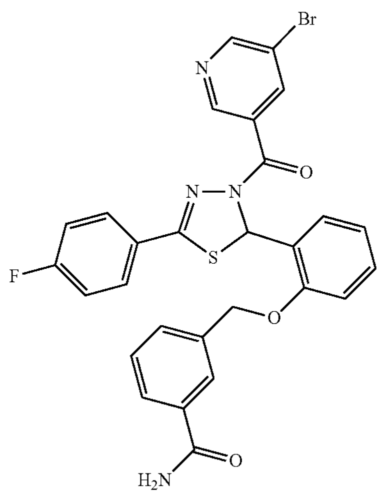 [SMILES: NC(=O)c1cccc(COc2ccccc2C2SC(c3ccc(F)cc3)=NN2C(=O)c2cncc(Br)c2)c1] | 591.0 |
| 254 | 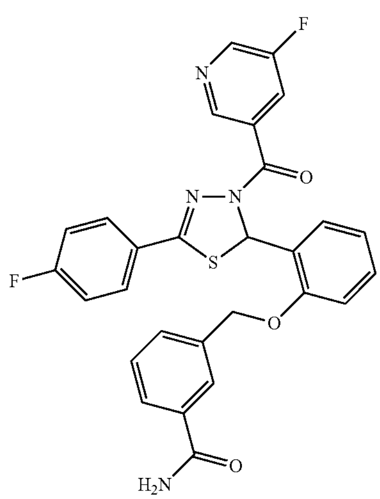 [SMILES: NC(=O)c1cccc(COc2ccccc2C2SC(c3ccc(F)cc3)=NN2C(=O)c2cncc(F)c2)c1] | 531.0 |

TABLE 2-continued

| Example | Structure | MS (m/z) (M + 1)+ |
|---|---|---|
| 255 | 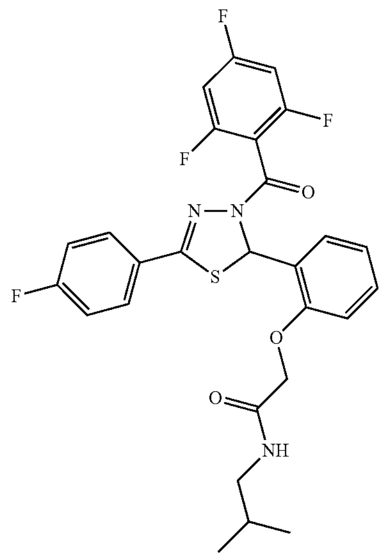 [SMILES: CC(C)CNC(=O)COc1ccccc1C1SC(c2ccc(F)cc2)=NN1C(=O)c1c(F)cc(F)cc1F] | 546.2 |
| 256 | 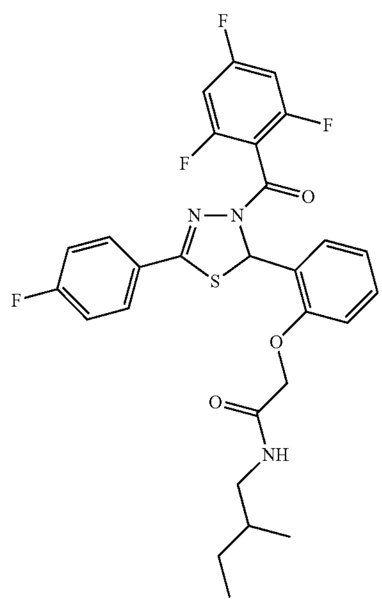 [SMILES: CCC(C)CNC(=O)COc1ccccc1C1SC(c2ccc(F)cc2)=NN1C(=O)c1c(F)cc(F)cc1F] | 560.2 |
| 257 | 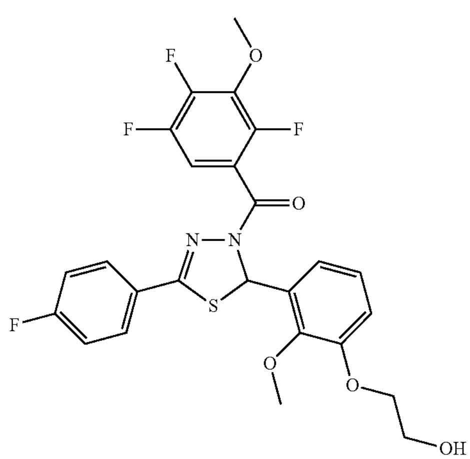 [SMILES: COc1c(OCCO)cccc1C1SC(c2ccc(F)cc2)=NN1C(=O)c1cc(F)c(F)c(OC)c1F] | 537.1 |

TABLE 2-continued
| Example | Structure | MS (m/z) (M + 1)+ |
|---|---|---|
| 258 | 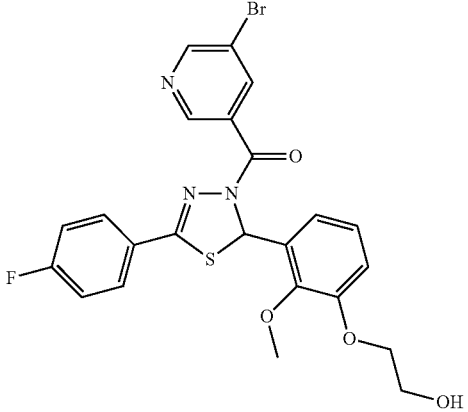 [SMILES: COc1c(OCCO)cccc1C1SC(c2ccc(F)cc2)=NN1C(=O)c1cncc(Br)c1] | 532.1 |
| 259 | 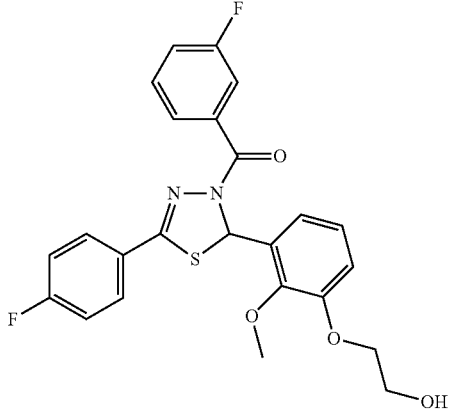 [SMILES: COc1c(OCCO)cccc1C1SC(c2ccc(F)cc2)=NN1C(=O)c1cccc(F)c1] | 471.1 |
| 260 | 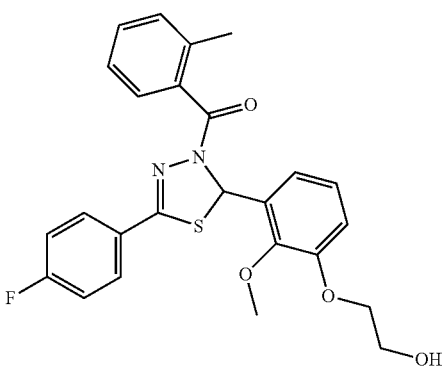 [SMILES: COc1c(OCCO)cccc1C1SC(c2ccc(F)cc2)=NN1C(=O)c1ccccc1C] | 468.2 |

TABLE 2-continued
| Example | Structure | MS (m/z) (M + 1)+ |
|---|---|---|
| 261 | 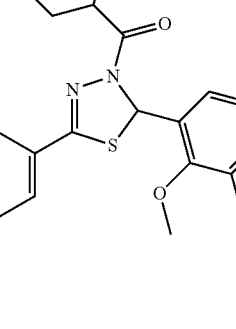 | 472.2 |
| 262 | 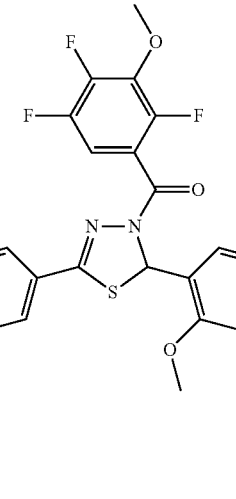 | 550.2 |
| 263 | 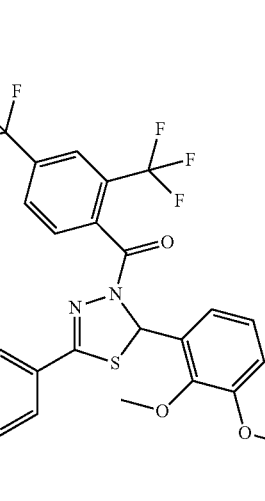 | 679.2 |

TABLE 2-continued
| Example | Structure | MS (m/z) (M + 1)+ |
|---|---|---|
| 264 | 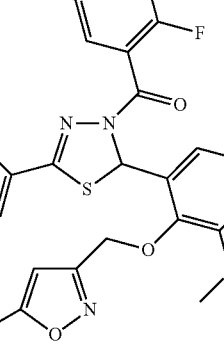 | 588.0 |
| 265 | 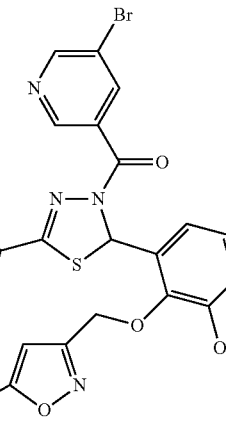 | 583.0 |
| 266 | 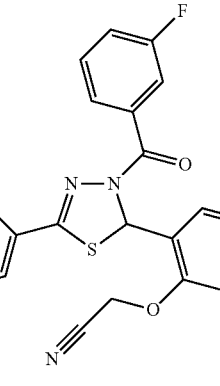 | 436.0 |
| 267 | 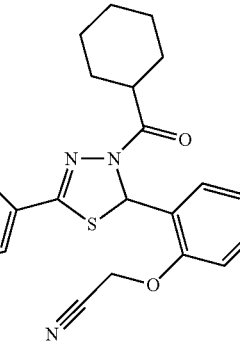 | 424.1 |

TABLE 2-continued

| Example | Structure | MS (m/z) (M + 1)+ |
|---------|-----------|-------------------|
| 268 | 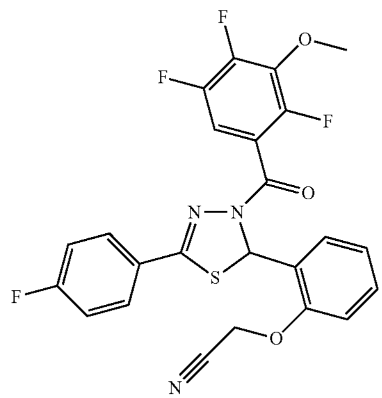 [SMILES: COc1c(F)c(F)cc(C(=O)N2N=C(c3ccc(F)cc3)SC2c2ccccc2OCC#N)c1F] | 502.0 |
| 269 | 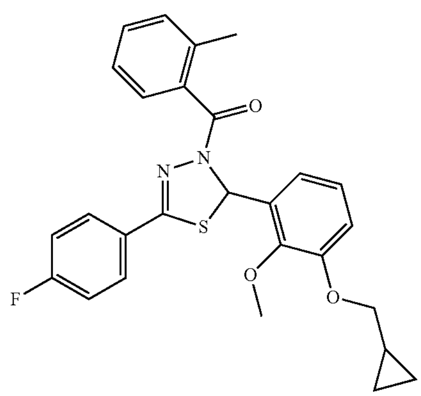 [SMILES: COc1c(OCC2CC2)cccc1C1SC(c2ccc(F)cc2)=NN1C(=O)c1ccccc1C] | 477.0 |
| 270 | 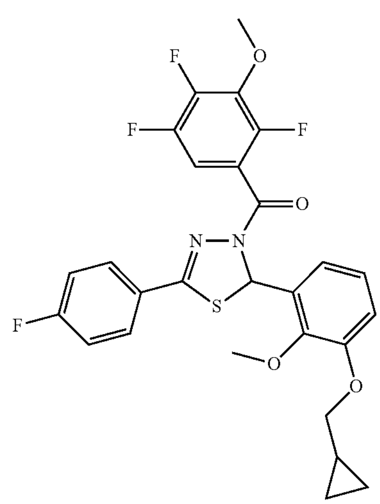 [SMILES: COc1c(OCC2CC2)cccc1C1SC(c2ccc(F)cc2)=NN1C(=O)c1cc(F)c(F)c(OC)c1F] | 547.1 |

TABLE 2-continued
| Example | Structure | MS (m/z) (M + 1)+ |
|---|---|---|
| 271 | 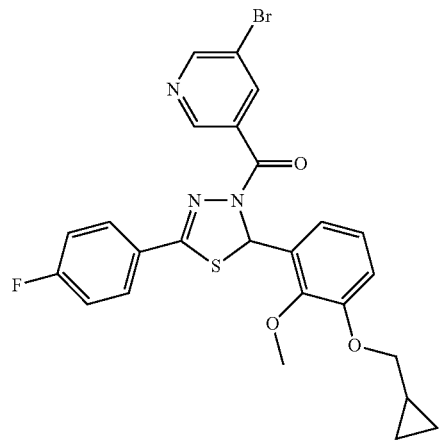 [SMILES: COc1c(OCC2CC2)cccc1C1SC(c2ccc(F)cc2)=NN1C(=O)c1cncc(Br)c1] | 542.0 |
| 272 | 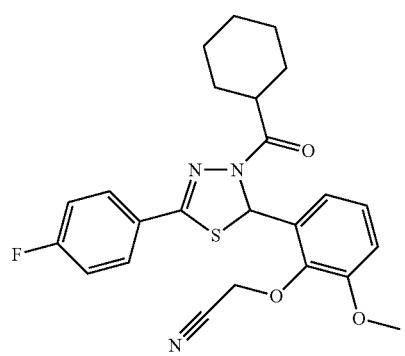 [SMILES: COc1cccc(C2SC(c3ccc(F)cc3)=NN2C(=O)C2CCCCC2)c1OCC#N] | 454.1 |
| 273 | 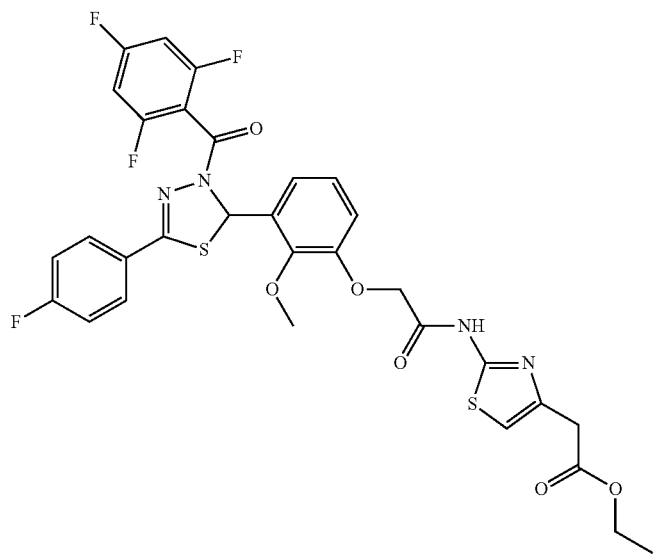 [SMILES: CCOC(=O)Cc1csc(NC(=O)COc2cccc(C3SC(c4ccc(F)cc4)=NN3C(=O)c3c(F)cc(F)cc3F)c2OC)n1] | 689.1 |

TABLE 2-continued
| Example | Structure | MS (m/z) (M + 1)+ |
|---|---|---|
| 274 | 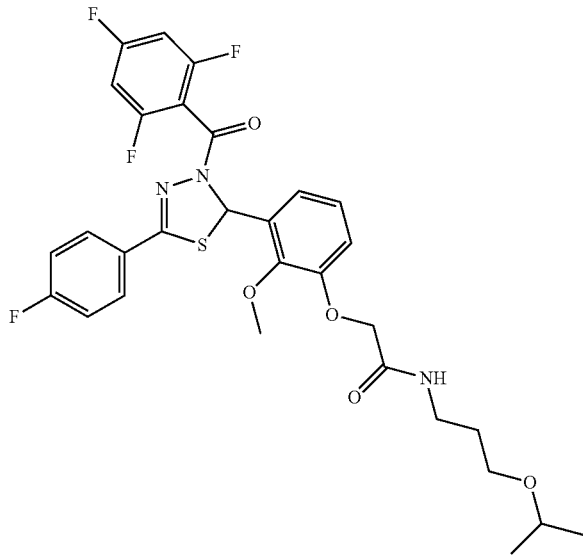 [SMILES: COc1c(OCC(=O)NCCCOC(C)C)cccc1C1SC(c2ccc(F)cc2)=NN1C(=O)c1c(F)cc(F)cc1F] | 620.2 |
| 275 | 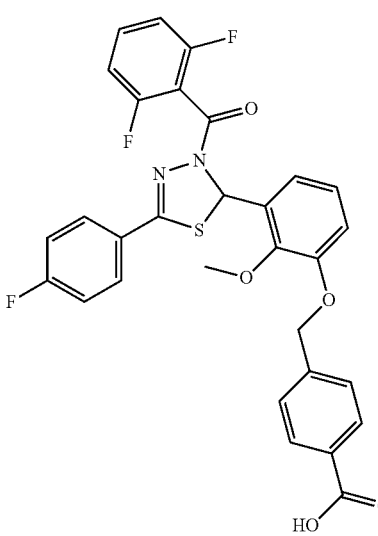 | 579.2 |
| 276 | 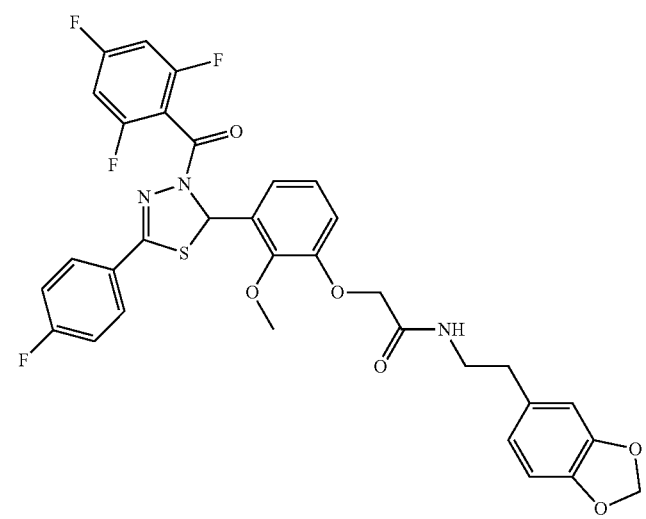 [SMILES: COc1c(OCC(=O)NCCc2ccc3c(c2)OCO3)cccc1C1SC(c2ccc(F)cc2)=NN1C(=O)c1c(F)cc(F)cc1F] | 668.2 |

TABLE 2-continued

| Example | Structure | MS (m/z) (M + 1)+ |
|---|---|---|
| 277 | 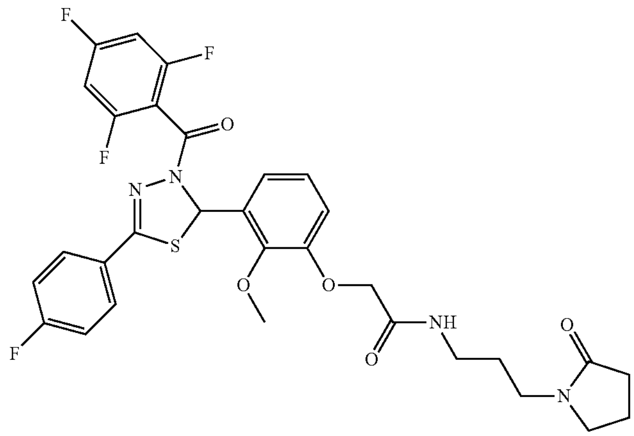 [SMILES: COc1c(OCC(=O)NCCCN2CCCC2=O)cccc1C1SC(c2ccc(F)cc2)=NN1C(=O)c1c(F)cc(F)cc1F] | 645.2 |
| 278 | 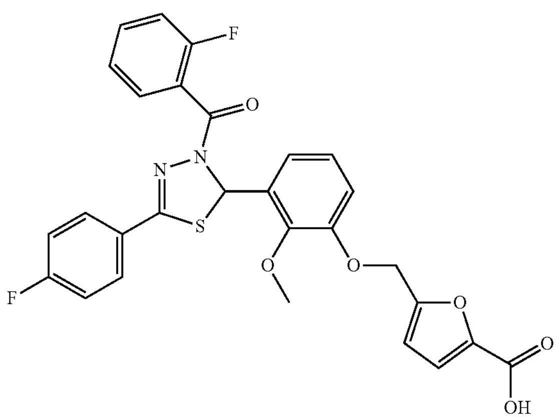 [SMILES: COc1c(OCc2ccc(C(=O)O)o2)cccc1C1SC(c2ccc(F)cc2)=NN1C(=O)c1ccccc1F] | 551.1 |
| 279 | 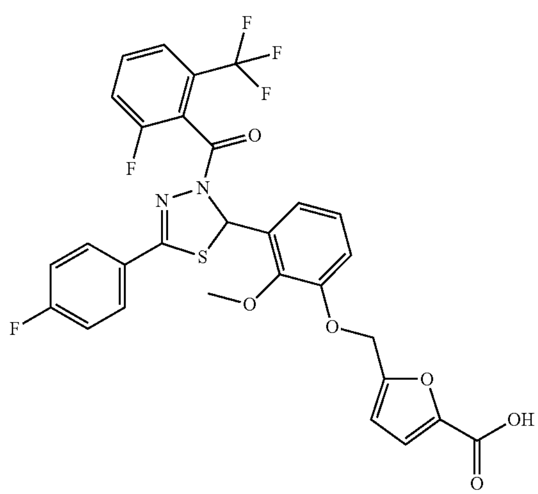 [SMILES: COc1c(OCc2ccc(C(=O)O)o2)cccc1C1SC(c2ccc(F)cc2)=NN1C(=O)c1c(F)cccc1C(F)(F)F] | 619.2 |

TABLE 2-continued

| Example | Structure | MS (m/z) (M + 1)+ |
|---|---|---|
| 280 | 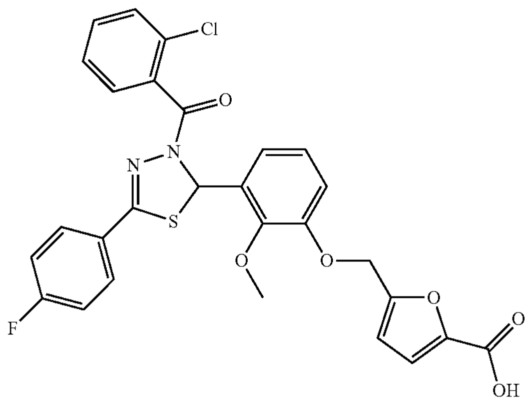 [SMILES: COc1c(OCc2ccc(C(=O)O)o2)cccc1C1SC(c2ccc(F)cc2)=NN1C(=O)c1ccccc1Cl] | 567.1 |
| 281 | 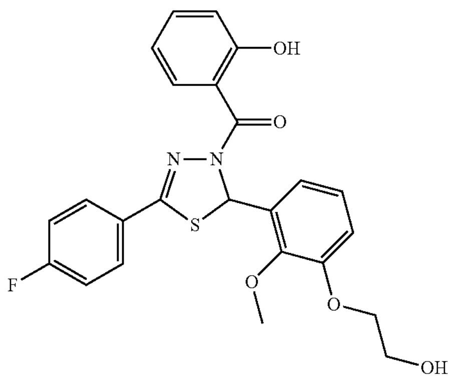 [SMILES: COc1c(OCCO)cccc1C1SC(c2ccc(F)cc2)=NN1C(=O)c1ccccc1O] | 469.1 |
| 282 | 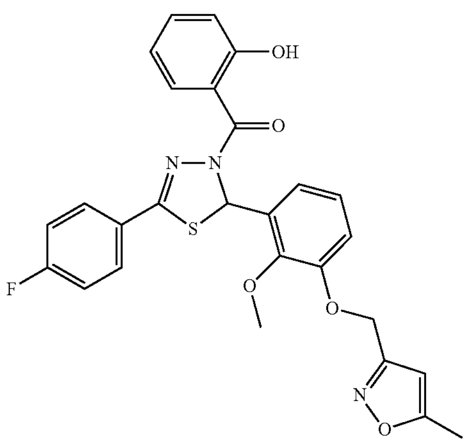 [SMILES: COc1c(OCc2cc(C)on2)cccc1C1SC(c2ccc(F)cc2)=NN1C(=O)c1ccccc1O] | 520.1 |
| 283 | 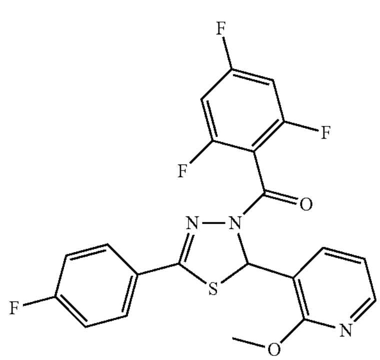 [SMILES: COc1ncccc1C1SC(c2ccc(F)cc2)=NN1C(=O)c1c(F)cc(F)cc1F] | 448.0 |

TABLE 2-continued

| Example | Structure | MS (m/z) (M + 1)+ |
|---------|-----------|-------------------|
| 284 | 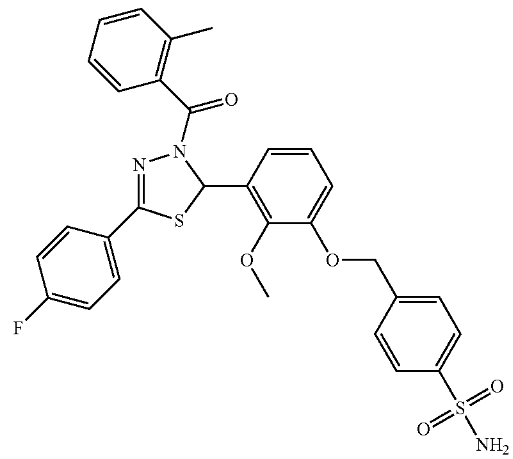 [SMILES: COc1c(OCc2ccc(S(N)(=O)=O)cc2)cccc1C1SC(c2ccc(F)cc2)=NN1C(=O)c1ccccc1C] | 592.0 |
| 285 | 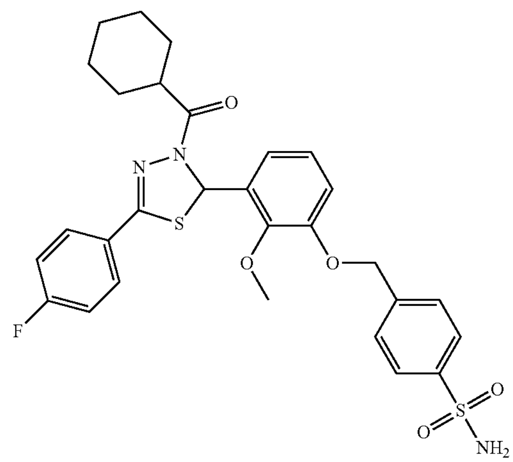 [SMILES: COc1c(OCc2ccc(S(N)(=O)=O)cc2)cccc1C1SC(c2ccc(F)cc2)=NN1C(=O)C1CCCCC1] | 584.1 |
| 286 | 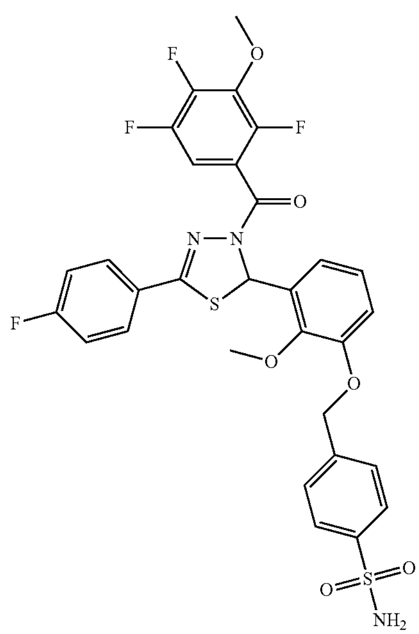 [SMILES: COc1c(OCc2ccc(S(N)(=O)=O)cc2)cccc1C1SC(c2ccc(F)cc2)=NN1C(=O)c1cc(F)c(F)c(OC)c1F] | 662.0 |

TABLE 2-continued

| Example | Structure | MS (m/z) (M + 1)+ |
|---|---|---|
| 287 | 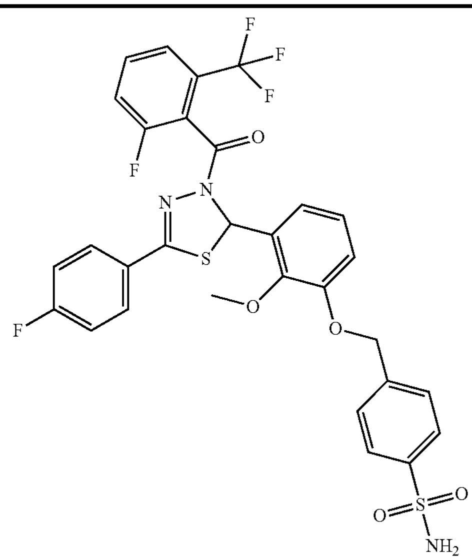 | 664.0 |
| 288 | 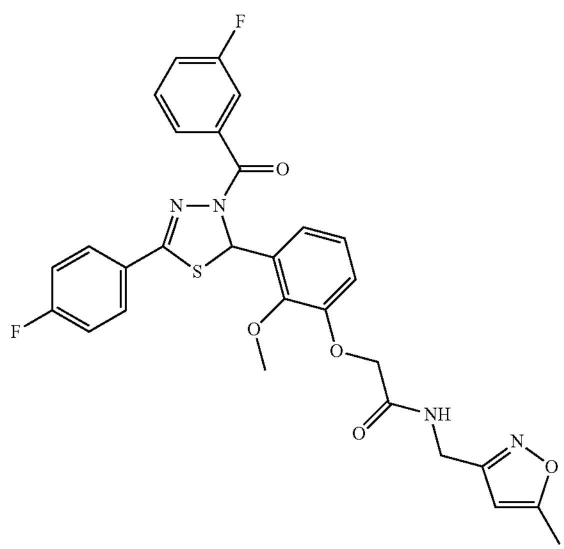 [SMILES: COc1c(OCC(=O)NCc2cc(C)on2)cccc1C1SC(c2ccc(F)cc2)=NN1C(=O)c1cccc(F)c1] | 579.1 |
| 289 | 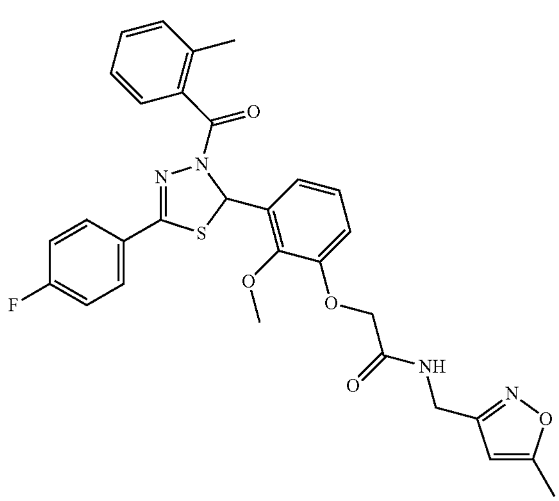 [SMILES: COc1c(OCC(=O)NCc2cc(C)on2)cccc1C1SC(c2ccc(F)cc2)=NN1C(=O)c1ccccc1C] | 575.0 |

TABLE 2-continued
| Example | Structure | MS (m/z) (M + 1)+ |
|---|---|---|
| 290 | 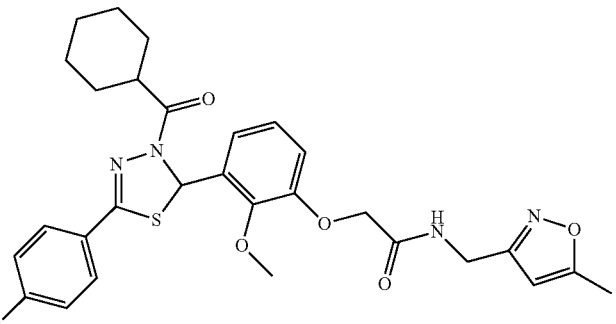 | 567.1 |
| 291 | 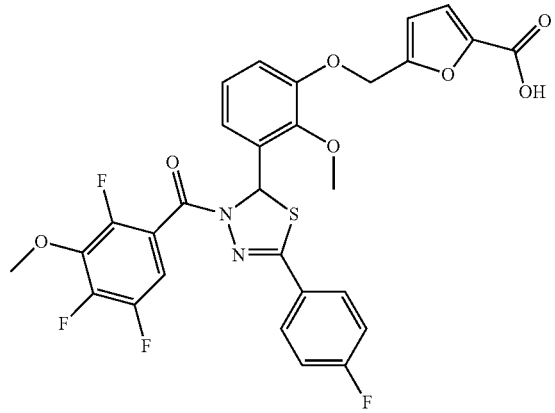 [SMILES: COc1c(OCc2ccc(C(=O)O)o2)cccc1C1SC(c2ccc(F)cc2)=NN1C(=O)c1cc(F)c(F)c(OC)c1F] | 617.2 |
| 292 | 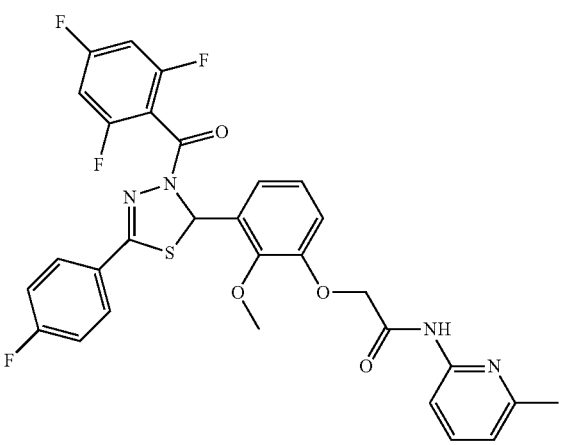 [SMILES: COc1c(OCC(=O)Nc2cccc(C)n2)cccc1C1SC(c2ccc(F)cc2)=NN1C(=O)c1c(F)cc(F)cc1F] | 611.2 |

TABLE 2-continued

| Example | Structure | MS (m/z) (M + 1)+ |
|---|---|---|
| 293 | 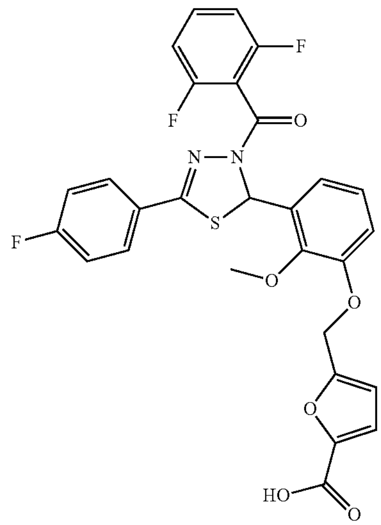 [SMILES: COc1c(OCc2ccc(C(=O)O)o2)cccc1C1SC(c2ccc(F)cc2)=NN1C(=O)c1c(F)cccc1F] | 569.1 |
| 294 | 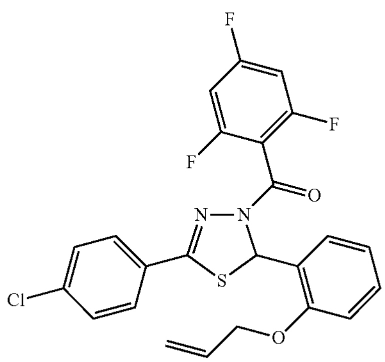 [SMILES: C=CCOc1ccccc1C1SC(c2ccc(Cl)cc2)=NN1C(=O)c1c(F)cc(F)cc1F] | 489.0 |
| 295 | 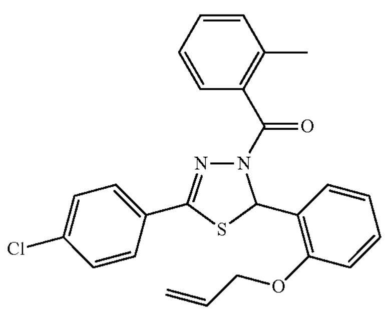 [SMILES: C=CCOc1ccccc1C1SC(c2ccc(Cl)cc2)=NN1C(=O)c1ccccc1C] | 449.1 |
| 296 | 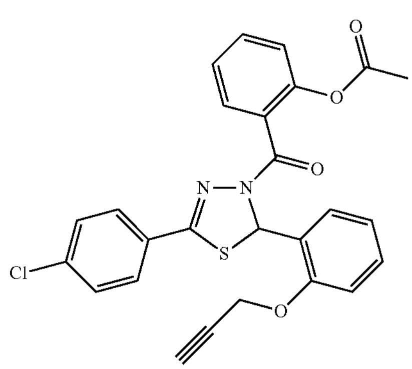 [SMILES: C#CCOc1ccccc1C1SC(c2ccc(Cl)cc2)=NN1C(=O)c1ccccc1OC(C)=O] | 491.0 |

TABLE 2-continued

| Example | Structure | MS (m/z) (M + 1)+ |
|---|---|---|
| 297 | 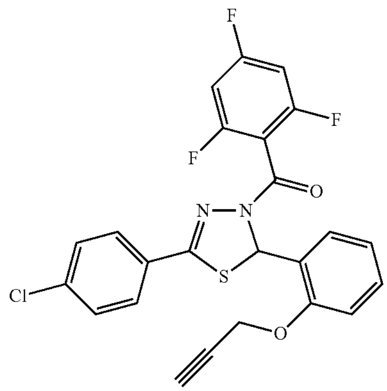 [SMILES: C#CCOc1ccccc1C1SC(c2ccc(Cl)cc2)=NN1C(=O)c1c(F)cc(F)cc1F] | 487.0 |
| 298 | 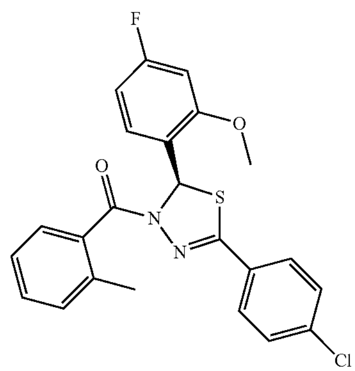 [SMILES: COc1cc(F)ccc1[C@H]1SC(c2ccc(Cl)cc2)=NN1C(=O)c1ccccc1C] | 441.0 |
| 299 | 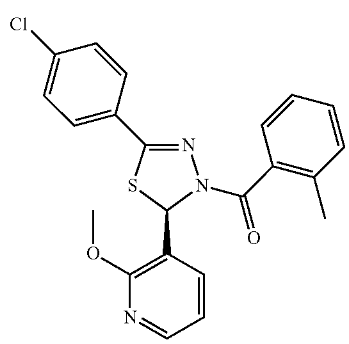 [SMILES: COc1ncccc1[C@H]1SC(c2ccc(Cl)cc2)=NN1C(=O)c1ccccc1C] | 424.0 |
| 300 | 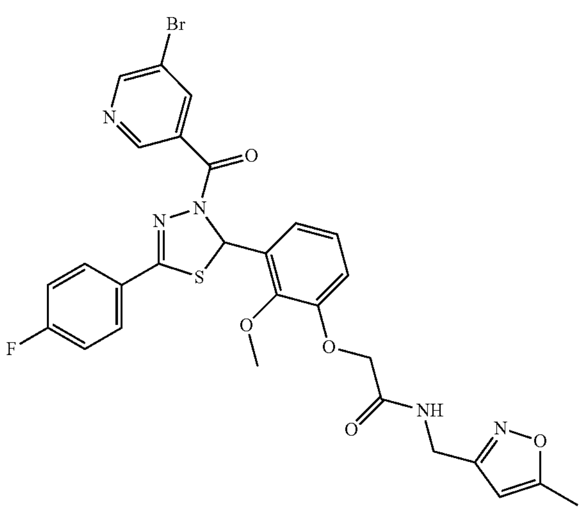 [SMILES: COc1c(OCC(=O)NCc2cc(C)on2)cccc1C1SC(c2ccc(F)cc2)=NN1C(=O)c1cncc(Br)c1] | 640.0 |

TABLE 2-continued
| Example | Structure | MS (m/z) (M + 1)+ |
|---|---|---|
| 301 | 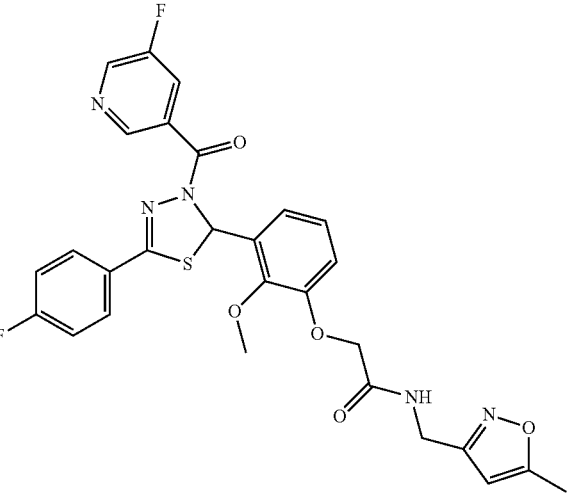 | 580.1 |
| 302 | 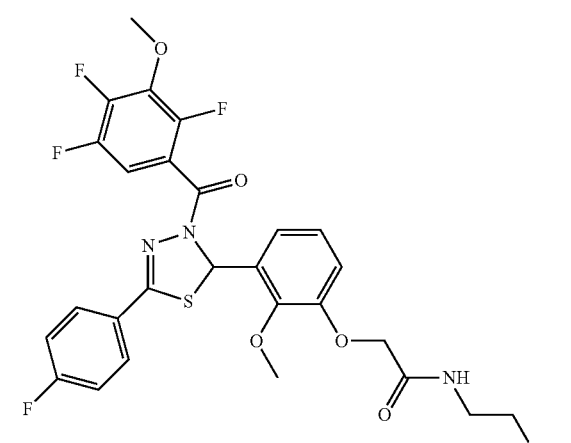 | 596.1 |
| 303 | 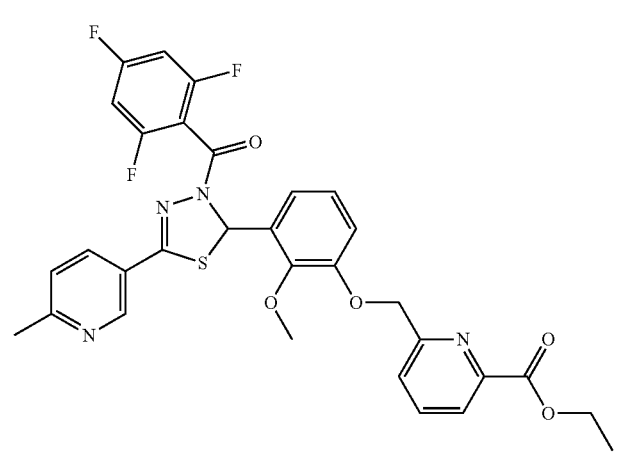 [SMILES: CCOC(=O)c1cccc(COc2cccc(C3SC(c4ccc(C)nc4)=NN3C(=O)c3c(F)cc(F)cc3F)c2OC)n1] | 623.1 |

TABLE 2-continued

| Example | Structure | MS (m/z) (M + 1)+ |
|---------|-----------|-------------------|
| 304 | 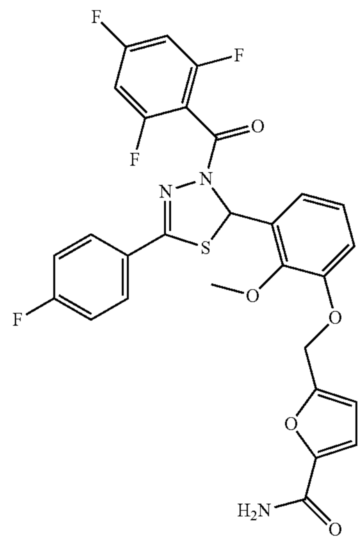 [SMILES: COc1c(OCc2ccc(C(N)=O)o2)cccc1C1SC(c2ccc(F)cc2)=NN1C(=O)c1c(F)cc(F)cc1F] | 586.0 |
| 305 | 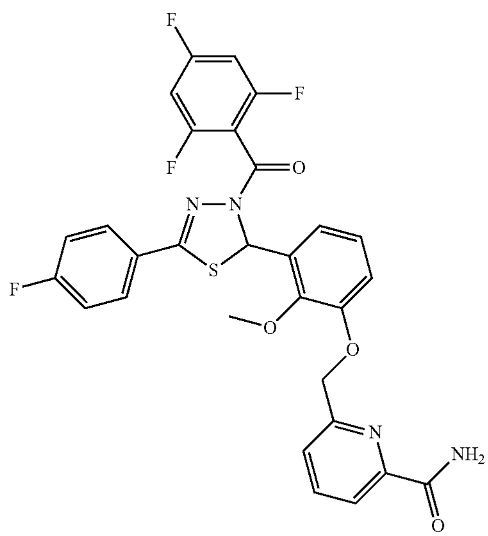 [SMILES: COc1c(OCc2cccc(C(N)=O)n2)cccc1C1SC(c2ccc(F)cc2)=NN1C(=O)c1c(F)cc(F)cc1F] | 597.0 |
| 306 | 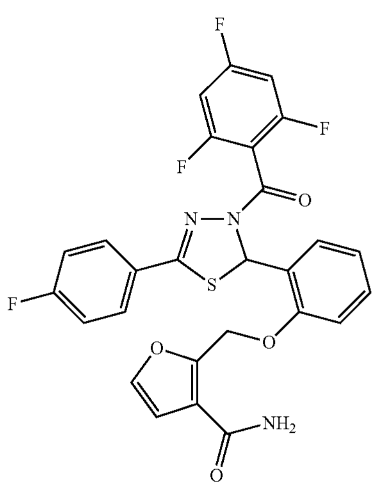 [SMILES: NC(=O)c1ccoc1COc1ccccc1C1SC(c2ccc(F)cc2)=NN1C(=O)c1c(F)cc(F)cc1F] | 556.0 |

TABLE 2-continued
| Example | Structure | MS (m/z) (M + 1)+ |
|---|---|---|
| 307 | 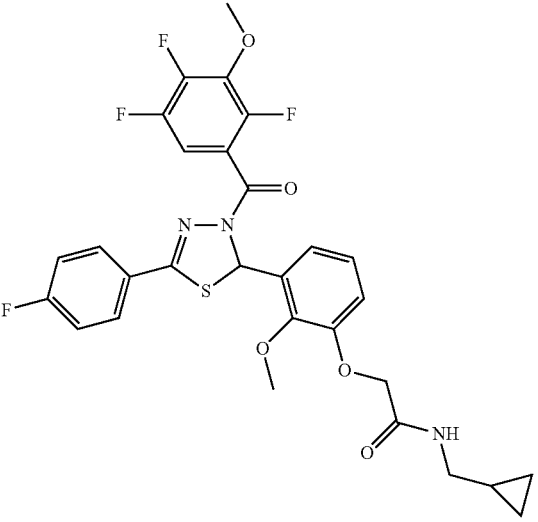 [SMILES: COc1c(OCC(=O)NCC2CC2)cccc1C1SC(c2ccc(F)cc2)=NN1C(=O)c1cc(F)c(F)c(OC)c1F] | 604.1 |
| 308 | 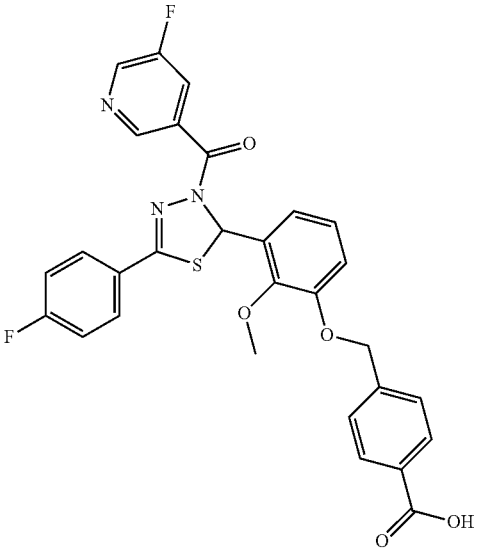 [SMILES: COc1c(OCc2ccc(C(=O)O)cc2)cccc1C1SC(c2ccc(F)cc2)=NN1C(=O)c1cncc(F)c1] | 562.0 |
| 309 | 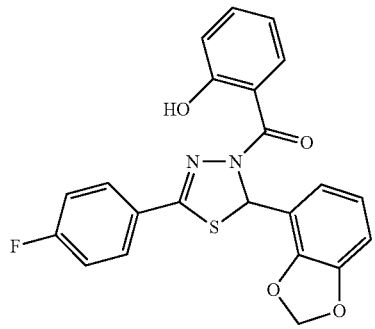 [SMILES: O=C(c1ccccc1O)N1N=C(c2ccc(F)cc2)SC1c1cccc2c1OCO2] | 423.1 |

TABLE 2-continued

| Example | Structure | MS (m/z) (M + 1)+ |
|---|---|---|
| 310 | 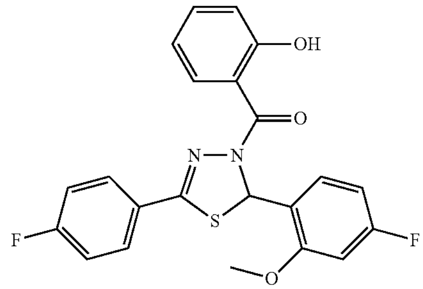 [SMILES: COc1cc(F)ccc1C1SC(c2ccc(F)cc2)=NN1C(=O)c1ccccc1O] | 427.1 |
| 311 | 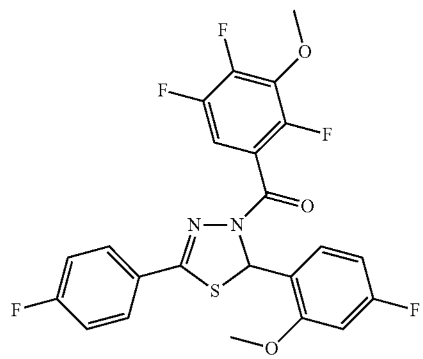 [SMILES: COc1cc(F)ccc1C1SC(c2ccc(F)cc2)=NN1C(=O)c1cc(F)c(F)c(OC)c1F] | 495.1 |
| 312 | 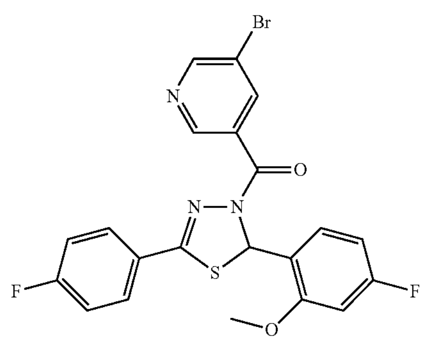 [SMILES: COc1cc(F)ccc1C1SC(c2ccc(F)cc2)=NN1C(=O)c1cncc(Br)c1] | 490.0 |
| 313 | 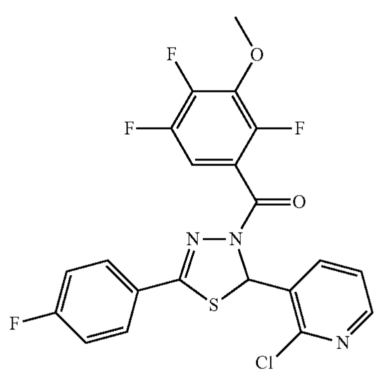 [SMILES: COc1c(F)c(F)cc(C(=O)N2N=C(c3ccc(F)cc3)SC2c2cccnc2Cl)c1F] | 482.0 |

TABLE 2-continued
| Example | Structure | MS (m/z) (M + 1)+ |
|---|---|---|
| 314 | 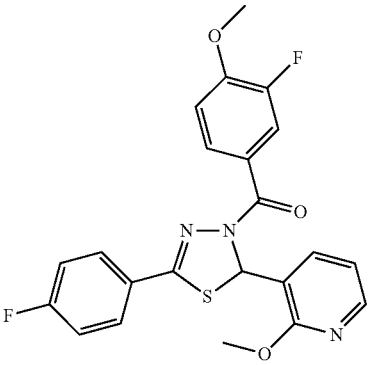 [SMILES: COc1ccc(C(=O)N2N=C(c3ccc(F)cc3)SC2c2cccnc2OC)cc1F] | 442.1 |
| 315 | 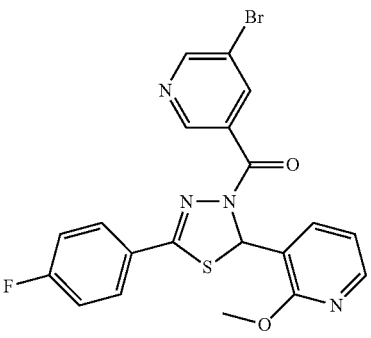 [SMILES: COc1ncccc1C1SC(c2ccc(F)cc2)=NN1C(=O)c1cncc(Br)c1] | 473.0 |
| 316 | 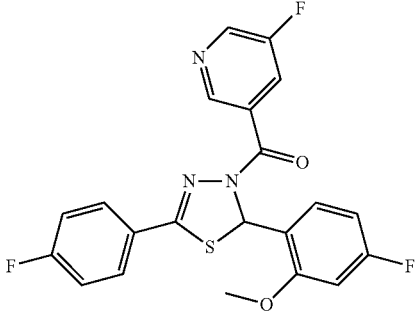 [SMILES: COc1cc(F)ccc1C1SC(c2ccc(F)cc2)=NN1C(=O)c1cncc(F)c1] | 430.1 |
| 317 | 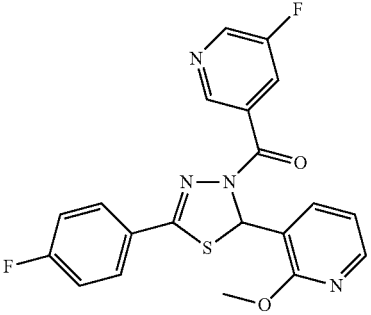 [SMILES: COc1ncccc1C1SC(c2ccc(F)cc2)=NN1C(=O)c1cncc(F)c1] | 413.1 |

TABLE 2-continued
| Example | Structure | MS (m/z) (M + 1)+ |
|---|---|---|
| 318 | 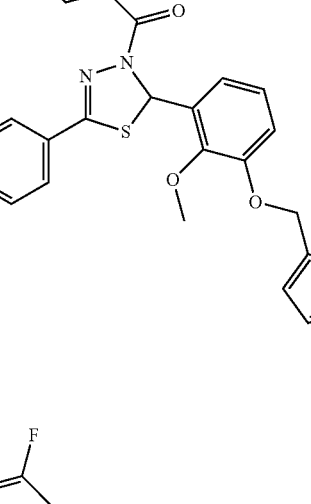 | 552.0 |
| 319 | 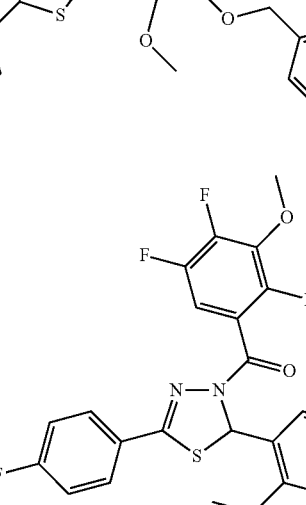 | 560.1 |
| 320 | 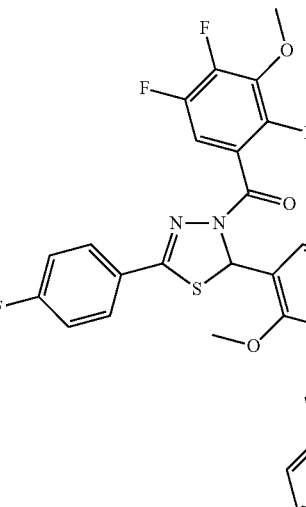 | 626.1 |

TABLE 2-continued

| Example | Structure | MS (m/z) (M + 1)+ |
|---|---|---|
| 321 | 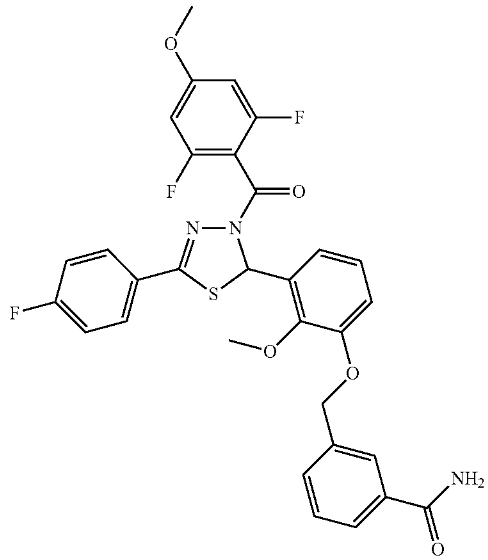 [SMILES: COc1cc(F)c(C(=O)N2N=C(c3ccc(F)cc3)SC2c2cccc(OCc3cccc(C(N)=O)c3)c2OC)c(F)c1] | 608.0 |
| 322 | 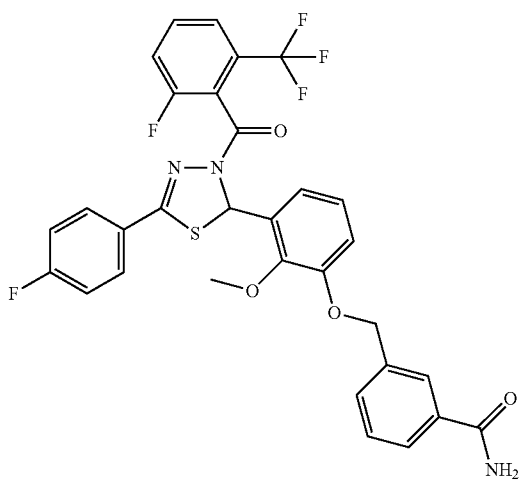 [SMILES: COc1c(OCc2cccc(C(N)=O)c2)cccc1C1SC(c2ccc(F)cc2)=NN1C(=O)c1c(F)cccc1C(F)(F)F] | 628.0 |
| 323 | 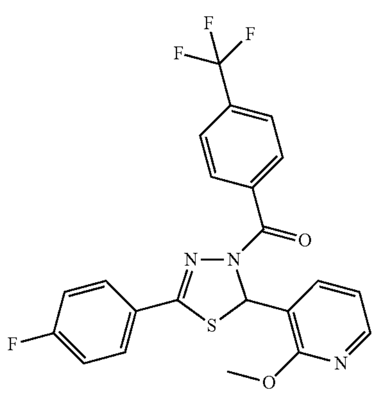 [SMILES: COc1ncccc1C1SC(c2ccc(F)cc2)=NN1C(=O)c1ccc(C(F)(F)F)cc1] | 462.0 |

TABLE 2-continued
| Example | Structure | MS (m/z) (M + 1)+ |
|---|---|---|
| 324 | 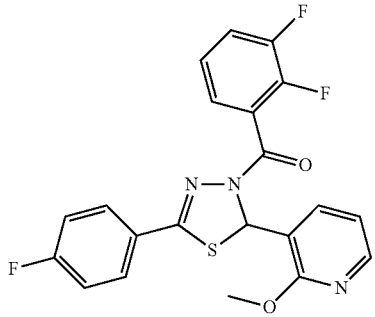 [SMILES: COc1ncccc1C1SC(c2ccc(F)cc2)=NN1C(=O)c1cccc(F)c1F] | 430.0 |
| 325 | 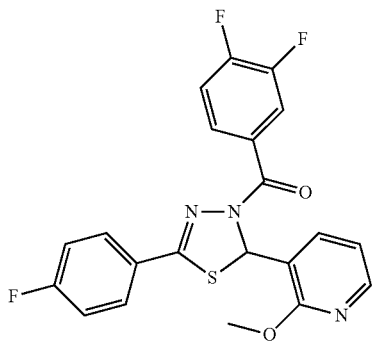 [SMILES: COc1ncccc1C1SC(c2ccc(F)cc2)=NN1C(=O)c1ccc(F)c(F)c1] | 430.0 |
| 326 | 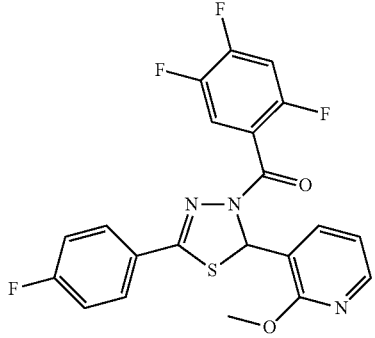 [SMILES: COc1ncccc1C1SC(c2ccc(F)cc2)=NN1C(=O)c1cc(F)c(F)cc1F] | 448.0 |
| 327 | 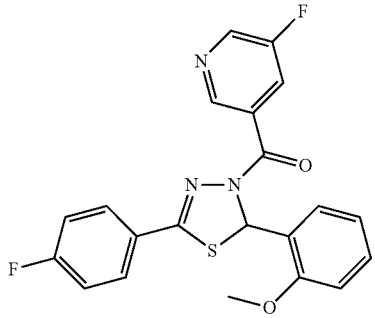 [SMILES: COc1ccccc1C1SC(c2ccc(F)cc2)=NN1C(=O)c1cncc(F)c1] | 412.1 |

TABLE 2-continued

| Example | Structure | MS (m/z) (M + 1)+ |
|---|---|---|
| 328 | 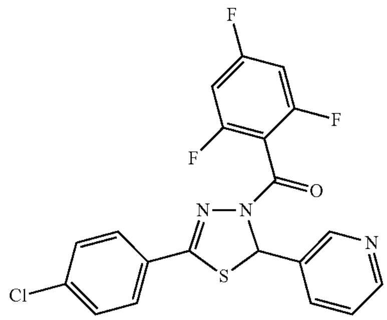 [SMILES: O=C(c1c(F)cc(F)cc1F)N1N=C(c2ccc(Cl)cc2)SC1c1cccnc1] | 433.9 |
| 329 | 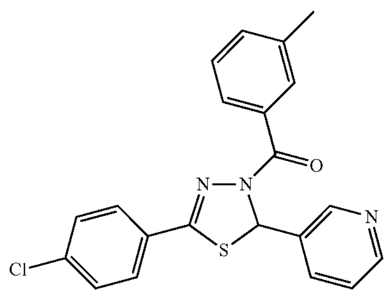 [SMILES: Cc1cccc(C(=O)N2N=C(c3ccc(Cl)cc3)SC2c2cccnc2)c1] | 394.0 |
| 330 | 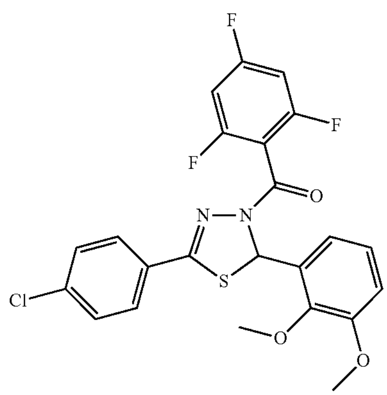 [SMILES: COc1cccc(C2SC(c3ccc(Cl)cc3)=NN2C(=O)c2c(F)cc(F)cc2F)c1OC] | 493.0 |
| 331 | 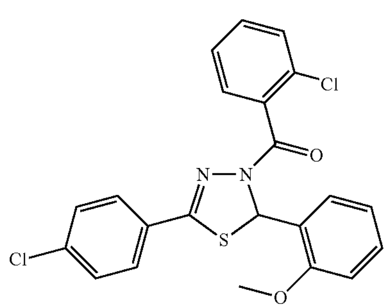 [SMILES: COc1ccccc1C1SC(c2ccc(Cl)cc2)=NN1C(=O)c1ccccc1Cl] | 443.0 |

TABLE 2-continued

| Example | Structure | MS (m/z) (M + 1)⁺ |
|---|---|---|
| 332 | 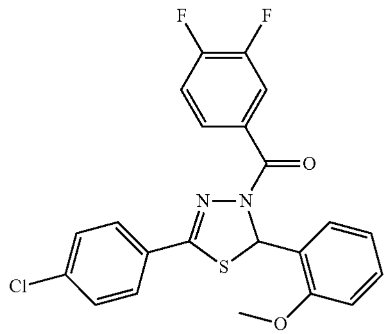 [SMILES: COc1ccccc1C1SC(c2ccc(Cl)cc2)=NN1C(=O)c1ccc(F)c(F)c1] | 445.0 |
| 333 | 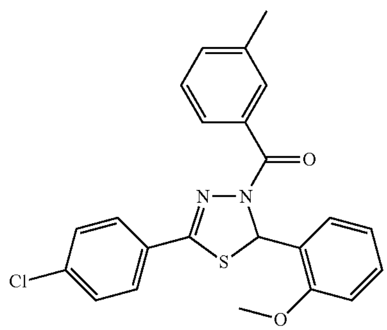 [SMILES: COc1ccccc1C1SC(c2ccc(Cl)cc2)=NN1C(=O)c1cccc(C)c1] | 423.2 |
| 334 | 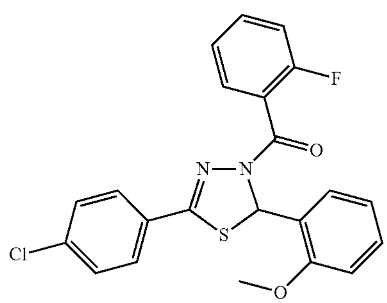 [SMILES: COc1ccccc1C1SC(c2ccc(Cl)cc2)=NN1C(=O)c1ccccc1F] | 427.0 |
| 335 | 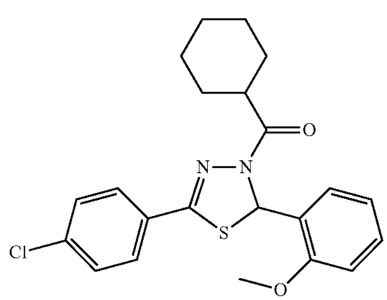 [SMILES: COc1ccccc1C1SC(c2ccc(Cl)cc2)=NN1C(=O)C1CCCCC1] | 415.1 |

TABLE 2-continued

| Example | Structure | MS (m/z) (M + 1)+ |
|---|---|---|
| 336 | 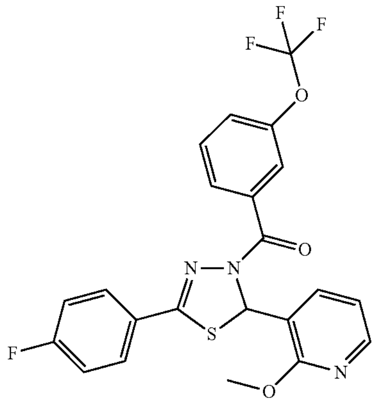 [SMILES: COc1ncccc1C1SC(c2ccc(F)cc2)=NN1C(=O)c1cccc(OC(F)(F)F)c1] | 478.0 |
| 337 | 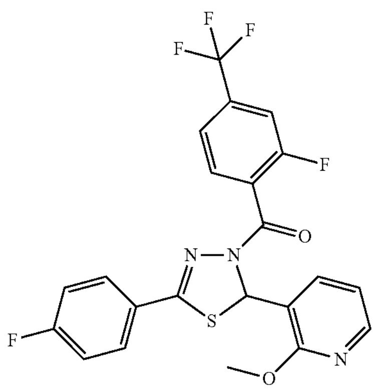 [SMILES: COc1ncccc1C1SC(c2ccc(F)cc2)=NN1C(=O)c1ccc(C(F)(F)F)cc1F] | 480.0 |
| 338 | 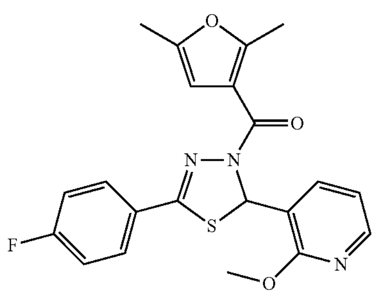 [SMILES: COc1ncccc1C1SC(c2ccc(F)cc2)=NN1C(=O)c1cc(C)oc1C] | 412.1 |
| 339 | 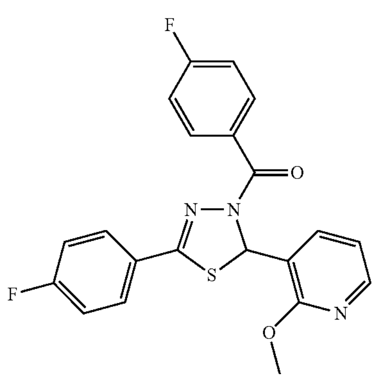 [SMILES: COc1ncccc1C1SC(c2ccc(F)cc2)=NN1C(=O)c1ccc(F)cc1] | 412.0 |

TABLE 2-continued

| Example | Structure | MS (m/z) (M + 1)+ |
|---------|-----------|-------------------|
| 340 | 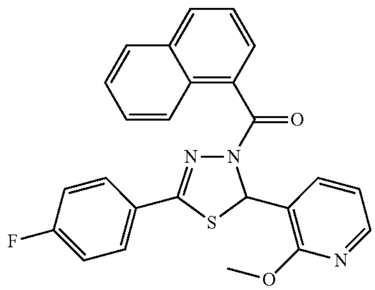 [SMILES: COc1ncccc1C1SC(c2ccc(F)cc2)=NN1C(=O)c1cccc2ccccc12] | 444.1 |
| 341 | 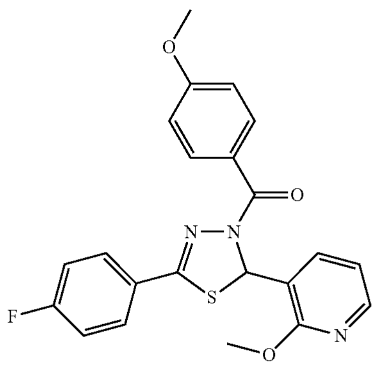 [SMILES: COc1ccc(C(=O)N2N=C(c3ccc(F)cc3)SC2c2cccnc2OC)cc1] | 424.1 |
| 342 | 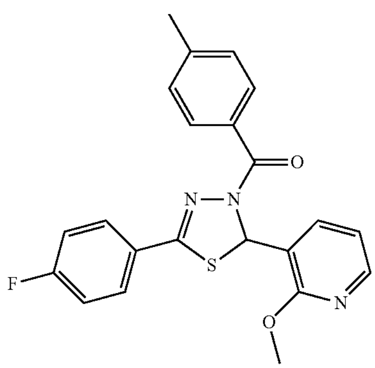 [SMILES: COc1ncccc1C1SC(c2ccc(F)cc2)=NN1C(=O)c1ccc(C)cc1] | 408.1 |
| 343 | 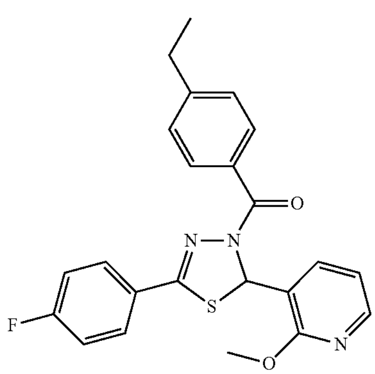 [SMILES: CCc1ccc(C(=O)N2N=C(c3ccc(F)cc3)SC2c2cccnc2OC)cc1] | 422.1 |

TABLE 2-continued
| Example | Structure | MS (m/z) (M + 1)+ |
|---|---|---|
| 344 | 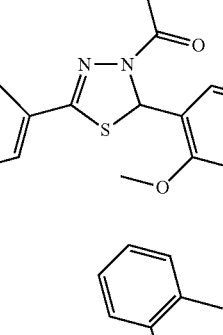 | 454.1 |
| 345 | 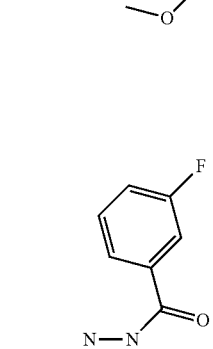 | 423.3 |
| 346 | 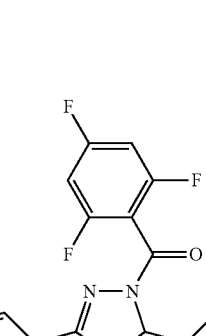 | 427.0 |
| 347 | 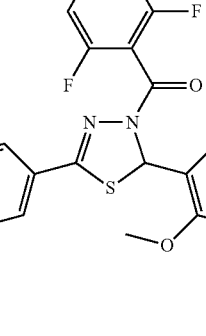 | 463.0 |

TABLE 2-continued

| Example | Structure | MS (m/z) (M + 1)+ |
|---|---|---|
| 348 | 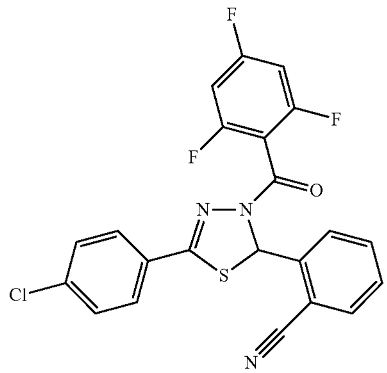 | 458.0 |
| 349 | 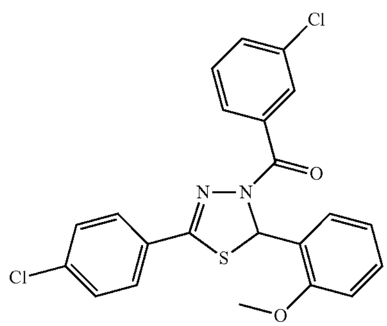 [SMILES: COc1ccccc1C1SC(c2ccc(Cl)cc2)=NN1C(=O)c1cccc(F)c1] | 443.0 |
| 350 | 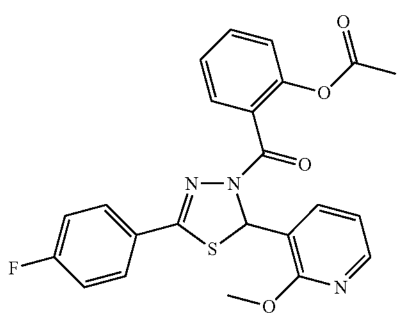 [SMILES: COc1ncccc1C1SC(c2ccc(F)cc2)=NN1C(=O)c1ccccc1OC(C)=O] | 452.0 |
| 351 | 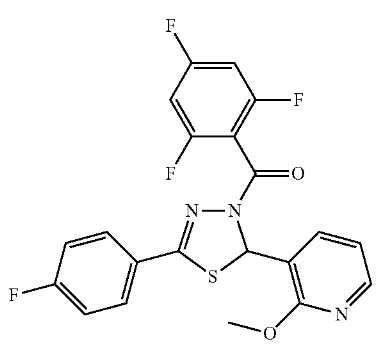 [SMILES: COc1ncccc1C1SC(c2ccc(F)cc2)=NN1C(=O)c1c(F)cc(F)cc1F] | 448.0 |

TABLE 2-continued

| Example | Structure | MS (m/z) (M + 1)+ |
|---|---|---|
| 352 | 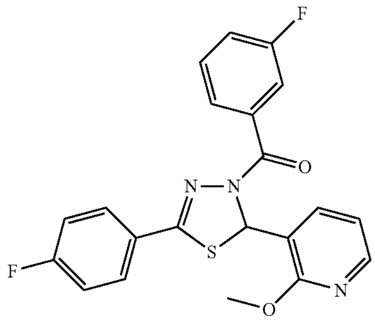 | 412.0 |
| 353 | 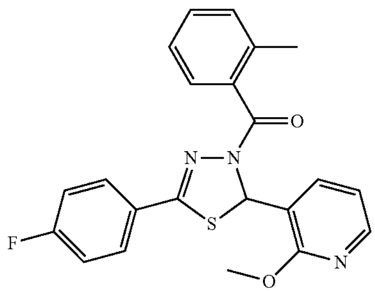 | 408.3 |
| 354 | 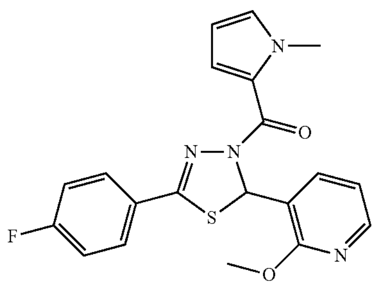 [SMILES: COc1ncccc1C1SC(c2ccc(F)cc2)=NN1C(=O)c1cccn1C] | 397.1 |
| 355 | 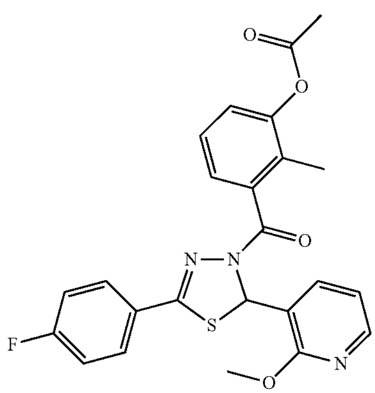 [SMILES: COc1ncccc1C1SC(c2ccc(F)cc2)=NN1C(=O)c1cccc(OC(C)=O)c1C] | 466.1 |
| 356 | 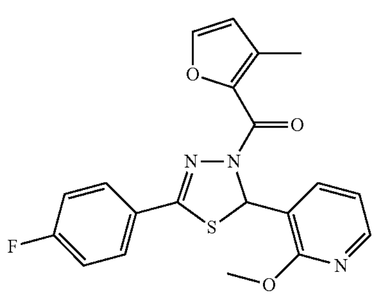 [SMILES: COc1ncccc1C1SC(c2ccc(F)cc2)=NN1C(=O)c1occc1C] | 398.0 |

TABLE 2-continued
| Example | Structure | MS (m/z) (M + 1)+ |
|---|---|---|
| 357 | 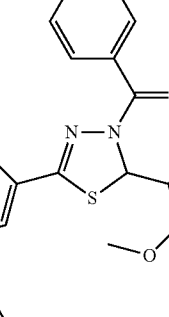 | 438.0 |
| 358 | 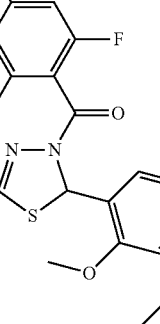 | 593.0 |
| 359 | 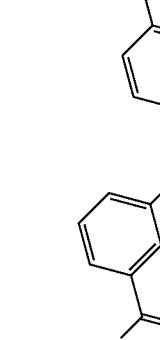 | 428.0 |
| 360 | 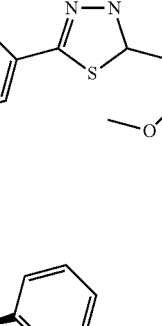 | 559.1 |

TABLE 2-continued
| Example | Structure | MS (m/z) (M + 1)+ |
|---|---|---|
| 361 | 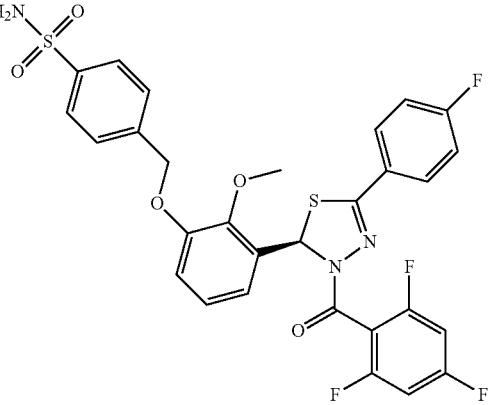 | 632.0 |
| 362 | 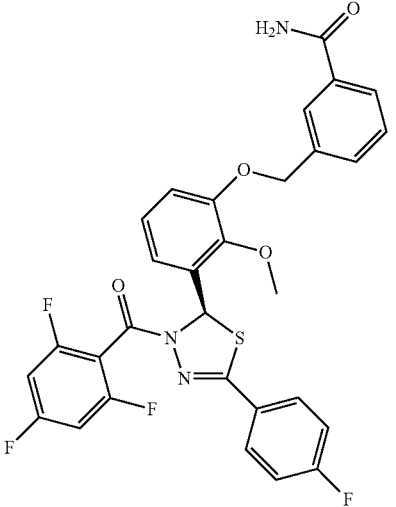 [SMILES: COc1c(OCc2cccc(C(N)=O)c2)cccc1[C@H]1SC(c2ccc(F)cc2)=NN1C(=O)c1c(F)cc(F)cc1F] | 596.0 |
| 363 | 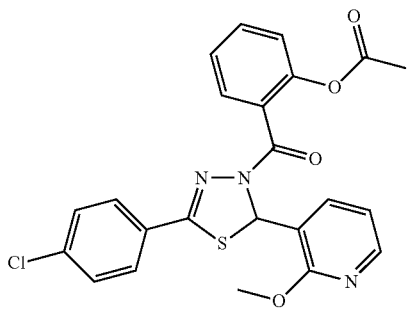 [SMILES: COc1ncccc1C1SC(c2ccc(Cl)cc2)=NN1C(=O)c1ccccc1OC(C)=O] | 468.2 |
| 364 | 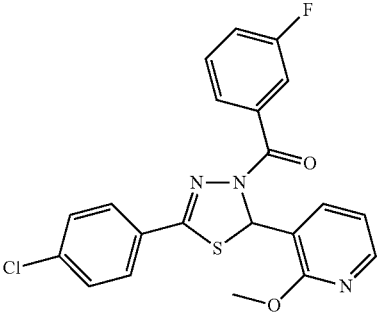 [SMILES: COc1ncccc1C1SC(c2ccc(Cl)cc2)=NN1C(=O)c1cccc(F)c1] | 428.0 |

TABLE 2-continued

| Example | Structure | MS (m/z) (M + 1)+ |
|---|---|---|
| 365 | 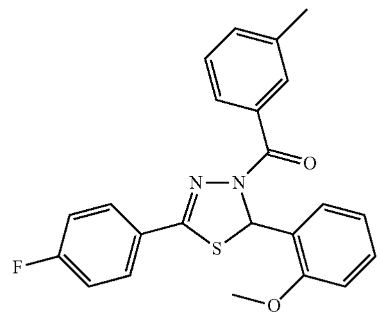 [SMILES: COc1ccccc1C1SC(c2ccc(F)cc2)=NN1C(=O)c1cccc(C)c1] | 407.1 |
| 366 | 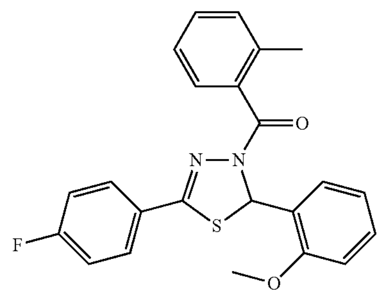 [SMILES: COc1ccccc1C1SC(c2ccc(F)cc2)=NN1C(=O)c1ccccc1C] | 407.1 |
| 367 | 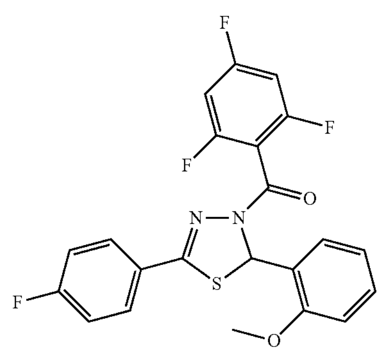 [SMILES: COc1ccccc1C1SC(c2ccc(F)cc2)=NN1C(=O)c1c(F)cc(F)cc1F] | 447.0 |
| 368 | 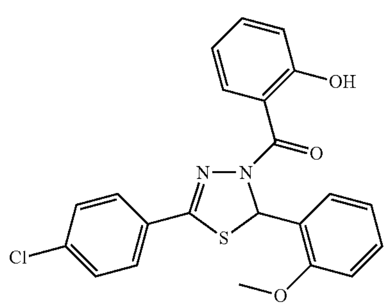 [SMILES: COc1ccccc1C1SC(c2ccc(Cl)cc2)=NN1C(=O)c1ccccc1O] | 425.3 |

TABLE 2-continued

| Example | Structure | MS (m/z) (M + 1)+ |
|---|---|---|
| 369 | 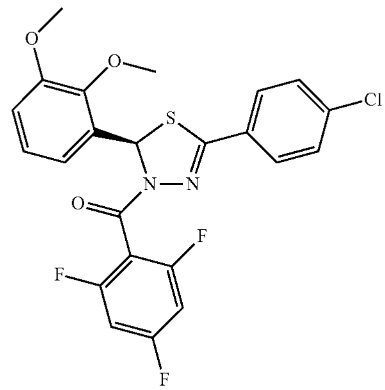 [SMILES: COc1cccc([C@H]2SC(c3ccc(Cl)cc3)=NN2C(=O)c2c(F)cc(F)cc2F)c1OC] | 493.0 |
| 370 | 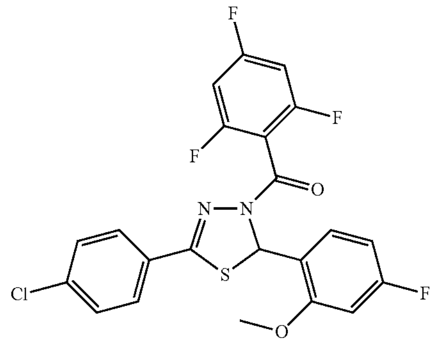 [SMILES: COc1cc(F)ccc1C1SC(c2ccc(Cl)cc2)=NN1C(=O)c1c(F)cc(F)cc1F] | 481.0 |
| 371 | 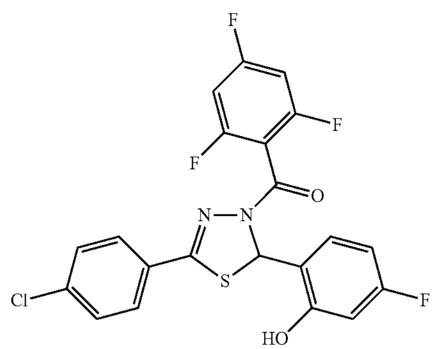 [SMILES: O=C(c1c(F)cc(F)cc1F)N1N=C(c2ccc(Cl)cc2)SC1c1ccc(F)cc1O] | 467.0 |
| 372 | 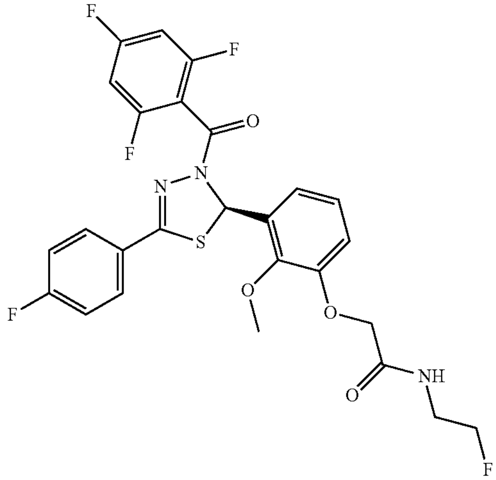 [SMILES: COc1c(OCC(=O)NCCF)cccc1[C@H]1SC(c2ccc(F)cc2)=NN1C(=O)c1c(F)cc(F)cc1F] | 566.2 |

TABLE 2-continued

| Example | Structure | MS (m/z) (M + 1)+ |
|---|---|---|
| 373 | 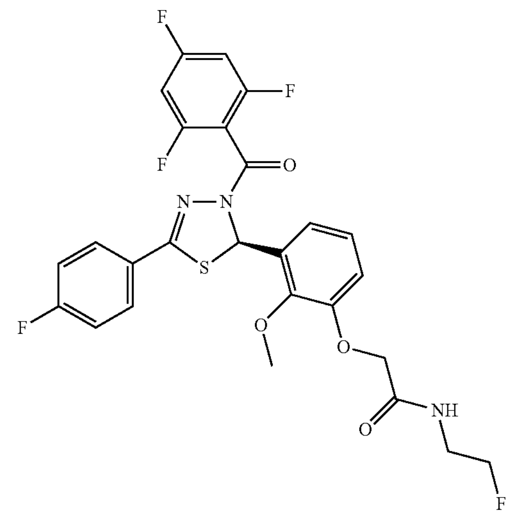 [SMILES: COc1c(OCC(=O)NCCF)cccc1[C@H]1SC(c2ccc(F)cc2)=NN1C(=O)c1c(F)cc(F)cc1F] | 566.0 |
| 374 | 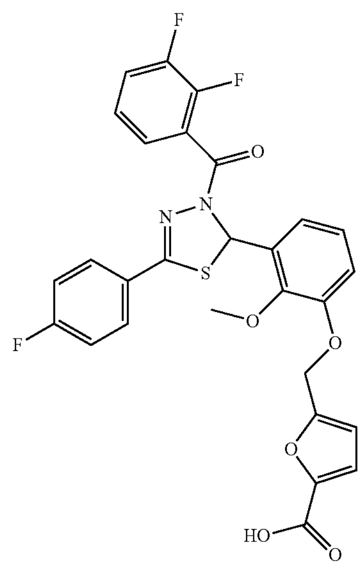 [SMILES: COc1c(OCc2ccc(C(=O)O)o2)cccc1C1SC(c2ccc(F)cc2)=NN1C(=O)c1cccc(F)c1F] | 569.0 |
| 375 | 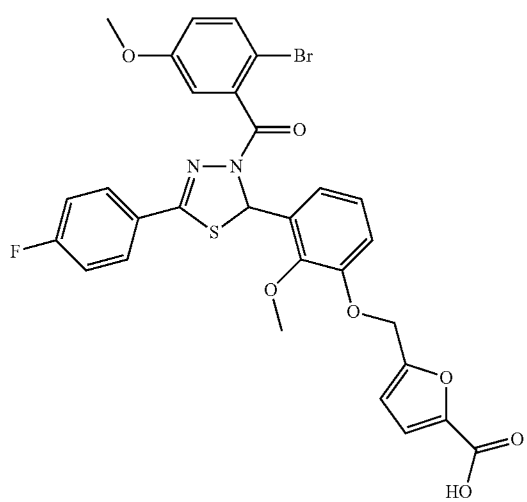 [SMILES: COc1ccc(Br)c(C(=O)N2N=C(c3ccc(F)cc3)SC2c2cccc(OCc3ccc(C(=O)O)o3)c2OC)c1] | 641.0 |

TABLE 2-continued
| Example | Structure | MS (m/z) (M + 1)+ |
|---|---|---|
| 376 | 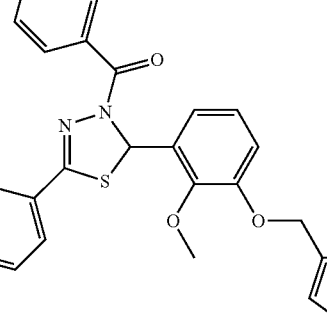 | 551.0 |
| 377 | 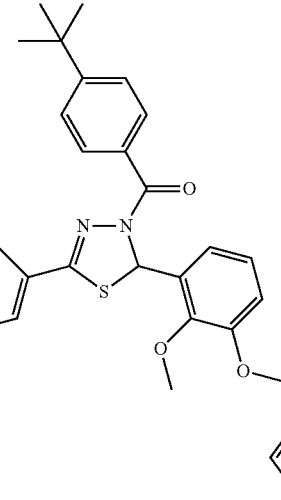 | 589.1 |
| 378 | 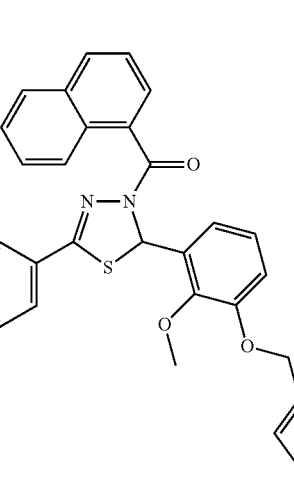 | 583.1 |

TABLE 2-continued

| Example | Structure | MS (m/z) (M + 1)+ |
|---|---|---|
| 379 | 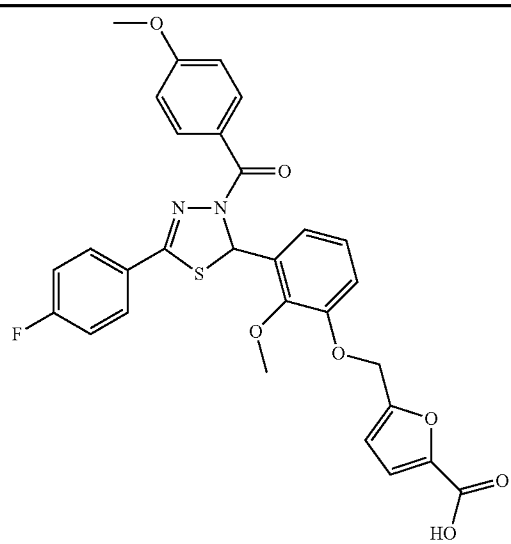 | 563.1 |
| 380 | 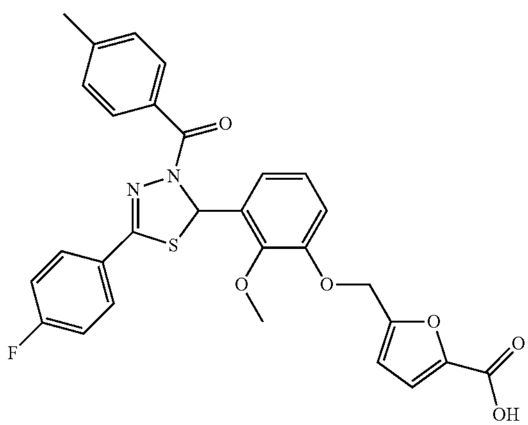 [SMILES: COc1c(OCc2ccc(C(=O)O)o2)cccc1C1SC(c2ccc(F)cc2)=NN1C(=O)c1ccc(C)cc1] | 547.0 |
| 381 | 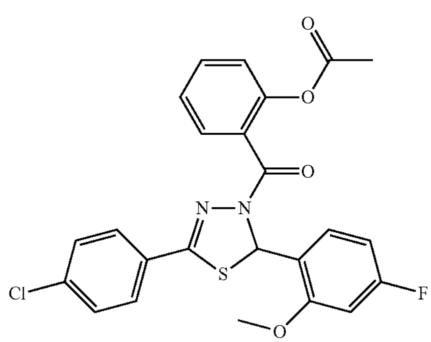 [SMILES: COc1cc(F)ccc1C1SC(c2ccc(Cl)cc2)=NN1C(=O)c1ccccc1OC(C)=O] | 485.0 |
| 382 | 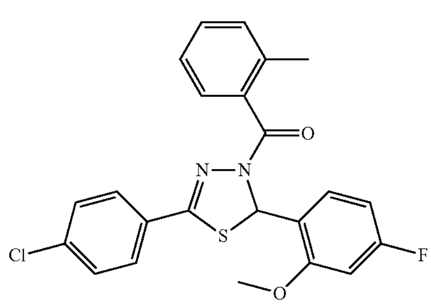 [SMILES: COc1cc(F)ccc1C1SC(c2ccc(Cl)cc2)=NN1C(=O)c1ccccc1C] | 441.0 |

TABLE 2-continued

| Example | Structure | MS (m/z) (M + 1)+ |
|---|---|---|
| 383 | 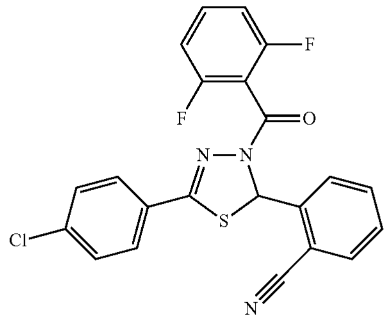 [SMILES: N#Cc1ccccc1C1SC(c2ccc(Cl)cc2)=NN1C(=O)c1c(F)cccc1F] | 440.0 |
| 384 | 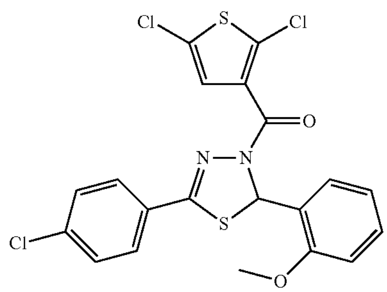 [SMILES: COc1ccccc1C1SC(c2ccc(Cl)cc2)=NN1C(=O)c1cc(Cl)sc1Cl] | 481.0 |
| 385 | 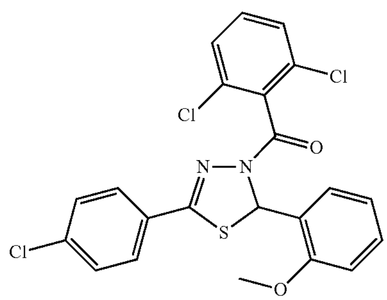 [SMILES: COc1ccccc1C1SC(c2ccc(Cl)cc2)=NN1C(=O)c1c(Cl)cccc1Cl] | 477.0 |
| 386 | 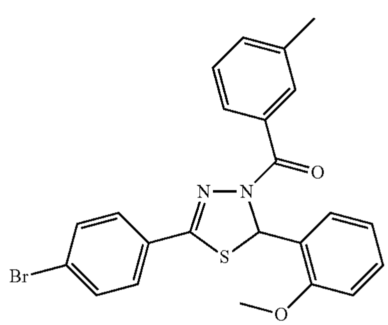 [SMILES: COc1ccccc1C1SC(c2ccc(Br)cc2)=NN1C(=O)c1cccc(C)c1] | 467.0 |
| 387 | 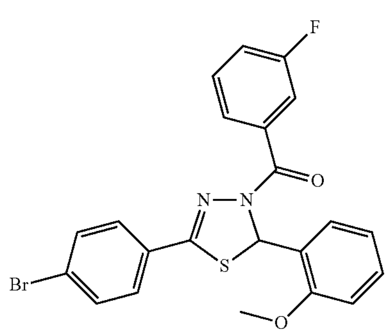 [SMILES: COc1ccccc1C1SC(c2ccc(Br)cc2)=NN1C(=O)c1cccc(F)c1] | 471.0 |

TABLE 2-continued

| Example | Structure | MS (m/z) (M + 1)+ |
|---|---|---|
| 388 | 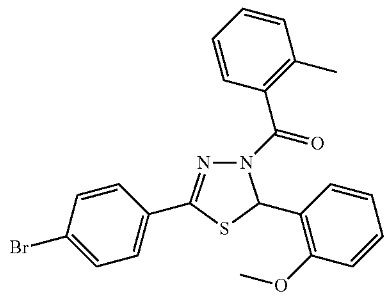 [SMILES: COc1ccccc1C1SC(c2ccc(Br)cc2)=NN1C(=O)c1ccccc1C] | 467.0 |
| 389 | 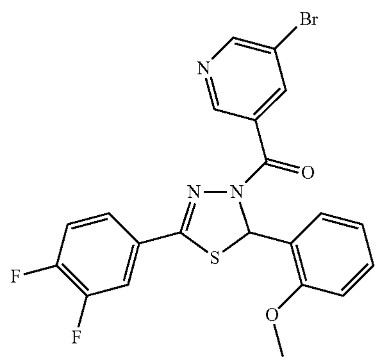 [SMILES: COc1ccccc1C1SC(c2ccc(F)c(F)c2)=NN1C(=O)c1cncc(Br)c1] | 490.2 |
| 390 | 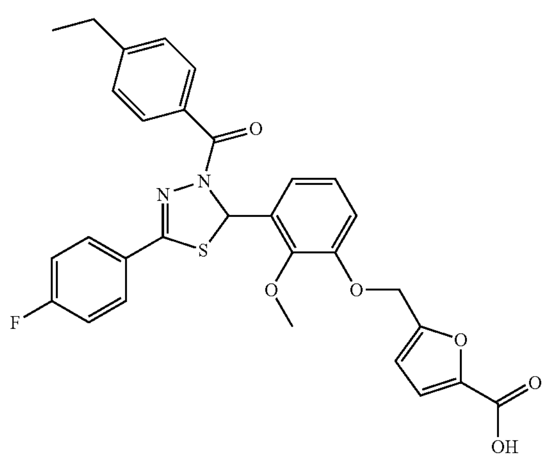 [SMILES: CCc1ccc(C(=O)N2N=C(c3ccc(F)cc3)SC2c2cccc(OCc3ccc(C(=O)O)o3)c2OC)cc1] | 561.1 |

TABLE 2-continued

| Example | Structure | MS (m/z) (M + 1)+ |
|---|---|---|
| 391 | 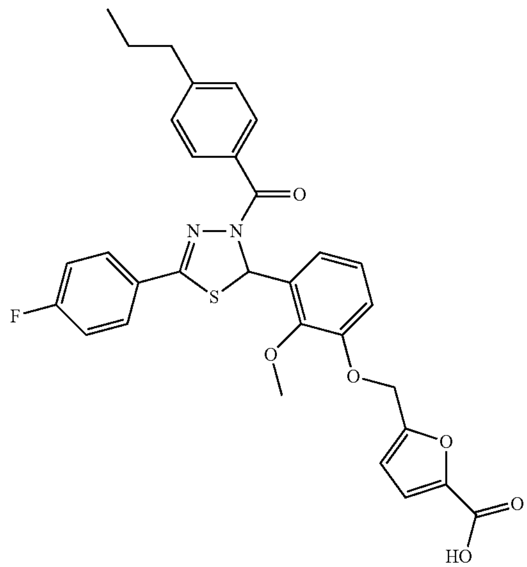 [SMILES: CCCc1ccc(C(=O)N2N=C(c3ccc(F)cc3)SC2c2cccc(OCc3ccc(C(=O)O)o3)c2OC)cc1] | 575.1 |
| 392 | 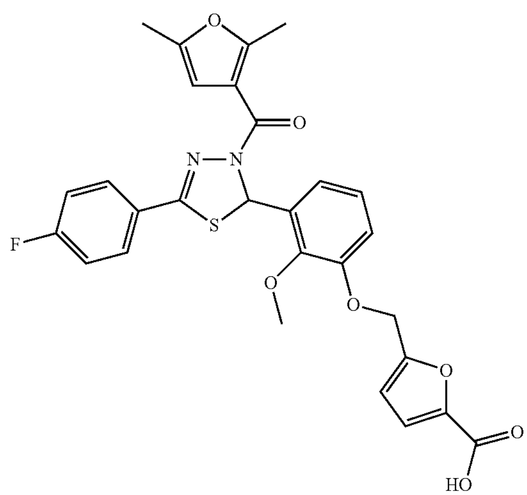 [SMILES: COc1c(OCc2ccc(C(=O)O)o2)cccc1C1SC(c2ccc(F)cc2)=NN1C(=O)c1cc(C)oc1C] | 551.1 |
| 393 | 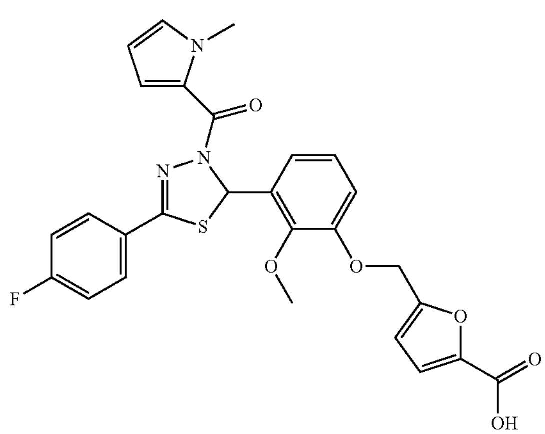 [SMILES: COc1c(OCc2ccc(C(=O)O)o2)cccc1C1SC(c2ccc(F)cc2)=NN1C(=O)c1cccn1C] | 536.1 |

TABLE 2-continued
| Example | Structure | MS (m/z) (M + 1)+ |
|---|---|---|
| 394 | 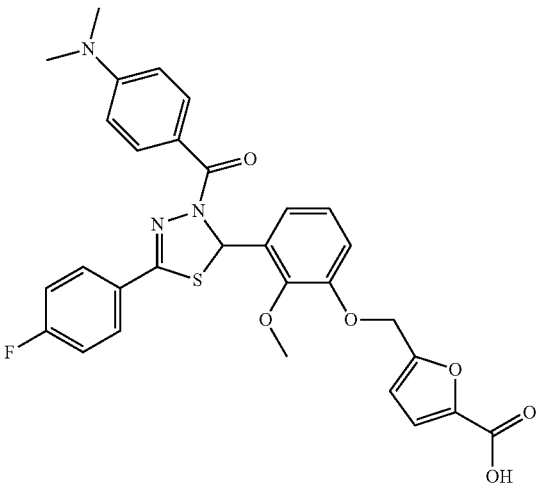 [SMILES: COc1c(OCc2ccc(C(=O)O)o2)cccc1C1SC(c2ccc(F)cc2)=NN1C(=O)c1ccc(N(C)C)cc1] | 576.1 |
| 395 | 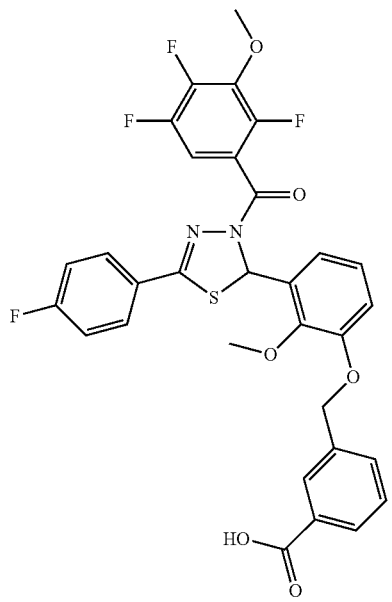 [SMILES: COc1c(OCc2cccc(C(=O)O)c2)cccc1C1SC(c2ccc(F)cc2)=NN1C(=O)c1cc(F)c(F)c(OC)c1F] | 627.1 |

TABLE 2-continued

| Example | Structure | MS (m/z) (M + 1)+ |
|---|---|---|
| 396 | 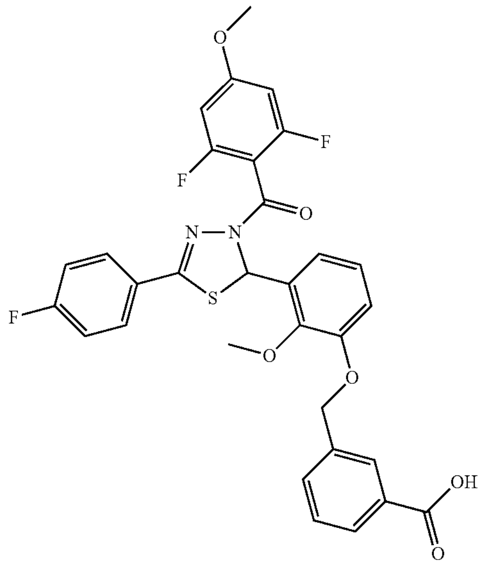 [SMILES: COc1cc(F)c(C(=O)N2N=C(c3ccc(F)cc3)SC2c2cccc(OCc3cccc(C(=O)O)c3)c2OC)c(F)c1] | 609.0 |
| 397 | 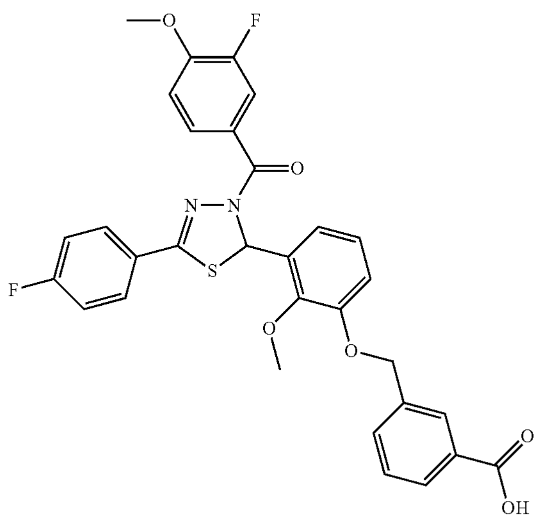 [SMILES: COc1ccc(C(=O)N2N=C(c3ccc(F)cc3)SC2c2cccc(OCc3cccc(C(=O)O)c3)c2OC)cc1F] | 591.1 |
| 398 | 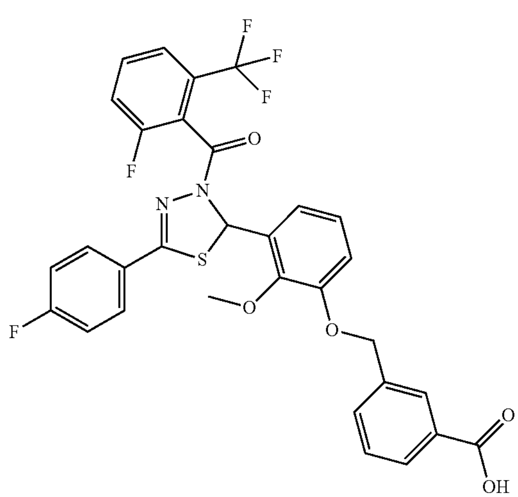 [SMILES: COc1c(OCc2cccc(C(=O)O)c2)cccc1C1SC(c2ccc(F)cc2)=NN1C(=O)c1c(F)cccc1C(F)(F)F] | 629.0 |

TABLE 2-continued
| Example | Structure | MS (m/z) (M + 1)+ |
|---|---|---|
| 399 | 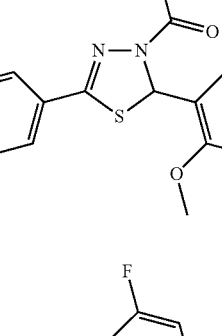 | 425.3 |
| 400 | 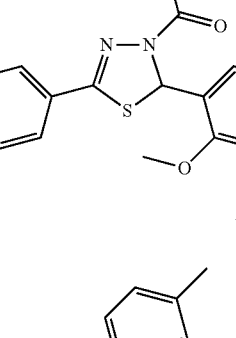 | 495.1 |
| 401 | 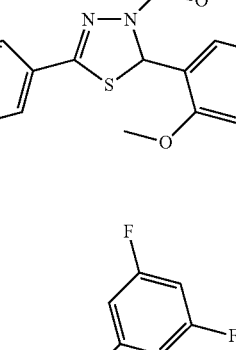 | 455.1 |
| 402 | 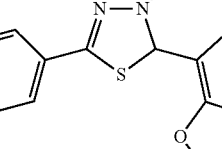 | 479.0 |

TABLE 2-continued

| Example | Structure | MS (m/z) (M + 1)+ |
|---|---|---|
| 403 | 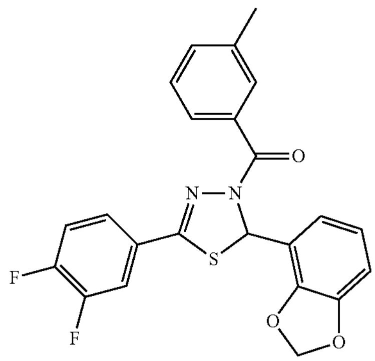 [SMILES: Cc1cccc(C(=O)N2N=C(c3ccc(F)c(F)c3)SC2c2cccc3c2OCO3)c1] | 439.0 |
| 404 | 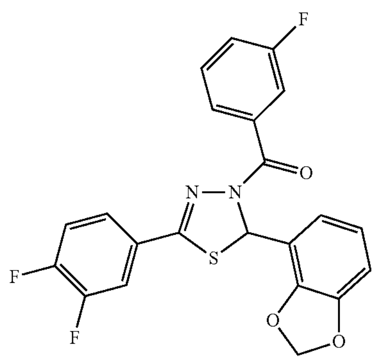 [SMILES: O=C(c1cccc(F)c1)N1N=C(c2ccc(F)c(F)c2)SC1c1cccc2c1OCO2] | 443.0 |
| 405 | 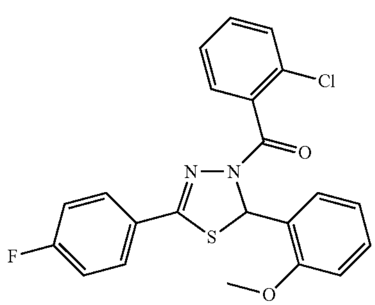 [SMILES: COc1ccccc1C1SC(c2ccc(F)cc2)=NN1C(=O)c1ccccc1Cl] | 427.0 |
| 406 | 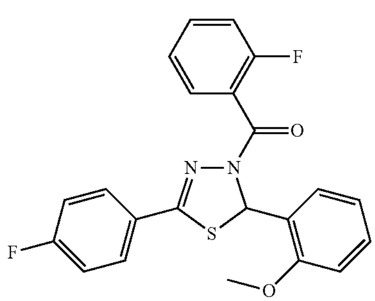 | 411.3 |

TABLE 2-continued

| Example | Structure | MS (m/z) (M + 1)+ |
|---|---|---|
| 407 | 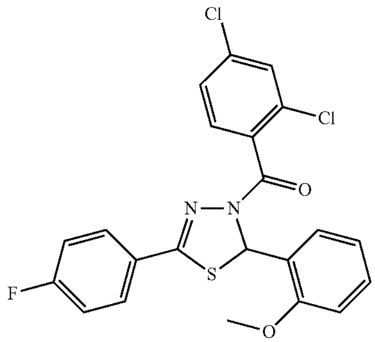 [SMILES: COc1ccccc1C1SC(c2ccc(F)cc2)=NN1C(=O)c1ccc(Cl)cc1Cl] | 461.0 |
| 408 | 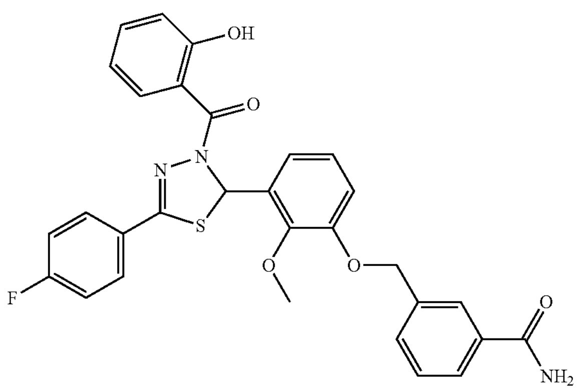 [SMILES: COc1c(OCc2cccc(C(N)=O)c2)cccc1C1SC(c2ccc(F)cc2)=NN1C(=O)c1ccccc1O] | 558.1 |
| 409 | 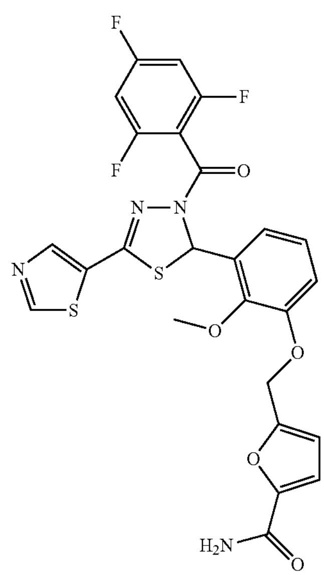 [SMILES: COc1c(OCc2ccc(C(N)=O)o2)cccc1C1SC(c2cncs2)=NN1C(=O)c1c(F)cc(F)cc1F] | 575.0 |

TABLE 2-continued
| Example | Structure | MS (m/z) (M + 1)+ |
|---|---|---|
| 410 | 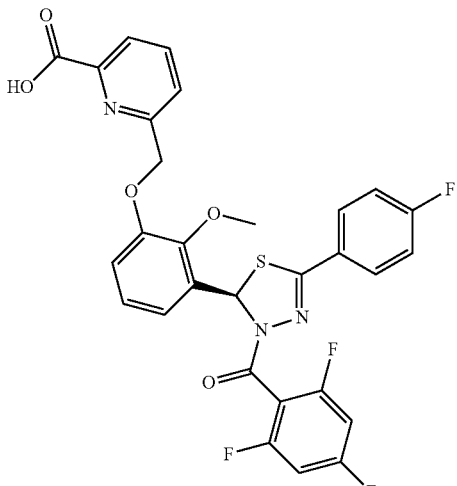 | 598.0 |
| 411 | 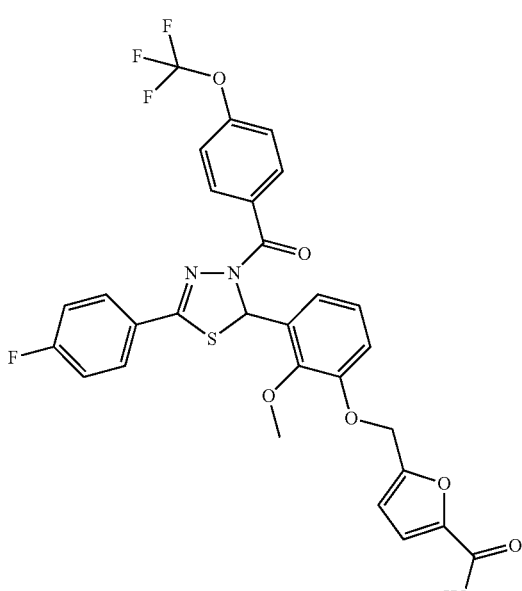 | 617.0 |
| 412 | 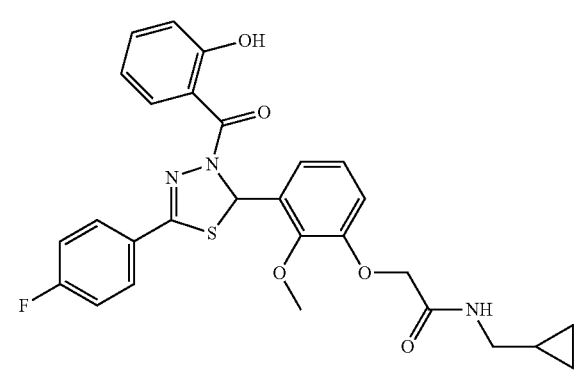 [SMILES: COc1c(OCC(=O)NCC2CC2)cccc1C1SC(c2ccc(F)cc2)=NN1C(=O)c1ccccc1O] | 536.1 |

TABLE 2-continued

| Example | Structure | MS (m/z) (M + 1)+ |
|---|---|---|
| 413 | 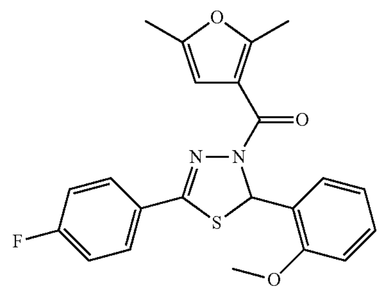 [SMILES: COc1ccccc1C1SC(c2ccc(F)cc2)=NN1C(=O)c1cc(C)oc1C] | 411.0 |
| 414 | 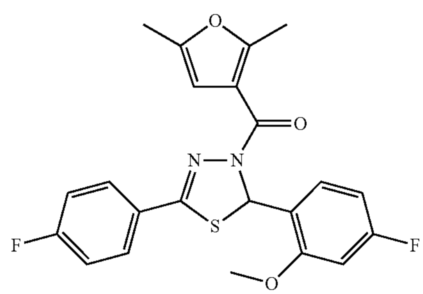 [SMILES: COc1cc(F)ccc1C1SC(c2ccc(F)cc2)=NN1C(=O)c1cc(C)oc1C] | 429.0 |
| 415 | 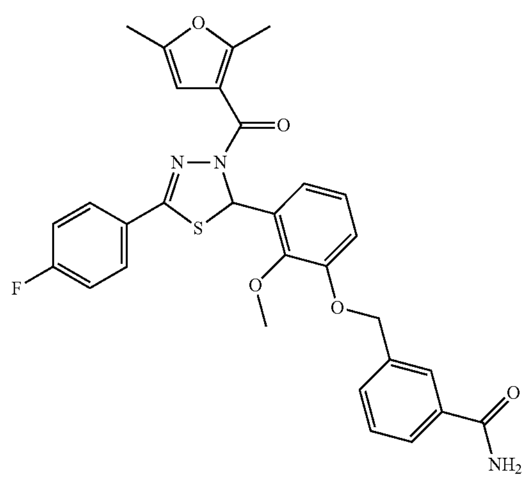 [SMILES: COc1c(OCc2cccc(C(N)=O)c2)cccc1C1SC(c2ccc(F)cc2)=NN1C(=O)c1cc(C)oc1C] | 560.1 |
| 416 | 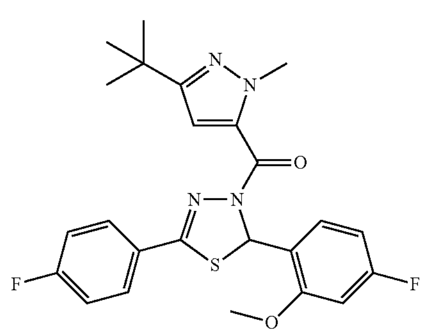 [SMILES: COc1cc(F)ccc1C1SC(c2ccc(F)cc2)=NN1C(=O)c1cc(C(C)(C)C)nn1C] | 471.1 |

TABLE 2-continued

| Example | Structure | MS (m/z) (M + 1)+ |
|---|---|---|
| 417 | 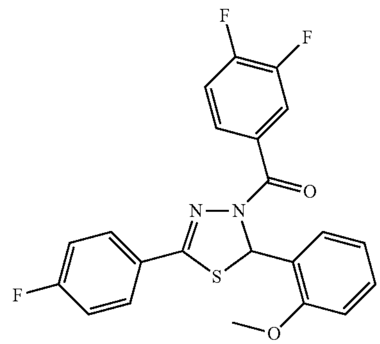 [SMILES: COc1ccccc1C1SC(c2ccc(F)cc2)=NN1C(=O)c1ccc(F)c(F)c1] | 429.1 |
| 418 | 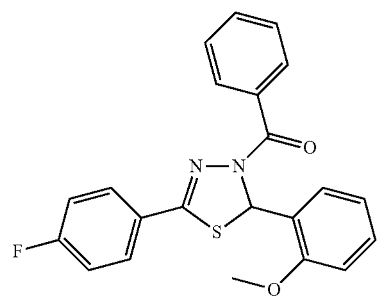 [SMILES: COc1ccccc1C1SC(c2ccc(F)cc2)=NN1C(=O)c1ccccc1] | 393.1 |
| 419 | 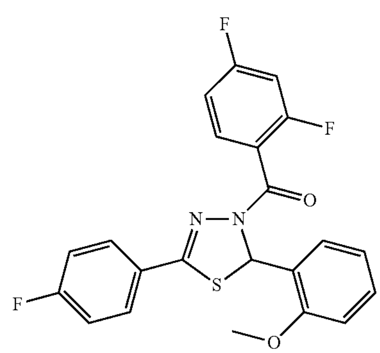 [SMILES: COc1ccccc1C1SC(c2ccc(F)cc2)=NN1C(=O)c1ccc(F)cc1F] | 429.1 |
| 420 | 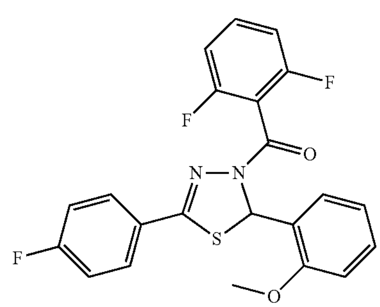 [SMILES: COc1ccccc1C1SC(c2ccc(F)cc2)=NN1C(=O)c1c(F)cccc1F] | 429.1 |

TABLE 2-continued

| Example | Structure | MS (m/z) (M + 1)+ |
|---|---|---|
| 421 | 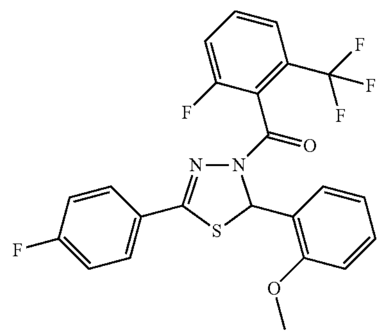 [SMILES: COc1ccccc1C1SC(c2ccc(F)cc2)=NN1C(=O)c1c(F)cccc1C(F)(F)F] | 479.0 |
| 422 | 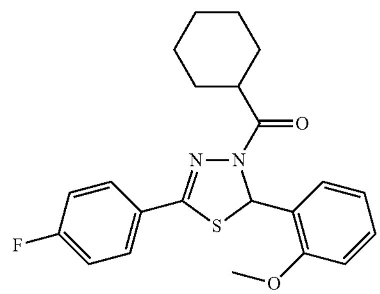 [SMILES: COc1ccccc1C1SC(c2ccc(F)cc2)=NN1C(=O)C1CCCCC1] | 399.1 |
| 423 | 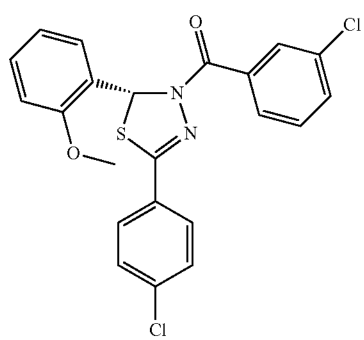 [SMILES: COc1ccccc1[C@H]1SC(c2ccc(Cl)cc2)=NN1C(=O)c1cccc(Cl)c1] | 443.2 |
| 424 | 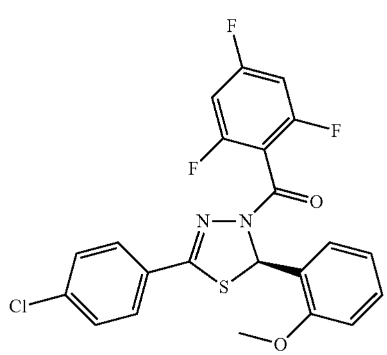 [SMILES: COc1ccccc1[C@H]1SC(c2ccc(Cl)cc2)=NN1C(=O)c1c(F)cc(F)cc1F] | 463.2 |

TABLE 2-continued
| Example | Structure | MS (m/z) (M + 1)+ |
|---|---|---|
| 425 | 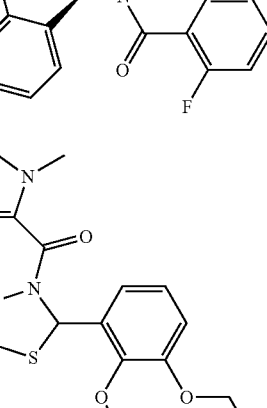 | 477.3 |
| 426 | 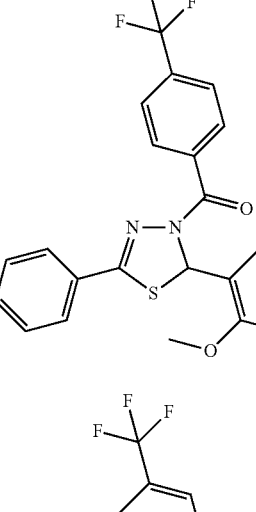 | 545.1 |
| 427 | 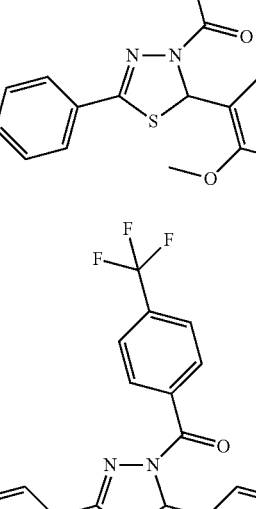 | 461.0 |
| 428 | 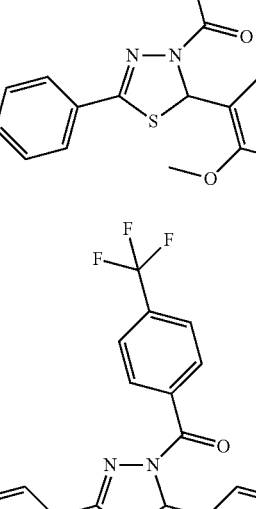 | 479.0 |

TABLE 2-continued

| Example | Structure | MS (m/z) (M + 1)+ |
|---------|-----------|-------------------|
| 429 | 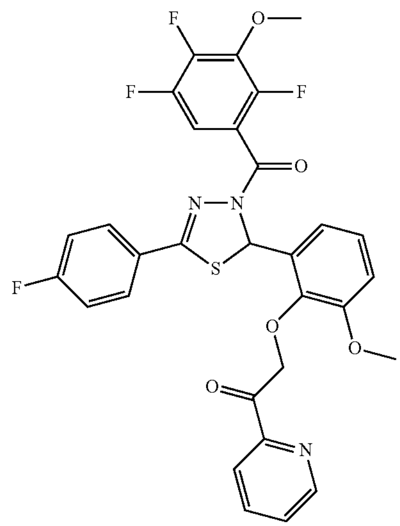 [SMILES: COc1cccc(C2SC(c3ccc(F)cc3)=NN2C(=O)c2cc(F)c(F)c(OC)c2F)c1OCC(=O)c1ccccn1] | 612.0 |
| 430 | 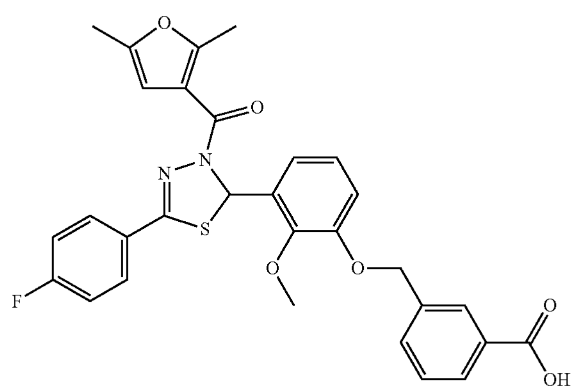 [SMILES: COc1c(OCc2cccc(C(=O)O)c2)cccc1C1SC(c2ccc(F)cc2)=NN1C(=O)c1cc(C)oc1C] | 561.1 |
| 431 | 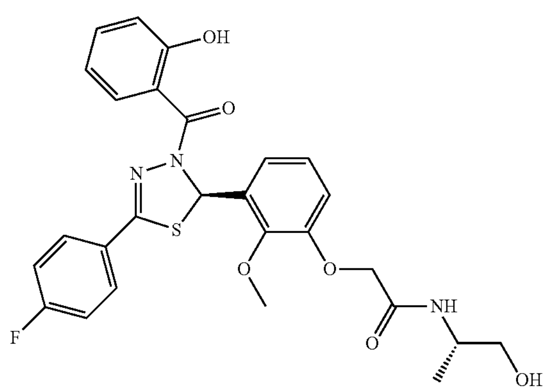 [SMILES: COc1c(OCC(=O)N[C@@H](C)CO)cccc1[C@H]1SC(c2ccc(F)cc2)=NN1C(=O)c1ccccc1O] | 540.1 |

TABLE 2-continued

| Example | Structure | MS (m/z) (M + 1)+ |
|---|---|---|
| 432 | 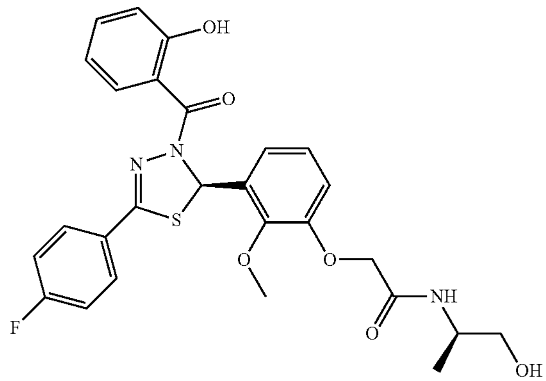 [SMILES: COc1c(OCC(=O)N[C@H](C)CO)cccc1[C@H]1SC(c2ccc(F)cc2)=NN1C(=O)c1ccccc1O] | 540.1 |
| 433 | 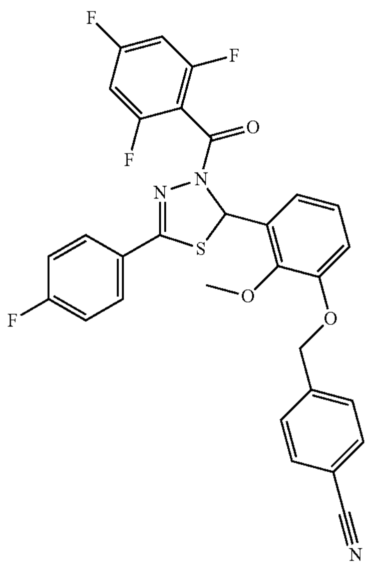 [SMILES: COc1c(OCc2ccc(C#N)cc2)cccc1C1SC(c2ccc(F)cc2)=NN1C(=O)c1c(F)cc(F)cc1F] | 578.1 |
| 434 | 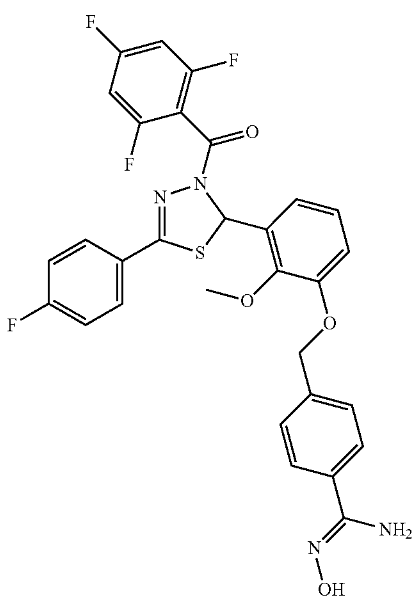 [SMILES: COc1c(OCc2ccc(/C(N)=N/O)cc2)cccc1C1SC(c2ccc(F)cc2)=NN1C(=O)c1c(F)cc(F)cc1F] | 611.2 |

TABLE 2-continued

| Example | Structure | MS (m/z) (M + 1)+ |
|---|---|---|
| 435 | 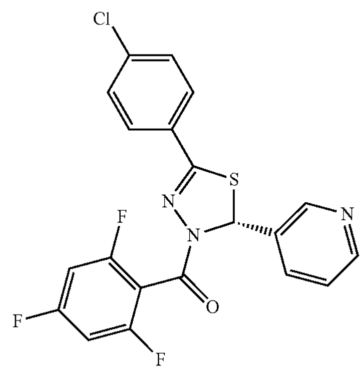 [SMILES: O=C(c1c(F)cc(F)cc1F)N1N=C(c2ccc(Cl)cc2)S[C@@H]1c1cccnc1] | 434.2 |
| 436 | 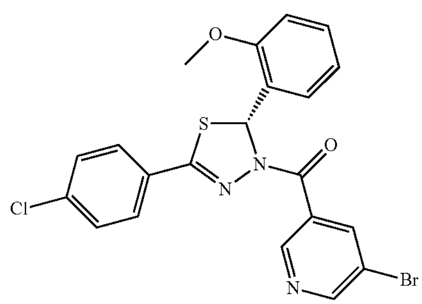 [SMILES: COc1ccccc1[C@H]1SC(c2ccc(Cl)cc2)=NN1C(=O)c1cncc(Br)c1] | 488.2 |
| 437 | 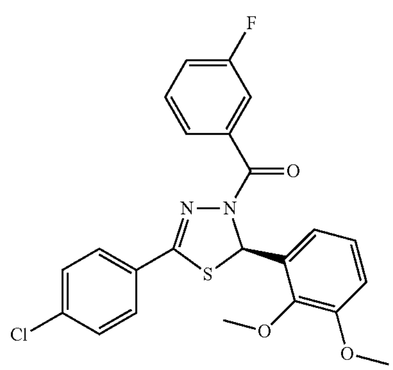 [SMILES: COc1cccc([C@H]2SC(c3ccc(Cl)cc3)=NN2C(=O)c2cccc(F)c2)c1OC] | 457.3 |
| 438 | 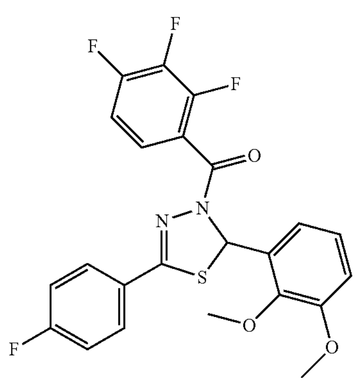 [SMILES: COc1cccc(C2SC(c3ccc(F)cc3)=NN2C(=O)c2ccc(F)c(F)c2F)c1OC] | 477.2 |

TABLE 2-continued

| Example | Structure | MS (m/z) (M + 1)+ |
|---|---|---|
| 439 | 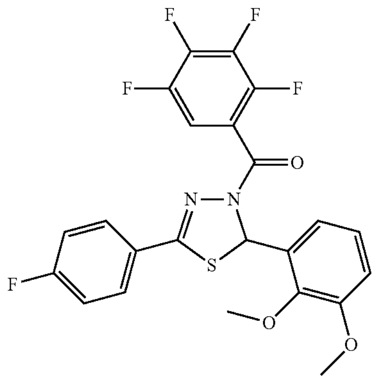 [SMILES: COc1cccc(C2SC(c3ccc(F)cc3)=NN2C(=O)c2cc(F)c(F)c(F)c2F)c1OC] | 495.2 |
| 440 | 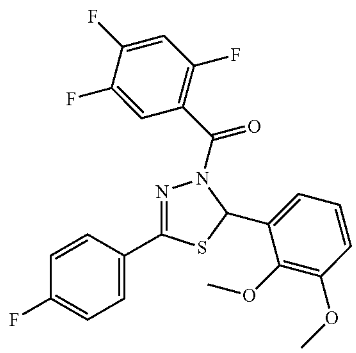 [SMILES: COc1cccc(C2SC(c3ccc(F)cc3)=NN2C(=O)c2cc(F)c(F)cc2F)c1OC] | 477.3 |
| 441 | 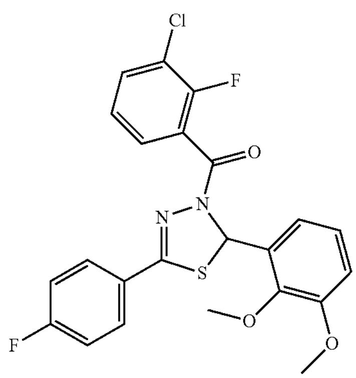 [SMILES: COc1cccc(C2SC(c3ccc(F)cc3)=NN2C(=O)c2cccc(Cl)c2F)c1OC] | 475.2 |
| 442 | 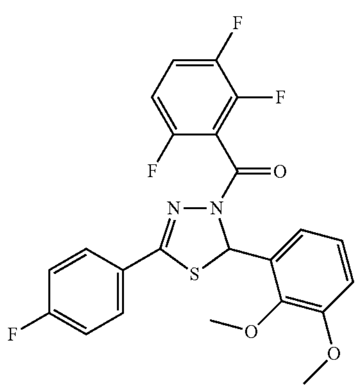 [SMILES: COc1cccc(C2SC(c3ccc(F)cc3)=NN2C(=O)c2c(F)ccc(F)c2F)c1OC] | 477.3 |

TABLE 2-continued
| Example | Structure | MS (m/z) (M + 1)+ |
|---|---|---|
| 443 | 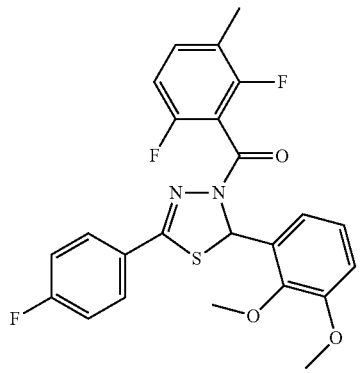 [SMILES: COc1cccc(C2SC(c3ccc(F)cc3)=NN2C(=O)c2c(F)ccc(C)c2F)c1OC] | 473.3 |
| 444 | 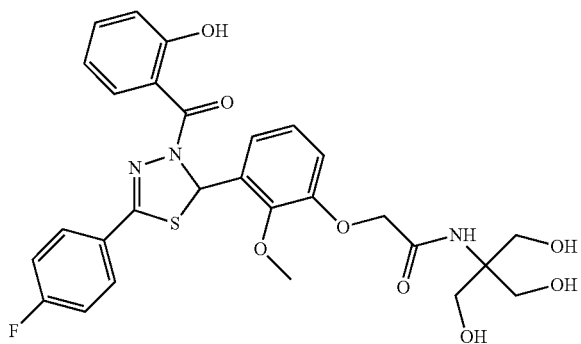 [SMILES: COc1c(OCC(=O)NC(CO)(CO)CO)cccc1C1SC(c2ccc(F)cc2)=NN1C(=O)c1ccccc1O] | 586.1 |
| 445 | 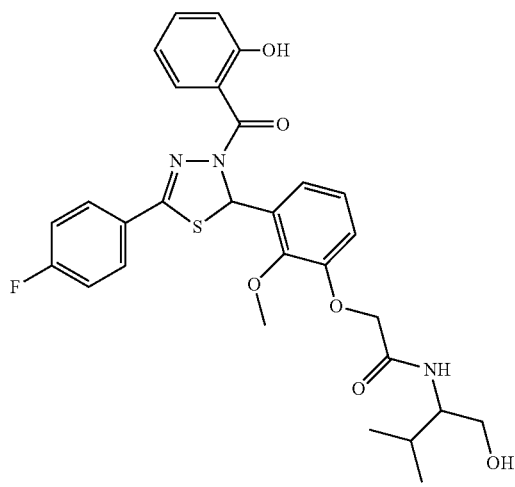 [SMILES: COc1c(OCC(=O)NC(CO)C(C)C)cccc1C1SC(c2ccc(F)cc2)=NN1C(=O)c1ccccc1O] | 568.1 |

TABLE 2-continued

| Example | Structure | MS (m/z) (M + 1)+ |
|---|---|---|
| 446 | 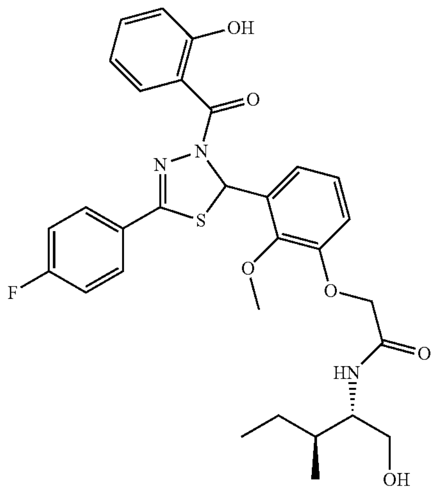 [SMILES: CC[C@H](C)[C@@H](CO)NC(=O)COc1cccc(C2SC(c3ccc(F)cc3)=NN2C(=O)c2ccccc2O)c1OC] | 582.2 |
| 447 | 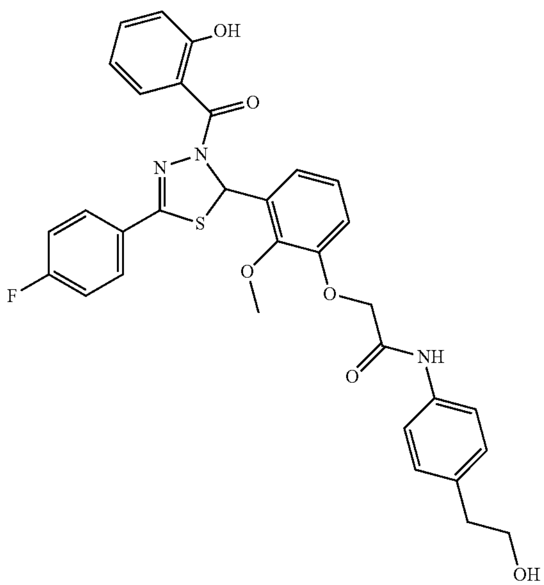 [SMILES: COc1c(OCC(=O)Nc2ccc(CCO)cc2)cccc1C1SC(c2ccc(F)cc2)=NN1C(=O)c1ccccc1O] | 602.1 |
| 448 | 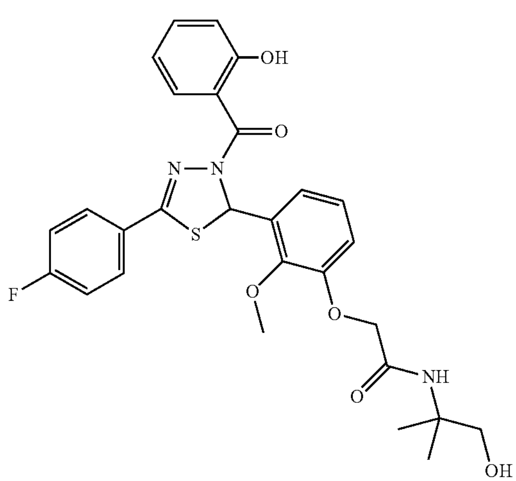 [SMILES: COc1c(OCC(=O)NC(C)(C)CO)cccc1C1SC(c2ccc(F)cc2)=NN1C(=O)c1ccccc1O] | 554.1 |

TABLE 2-continued

| Example | Structure | MS (m/z) (M + 1)+ |
|---|---|---|
| 449 | 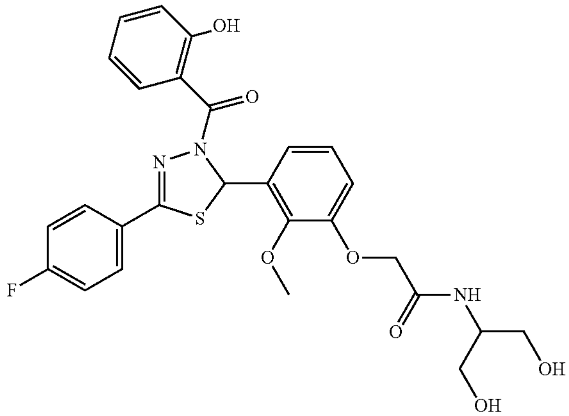 [SMILES: COc1c(OCC(=O)NC(CO)CO)cccc1C1SC(c2ccc(F)cc2)=NN1C(=O)c1ccccc1O] | 556.1 |
| 450 | 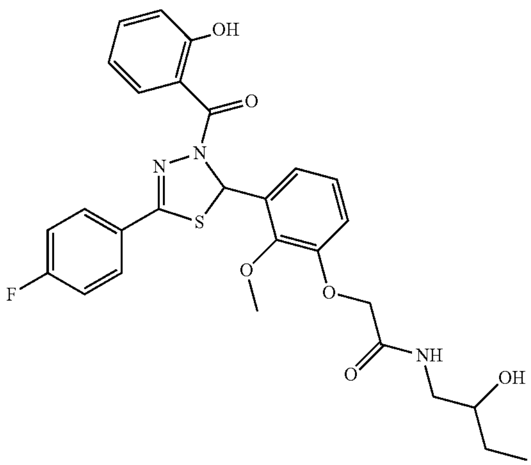 [SMILES: CCC(O)CNC(=O)COc1cccc(C2SC(c3ccc(F)cc3)=NN2C(=O)c2ccccc2O)c1OC] | 554.1 |
| 451 | 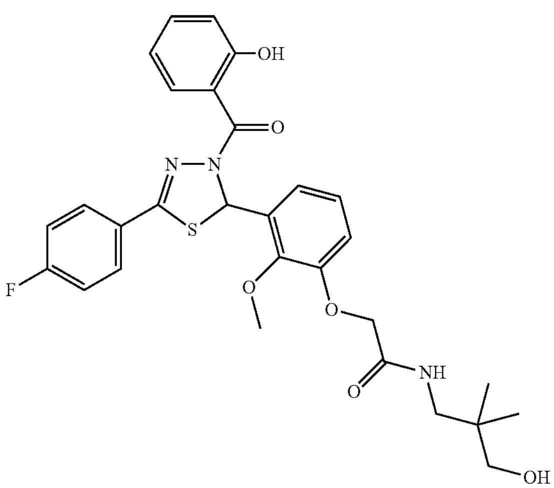 [SMILES: COc1c(OCC(=O)NCC(C)(C)CO)cccc1C1SC(c2ccc(F)cc2)=NN1C(=O)c1ccccc1O] | 568.1 |

TABLE 2-continued

| Example | Structure | MS (m/z) (M + 1)+ |
|---|---|---|
| 452 | 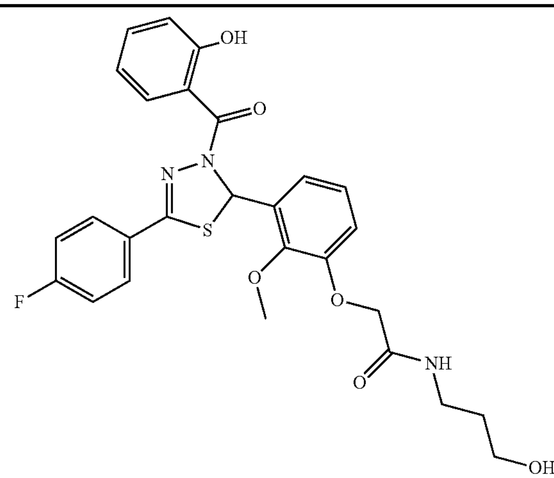 | 540.1 |
| 453 | 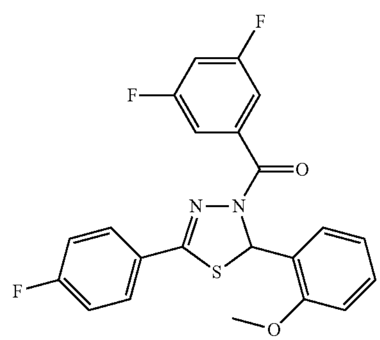 [SMILES: COc1ccccc1C1SC(c2ccc(F)cc2)=NN1C(=O)c1cc(F)cc(F)c1] | 429.2 |
| 454 | 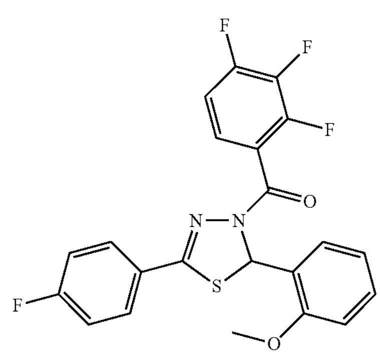 [SMILES: COc1ccccc1C1SC(c2ccc(F)cc2)=NN1C(=O)c1ccc(F)c(F)c1F] | 447.2 |
| 455 | 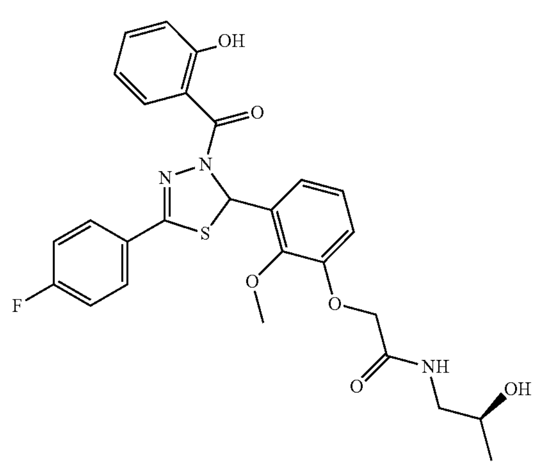 [SMILES: COc1c(OCC(=O)NC[C@H](C)O)cccc1C1SC(c2ccc(F)cc2)=NN1C(=O)c1ccccc1O] | 540.1 |

TABLE 2-continued

| Example | Structure | MS (m/z) (M + 1)+ |
|---|---|---|
| 456 | 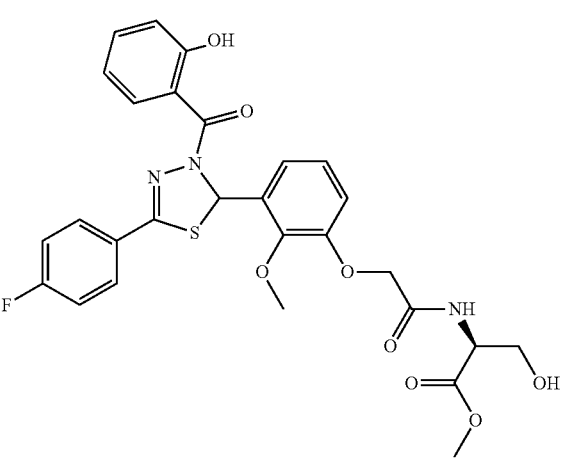 [SMILES: COC(=O)[C@H](CO)NC(=O)COc1cccc(C2SC(c3ccc(F)cc3)=NN2C(=O)c2ccccc2O)c1OC] | 584.2 |
| 457 | 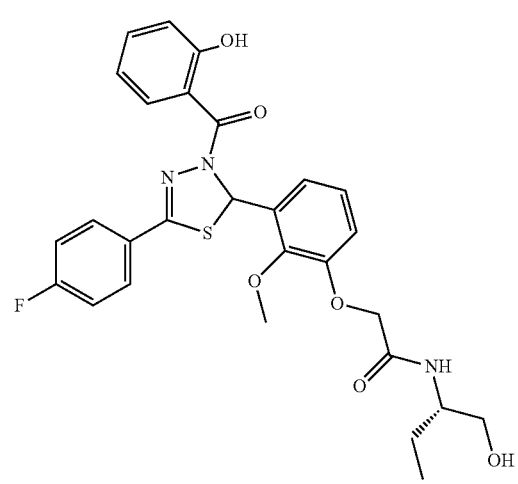 [SMILES: CC[C@@H](CO)NC(=O)COc1cccc(C2SC(c3ccc(F)cc3)=NN2C(=O)c2ccccc2O)c1OC] | 554.1 |
| 458 | 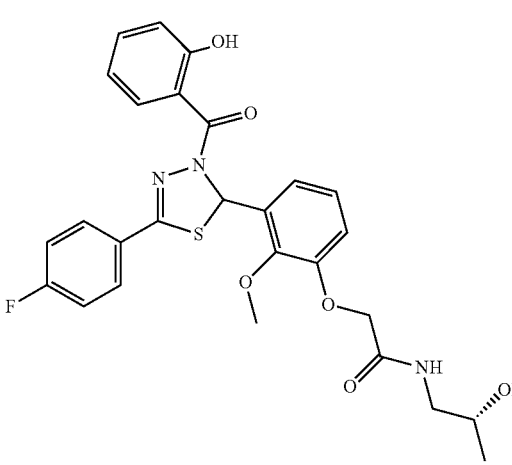 | 540.1 |

Assay 1

Transcriptional Assay

Transfection assays are used to assess the ability of compounds of the invention to modulate the transcriptional activity of the LXRs. Briefly, expression vectors for chimeric proteins containing the DNA binding domain of yeast GAL4 fused to the ligand-binding domain (LBD) of either LXRα or LXRβ are introduced via transient transfection into mammalian cells, together with a reporter plasmid where the luciferase gene is under the control of a GAL4 binding site. Upon exposure to an LXR modulator, LXR transcriptional activity varies, and this can be monitored by changes in luciferase levels. If transfected cells are exposed to an LXR agonist, LXR-dependent transcriptional activity increases and luciferase levels rise.

293T human embryonic kidney cells ($8 \times 10^6$) are seeded in a 175 cm$^2$ flask 2 days prior to the start of the experiment in 10% FBS, 1% Penicillin/Streptomycin/Fungizome, DMEM Media. The transfection mixture for chimeric proteins is prepared using GAL4-LXR LBD expression plasmid (4 μg), UAS-luciferase reporter plasmid (5 μg), Fugene (3:1 ratio; 27 μL) and serum-free media (210 μL). The transfection mixture is incubated for 20 minutes at room temperature. The cells are harvested by washing with PBS (30 mL) and then dissociated using trypsin (0.05%; 3 mL). The trypsin is inactivated by the addition of assay media (DMEM, lipoprotein-deficient fetal bovine serum (5%), statin (e.g. lovastatin 7.5 μM), and mevalonic acid (100 μM)) (10 mL). The cells are counted using a 1:10 dilution and the concentration of cells adjusted to 160,000 cells/mL. The cells are mixed with the transfection mixture (10 mL of cells per 250 μl of transfection mixture) and are further incubated for 30 minutes at room temperature with periodic mixing by inversion. Cells (50 μl/well) are then plated into 384 white, solid-bottom, TC-treated plates. The cells are further incubated at 37° C., 5.0% CO$_2$ for 24 hours. A 12-point series of dilutions (half-log serial dilutions) are prepared for each test compound in DMSO with a starting concentration of compound of 1 μM. Test compound (500n1) is added to each well of cells in the assay plate and the cells are incubated at 37° C., 5.0% CO$_2$ for 24 hours. The cell lysis/luciferase assay buffer Bright-Glo™ (25%; 25 μl; Promega), is added to each well. After a further incubation for 5 minutes at room temperature, the luciferase activity is measured.

Raw luminescence values are normalized by dividing them by the value of the DMSO control present on each plate. Normalized data is visualized using XLfit3 and dose-response curves are fitted using a 4-parameter logistic model or sigmoidal single-site dose-response equation (equation 205 in XLfit3.05). EC50 is defined as the concentration at which the compound elicits a response that is half way between the maximum and minimum values. Relative efficacy (or percent efficacy) is calculated by comparison of the response elicited by the compound with the maximum value obtained for the known LXR modulator, (3-{3-[(2-Chloro-3-trifluoromethyl-benzyl)-(2,2-diphenyl-ethyl)-amino]-propoxy}-phenyl)-acetic acid.

Assay 2

Method for Assessing Endogenous Gene Expression Induced by LXR Modulator

ABCA1 Gene Expression

Human THP1 cells are grown in propagation media (10% defined FBS, 2 mM L-glutamine, 10 mM HEPES, 1.0 mM sodium pyruvate, 4.5 g/L glucose, 1.5 g/L bicarbonate, 0.05 mM 2-Mercaptoethanol in RPMI 1640). On day 1, 0.5 mL of cells at a concentration of 250,000 cells/mL in propagation media plus 40 ng/mL PMA are plated per well on a 48-well dish. Plate is incubated for 24 hours at 37 degrees celsius. On day 2, media is replaced with 0.5 mL fresh assay media (same as propagation media but with 2% lipoprotein deficient FBS as the serum supplement) and compounds are added 6 hours later (1 or 10 μM in DMSO). Plate is then incubated at 37 degrees for 24 hours. On day 3, cells are harvested and RNA is isolated using the RNeasy kit (Qiagen) with DNaseI option. RNA is eluted in 100 ul of water, quantitated (UV absorbance at 260 nm) and stored at −80 degrees till use.

ABCA1 gene expression is measured using TaqMan quantitative PCR using the following primers/probe set for human ABCA1, forward 5'TGTCCAGTCCAGTAATGGT-TCTGT3' (SEQ ID NO. 1), reverse 5'AAGCGAGATATG-GTCCGGATT3'(SEQ ID NO. 2), probe 5'FAM ACACCTG-GAGAGAAGCTTTCAACGAGACTAACCTAMRA3' (SEQ ID NO. 3), and human 36B4, forward 5'CCACGCT-GCTGAACATGC3' (SEQ ID NO. 4), reverse 5'TCGAA-CACCTGCTGGATGAC3' (SEQ ID NO. 5), probe 5'VIC AACATCTCCCCCTTCTCCTTTGGGCT TAMRA3' (SEQ ID NO. 6). Reverse transcription and PCR reactions are run in sequence in the same sample mixture using the Superscript Platinum III Q-PCR reagent (Invitrogen). Reaction mixes (Superscript RT/platinum Taq—0.4 μl, 2× Reaction Mix—10 μl, 36B4 primers—0.4 μl of 10 μM stock, ABCA1 primers—1.8 μl of 10 μM stock, ABCA1 probe-FAM—0.04 μl of 100 μM stock, 36B4 probe-VIC—0.04 μl of 50 μM stock, RNA (50 ng/μl)—2 μl, 50×ROX dye—0.4 μl, MgSO4-0.4 μl of 50 mM stock, water—4.52 μl) are placed in a 384-well plate and run on an ABI HT7900 machine using standard conditions. ABCA1 gene expression is evaluated in reference to a curve of diluted RNA, and normalized to the levels of 36B4 RNA present in the sample. Fold induction induced by compound is calculated in reference to DMSO. Relative efficacy (or percent efficacy) is calculated by comparison of the response elicited by the compound with the maximum value obtained for the known LXR modulator, (3-{3-[(2-Chloro-3-trifluoromethyl-benzyl)-(2,2-diphenyl-ethyl)-amino]-propoxy}-phenyl)-acetic acid.

Fas Gene Expression

Human HepG2 cells are grown in propagation media (10% FBS, 2 mM L-glutamine, 1.5 g/L bicarbonate, 0.1 mM non-essential amino acids, 1.0 mM sodium pyruvate in DMEM). On day 1, 0.5 mL of cells in propagation media at a concentration of 150,000 cells/mL are plated per well on a 48-well plate. Plate is then incubated at 37 degrees for 24 hours. On day 2, media is changed to 0.5 mL of assay media (same as propagation media but with 2% lipoprotein deficient FBS as the serum supplement) and compounds are added 6 hours later (1 or 10 μM in DMSO). Plate is then incubated at 37 degrees for 36-48 hours. Cells are harvested and RNA is isolated using the RNeasy kit (Qiagen) with DNaseI option. RNA is eluted in 100 ul of water, quantitated (UV absorbance at 260 nm) and stored at −80 degrees till use. Fas gene expression is measured using TaqMan quantitative PCR using the following primers/probe set for human Fas, forward 5'GCAAATTCGACCTTTCTCAGAAC3' (SEQ ID NO. 7), reverse 5'GGACCCCGTGGAATGTCA3' (SEQ ID NO. 8), probe 5'FAM ACCCGCTCGGCATGGCTATCTTC TAMRA3' (SEQ ID NO. 9) and human 36B4, forward 5'CCACGCTGCTGAACATGC3' (SEQ ID NO. 10), reverse 5'TCGAACACCTGCTGGATGAC3' (SEQ ID NO. 11), probe 5'VIC AACATCTCCCCCTTCTCCTTTGGGCT-TAMRA3' (SEQ ID NO. 12). Reverse transcription and PCR reactions are run in sequence in the same sample mixture using the Superscript Platinum III Q-PCR reagent (Invitrogen). Reaction mixes (Superscript RT/platinum Taq—0.4 μl, 2× Reaction Mix—10 μl, 36B4 primers—1.2 μl of 10 μM stock, Fas primers—1.2 μl of 10 μM stock, Fas probe-FAM—0.045 μl of 100 μM stock, 36B4 probe-VIC—0.08 μl of 50 μM stock, RNA (50 ng/μl)—2 μl, 50×ROX dye—0.4 μl, MgSO4-1 μl of 50 mM stock, water—3.68 μl) are placed in a 384-well plate and run on an ABI HT7900 machine with standard conditions. Fas gene expression is evaluated in reference to a curve of diluted RNA, and normalized to the levels of 36B4 RNA present in the sample. Fold induction induced by compound is calculated in reference to DMSO.

Assay 3

FRET Co-Activator Recruitment Assay

A FRET assay is used to assess the ability of a compound of the invention to bind directly to the LXR ligand-binding domain (LBD) and promote the recruitment of proteins that potentiate the transcriptional activity of LXRs (e.g. co-activators). This cell-free assay uses a recombinant fusion protein composed of the LXR LBD and a tag (e.g. GST, His, FLAG) that simplifies its purification, and a synthetic biotinylated peptide derived from the nuclear receptor interacting domain of a transcriptional co-activator protein, such as steroid receptor co-activator 1 (SRC-1). In one format, the tagged LBD fusion protein can be labeled using an antibody against the LBD tag coupled to europium (e.g. EU-labeled anti-GST antibody), and the co-activator peptide can be labeled with allophycocyanin (APC) coupled to streptavidin. In the presence of an agonist for LXR, the co-activator peptide is recruited to the LXR LBD, bringing the EU and APC moieties in close proximity. Upon excitation of the complex with light at 340 nM, EU absorbs and transfers energy to the APC moiety resulting in emission at 665 nm. If there is no energy transfer (indicating lack of EU-APC proximity), EU emits at 615 nm. Thus the ratio of the 665 to 615 nm light emitted gives an indication of the strength of co-activator peptide recruitment, and thus of agonist binding to the LXR LBD.

Fusion proteins, amino acids 205-447 (Genbank NM_005693) for LXRα (NR1H3) and amino acids 203-461 (NM_007121 for β) for LXRβ (NR1H3), were cloned in-frame at the Sal1 and Not1 sites of pGEX4T-3 (27-4583-03 Amersham Pharmacia Biotech). A biotinylated peptide sequence was derived from SRC-1 (amino acids 676 to 700): biotin-CPSSHSSLTERHKILHRLLQEGSPSC-OH (SEQ ID NO. 13).

A master mix is prepared (5 nM GST-LXR-LBD, 5 nM Biotinylated SRC-1 peptide, 10 nM APC-Streptavidin (Prozyme Phycolink streptavidin APC, PJ25S), and 5n MEU-Anti-GST Antibody) in FRET buffer (50 mM Tris pH 7.5, 50 mM KCl 1 mM DTT, 0.1% BSA). To each well of a 384 well plate, 20 μL of this master mix is added. Final FRET reaction: 5 nM fusion protein, 5 nM SRC-1 peptide, 10 nM APC-Streptavidin, 5 nm EU-Anti-GST Antibody (PerkinElmer AD0064). Test compounds are diluted in half-log, 12-point serial dilutions in DMSO, starting at 1 mM and 100 mL of compound is transferred to the master mix for a final concentration of 5 μM-28 pM in the assay wells. Plates are incubated at room temperature for 3 hours and fluorescence resonance energy transfer read. Results are expressed as the ratio of APC fluorescence to EU fluorescence times one thousand.

The ratio of 665 nm to 615 nm is multiplied by a factor of 1000 to simplify data analysis. DMSO values are subtracted from ratios to account for background. Data is visualized using XLfit3 and dose-response curves are fitted using a 4-parameter logistic model or sigmoidal single-site dose-response equation (equation 205 in XLfit3.05). EC50 is defined as the concentration at which the compound elicits a response that is half way between the maximum and minimum values. Relative efficacy (or percent efficacy) is calculated by comparison of the response elicited by the compound with the maximum value obtained for a reference LXR modulator.

Compounds of Formula I, in free form or in pharmaceutically acceptable salt form, exhibit valuable pharmacological properties, for example, as indicated by the in vitro tests described in this application. Compounds of the invention display % Efficacy for expression of endogenous ABCA1 ranging from 10% to 130%. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

---

We claim:

1. A compound of Formula I:

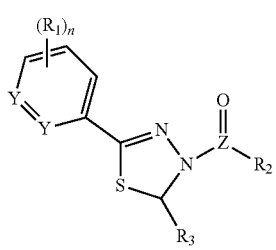

in which
n is selected from 0, 1, 2 and 3;
Z is selected from C and S(O);
each Y is $CR_4$;
or one Y is $CR_4$ and the other is N, thereby forming a pyridine-3-yl;
or one Y is $CR_4$ and the other is N, thereby forming a pyridine-2-yl;
wherein $R_4$ is selected from hydrogen, cyano, hydroxyl, $C_{1-6}$alkyl, $C_{1-6}$alkoxy, halo-substituted-$C_{1-6}$alkyl and halo-substituted-$C_{1-6}$alkoxy;
$R_1$ is selected from halo, cyano, hydroxyl, $C_{1-6}$alkyl, $C_{1-6}$alkoxy, halo-substituted-$C_{1-6}$alkyl, halo-substituted-$C_{1-6}$alkoxy and —$C(O)OR_4$; wherein is selected from hydrogen, cyano, hydroxyl, $C_{1-6}$alkyl, $C_{1-6}$alkoxy, halo-substituted-$C_{1-6}$alkyl and halo-substituted-$C_{1-6}$alkoxy;
$R_2$ is selected from $C_{6-10}$aryl, and $C_{3-12}$cycloalkyl;
wherein any aryl, or cycloalkyl of $R_2$ is optionally substituted with 1 to 5 radicals independently selected from halo, hydroxy, cyano, nitro, $C_{1-6}$alkyl, $C_{1-6}$alkoxy, halo-substituted-$C_{1-6}$alkyl, halo-substituted-$C_{1-6}$alkoxy, —C(O)NR$_5$R$_5$, —OR$_5$, —OC(O)R$_5$, —NR$_5$R$_6$, —C(O)R$_5$ and —NR$_5$C(O)R$_5$;

wherein R$_5$ and R$_6$ are independently selected from hydrogen, $C_{1-6}$alkyl, $C_{1-6}$alkoxy, halo-substituted-$C_{1-6}$alkyl, halo-substituted-$C_{1-6}$alkoxy, $C_{6-10}$aryl-$C_{0-4}$alkyl, and $C_{3-12}$cycloalkyl-$C_{0-4}$alkyl;

wherein any aryl, or cycloalkyl of R$_5$ is optionally substituted with 1 to 4 radicals independently selected from halo, hydroxy, cyano, nitro, $C_{1-6}$alkyl, $C_{1-6}$alkoxy, halo-substituted-$C_{1-6}$alkyl and halo-substituted-$C_{1-6}$alkoxy;

R$_3$ is $C_{5-10}$heteroaryl;

wherein any heteroaryl of R$_3$ is substituted with 1 to 5 radicals independently selected from halo, $C_{1-6}$alkyl, halo-substituted-$C_{1-6}$alkyl, halo-substituted-$C_{1-6}$alkoxy, —OXR$_7$, —OXC(O)NR$_7$R$_8$, —OXC(O)NR$_7$XC(O)OR$_8$, —OXC(O)NR$_7$OR$_8$, —OXC(O)NR$_7$XNR$_7$R$_8$, —OXC(O)NR$_7$XS(O)$_{0-2}$R$_8$, —OXC(O)NR$_7$XNR$_7$C(O)R$_8$, —OXC(O)NR$_7$C(O)XC(O)OR$_8$, —OXC(O)NR$_7$R$_9$, —OXC(O)OR$_7$, —OXOR$_7$, —OXR$_9$, —XR$_9$, —OXC(O)R$_9$, —OXS(O)$_{0-2}$R$_9$ and —OXC(O)NR$_7$CR$_7$[C(O)R$_8$]$_2$;

wherein:

X is a selected from a bond and $C_{1-6}$alkylene wherein any methylene of X can optionally be replaced with a divalent radical selected from C(O), NR$_7$, S(O)$_2$ and O;

R$_7$ and R$_8$ are independently selected from hydrogen, cyano, $C_{1-6}$alkyl, halo-substituted-$C_{1-6}$alkyl, $C_{2-6}$alkenyl and $C_{3-12}$cycloalkyl-$C_{0-4}$-alkyl;

and wherein:

when R$_3$ is $C_{5-10}$heteroaryl, then R$_9$ is selected from $C_{6-10}$aryl-$C_{0-4}$-alkyl, and $C_{3-12}$cycloalkyl-$C_{0-4}$alkyl;

wherein any alkyl of R$_9$ can have a hydrogen replaced with —C(O)OR$_{10}$; and any aryl, or cycloalkyl of R$_9$ is optionally substituted with 1 to 4 radicals independently selected from halo, $C_{1-6}$alkyl, $C_{3-12}$cycloalkyl, halo-substituted-$C_{1-6}$ alkyl, $C_{1-6}$alkoxy, halo-substituted-$C_{1-6}$alkoxy, —XC(O)OR$_{10}$, —XC(O)R$_{10}$, —XC(O)NR$_{10}$R$_{10}$, —XS(O)$_{0-2}$NR$_{10}$R$_{10}$ and —XS(O)$_{0-2}$ R$_{10}$;

wherein R$_{10}$ is independently selected from hydrogen and $C_{1-6}$alkyl;

and a pharmaceutically acceptable salt or isomer thereof.

2. The compound of claim 1 of Formula Ia:

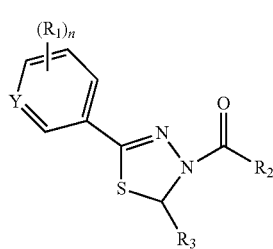

(Ia)

in which n is selected from 1, 2 and 3;

Y is CH or N;

R$_1$ is selected from halo, $C_{1-6}$alkyl, and —C(O)OR$_4$;

wherein R$_4$ is selected from hydrogen and $C_{1-6}$alkyl;

R$_2$ is selected from $C_{6-10}$aryl and $C_{3-12}$cycloalkyl;

wherein any aryl or cycloalkyl of R$_2$ is optionally substituted with 1 to 4 radicals independently selected from halo, hydroxy, $C_{1-6}$alkyl, halo-substituted-$C_{1-6}$ alkyl and —OC(O)R$_5$;

wherein R$_5$ is selected from hydrogen and $C_{1-6}$alkyl; and

R$_3$ is $C_{5-10}$heteroaryl;

wherein any heteroaryl of R$_3$ is substituted with 1 to 5 radicals independently selected from halo, $C_{1-6}$alkoxy, halo-substituted-$C_{1-6}$alkyl, halo-substituted-$C_{1-6}$alkoxy, —OXR$_7$, —OXC(O)NR$_7$R$_8$, —OXC(O)NR$_7$C(O)OR$_8$, —OXC(O)NR$_7$XOR$_8$, —OXC(O)NR$_7$XNR$_7$R$_8$, —OXC(O)NR$_7$XS(O)$_{0-2}$R$_8$, —OXC(O)NR$_7$XNR$_7$C(O)R$_8$, —OXC(O)NR$_7$C(O)XC(O)OR$_8$, —OXC(O)NR$_7$R$_9$, —OXC(O)OR$_7$, —OXOR$_7$, —OXR$_9$, —XR$_9$, —OXC(O)R$_9$ and —OXC(O)NR$_7$CR$_7$[C(O)R$_8$]$_2$;

wherein X is a selected from a bond and $C_{1-6}$alkylene;

R$_7$ and R$_8$ are independently selected from hydrogen, cyano, $C_{1-6}$alkyl, halo-substituted-$C_{1-6}$alkyl, $C_{2-6}$alkenyl and $C_{3-12}$cycloalkyl-$C_{0-4}$alkyl;

and wherein:

when R$_3$ is $C_{5-10}$heteroaryl, then R$_9$ is selected from $C_{6-10}$aryl-$C_{0-4}$alkyl, and $C_{3-12}$cycloalkyl-$C_{0-4}$alkyl;

wherein any alkyl of R$_9$ can have a hydrogen replaced with —C(O)OR$_{10}$; and any aryl, or cycloalkyl of R$_9$ is optionally substituted with 1 to 4 radicals independently selected from halo, $C_{1-6}$alkyl, $C_{3-12}$cycloalkyl, halo-substituted-$C_{1-6}$ alkyl, $C_{1-6}$alkoxy, halo-substituted-$C_{1-6}$ alkoxy, —XC(O)OR$_{10}$, —XC(O)R$_{10}$, —XC(O)NR$_{10}$R$_{10}$, —XS(O)$_{0-2}$NR$_{10}$R$_{10}$ and —XS(O)$_{0-2}$ R$_{10}$;

wherein R$_{10}$ is independently selected from hydrogen and $C_{1-6}$alkyl.

3. The compound of claim 2 in which

R$_1$ is selected from fluoro, chloro, methyl and —C(O)OCH$_3$; and

R$_2$ is selected from phenyl, cyclohexyl, cyclopentyl, and naphthyl,;

wherein any aryl or cycloalkyl of R$_2$ is optionally substituted with 1 to 4 radicals independently selected from fluoro, chloro, bromo, hydroxy, methyl, ethyl, propyl, t-butyl, amino, dimethyl-amino, methoxy, trifluoromethyl, trifluoromethoxy and —OC(O)CH$_3$.

4. The compound of claim 3 in which

R$_3$ is selected from pyridinyl substituted with 1 to 5 radicals independently selected from fluoro, chloro, bromo, methoxy, hydroxyl, difluoromethoxy, —OCH$_2$C(O)NH$_2$, —OCH$_2$C(O)OCH$_3$, —OCH$_2$C(O)NHCH$_3$, —OCH$_2$C(O)N(CH$_3$)$_2$, —R$_9$, —OR$_9$, —OCH$_2$R$_9$, —OCH$_2$C(O)R$_9$, —OCH$_2$C(O)NHR$_9$, —OCH$_2$C(O)N(CH$_3$)R$_9$, —OCH$_2$C(O)NHCH$_2$R$_9$, —OCH$_2$CN, —OCH$_2$C$_2$H$_3$, —OCH$_2$C$_2$H$_4$, —O—(CH$_2$)$_2$OH, —OCH$_2$C(O)NH(CH$_2$)$_2$C(O)OC$_2$H$_5$, —OCH$_2$C(O)NH(CH$_2$)$_2$CH$_2$F, —OCH$_2$C(O)NHCH$_2$CH$_2$F, —OCH$_2$C(O)NH(CH$_2$)$_2$C(O)OH, —OCH$_2$C(O)NHC(O)(CH$_2$)$_2$C(O)OCH$_3$, —OCH$_2$C(O)NH(CH$_2$)$_2$NHC(O)CH$_3$, —OCH$_2$C(O)NH(CH$_2$)$_2$C(O)OC$_4$H$_9$, —OCH$_2$C(O)NHCH$_2$C(O)OC$_2$H$_5$, —S(O)$_2$CH$_3$, —OCH$_2$C(O)NHCH$_2$CF$_3$, —OCH$_2$C(O)NHCH$_2$C(O)(CH$_2$)$_2$C(O)OCH$_3$, —OCH$_2$C(O)N(CH$_3$)CH$_2$C(O)OCH$_3$, —OCH$_2$C(O)NH(CH$_2$)$_3$OC$_2$H$_5$, —OCH$_2$C(O)

NH(CH₂)₃OCH(CH₃)₂, —OCH₂C(O)NH(CH₂)₂SCH₃, —OCH₂C(O)NHCH₂CH(CH₃)₂, —OCH₂C(O)NHCH(CH₃)CH₂OH, —OCH₂C(O)NHCH₂CH(CH₃)C₂H₅, —OCH₂C(O)NHCH(CH₃)C(O)OC₂H₅, —OCH₂C(O)NHCH₂CH(CH₃)₂ and —OCH₂C(O)(CH₂)₃OCH(CH₃)₂;

wherein R₉ is phenyl, cyclopropyl-methyl, and phenethyl; wherein any alkyl of R₉ can have a hydrogen replaced with —C(O)OC₂H₅; and wherein any aryl, of R₉ is optionally substituted with 1 to 4 radicals independently selected from methyl, ethyl, cyclopropyl, methoxy, trifluoromethyl, —OC(O)CH₃, —COOH, —S(O)₂NH₂, —C(O)OC₂H₅, —CH₂C(O)OH, —CH₂C(O)OC₂H₅, —CH₂C(O)OCH₃, —C(O)OCH₃, —C(O)NH₂, —C(O)NHCH₃ and —C(O)CH₃.

5. A pharmaceutical composition comprising a therapeutically effective amount of a compound of claim 1 in combination with a pharmaceutically acceptable excipient.

6. The compound of claim 1 selected from:

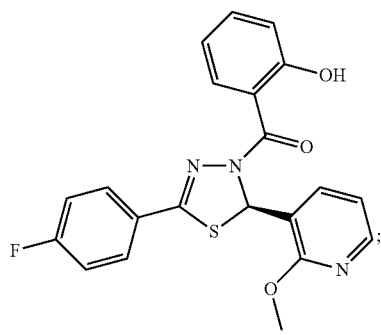

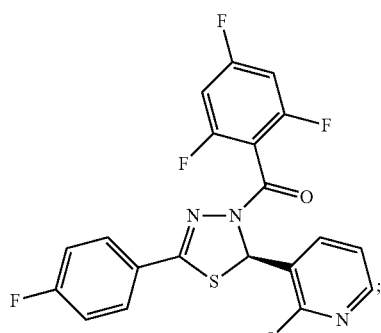

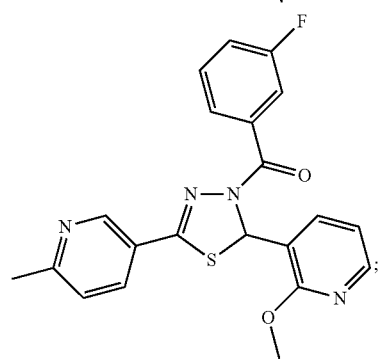

-continued

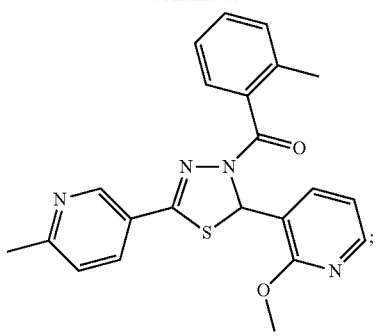

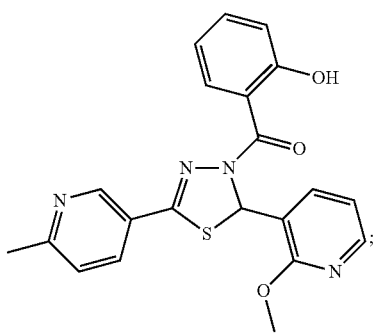

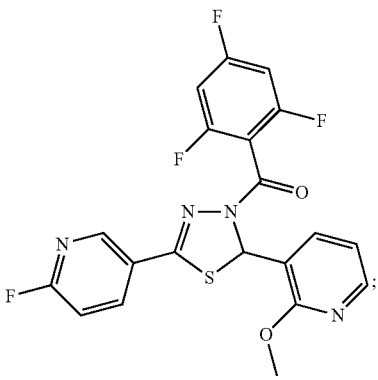

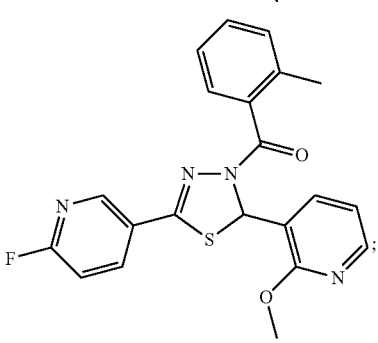

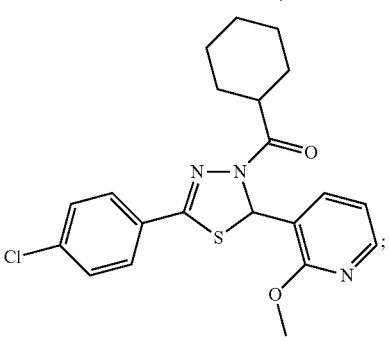

319
-continued
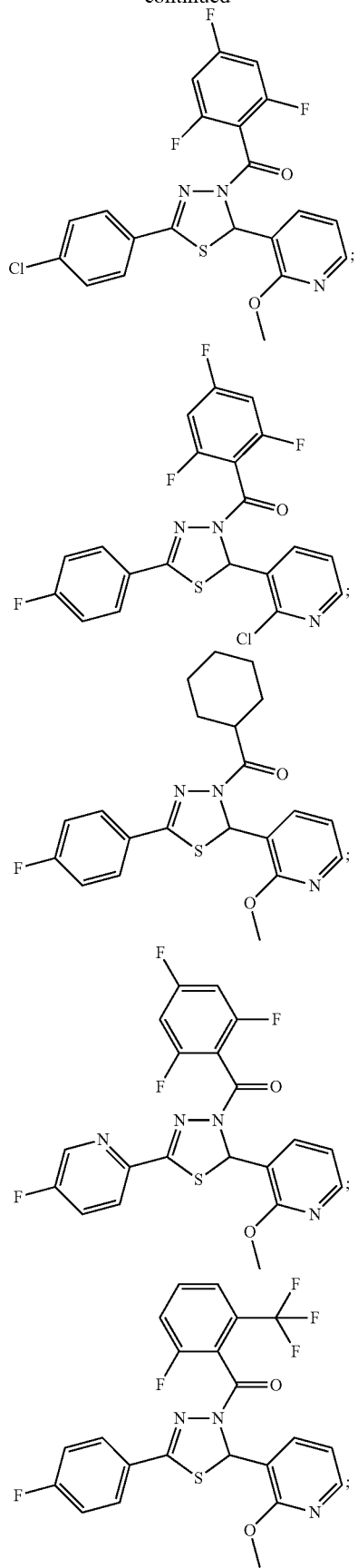
320
-continued
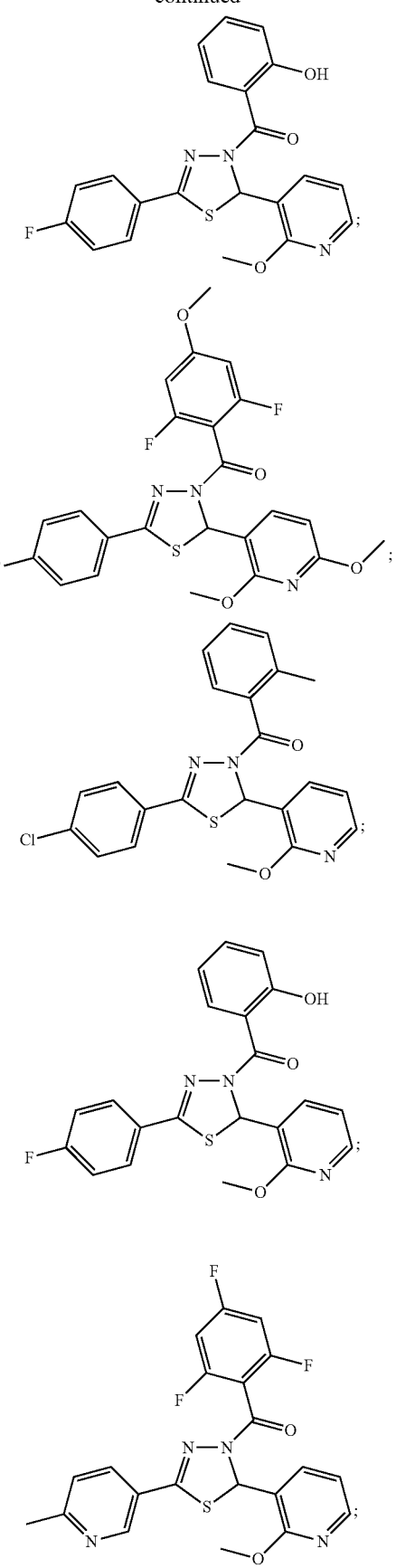

321
-continued
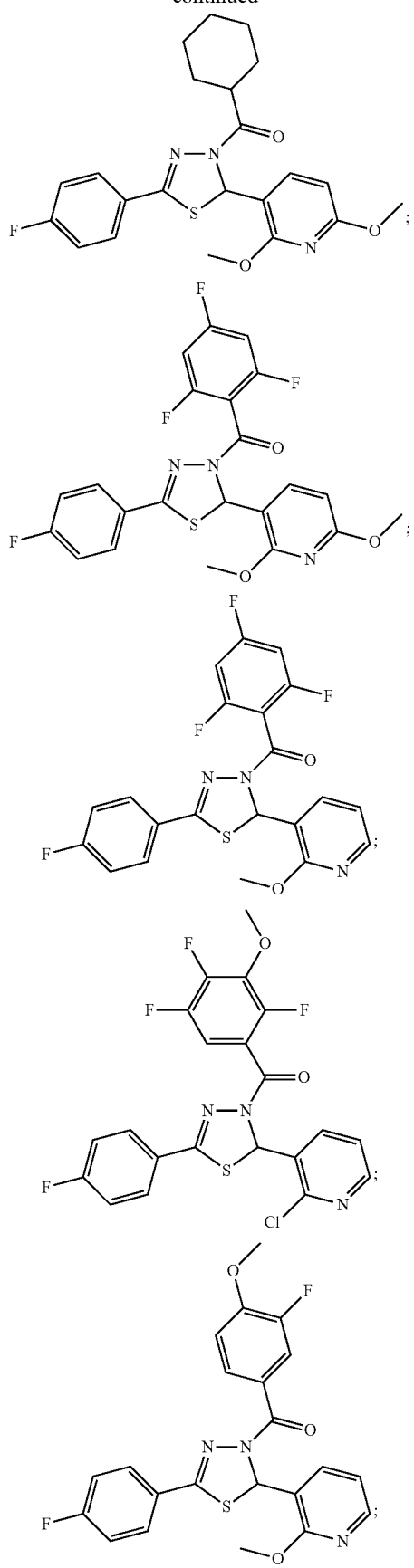
322
-continued
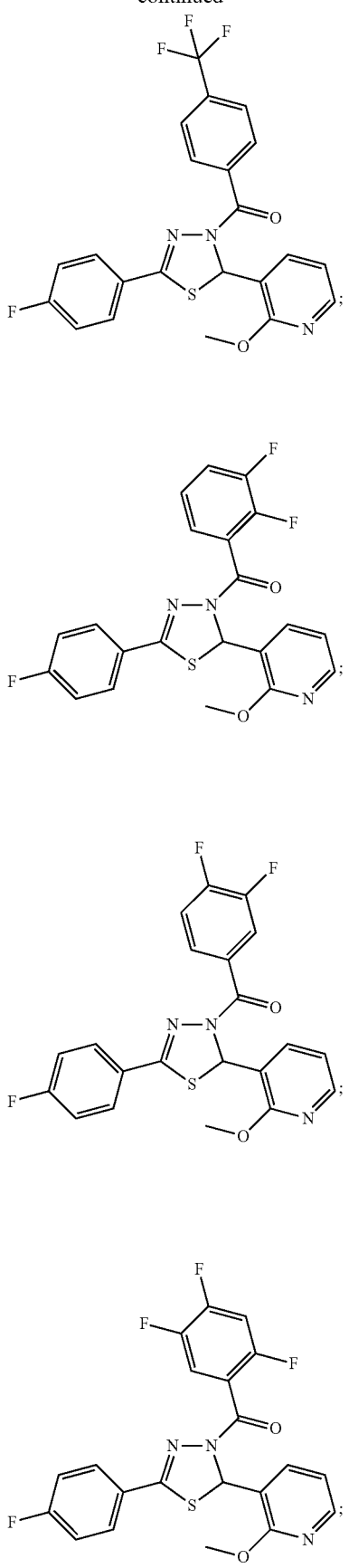

323
-continued
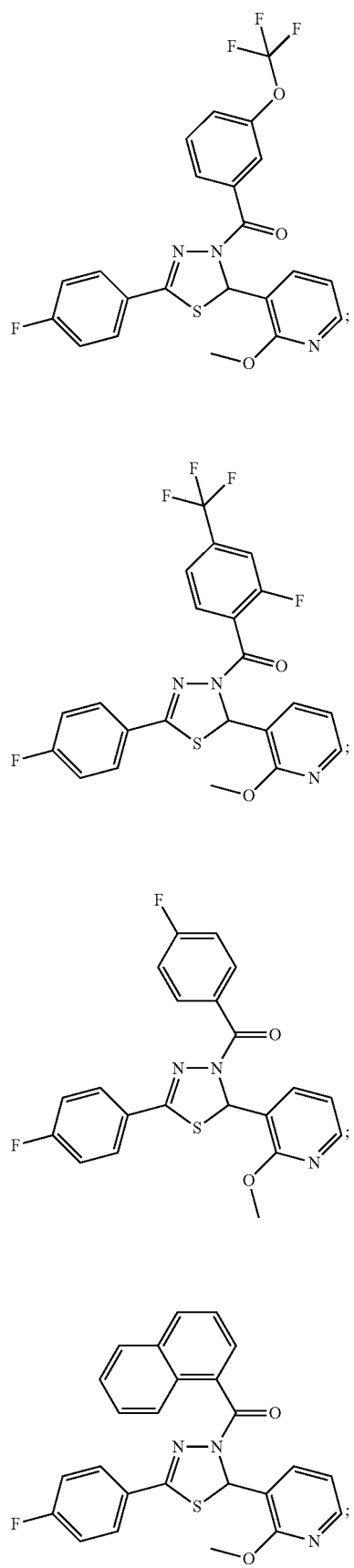
324
-continued
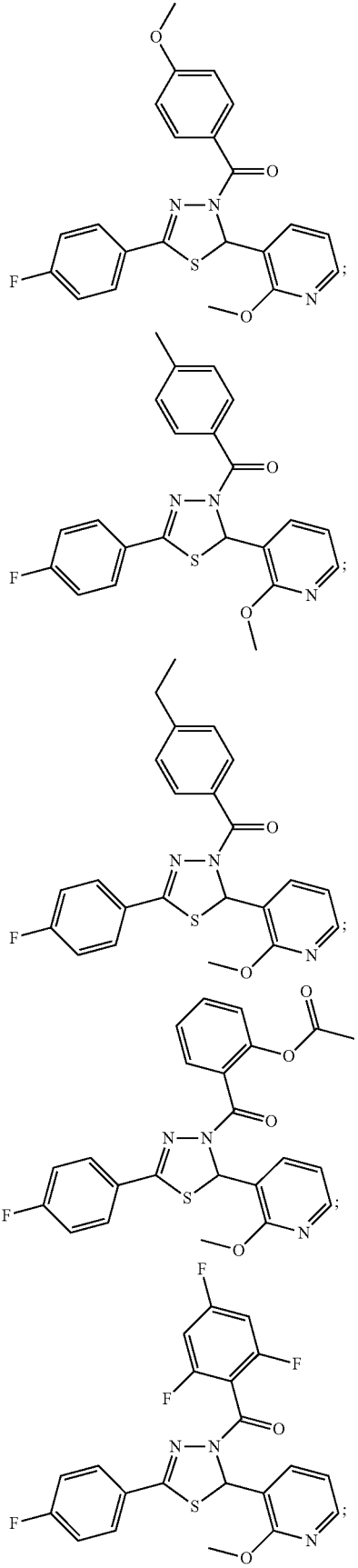

325
-continued
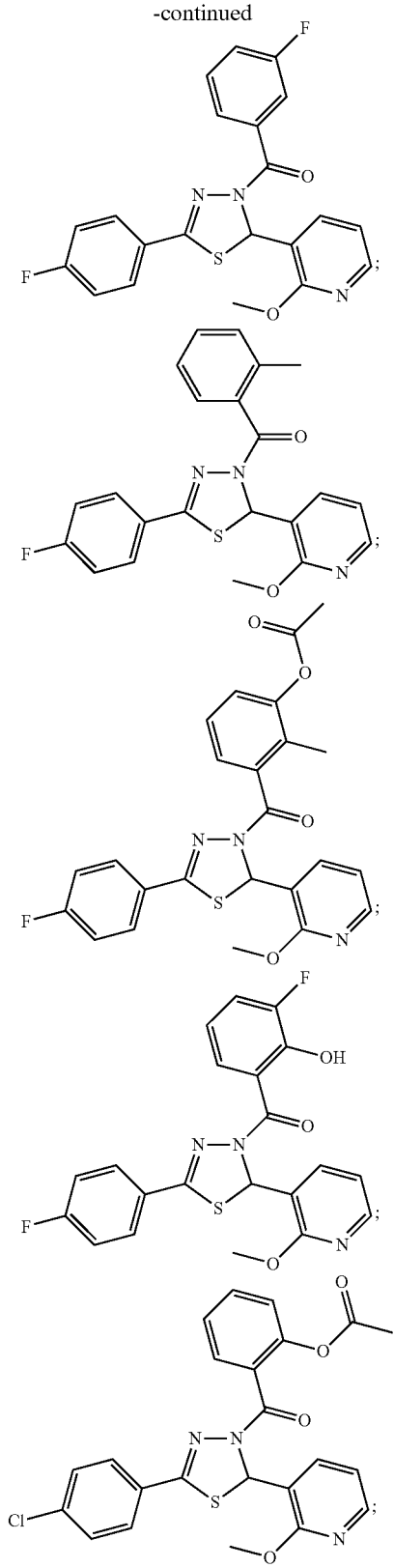
326
-continued
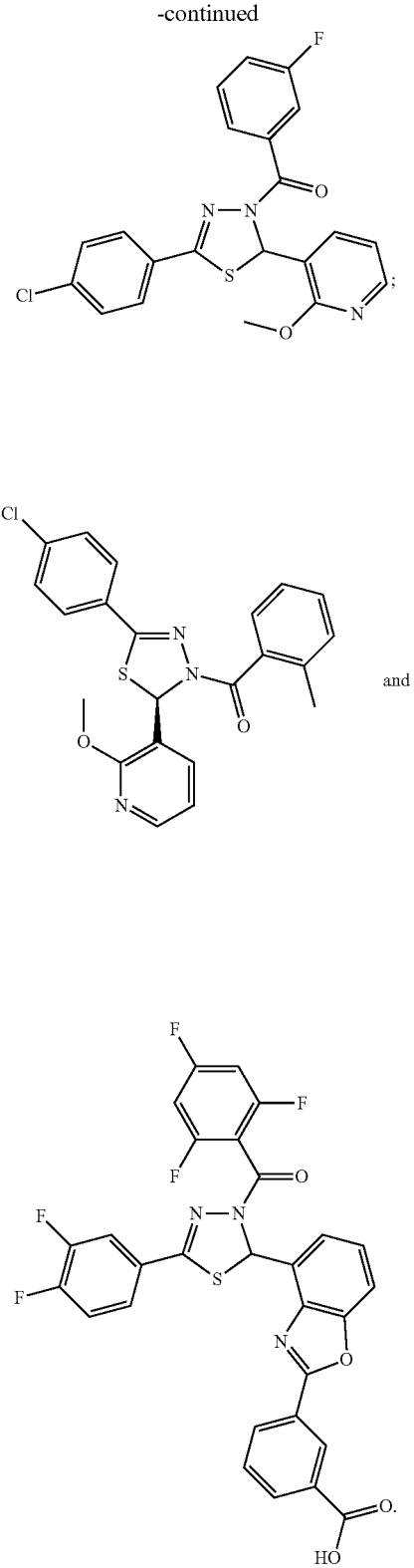
* * * * *